(12) United States Patent
Gandhi et al.

(10) Patent No.: US 11,325,983 B2
(45) Date of Patent: May 10, 2022

(54) BISPECIFIC ANTIBODIES

(71) Applicant: Novo Nordisk A/S, Bagsvaerd (DK)

(72) Inventors: Prafull S. Gandhi, Ballerup (DK); Jens Breinholt, Dyssegaard (DK); Henrik Oestergaard, Oelstykke (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 17/501,548

(22) Filed: Oct. 14, 2021

(65) Prior Publication Data

US 2022/0064329 A1   Mar. 3, 2022

Related U.S. Application Data

(63) Continuation of application No. PCT/EP2020/060579, filed on Apr. 15, 2020.

(30) Foreign Application Priority Data

Apr. 17, 2019 (EP) .................... 19169704
Dec. 5, 2019 (EP) .................... 19213867

(51) Int. Cl.
  *C07K 16/36* (2006.01)
  *C07K 16/28* (2006.01)
  *A61P 7/04* (2006.01)
  *A61K 39/00* (2006.01)

(52) U.S. Cl.
  CPC .............. *C07K 16/36* (2013.01); *A61P 7/04* (2018.01); *C07K 16/2803* (2013.01); *A61K 39/00* (2013.01); *A61K 2039/505* (2013.01); *C07K 2317/31* (2013.01); *C07K 2317/56* (2013.01); *C07K 2317/565* (2013.01)

(58) Field of Classification Search
  None
  See application file for complete search history.

(56) References Cited

U.S. PATENT DOCUMENTS

| | | | |
|---|---|---|---|
| 5,496,549 A | 3/1996 | Yamazaki et al. | |
| 5,506,134 A | 4/1996 | Soule et al. | |
| 6,541,275 B1 | 4/2003 | Ruiz et al. | |
| 7,553,936 B2 | 6/2009 | Mori et al. | |
| 8,062,635 B2 * | 11/2011 | Hattori | C07K 16/36 514/14.1 |
| 8,063,180 B2 | 11/2011 | Teigelkamp et al. | |
| 9,334,331 B2 * | 5/2016 | Igawa | C07K 16/40 |
| 2003/0003096 A1 | 1/2003 | Jurgen Romisch et al. | |
| 2004/0180409 A1 | 9/2004 | McVicar et al. | |
| 2019/0083587 A1 | 3/2019 | Hilden et al. | |

FOREIGN PATENT DOCUMENTS

| | | |
|---|---|---|
| EP | 0513778 A2 | 11/1992 |
| WO | 9601653 A1 | 1/1996 |
| WO | 2006/096828 A2 | 9/2006 |
| WO | 2009/140598 A1 | 11/2009 |
| WO | 2010066803 | 6/2010 |
| WO | 2010/132370 A2 | 11/2010 |
| WO | 2011/023785 A1 | 3/2011 |
| WO | 2011/124685 A1 | 10/2011 |
| WO | 2012/006633 A1 | 1/2012 |
| WO | 2012/117091 A1 | 9/2012 |
| WO | WO-2012117091 A1 * | 9/2012 ............. A61K 38/36 |
| WO | 2018053597 A1 | 3/2018 |

OTHER PUBLICATIONS

Agersoe et al. "Recombinant human factor VIIa (rFVIIa) cleared principally by antithrombin following intravenous administration in hemophilia patients." Journal of Thrombosis and Haemostasis, Nov. 2010, vol. 9, No. 2, pp. 333-338.
Klein et al., "Progress in overcoming the chain association issue in bispecific heterodimeric IgG antibodies", MABS, Nov. 2012, vol. 4, No. 6, pp. 653-663.
Kontermann, Ronald E., "Dual Targeting Strategies with Bispecific Antibodies", MABS, Mar. 2012, vol. 4, No. 2, pp. 182-197.
Washington A. V. et al., "A TREM family member, TLT-1, is found exclusively in the alpha-granules of megakaryocytes and platelets", Blood, Aug. 15, 2004, vol. 104, No. 4, pp. 1042-1047.
Gattis J. L. et al., "The Structure of the Extracellular Domain of Triggering Receptor Expressed on Myeloid Cells Like Transcript-1 and Evidence for a Naturally Occurring Soluble Fragment", The Journal of Biological Chemistry, May 12, 2006, vol. 281, No. 19, pp. 13396-13403.
Emsley J. et al., "Structure and function of factor XI", Blood, Apr. 2010, vol. 115, No. 13, pp. 2569-2577.
Giomarelli B. et al., "Inhibition of thrombin-induced platelet aggregation using human single-chain Fv antibodies specific for TREM-like transcript-1", Thrombosis and Haemostasis, Schattauer, GMBH, Jun. 2007, vol. 97, No. 6, pp. 955-964.
Lu Yen-Ta et al.,"Preparation and Characterization of Monoclonal Antibody Against Protein TREM-Like Transcript-1 (TLT-1)", Hybridoma, Feb. 2006, vol. 25, No. 1, pp. 20-26.
Andersen L. M. et al., "Antibody-induced Enhancement of Factor VIIa Activity through Distinct Allosteric Pathways", The Journal of Biological Chemistry, Mar. 16, 2012, vol. 287, No. 12, pp. 8994-9001.
Grounds M., "Recombinant factor VIIa (rFVIIa) and its use in severe bleeding in surgery and trauma: a review", Blood Reviews, Sep. 2003, vol. 17, No. Suppl. 1, pp. S11-S21.

* cited by examiner

Primary Examiner — Michael Szperka
(74) Attorney, Agent, or Firm — Leon Y. Lum

(57) ABSTRACT

The invention relates to a bispecific antibody comprising a first antigen-binding site capable of binding Factor VII(a) and a second antigen-binding site capable of binding TLT-1, pharmaceutical formulations comprising such bispecific antibodies and uses thereof.

9 Claims, No Drawings

Specification includes a Sequence Listing.

BISPECIFIC ANTIBODIES

CROSS-REFERENCE TO RELATED APPLICATIONS

This application is continuation of International Application No. PCT/EP2020/060579, filed Apr. 15, 2020, which claims priority to European Patent Application 19213867.5, filed Dec. 5, 2019 and European Patent Application 19169704.4, filed Apr. 17, 2019; the contents of which are incorporated herein by reference

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on Oct. 14, 2021, is named "Untitled_ST25", and is 418 kilobytes in size.

TECHNICAL FIELD OF THE INVENTION

The present invention pertains to bispecific antibodies exhibiting improved pharmaceutical properties, compositions comprising such antibodies and uses of such antibodies and compositions, such as pharmaceutical and therapeutic uses.

SEQUENCE LISTING

The present application is filed with a Sequence Listing in electronic form. The entire contents of the sequence listing are hereby incorporated by reference.

BACKGROUND OF THE INVENTION

The process of blood coagulation involves several proteins that act together following vascular injury to generate a blood clot that prevents severe loss of body fluids and/or pathogenic invasion. The cascade of events leading to the formation of a blood clot can be initiated through two pathways known as the intrinsic (contact) and extrinsic (tissue factor) pathways. Each pathway consists of a series of zymogen activation steps where a newly activated enzyme catalyzes the activation of the next zymogen in the series until prothrombin is converted to thrombin. Thrombin coverts fibrinogen to fibrin meshwork and activates platelets to form a platelet plug, together resulting in the formation of a stable blood clot. Initiation of the extrinsic clotting pathway is mediated by formation of the complex between membrane bound tissue factor (TF), which is exposed as a result of injury to a vessel wall, and low levels of circulating factor VIIa (FVIIa). The FVIIa:TF complex initiates the coagulation cascade by activating small quantities of coagulation factor IX (FIX) and factor X (FX). During the initial phase, the small concentration of FXa produces minute amounts of thrombin that can activate factor XI and cofactors VIII and V. During the propagation phase, the procoagulant complexes are assembled and they significantly enhance the generation of FXa and thrombin by the tenase (FIXa, FVIIIa, $Ca^{2+}$, phospholipids) and prothrombinase (FXa, FVa, $Ca^{2+}$, phospholipids) complexes respectively.

In people with haemophilia A and B (HA and HB, respectively) various steps of the coagulation cascade are rendered dysfunctional due to the absence or insufficient presence of functional FVIII and FIX, respectively. This leads to an impaired and insufficient blood coagulation and potentially life-threatening bleeding or damage to internal organs, such as the joints.

Recombinant FVIIa (rFVIIa) has been widely used as a bypassing agent for on-demand (OD) treatment of bleeds in people with haemophilia (A and B) with inhibitors (HwI). rFVIIa has a short systemic half-life of 2-3 hrs when administered intravenously (IV) and a low bioavailability when administered subcutaneously (SC). The short systemic half-life of rFVIIa is believed to be due to involvement of several mechanisms including inhibition by plasma inhibitors antithrombin III (AT) (Agersø H et al. (2010) J. Thromb. Haemost. 9:333-8.) and alpha-2-macroglobulin (α2M) as well as renal clearance. The short systemic half-life and low SC bioavailability of rFVIIa makes it challenging to utilize rFVIIa for prophylactic treatment. Additionally, low intrinsic activity of rFVIIa requires administration of higher rFVIIa doses.

Consequently, there is a need for improved compounds that can support prophylactic treatment with less frequent dosing and SC administration.

Roche recently launched a bispecific antibody, emicizumab, that is indicated for routine prophylaxis dosed once-weekly through SC administration for people with HA and HA with inhibitors (HAwI). Nonetheless, development of safe, efficacious molecules with alternative mechanism of action remains an area of key interest in order to improve and supplement the standard of care for people with Haemophilia.

SUMMARY OF INVENTION

The present invention relates to bispecific antibodies exhibiting improved pharmaceutical properties, particularly it relates to bispecific antibodies that could be used in the treatment of subjects with congenital and/or acquired coagulopathies, for example in the treatment of people with hemophilia A or B with or without inhibitors. Further, the present invention particularly pertains to bispecific antibodies that are capable of binding coagulation Factor VII (FVII(a)) and TREM-like Transcript 1 (TLT-1).

In one aspect, the bispecific antibodies of the invention comprise (i) a first antigen binding site that binds FVII(a), and (ii) a second antigen binding site that binds TLT-1.

In an aspect of the invention, the bispecific antibody prolongs the active circulatory half-life of endogenous FVIIa without loss in endogenous FVIIa activity and stimulate endogenous FVIIa activity by localizing it selectively to activated platelets.

In an embodiment of the invention, the bispecific antibody comprises a Fc region. The Fc region mediates recycling of the bispecific antibody prolonging its half-life in circulation.

In an embodiment of the invention, the first antigen-binding site competes for binding to FVII(a) in a competitive ELISA assay with any one of the anti-FVII(a) antibodies comprising a light chain variable domain (VL) and a heavy chain variable domain (VH) as indicated below:

mAb0522 (VL: SEQ ID NO 846 and VH: SEQ ID NO: 850),
Fab0883 (VL: SEQ ID NO 814 and VH: SEQ ID NO: 818),
mAb0005 (VL: SEQ ID NO 750 and VH: SEQ ID NO: 754),
mAb0004 (VL: SEQ ID NO 14 and VH: SEQ ID NO: 18),
mAb0013 (VL: SEQ ID NO 46 and VH: SEQ ID NO: 50),
mAb0018 (VL: SEQ ID NO 62 and VH: SEQ ID NO: 66), mAb0544 (VL: SEQ ID NO 694 and VH: SEQ ID NO: 698), mAb0552 (VL: SEQ ID NO 702 and VH: SEQ ID NO: 706), mAb0001 (VL: SEQ ID NO 710 and VH: SEQ ID NO: 714), mAb0007 (VL: SEQ ID NO 718 and VH: SEQ ID NO: 722), mAb0578 (VL: SEQ ID NO 726 and VH: SEQ ID NO: 730), mAb0701 (VL: SEQ ID NO 734 and VH: SEQ ID NO: 738), and mAb0587 (VL: SEQ ID NO 742 and VH: SEQ ID NO: 746).

In a further embodiment of the invention, the first antigen-binding site of the bispecific antibody is capable of binding an epitope comprising amino acid residues H115, T130, V131, and R392 of FVII(a) (SEQ ID NO: 1).

In an aspect of the invention, the bispecific antibodies are formulated in pharmaceutical formulations comprising a bispecific antibody of the invention and a pharmaceutically acceptable carrier.

In an aspect of the invention, the bispecific antibodies are parenterally administered, such as intravenously, intramuscularly or subcutaneously. In an aspect of the invention the bispecific antibodies allow for the prophylactic treatment of subjects with a congenital and/or acquired coagulopathy, such as haemophilia A, haemophilia B, haemophilia A with inhibitors or haemophilia B with inhibitors. Hence, the bispecific antibodies are designed to provide haemostatic coverage against bleeds. In an aspect of the invention the bispecific antibodies are designed such as to be suitable for once weekly, once monthly or less frequent administration.

Medical treatment with the bispecific antibodies of the invention may offer a number of advantages, such as longer duration between injections, more convenient administration and potentially improved haemostatic protection between injections. Hence, the bispecific antibodies described herein may have a substantial impact upon the quality of life of individuals with haemophilia A or B, with or without inhibitors.

Brief Description of Sequence Listing

Table 1 is an overview of antibodies and their corresponding SEQ ID NOs for corresponding VL and VL domain sequences. The type of heavy chain constant domains is as defined in Table 2a ("M" denotes a murine IgG1 constant domain).

Table 2a is an overview of different formats used for recombinant expression of bivalent antibodies, monovalent (OA) antibodies and bispecific antibodies. Listed are SEQ ID NOs corresponding to first heavy chain (HC-1) and second heavy chain (HC-2, or for OA antibodies the truncated heavy chain (trHC)). The light chain constant domain was in all cases human kappa corresponding to SEQ ID NO: 12.

Table 2b is an overview of murine anti-FVII(a) antibodies of the current invention. Correspondence between clone name, abbreviation for fully murine (hybridoma-derived except for mAb0765, which was recombinantly expressed) antibodies and corresponding murine/human chimeric variants (murine variable domains, human IgG4 S228P constant domains).

Table 2c is an overview of antibodies in the murine and humanized 11F2 lineage

Table 2d is an overview of antibodies of the anti-TLT-1 mAb0012 lineage

TABLE 1

| Antibody | Target | VL SEQ ID NO | VH SEQ ID NO | Constant domain |
|---|---|---|---|---|
| mAb0004 | FVII(a) | 14 | 18 | M |
| mAb0048 | FVII(a) | 22 | 26 | A |
| Fab0076 | FVII(a) | 30 | 34 | G |
| mAb0077(OA) | FVII(a) | 38 | 42 | E |
| mAb0013 | FVII(a) | 46 | 50 | M |
| mAb0099 | FVII(a) | 54 | 58 | F |
| mAb0018 | FVII(a) | 62 | 66 | M |
| mAb0108 | FVII(a) | 70 | 74 | A |
| mAb0109 | FVII(a) | 78 | 82 | A |
| mAb0110 | FVII(a) | 86 | 90 | A |
| mAb0111 | FVII(a) | 94 | 98 | A |
| mAb0112 | FVII(a) | 102 | 106 | A |
| mAb0113 | FVII(a) | 110 | 114 | A |
| mAb0114 | FVII(a) | 118 | 122 | A |
| mAb0115 | FVII(a) | 126 | 130 | A |
| mAb0116 | FVII(a) | 134 | 138 | A |
| mAb0117 | FVII(a) | 142 | 146 | A |
| mAb0118 | FVII(a) | 150 | 154 | A |
| mAb0119 | FVII(a) | 158 | 162 | A |
| mAb0120 | FVII(a) | 166 | 170 | A |
| mAb0121 | FVII(a) | 174 | 178 | A |
| mAb0122 | FVII(a) | 182 | 186 | A |
| mAb0123 | FVII(a) | 190 | 194 | A |
| mAb0124 | FVII(a) | 198 | 202 | A |
| mAb0125 | FVII(a) | 206 | 210 | A |
| mAb0126 | FVII(a) | 214 | 218 | A |
| mAb0127 | FVII(a) | 222 | 226 | A |
| mAb0128 | FVII(a) | 230 | 234 | A |
| mAb0129 | FVII(a) | 238 | 242 | A |
| mAb0130 | FVII(a) | 246 | 250 | A |
| mAb0137(OA) | FVII(a) | 254 | 258 | E |
| mAb0138(OA) | FVII(a) | 262 | 266 | E |
| mAb0139(OA) | FVII(a) | 270 | 274 | E |
| mAb0140(OA) | FVII(a) | 278 | 282 | E |
| mAb0141(OA) | FVII(a) | 286 | 290 | E |
| mAb0142(OA) | FVII(a) | 294 | 298 | E |
| mAb0143(OA) | FVII(a) | 302 | 306 | E |
| mAb0153 | FVII(a) | 310 | 314 | A |
| mAb0154 | FVII(a) | 318 | 322 | A |
| mAb0155 | FVII(a) | 326 | 330 | A |
| mAb0156 | FVII(a) | 334 | 338 | A |
| mAb0157 | FVII(a) | 342 | 346 | A |
| mAb0158 | FVII(a) | 350 | 354 | A |
| mAb0159 | FVII(a) | 358 | 362 | A |
| mAb0160 | FVII(a) | 366 | 370 | A |
| mAb0161 | FVII(a) | 374 | 378 | A |
| mAb0162 | FVII(a) | 382 | 386 | A |
| mAb0163 | FVII(a) | 390 | 394 | A |
| mAb0164 | FVII(a) | 398 | 402 | A |
| mAb0165 | FVII(a) | 406 | 410 | A |
| mAb0166 | FVII(a) | 414 | 418 | A |
| mAb0167 | FVII(a) | 422 | 426 | A |
| mAb0168 | FVII(a) | 430 | 434 | A |
| mAb0169 | FVII(a) | 438 | 442 | A |
| mAb0170 | FVII(a) | 446 | 450 | A |
| mAb0171 | FVII(a) | 454 | 458 | A |
| mAb0172 | FVII(a) | 462 | 466 | A |
| mAb0173 | FVII(a) | 470 | 474 | A |
| mAb0174 | FVII(a) | 478 | 482 | A |
| mAb0175 | FVII(a) | 486 | 490 | A |
| mAb0176 | FVII(a) | 494 | 498 | A |
| mAb0177 | FVII(a) | 502 | 506 | A |
| mAb0178 | FVII(a) | 510 | 514 | A |
| mAb0203 | FVII(a) | 518 | 522 | A |
| mAb0228 | FVII(a) | 526 | 530 | A |
| mAb0253 | FVII(a) | 534 | 538 | A |
| mAb0278 | FVII(a) | 542 | 546 | A |
| mAb0303 | FVII(a) | 550 | 554 | A |
| mAb0328 | FVII(a) | 558 | 562 | A |
| mAb0353 | FVII(a) | 566 | 570 | A |
| mAb0378 | FVII(a) | 574 | 578 | A |
| mAb0403 | FVII(a) | 582 | 586 | A |
| mAb0428 | FVII(a) | 590 | 594 | A |
| mAb0453 | FVII(a) | 598 | 602 | A |
| mAb0478 | FVII(a) | 606 | 610 | A |
| mAb0503 | FVII(a) | 614 | 618 | A |
| mAb0528 | FVII(a) | 622 | 626 | A |

TABLE 1-continued

| Antibody | Target | VL SEQ ID NO | VH SEQ ID NO | Constant domain |
|---|---|---|---|---|
| mAb0553 | FVII(a) | 630 | 634 | A |
| mAb0578 | FVII(a) | 638 | 642 | A |
| mAb0603 | FVII(a) | 646 | 650 | A |
| mAb0705(OA) | FVII(a) | 654 | 658 | F |
| mAb0706(OA) | FVII(a) | 662 | 666 | F |
| mAb0707(OA) | FVII(a) | 670 | 674 | F |
| mAb0709(OA) | FVII(a) | 678 | 682 | F |
| mAb0710(OA) | FVII(a) | 686 | 690 | F |
| mAb0544 | FVII(a) | 694 | 698 | M |
| mAb0552 | FVII(a) | 702 | 706 | M |
| mAb0001 | FVII(a) | 710 | 714 | M |
| mAb0007 | FVII(a) | 718 | 722 | M |
| mAb0578 | FVII(a) | 726 | 730 | M |
| mAb0701 | FVII(a) | 734 | 738 | M |
| mAb0587 | FVII(a) | 742 | 746 | M |
| mAb0005 | FVII(a) | 750 | 754 | M |
| mAb0842(OA) | FVII(a) | 758 | 762 | F |
| mAb0864 | FVII(a) | 766 | 770 | B |
| mAb0865 | FVII(a) | 774 | 778 | B |
| mAb0872 | FVII(a) | 782 | 786 | B |
| mAb0873 | FVII(a) | 790 | 794 | B |
| mAb0874 | FVII(a) | 798 | 802 | B |
| mAb0875 | FVII(a) | 806 | 810 | B |
| Fab0883 | FVII(a) | 814 | 818 | G |
| mAb7250 | FVII(a) | 822 | 826 | M |
| mAb0350 | FVII(a) | 830 | 834 | D |
| mAb0351 | FVII(a) | 838 | 842 | C |
| mAb0522 | FVII(a) | 846 | 850 | K |
| mAb0524 | TLT-1 | 854 | 858 | J |
| mAb0012 | TLT-1 | 862 | 866 | A |
| mAb0023 | TLT-1 | 870 | 874 | A |
| mAb0051 | TLT-1 | 878 | 882 | A |
| mAb0061 | TLT-1 | 886 | 890 | A |
| mAb0062 | TLT-1 | 894 | 898 | A |
| mAb0082 | TLT-1 | 902 | 906 | A |
| mAb1038 | TLT-1 | 910 | 914 | A |
| mAb1047 | TLT-1 | 918 | 922 | A |
| mAb1049 | TLT-1 | 926 | 930 | A |
| mAb1076 | TLT-1 | 934 | 938 | A |

TABLE 2a

| Constant domain type | Description | HC-1 SEQ ID NO: | HC-2 (or trHC) SEQ ID NO: |
|---|---|---|---|
| A | Bivalent antibody | 4 | 4 |
| B | Bivalent antibody (Duobody) | 5 | 5 |
| C | Bivalent antibody (YTE) | 6 | 6 |
| D | Bivalent antibody (Duobody and YTE) | 7 | 7 |
| E | OA antibody (Duobody) | 4 | 8 |
| F | OA antibody (Knob-in-hole) | 9 | 10 |
| G | Fab fragment | 11 | NA |
| H | Bispecific antibody (Duobody) | 5 | 4 |
| I | Bispecific antibody (Duobody and YTE) | 7 | 6 |
| J | Bivalent antibody (delta-Lys) | 942 | 942 |
| K | Bivalent antibody (Duobody, delta-Lys) | 943 | 943 |
| L | Bispecific antibody (Duobody, delta-Lys) | 943 | 942 |

TABLE 2b

| Clone | Murine | Chimera |
|---|---|---|
| 11F2 | mAb0005/mAb0765 | mAb0048 |
| 11F34 | mAb0007 | mAb0760 |
| 11F9 | mAb0544 | mAb0756 |
| 11F18 | mAb0552 | mAb0757 |
| 8F19 | mAb0018 | mAb0100 |
| 11F19 | mAb0004 | mAb0047 |
| 11F26 | mAb0001 | mAb0759 |
| 12F19 | mAb0578 | mAb0762 |
| 12F39 | mAb0587 | mAb0764 |

TABLE 2b-continued

| Clone | Murine | Chimera |
|---|---|---|
| 12F25 | mab0013 | mAb0096 |
| 17F227 | mAb0701 | mAb0763 |

TABLE 2c

| Antibody | Variable domain | Constant domain |
|---|---|---|
| mAb0005 | Murine VL/VH | M |
| mAb0048 | Murine VL/VH | A |
| Fab0076 | Murine VL/VH | G |
| mAb0077(OA) | Murine VL/VH | E |
| mAb0705(OA) | Humanized VL/VH | F |
| Fab0883 | Humanized VL/VH | G |
| mAb0865 | Humanized VL/VH | B |
| mAb0522 | Humanized VL/VH | K |

TABLE 2d

| Antibody | Variable domain | Constant domain |
|---|---|---|
| mAb0012 | Murine VL/VH | M |
| mAb0082 | Murine VL C41A/VH T61A | A |
| mAb1076 | Humanized VL/VH | A |
| mAb0524 | Humanized VL/VH | J |

In the present invention recombinantly produced antibodies were all expressed in a human IgG4 background, and all contained the standard hinge-stabilizing substitution S228P (EU numbering). In some variants the C-terminal lysine of the heavy chain (K447, which is rapidly cleaved off in vivo; see Cai et al. Biotechnol. Bioeng. 2011 vol. 108, pp 404-412) was omitted (referred to as delta-lys). Additional substitutions were according to Table 2a introduced in the heavy chain constant domain to secure desired chain-pairing in bispecific and monovalent antibodies (Duobody mutations F405L R409K (Labrijn et al. PNAS 2013, vol. 110, pp. 5145-5150) and knob-in-hole mutations (see Carter et al. J. Imm. Methods 2001, vol. 248, pp. 7-15) T366W (knob) and T366S L368A Y407V (hole)), or to prolong the in vivo half-life (YTE mutations, M252Y S254T T256E (Dall'Acqua et al. J. Biol. Chem. 2006, vol. 18, pp. 23514-23524)). All recombinantly produced antibodies of the present invention has the human kappa light chain constant domain (SEQ ID NO: 12).

DETAILED DESCRIPTION OF THE INVENTION

The present invention relates to the design and use of antibody compositions exhibiting improved pharmaceutical properties. Particularly it pertains to bispecific antibodies that are capable of binding coagulation FVII(a) and TLT-1.

Antibodies

The term "antibody" herein refers to a protein, derived from an immunoglobulin sequence, which is capable of binding to an antigen or a portion thereof. The term antibody includes, but is not limited to, full length antibodies of any class (or isotype), that is, IgA, IgD, IgE, IgG, IgM and/or IgY.

Of particular interest for therapeutic antibodies is the IgG sub-class which in humans is divided into four sub-classes IgG1, IgG2, IgG3 and IgG4, based on the sequence of their heavy chain constant regions. The light chains can be divided into two types, kappa and lambda chains, based on differences in their sequence composition. IgG molecules are composed of two heavy chains, interlinked by two or more disulfide bonds, and two light chains, each attached to a heavy chain by a disulfide bond. An IgG heavy chain may comprise a heavy chain variable domain ($V_H$) and up to three heavy chain constant ($C_H$) domains: $C_H1$, $C_H2$ and $C_H3$. A light chain may comprise a light chain variable domain (VL) and a light chain constant domain ($C_L$). $V_H$ and $V_L$ regions can be further subdivided into regions of hypervariability, termed complementarity determining regions (CDRs), interspersed with regions that are more conserved, termed framework regions (FR). $V_H$ and $V_L$ domains are typically composed of three CDRs and four FRs, arranged from amino-terminus to carboxy-terminus in the following order: FR1, CDR1, FR2, CDR2, FR3, CDR3, FR4. The heavy and light chain variable domains containing the hypervariable regions (CDRs) form a structure that is capable of interacting with an antigen, whilst the constant region of an antibody may mediate binding of the antibody to Fc receptors and the first component, C1q, of the C1 complex of the classical complement system.

The term "antigen binding site" or "binding portion" refers to the part of the antibody that enables antigen binding.

The term "antigen-binding fragment" of an antibody refers to a fragment of an antibody that retains the ability to bind to its cognate antigen, such as FVII(a), TLT-1 or another target molecule, as described herein. Examples of antigen-binding fragments include (but is not limited to) Fab, Fab', Fab$_2$, Fab'$_2$, Fv, single-chain Fv (scFv) or a single $V_H$ or $V_L$ domain.

The term "one-armed antibody" as used herein, refers to a particular type of monovalent antibody fragment composed of an antibody heavy chain, a truncated heavy chain lacking the Fab region, and a single light chain.

The term "monospecific" antibody as used herein, refers to an antibody which is capable of binding to one particular epitope (including but not limited to bivalent antibodies).

The terms "bispecific antibody" and "biAb" herein refers to an antibody which is capable of binding to two different antigens, such as FVII(a) and TLT-1, or two different epitopes on the same antigen.

Bispecific antibodies of the invention are derived from antibodies or antigen-binding fragment thereof. Bispecific antibodies of the inventions may be fusions or conjugates of antibodies and antigen binding fragments of antibodies, such as e.g. Fab, Fab', Fab2, Fab'2 or scFv. Bispecific antibodies of the invention may also be fusions or conjugates of antibody fragments. A wide range of molecular formats for bispecific antibodies derived from antibodies and antibody fragments are known in the art, see e.g. (Spiess et al.: Molecular Immunology 67, (2015), pp. 95-106) and (Brinkmann and Kontermann: MABS, 9 (2017), pp 182-212).

Bispecific antibodies may be made in a variety of ways described in the art see e.g. (Spiess et al.: Molecular Immunology 67, (2015), pp. 95-106) and (Brinkmann and Kontermann: MABS, 9 (2017), pp 182-212). For example, desired heavy chain pairing can be achieved by engineering the dimerisation interface of the Fc region to promote heterodimerisation. One example hereof is the so-called knob-in-hole mutations where sterically bulky side chains (knobs) are introduced in one Fc matched by sterically small side chains (holes) on the opposite Fc thereby creating steric complementarity promoting heterodimerisation. Other methods for engineered heterodimerisation Fc interfaces are electrostatic complementarity, fusion to non-IgG heterodimerisation domains or utilising the natural Fab-arm exchange phenomenon of human IgG4 to conduct heterodimerisation in vitro. Examples of heterodimerised bispecific antibodies are well described in the literature, e.g. (Klein C, et al.; MAbs. 2012 4, pp 653-663). Special attention has to be paid to the light chains in heterodimeric antibodies. Correct pairing of LCs and HCs can be accomplished by the use of a common light chain. Engineering of the LC/HC interface can be used to promote heterodimerisation or light chain cross-over engineering as in CrossMabs. In vitro re-assembly under mildly reducing conditions of antibodies from two individual IgGs containing appropriate mutations can also be used to generate bispecific antibodies (e.g. Labrijn et al., PNAS, 110 (2013), pp 5145-5150). Also, the natural Fab-arm exchange method is reported to ensure correct light chains paring.

The term "multispecific" antibody as used herein, refers to an antibody which is capable of binding to two or more different antigens or two or more different epitopes on the same antigen. Multispecific antibodies thus comprise bispecific antibodies.

The antibodies of the invention may be combined with other antibodies and antibody fragments known in the art creating bispecific, trispecific or multispecific antibody molecules.

In one aspect, an antibody of the invention is a chimeric antibody, a human antibody or a humanised antibody. Such antibody can be generated by using, for example, suitable antibody display or immunization platforms or other suitable platforms or methods known in the field.

Furthermore, if the antibody contains a constant region, the constant region or a portion thereof is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

Human antibodies may be isolated from sequence libraries built on selections of human germline sequences, further diversified with natural and synthetic sequence diversity. Human antibodies may be prepared by in vitro immunisation of human lymphocytes followed by transformation of the lymphocytes with Epstein-Barr virus. Human antibodies may be produced by recombinant methods known in the art.

The term "humanised antibody", as used herein, refers to a human/non-human antibody that contains a sequence (CDR regions or parts thereof) derived from a non-human immunoglobulin. A humanised antibody is, thus, a human immunoglobulin (recipient antibody) in which residues from at least a hypervariable region of the recipient are replaced by residues from a hypervariable region of an antibody from a non-human species (donor antibody) such as from a mouse, rat, rabbit or non-human primate, which have the desired specificity, affinity, sequence composition and functionality. In some instances, framework (FR) residues of the human immunoglobulin are replaced by corresponding non-human residues. An example of such a modification is the introduction of one or more so-called back-mutations, which are typically amino acid residues derived from the donor antibody. Humanisation of an antibody may be carried out using recombinant techniques known to the person skilled in the art (see, e.g., Antibody Engineering, Methods in Molecular Biology, vol. 248, edited by Benny K. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanised antibody can be further optimised for e.g. affinity, functionality and biophysical properties by identification of critical framework positions where re-introduction (back-mutation) of the amino acid residue from the donor antibody has beneficial impact on the properties of the humanised antibody. In addition to donor antibody derived back-mutations, the humanised antibody can be engineered by introduction of germline residues in the CDR or framework regions, elimination of immunogenic epitopes, site-directed mutagenesis, affinity maturation, etc. Furthermore, humanised antibodies may comprise residues that are not found in the recipient antibody or in the donor antibody. These modifications are made to further refine antibody performance. The humanised antibody can, optionally, also comprise at least a portion of an immunoglobulin constant region (Fc), typically that of a human immunoglobulin.

The term "chimeric antibody", as used herein, refers to an antibody comprising portions of antibodies derived from two or more species. For example, the genes encoding such antibody comprise genes encoding variable domains and genes encoding constant domains originated from two different species. For example, the genes encoding variable domains of a mouse monoclonal antibody may be joined to the genes encoding the constant domains of an antibody of human origin.

Antibodies or fragment thereof may be defined in terms of their complementarity-determining regions (CDRs). The term "complementarity-determining region", when used herein, refers to the regions of an antibody in which amino acid residues involved in antigen-binding are typically situated. The CDRs can be identified as the regions with the highest variability among antibody variable domains. Databases can be used for CDR identification such as the Kabat database, the CDRs e.g. being defined as comprising amino acid residues 24-34 (L1), 50-56 (L2) and 89-97 (L3) of the light-chain variable domain and 31-35 (H1), 50-65 (H2) and 95-102 (H3) in the heavy-chain variable domain; (Kabat et al. 1991; Sequences of Proteins of Immunological Interest, Fifth Edition, U.S. Department of Health and Human Services, NIH Publication No. 91-3242). Typically, the numbering of amino acid residues in this region is performed by the method described in Kabat et al. supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence. Numbering is according to Kabat only if specifically stated, otherwise numbering is consecutive according to a specified SEQ ID NO.

The term "framework region" or "FR" residues refer to those $V_H$ or $V_L$ amino acid residues that are not within the CDRs, as defined herein.

An antibody of the invention may comprise a CDR region from one or more of the specific antibodies disclosed herein.

The term "antigen" (Ag) refers to the molecular entity used for immunisation of an immunocompetent vertebrate to produce the antibody (Ab) that recognizes the Ag. Herein, Ag is termed more broadly and is generally intended to include target molecules that are recognized by the Ab.

The present invention encompasses variants of the antibodies, or antigen-binding fragments thereof of the invention, which may comprise 1, 2, 3, 4 or 5 amino acid substitutions and/or deletions and/or insertions in the individual sequences disclosed herein.

"Substitution" variants preferably involve the replacement of one or more amino acids with the same number of amino acids.

The term "epitope", as used herein, is defined in the context of a molecular interaction between an "antigen binding polypeptide", such as an antibody (Ab), and its corresponding antigen (Ag). Generally, "epitope" refers to the area or region on an Ag to which an Ab binds, i.e. the area or region in physical contact with the Ab. In the present invention epitopes are determined using an X-ray derived crystal structure, defining the spatial coordinates of a complex between an Ab, such as a Fab fragment, and its Ag. The term epitope is herein, unless otherwise specified or contradicted by context, defined as Ag (here FVII(a) or TLT-1) residues characterized by having a heavy atom (i.e. a non-hydrogen atom) within a distance of 4 Å from a heavy atom in the Fab.

Epitopes described at the amino acid level, e.g. determined from an X-ray structure, are said to be identical if they contain the same set of amino acid residues. Epitopes are said to overlap if at least one amino acid residue is shared by the epitopes. Epitopes are said to be separate (unique) if no amino acid residue is shared by the epitopes.

The definition of the term "paratope" is derived from the above definition of "epitope" by reversing the perspective. Thus, the term "paratope" refers to the area or region on the antibody, or fragment thereof to which an antigen binds, i.e. to which it makes physical contact to the antigen. The term paratope is herein, unless otherwise specified or contradicted by context, defined as Ab residues characterized by having a heavy atom (i.e. a non-hydrogen atom) within a distance of 4 Å from a heavy atom in FVII(a) or TLT-1. Epitopes on an antigen may comprise one or more hot-spot residues, i.e. residues which are particularly important for the interaction with the cognate antibody, and where interactions mediated by the side chain of said hot-spot residue contribute significantly to the binding energy for the antibody/antigen interaction (Peng et al. *PNAS* 111 (2014), E2656-E2665). Hotspot residues can be identified by testing variants of the antigen, where single epitope residues have been substituted by e.g. alanine, for binding to the cognate antibody. If substitution of an epitope residue with alanine has a strong impact on binding to the antibody, said epitope residue is considered a hot-spot residue, and therefore of particular importance for binding of the antibody to the antigen.

Antibodies that bind to the same antigen can be characterised with respect to their ability to bind to their common antigen simultaneously and may be subjected to "competition binding"/"binning". In the present context, the term "binning" refers to a method of grouping antibodies that bind to the same antigen. "Binning" of antibodies may be based on competition binding of two antibodies to their common antigen in assays based on standard techniques. An antibody's "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Competition assays for determining whether an antibody competes for binding with an anti-FVII(a) or anti-TLT-1 antibody disclosed herein are known in the art. Exemplary competition assays include immunoassays (e.g., ELISA assays, RIA assays), surface plasmon resonance analysis (e.g. using a BIAcore™ instrument), biolayer interferometry (ForteBio®) and flow cytometry.

Typically, a competition assay involves the use of an antigen bound to a solid surface or expressed on a cell surface, a test FVII- or FVIIa binding antibody and a reference antibody. The reference antibody is labelled and the test antibody is unlabeled. Competitive inhibition is measured by determining the amount of labelled reference antibody bound to the solid surface or cells in the presence of the test antibody. Usually the test antibody is present in excess (e.g., 1, 5, 10, 20, 100, 1000, 10000 or 100000-fold). Antibodies identified as being competitive in the competition assay (i.e., competing antibodies) include antibodies binding to the same epitope, or overlapping epitopes, as the reference antibody, and antibodies binding to an adjacent epitope sufficiently proximal to the epitope bound by the reference antibody for steric hindrance to occur.

In an exemplary competition assay, a reference anti-FVII or anti-FVIIa antibody is biotinylated using commercially available reagents. The biotinylated reference antibody is mixed with serial dilutions of the test antibody or unlabeled reference antibody (self-competition control) resulting in a mixture of various molar ratios (e.g., 1, 5, 10, 20, 100, 1000, 10000 or 100000-fold) of test antibody (or unlabeled reference antibody) to labelled reference antibody. The antibody mixture is added to a FVII or FVIIa polypeptide coated-ELISA plate. The plate is then washed, and horseradish peroxidase (HRP)-strepavidin is added to the plate as the detection reagent. The amount of labelled reference antibody bound to the target antigen is detected following addition of a chromogenic substrate (e.g., TMB (3,3',5,5'-tetramethylbenzidine) or ABTS (2,2"-azino-di-(3-ethylbenzthiazoline-6-sulfonate)), which are known in the art. Optical density readings (OD units) are made using a spectrometer (e.g. SpectraMax® M2 spectrometer (Molecular Devices)). The response (OD units) corresponding to zero percent inhibition is determined from wells without any competing antibody. The response (OD units) corresponding to 100% inhibition, i.e. the assay background, is determined from wells without any labelled reference antibody or test antibody. Percent inhibition of labelled reference antibody to FVII or FVIIa by the test antibody (or the unlabeled reference antibody) at each concentration is calculated as follows: % inhibition=(1−(OD units−100% inhibition)/(0% inhibition−100% inhibition))*100.

The person skilled in the art will understand that similar assays may be performed to determine if two or more anti-TLT-1 antibodies shares a binding region, a bin and/or competitively binds the antigen. Persons skilled in the art will also appreciate that the competition assay can be performed using various detection systems known in the art. A test antibody competes with the reference antibody for binding to the antigen if an excess of one antibody (e.g., 1, 5, 10, 20, 100, 1000, 10000 or 100000-fold) inhibits binding of the other antibody, e.g., by at least 50%, 75%, 90%, 95% or 99%, as measured in a competitive binding assay.

Unless otherwise indicated competition is determined using a competitive ELISA assay as described above and provided in Example 7 and Example 32.

The term "binding affinity" is herein used as a measure of the strength of a non-covalent interaction between two molecules, e.g. an antibody, or fragment thereof, and an antigen. The term "binding affinity" is used to describe monovalent interactions. Binding affinity between two molecules, e.g. an antibody, or fragment thereof, and an antigen, through a monovalent interaction may be quantified by determining the equilibrium dissociation constant ($K_D$). $K_D$ can be determined by measurement of the kinetics of complex formation and dissociation, e.g. by the Surface Plasmon Resonance (SPR) as done in Examples 6 and 16 or other methods known in the art. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D=k_d/k_a$. Following the above definition, binding affinities associated with different molecular interactions, such as comparison of the binding affinity of different antibodies for a given antigen, may be compared by comparison of the $K_D$ values for the individual antibody/antigen complexes.

The $K_D$ of an antibody of the invention for its target may be less than 1 pM such as less than 10 pM, such as less than 100 pM, such as less than 200 pM, such as less than 400 pM, such as less than 600 pM, such as less than 1 nM, such as less than 5 nM, such as less than 10 nM, such as less than 20 nM, such as less than 50 nM, such as less than 100 nM, such as less than 200 nM, such as less than 400 nM, such as less than 600 nM, such as less than 800 nM.

In one such embodiment the antibody is a bispecific antibody comprising an anti-FVII(a) arm with a $K_D$ towards FVIIa of less than 1 pM such as less than 10 pM, such as less than 100 pM, such as less than 200 pM, such as less than 400 pM, such as less than 600 pM, such as less than 1 nM, such as less than 5 nM, such as less than 10 nM, such as less than 20 nM, such as less than 50 nM, such as less than 100 nM, such as less than 200 nM, such as less than 400 nM, such as less than 600 nM, such as less than 800 nM, and a second anti-TLT-1 arm with a $K_D$ towards TLT-1 of less than 1 pM such as less than 10 pM, such as less than 100 pM, such as less than 200 pM, such as less than 400 pM, such as less than 600 pM, such as less than 1 nM, such as less than 5 nM, such as less than 10 nM, such as less than 20 nM, such as less than 50 nM, such as less than 100 nM, such as less than 200 nM, such as less than 400 nM, such as less than 600 nM, such as less than 800 nM.

The term "identity" as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. In the present invention similarity and identity were determined using Needleman (Needleman et al. J. Mol. Biol. 1970; 48:443-453) from EMBOSS-6.6.0 using the parameters 10 and 0.5 for gaps opening and extensions, respectively (gapopen=10, gapextend=0.5).

The fragment crystallisable region ("Fc region"/"Fc domain") of an antibody is the C-terminal region of an antibody, which comprises the hinge and the constant $C_H2$ and $C_H3$ domains.

Antibodies of the invention may comprise an Fc region which may have a wild-type amino acid sequence, or it may comprise amino acid substitutions which modulates the effector functions of the antibody, see e.g. (Wang et al.: Protein Cell. 9 (2018), pp. 63-73). Specific examples of Fc variants with modified effector functions are variants where binding to Fcγ receptors has been reduced. One specific example of such a variant is IgG1 comprising the substitutions L234A, L235E, G237A, A330S and P331S (residue numbering according to the EU index) with decreased affinity for certain Fcγ receptors and C1q.

Bispecific Molecules

The term "bispecific molecules" herein refers to molecules capable of binding to different targets, such as FVII (a) and TLT-1. The binding moieties of the bispecific molecule may be derived from an antibody or may be of non-antibody origin. One particular example of a bispecific molecule is a bispecific antibody.

In an aspect of the invention, the bispecific molecule comprises a first antigen binding site capable of binding Factor VII(a), and a second antigen binding site capable of binding TREM-like Transcript 1 (TLT-1).

Bispecific molecules of the invention may comprise non-antibody derived binding moieties, also referred to as alternative scaffolds. Bispecific molecules of the invention may be fusions or conjugates of alternative scaffolds. Bispecific molecules of the invention may be fusions or conjugates of antibodies and alternative scaffolds. Bispecific molecules of the invention may also be fusions or conjugates of antibody fragments and alternative scaffolds.

A large number and variety of alternative scaffolds are known in the art, see e.g. (Simeon and Chen: Protein Cell 9 (2018), pp. 3-14), (Könning and Kolmar: Microbial Cell Factories (2018), pp. 17-32), and (Nygren and Skerra: Journal of Immunological Methods 290 (2004), pp 3-28).

Specific examples of alternative scaffolds are Adnectins, Affilins, Anticalins, Avimers, Atrimers, FN3 scaffolds, Fynomers, OBodies, Kringle domains, Kunitz domains, Knottins, Affibodies, DARPins, Bicyclic peptides and Cysknots.

Factor VII(a)

The terms "Factor VII" and "FVII" herein refer to the zymogen of coagulation factor VII. The terms "Factor VIIa" and "FVIIa" herein refer to activated coagulation factor VII, which is a serine protease. The terms "Factor VII(a)" and "FVII(a)" herein encompass the uncleaved zymogen, Factor VII (FVII), as well as the cleaved and thus activated protease, Factor VIIa (FVIIa). The terms "Factor VII(a)" and "FVII(a)" herein include natural allelic variants of FVII(a) that may exist. One wild type human Factor VII(a) sequence is provided in SEQ ID NO: 1.

```
Wild type human coagulation Factor VII(a)
(SEQ ID NO. 1):
ANAFLEELRPGSLERECKEEQCSFEEAREIFKDAERTKLFW

ISYSDGDQCASSPCQNGGSCKDQLQSYICFCLPAFEGRNCE

THKDDQLICVNENGGCEQYCSDHTGTKRSCRCHEGYSLLAD

GVSCTPTVEYPCGKIPILEKRNASKPQGRIVGGKVCPKGEC

PWQVLLLVNGAQLCGGTLINTIWVVSAAHCFDKIKNWRNLI

AVLGEHDLSEHDGDEQSRRVAQVIIPSTYVPGTTNHDIALL

RLHQPVVLTDHVVPLCLPERTFSERTLAFVRFSLVSGWGQL

LDRGATALELMVLNVPRLMTQDCLQQSRKVGDSPNITEYMF

CAGYSDGSKDSCKGDSGGPHATHYRGTWYLTGIVSWGQGCA

TVGHFGVYTRVSQYIEWLQKLMRSEPRPGVLLRAPFP
```

Wild type FVII(a) consists of 406 amino acid residues and is composed of four domains. There is an N-terminal gamma-carboxyglutamic acid-rich (Gla) domain, where ten glutamate residues (highlighted in bold in the sequence above) may be gamma-carboxylated. The gla domain is followed by two epidermal growth factor (EGF)-like domains and a C-terminal serine protease domain. Both FVII and FVIIa are present in circulation, but FVIIa only at low abundance (approximately 1% of the total FVII(a) pool; Morrissey J H, Broze Jr G J. Tissue factor and the initiation and regulation (TFPI) of coagulation. In: Marder V J, Aird W C, Bennett J S, Schulman S, White II G C, editors. Hemostasis and thrombosis: basic principles and clinical practice. 6th ed. Wolters Kluwer & Lippincott Williams & Wilkins: Philadelphia; 2013. p. 163-78). FVII can be activated to FVIIa by proteolytic cleavage between residues Arg152 and Ile153, resulting in the two-chain FVIIa molecule consisting of a light chain and a heavy chain. The two chains in FVIIa are tethered by a disulfide bond. The light chain contains the Gla and EGF-like domains, and the heavy chain the protease domain. FVIIa requires binding to its cell-surface co-factor tissue factor (TF) to reach its full biological activity.

The predicted full-length cynomolgus monkey (*Macaca fascicularis*) FVII isoform X1 consists of 406 amino acids with the NCBI reference sequence ID XP_015295043.1. The term "cFVIIa-chimera" herein refers to the chimeric cynomolgus monkey FVIIa construct. The amino acid sequence of cFVIIa-chimera is such that the Gla and the first EGF-like domains (amino acids 1-88 when aligned with the human FVIIa sequence) are comprised of the human FVII sequence (Uniprot ID P08709); whereas, the second EGF-like and the protease domains (amino acids 89-406 when aligned with the human FVIIa sequence) are comprised of the cynomolgus monkey FVII isoform X1 sequence (NCBI reference sequence ID XP_015295043.1)

The active half-life of recombinant FVIIa (and endogenous FVIIa) in humans is about 2 to 3 hours, when dosed intravenously. Factor VII(a) may be endogenous, plasma-derived or recombinantly produced, using well known methods of production and purification. The degree and location of glycosylation, gamma-carboxylation and other post-translational modifications may vary depending on the chosen host cell and its growth conditions.

Factor VIIa may be found in different conformations. Factor VIIa circulates in the blood in an inactive conformation or inactive form. This conformation does not have catalytic activity. FVIIa may also be found in an active conformation or active form, herein also referred to as fully active or fully activated FVIIa. The term FVIIa encompasses FVIIa in the inactive form or conformation and FVIIa in the active form or conformation. For example, the active conformation of FVIIa may comprise a complex between FVIIa and tissue factor (FVIIa/TF), e.g. in the form of FVIIa/sTF (1-219), where sTF(1-219) is a truncated and soluble form of tissue factor, or the active conformation of FVIIa may comprise active-site inhibited FVIIa (FVIIai). FVIIai is a catalytically inert form of FVIIa that may be produced by the treatment of FVIIa with Dansyl-Glu-Gly-Arg chloromethyl ketone or Phe-Phe-Arg-chloromethyl ketone (FFR-chloromethyl ketone) (Wildgoose et al (1990) Biochemistry 29: 3413-3420 and Sorensen et al (1997) J Biol Chem 272: 11863-11868). FVIIai retains its affinity for TF and is thought to adopt the same conformation as that induced in FVIIa by TF binding. FVIIai thus has an activated conformation and binding of a test compound to FVIIai is indicative that the test compound will also bind to an activated form of wild-type FVIIa.

The target molecule of an anti-FVII(a) antibody may be any FVII(a) molecule as described herein.

TREM-Like Transcript 1 (TLT-1)

Triggering receptors expressed on myeloid cells (TREMs) have a well-established role in the biology of various myeloid lineages, playing important roles in the regulation of innate and adaptive immunity. TREM-like transcript (TLT)-1 belongs to this family of proteins, though the TLT-1 gene is expressed only in a single lineage, namely megakaryocytes and thrombocytes (platelets) and is exclusively found in the alpha-granules of megakaryocytes and platelets. TLT-1 is a transmembrane protein that is exposed on the surface of activated platelets upon alpha-granule release. To date, TLT-1 has not been found on the surface of resting platelets or on the surface of any other cell type.

TLT-1 contains an extracellular globular head, a stalk region, a transmembrane domain and an intracellular domain containing immunoreceptor tyrosine-based inhibitory motifs (Washington et al. Blood, 2002; 100: 3822-3824). The extracellular globular head of human TLT-1 (hTLT-1) is a single immunoglobulin-like (Ig-like) domain. It is connected to the platelet membrane by a 37-amino acid linker region referred to as the stalk (Gattis et al., Jour Biol Chem, 2006, 281, 19, 13396-13403).

The putative transmembrane segment of hTLT-1 is 20 amino acids long. TLT-1 also has a cytoplasmic Immune-receptor Tyrosine-based Inhibitory-Motif (ITIM), which may function as an intracellular signal transduction motif.

A fraction of TLT-1 is shed upon platelet activation, forming a soluble form (sTLT-1) (Gattis et al., Jour Biol Chem, 2006, 281, 19, 13396-13403). The cleavage site is situated in close proximity to the platelet membrane. A shorter isoform of TLT-1 with a truncated intracellular domain also exists in platelets.

TLT-1 is involved in regulating coagulation and possibly also inflammation at site of an injury. TLT-1 plays a role in platelet aggregation in response to sub-optimal concentration of some platelet agonists (Giomarelli et al, Thromb Haemost 2007; 97: 955-963.). The best described ligand to TLT-1 is fibrinogen (Washington et al. J Clin Invest 2009; 119: 1489-3824.). Recently it was shown that TLT-1 also binds von Willebrand Factor (Doerr A et al, abstract PB359 at International Society of Thrombosis and Haemostasis 2019). sTLT-1 is suggested to have a role in haemorrhage related to sepsis by dampening leukocyte activation and modulating platelet-neutrophil cross-talk (Derive, J Immunol 2012, 188: 5585-5592).

In terms of the current invention, TLT-1 may be from any vertebrate, such as any mammal, such as a rodent (such as a mouse, rat or guinea pig), a lagomorph (such as a rabbit), an artiodactyl (such as a pig, cow, sheep or camel) or a primate (such as a monkey or human being). TLT-1 is, preferably, human TLT-1. TLT-1 may be translated from any naturally occurring genotype or allele that gives rise to a functional TLT-1 protein. A non-limiting example of one human TLT-1 is the polypeptide sequence of SEQ ID NO: 2.

The target molecule of a TLT-1 antibody may be any TLT-1 molecule as described herein.

Anti-FVII(a) Antibodies

The term "anti-FVII(a) antibody" herein refers to antibody having FVII(a) as its target. The anti-FVII(a) antibody is capable of binding to FVII(a) molecules as described herein; including, but not limited to endogenous FVII(a) as found in human plasma, exogenous FVII(a), such as recombinant wild type human FVII(a), and endogenous FVII(a) as found in animal plasma, such as in the rabbit, mouse, rat, dog or monkey.

An anti-FVII(a) antibody" could be a monoclonal, monospecific antibody having FVII(a) as its target. A monospecific anti-FVII(a) antibody typically comprises two identical antigen binding sites that bind FVII(a); non-limiting examples being monoclonal IgG4 anti-FVII(a) antibodies.

Suitable anti-FVII(a) antibodies include, without limitation, any one of anti-FVII(a) antibodies shown in Table 3.

TABLE 3

| Antibody | Target | VL SEQ ID NO | VH SEQ ID NO | Constant domain |
| --- | --- | --- | --- | --- |
| mAb0522 | FVII(a) | 846 | 850 | K |
| Fab0883 | FVII(a) | 814 | 818 | G |
| mAb0005 | FVII(a) | 750 | 754 | M |
| mAb0004 | FVII(a) | 14 | 18 | M |
| mAb0013 | FVII(a) | 46 | 50 | M |
| mAb0018 | FVII(a) | 62 | 66 | M |
| mAb0544 | FVII(a) | 694 | 698 | M |
| mAb0552 | FVII(a) | 702 | 706 | M |
| mAb0001 | FVII(a) | 710 | 714 | M |
| mAb0007 | FVII(a) | 718 | 722 | M |
| mAb0578 | FVII(a) | 726 | 730 | M |
| mAb0701 | FVII(a) | 734 | 738 | M |
| mAb0587 | FVII(a) | 742 | 746 | M |

The anti-FVII(a) antibody may be capable of competing, with any one of the antibodies shown in Table 3, for binding to FVII(a). Whether or not an anti-FVII(a) antibody competes with any one of the antibodies shown in Table 3, for binding to FVII(a), may be determined using methods (that is, competitive binding assays) that are well-known, such as surface plasmon resonance (SPR), ELISA or flow cytometry. Example 7 describes how competition binding to FVII(a) may be determined using a competitive ELISA.

In one embodiment, the anti-FVII(a) antibody binds to FVII(a) with a high affinity. A anti-FVII(a) antibody may have a $K_D$ for its target of less than 1 pM, such as less than 10 pM, such as less than 100 pM, such as less than 200 pM, such as less than 400 pM, such as less than 600 pM, such as less than 1 nM, such as less than 5 nM, such as less than 10 nM, such as less than 20 nM, such as less than 50 nM, such as less than 100 nM, such as less than 200 nM, such as less than 400 nM, such as less than 600 nM, such as less than 800 nM. In vivo, the high-affinity anti-FVII(a) antibody reduces the clearance of FVII(a) by forming a complex with it. Thereby, it prolongs the half-life of FVII(a) and causes it to accumulate in the circulation. In this manner, the antibody can provide an elevated steady-state concentration of FVII (a).

In one embodiment, the anti-FVII(a) antibody does not interfere with the biological function of FVII(a). In an embodiment, the anti-FVII(a) antibody does not prevent endogenous FVII from being activated to FVIIa. For example, the anti-FVII(a) antibodies do not interfere with the ability of FVII to convert into FVIIa (i.e., to auto-activate), whilst bound to TF (as described in Example 12). It is also preferable that the anti-FVII(a) antibody does not prevent FVII(a) from forming the so-called initiation complex with tissue factor (TF) and to activate Factor X (FX) in a TF-dependent or independent manner (as described in Example 10). In an embodiment, the anti-FVII(a) antibody does not compete with FVII(a) substrates or co-factors. However, the anti-FVII(a) antibody might compete with inhibitors of FVIIa, such as antithrombin (AT) and alpha-2-macroglobulin (as described in Example 11).

Anti-TLT-1 Antibodies

The term "anti-TLT-1 antibody" herein refers to antibody having TLT-1 as its target. The anti-TLT-1 antibody is capable of binding to TLT-1 molecules as described herein. An TLT-1 antibody" could be a monoclonal, monospecific antibody.

Suitable anti-TLT-1 antibodies include, without limitation, the anti-TLT-1 antibodies shown in Table 4

TABLE 4

| Antibody | Target | VL SEQ ID NO | VH SEQ ID NO | Constant domain |
|---|---|---|---|---|
| mAb0524 | TLT-1 | 854 | 858 | J |
| mAb0012 | TLT-1 | 862 | 866 | A |
| mAb0082 | TLT-1 | 902 | 906 | A |
| mAb1038 | TLT-1 | 910 | 914 | A |
| mAb1047 | TLT-1 | 918 | 922 | A |
| mAb1049 | TLT-1 | 926 | 930 | A |
| mAb0061 | TLT-1 | 886 | 890 | A |
| mAb0023 | TLT-1 | 870 | 874 | A |
| mAb0051 | TLT-1 | 878 | 882 | A |
| mAb0062 | TLT-1 | 894 | 898 | A |

The anti-TLT-1 antibody may be capable of competing, with any one of the antibodies shown in Table 4 for binding to TLT-1. Whether or not an anti-TLT-1 antibody competes with any one of the antibodies shown in Table 4, for binding to TLT-1, may be determined using methods that are well-known (that is, competitive binding assays), such as surface plasmon resonance (SPR), ELISA or flow cytometry. Competition binding to TLT-1 may be determined using a competitive ELISA. Example 32 describes how competition binding to TLT-1 may be determined using a competitive ELISA.

A anti-TLT-1 antibody may have a $K_D$ for its target of less than 1 pM, such as less than 10 pM, such as less than 100 pM, such as less than 200 pM, such as less than 400 pM, such as less than 600 pM, such as less than 1 nM, such as less than 5 nM, such as less than 10 nM, such as less than 20 nM, such as less than 50 nM, such as less than 100 nM, such as less than 200 nM, such as less than 400 nM, such as less than 600 nM, such as less than 800 nM.

It is preferable that the anti-TLT-1 antibody does not interfere with functions of TLT-1 and—in particular—does not inhibit platelet aggregation.

In one preferred embodiment, anti-TLT-1 antibodies are capable of binding to TLT-1 without interfering with platelet aggregation.

In another preferred embodiment, anti-TLT-1 antibodies are capable of binding to TLT-1 without competing with fibrinogen for binding to TLT-1.

In another preferred embodiment, TLT-1 antibodies do not interfere with the shedding of TLT-1.

It is preferable that anti-TLT-1 antibodies do not bind to, or demonstrate little affinity for, any other triggering receptor expressed on myeloid cells (TREM) than TLT-1, or any other receptor on the resting or activated platelet.

In one embodiment, the anti-TLT-1 antibody binds to the stalk of TLT-1.

Bispecific Anti-FVII(a)/Anti-TLT-1 Antibodies

The bispecific antibodies of the invention comprise a first antigen binding site capable of binding FVII(a), and a second antigen binding site capable of binding TLT-1.

Anti-FVII(a) Antigen Binding Site

In an aspect, the bispecific antibodies of the invention comprise a first antigen binding site capable of binding FVII(a).

In some embodiments of the invention, the first antigen-binding site of the bispecific antibody competes for binding to FVII(a) with any one of the anti-FVII(a) antibodies identified in Table 3; have an epitope identical to any one of the antibodies identified in Table 3; have CDR regions identical to any one of the antibodies identified in Table 3; and have VL and VH regions identical to any one of the antibodies identified in Table 3.

Anti-TLT-1 Antigen Binding Site

In an aspect, the bispecific antibodies of the invention comprise a second antigen binding site capable of binding TLT-1.

In some embodiments of the invention, the second antigen-binding site of the bispecific antibody competes for binding to TLT-1 with any one of the anti-TLT-1 antibodies identified in Table 4; have an epitope identical to any one of the antibodies identified in Table 4; have CDR regions identical to any one of the antibodies identified in Table 4; and have VL and VH regions identical to any one of the antibodies identified in Table 4.

Modified Effector Functions

Bispecific antibodies of the invention may comprise an Fc region which may have a wild-type amino acid sequence, or it may comprise amino acid substitutions which modulates the effector functions of the antibody, see e.g. (Wang et al.: Protein Cell. 9 (2018), pp. 63-73). Specific examples of Fc variants with modified effector functions are variants where binding to Fcγ receptors has been reduced. One specific example of such a variant is IgG1 comprising the substitutions L234A, L235E, G237A, A330S and P331S (residue numbering according to the EU index) with decreased affinity for certain Fcγ receptors and C1q.

A desired property of the bispecific antibodies of the invention is a long in vivo half-life. Bispecific antibodies comprising a Fc-region may be recycled and rescued via the FcRn receptor which, in turn, may result in the desired long half-life. For bispecific antibodies of the invention lacking a Fc-region half-life may be extended by other means. Different methods and principles for obtaining a prolonged half-life of polypeptides and antibodies are known in the art, see e.g. Kontermann: Expert Opinion on Biological Therapy, 16 (2016), pp. 903-915 and references therein.

In addition to Fc-based half-life extension of polypeptides and antibodies, fusion or conjugation to albumin or albumin variants have proven effective in half-life prolongation. Another approach is attachment of polymers, such as XTEN or PEG (insert reference). Furthermore, prolonged in vivo half-life can be obtained by attachment of an albumin binding moiety, see e.g. Tan et al.: Current Pharmaceutical Design 24 (2018), pp. 4932-4946; Kontermann: Expert Opinion on Biological Therapy, 16 (2016), pp. 903-915) and Kontermann: Current Opinion in Biotechnology 22 (2011), pp 868-876).

Functional Features

By binding to FVII(a), the bispecific antibodies of the invention may prolong the active circulatory half-life of FVIIa present in circulation; by binding to TLT-1, the bispecific antibodies and bound FVII(a) is directed to the surface of the activated platelet. This, in turn, leads to increased accumulation of FVIIa on the activated platelet and thus enhanced FVIIa pro-coagulant activity at the site of vascular injury. The bispecific antibodies described herein are thus capable of endowing the endogenous pool of FVII(a) with improved pharmacokinetic (PK) and pharmacodynamic (PD) properties.

In humans, the active half-life of administered recombinant FVIIa is known to be about 2-3 hours. The short half-life of recombinant FVIIa is believed to be due to the involvement of several mechanisms, including inhibition by antithrombin III (AT), inhibition by alpha-2-macroglobulin ($\alpha$2M) and renal clearance. Similar mechanisms are believed to hold true for endogenous FVIIa, thereby endowing it with a similar short half-life.

In order to prolong the active half-life of FVIIa, including the half-life of endogenous FVIIa, the bispecific antibodies described herein aim to intercept one or more of these clearance mechanisms by means of its anti-FVII arm or so-called "first antigen-binding site", without loss of endogenous FVIIa activity. The Fc portion of the biAb:FVIIa complex will, in the endosome and via binding to FcRn, mediate recycling of the complex and rescue it from degradation. Furthermore, a high-affinity anti-FVII arm of the bispecific antibodies protect endogenous FVIIa from $\alpha$2M inhibition and renal clearance by virtue of the increased molecular size of the biAb:FVIIa complex, relative to the size of the free endogenous FVIIa. The anti-TLT-1 arm of the bispecific antibodies selectively localize the protracted endogenous FVIIa to activated platelets. This localization of FVIIa to activated platelets potentiates the FVIIa activity without increasing its susceptibility to AT inhibition.

The bispecific antibodies of the invention may increase the mean residence time (MRT) of endogenous or exogenous FVII(a). It is preferable that the bispecific antibodies are capable of potentiating the activity of FVII(a) in vivo.

Mean Residence Time

The mean residence time (MRT) is the average time a molecule stays in the body, available for therapeutic activity. The MRT is calculated according to equation 1 as a function of volume of distribution at steady-state (Vss) divided by systemic clearance (CL).

$$MRT = Vss/CL \qquad \text{Eq. 1}$$

The results are expressed in time. MRT is correlated with effective plasma half-life ($t_{1/2}$) according to equation 2.

$$MRT = \ln(2) * t_{1/2} \qquad \text{Eq. 2}$$

The ability of an antibody to increase MRT of FVII(a) may be determined by well-known methods, such as such as those described in Pharmacokinetic and Pharmacodynamic Data Analysis: Concepts & Applications (Gabrielsson and Weiner). For example, by analysis of plasma concentration or activity profiles of FVII(a) after IV or SC administration into experimental animals, e.g. mice, rats or monkeys. The ability of an antibody to increase the functional MRT of FVII(a) may be determined by analysis of plasma activity profiles of FVII(a) as measured with assays such as, but not limited to, the FVIIa activity assay described in Example 8.

The ability of an antibody to increase MRT and the functional MRT of FVII(a) may, for example, be determined as described in Examples 9, and 18.

In some embodiments, the bispecific antibodies of the invention are capable of increasing the MRT of FVII(a) by at least 2-fold, at least 3-fold, at least 5-fold, at least 10-fold, at least 20-fold, at least 30-fold, or at least 40-fold compared with administration of FVII(a) in the absence of an antibody of the invention (FVII(a) polypeptide alone).

In some embodiments, bispecific antibodies of the invention are capable of increasing the functional MRT of FVII (a), as measured with a FVIIa activity assay described in Example 8, by at least 2-fold, at least 3-fold, at least 5-fold, at least 10-fold, at least 20-fold, at least 30-fold, or at least 40-fold compared with administration of FVII(a) in the absence of the bispecific antibody of the invention.

Accumulation of Endogenous FVIIa

The ability of the bispecific antibodies of the invention to increase the level of circulating endogenous functionally active FVIIa may, for example, be determined by measuring the level of endogenous FVIIa before and after administration of the antibody into experimental animals, e.g. mice, rats or monkeys, measured with assays such as, but not limited to, the FVIIa activity assay described in Example 8.

The ability of an antibody to increase the level of circulating endogenous functionally active FVIIa may, for example, be determined as described in Examples 27 and 28.

In some embodiments, the bispecific antibodies of the invention are capable of increasing the level of the circulating endogenous FVIIa by at least 2-fold, at least 4-fold, at least 10-fold, at least 20-fold, at least 40-fold, at least 80-fold, at least 160-fold, at least 320-fold, at least 640-fold compared to the level of circulating endogenous FVIIa in the absence of administered bispecific antibody.

TLT-1- and TF-Independent Thrombin Generation

In an aspect, the bispecific antibodies of the invention are capable of maintaining or increasing the TLT-1- and TF-independent ability of Factor VIIa to generate thrombin.

The ability of an antibody to increase thrombin generation of a FVII(a) polypeptide may be determined by methods well-known in the art, such as, e.g., a thrombin generation assay as described in Example 5. In this assay, in this assay thrombin generation is measured in hemophilia A-induced human plasma in the presence of phospholipids, 25 nM FVIIa, and an antibody at a concentration approaching saturation of added FVIIa. Saturation is approached when >90% of FVIIa is bound by antibody according to the measured dissociation constant determined for the FVIIa-antibody interaction by e.g. SPR as exemplified in Example 6. Based on the ratio of peak thrombin formation in the presence and absence of antibodies, antibodies are categorized as stimulatory (>120%), inhibitory (<90%), or neutral (90-120%).

In some embodiments, the bispecific antibodies of the invention are capable of maintaining (neutral)/increasing (stimulatory) the ability of the Factor VII(a) polypeptide to generate thrombin as measured in a thrombin generation assay compared with FVII(a) in the absence of the antibody.

In some embodiments, the bispecific antibodies of the invention are capable of increasing the ability of Factor VII(a) to generate thrombin as measured in a thrombin generation assay to at least 20% compared with FVII(a) in the absence of the antibody.

Inhibition by Antithrombin and/or Alpha-2-Macroglobulin

In an aspect, the bispecific antibodies of the invention are capable of reducing the susceptibility of FVIIa to inhibition by antithrombin (AT) and/or alpha-2-macroglobulin.

The ability of an antibody of reducing the inhibition of FVIIa by antithrombin (AT) and/or alpha-2-macroglobulin may be determined by methods well-known in the art such as described in Example 5 and 11.

In some embodiments, the bispecific antibodies of the invention are capable of reducing the inhibition of FVIIa by antithrombin (AT) and/or alpha-2-macroglobulin compared with the inhibition of FVIIa in the absence of the antibody.

TLT-1-Dependent FXa Generation (Stimulatory Activity Assay)

In an aspect, the bispecific antibodies of the invention are capable of maintaining or increasing the ability of a FVIIa polypeptide to promote FX activation in the presence of a TLT-1-containing procoagulant membrane surface.

The ability of a bispecific antibody of the invention to increase the ability of a FVIIa polypeptide to promote FX activation may be determined by methods well-known in the art, such as, e.g. a TLT-1-dependent stimulatory activity assay as described in Example 21. In this assay, FX activation is measured in the presence of FX (150 nM), FVIIa (2.5 nM), phospholipid membranes containing TLT-1 (4 nM), and an anti-FVII(a)/anti-TLT-1 bispecific antibody. The so-called stimulatory activity of a bispecific antibody (expressed as fold increase), is the amount of generated FXa in the presence of 100 nM bispecific antibody relative to the amount generated by FVIIa in the absence of bispecific antibody.

In some embodiments, the stimulatory activities of the bispecific antibodies of the invention are at least 2-fold, at least 5-fold, at least 10-fold, at least 20-fold, at least 30-fold, at least 40-fold, at least 60-fold, at least 80-fold, at least 100-fold, or at least 150-fold.

TLT-1-Dependent Whole Blood Clot Formation

In an aspect, the bispecific antibodies of the invention are capable of promoting clot formation similar to or better than a therapeutic effective concentration of recombinant FVIIa under hemophilia A conditions.

The ability of a bispecific antibody to improve whole blood clot formation may be determined by methods well-known in the art, such as, e.g. a thromboelastography assay as described in Example 29. In this assay, clot formation is measured in human hemophilia-A induced whole blood to which bispecific antibody is added together with FVII, FVIIa, and FVIIa:AT at concentrations mimicking the in vivo steady state plasma levels of the corresponding endogenous factors upon repeated administration of the bispecific antibody as described in Examples 27, 28, and 29. Coagulation is induced by addition of the PAR1 agonist peptide SFLLRN and calcium. The clot time under these conditions are compared to the clot time achieved by addition of 25 nM FVIIa in the absence of antibody.

In some embodiments, bispecific antibodies of the invention are capable of reducing the clot time in human haemophilia A-induced whole blood to a level similar to or below that achieved by addition of 25 nM FVIIa. In some embodiments, bispecific antibodies of the invention are capable of reducing the clot time in human haemophilia A-induced whole blood to a level similar to or below that achieved by addition of 2 nM FVIIa, 4 nM FVIIa, 6 nM FVIIa, 8 nM FVIIa, 10 nM FVIIa, 12 nM FVIIa, 16 nM FVIIa or 20 nM FVIIa.

Pharmaceutical Formulations

In an aspect, the present invention provides compositions and formulations comprising the bispecific antibodies described herein. For example, the invention provides a pharmaceutical composition that comprises a bispecific antibody formulated together with a pharmaceutically acceptable carrier.

In an embodiment of the invention, the pharmaceutical formulation comprises a bispecific antibody present in a concentration from 80 mg/ml to 200 mg/ml, such as 100-180 mg/ml, and wherein said formulation has a pH from 2.0 to 10.0. The formulation may further comprise one or more of a buffer system, a preservative, a tonicity agent, a chelating agent, a stabilizer or a surfactant, as well as various combinations thereof. The use of preservatives, isotonic agents, chelating agents, stabilizers and surfactants in pharmaceutical compositions is well-known to the skilled person. Reference may be made to Remington: The Science and Practice of Pharmacy, $19^{th}$ edition, 1995.

In one embodiment, the pharmaceutical formulation is an aqueous formulation. Such a formulation is typically a solution or a suspension, but may also include colloids, dispersions, emulsions and multi-phase materials. The term "aqueous formulation" is defined as a formulation comprising at least 50% w/w water. Likewise, the term "aqueous solution" is defined as a solution comprising at least 50% w/w water and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of a FVII(a) polypeptide a bispecific antibody as described herein and a buffer, wherein the antibody is present in a concentration from 1 mg/ml or above and wherein said formulation has a pH from about 2.0 to about 10.0.

A composition of the invention may be administered parenterally, such as intravenously, such as intramuscularly, such as subcutaneously; preferably subcutaneously. The composition of the invention may be administered prophylactically.

A pharmaceutical composition of the invention may be used to treat a subject with a coagulopathy. As used herein, the term "subject" includes any human patient, or non-human vertebrate, with a coagulopathy.

Medical Uses

The term "treatment", as used herein, refers to the medical therapy of any human or other animal subject in need thereof. Said subject is expected to have undergone physical examination by a medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Preventative or prophylactic administration of pro-coagulant compounds of the invention is also contemplated, with prevention being defined as delaying or averting manifestation or aggravation of one or more symptoms of the disease or disorder. Thus, said treatment may be prophylactic, palliative, symptomatic ("on demand") and/or curative.

In terms of the present invention, prophylactic, palliative and/or symptomatic treatments may represent separate aspects of the invention.

A coagulopathy that results in an increased haemorrhagic tendency may be caused by any qualitative or quantitative deficiency of any pro-coagulant component of the normal coagulation cascade or any up-regulation of fibrinolysis. Such coagulopathies may be congenital and/or acquired and/or iatrogenic and are identified by a person skilled in the art.

Non-limiting examples of congenital hypocoagulopathies are haemophilia A, haemophilia B, Factor VII deficiency, Factor X deficiency, Factor XI deficiency, von Willebrand's disease and thrombocytopenias such as Glanzmann's thombasthenia and Bernard-Soulier syndrome.

A non-limiting example of an acquired coagulopathy is serine protease deficiency caused by vitamin K deficiency; such vitamin K-deficiency may be caused by administration of a vitamin K antagonist, such as warfarin. Acquired coagulopathy may also occur following extensive trauma. In this case otherwise known as the "bloody vicious cycle", it is characterised by haemodilution (dilutional thrombocytopaenia and dilution of clotting factors), hypothermia, consumption of clotting factors and metabolic derangements (acidosis). Fluid therapy and increased fibrinolysis may exacerbate this situation. Said haemorrhage may be from any part of the body.

Haemophilia A with "inhibitors" (that is, allo-antibodies against factor VIII) and haemophilia B with "inhibitors" (that is, allo-antibodies against factor IX) are non-limiting examples of coagulopathies that are partly congenital and partly acquired.

A non-limiting example of an iatrogenic coagulopathy is that which is induced by excessive and/or inappropriate fluid therapy, such as that which may be induced by a blood transfusion.

In one preferred embodiment of the current invention, haemorrhage is associated with haemophilia A. In another preferred embodiment of the current invention, haemorrhage is associated with haemophilia B. In another preferred embodiment, haemorrhage is associated with haemophilia A or B with acquired inhibitors. In another preferred embodiment, haemorrhage is associated with FVII deficiency. In another preferred embodiment, haemorrhage is associated with Glansmann's thrombasthenia. In another embodiment, haemorrhage is associated with von Willebrand's disease. In another embodiment, haemorrhage is associated with severe tissue damage. In another embodiment, haemorrhage is associated with severe trauma. In another embodiment, haemorrhage is associated with surgery. In another embodiment, haemorrhage is associated with haemorrhagic gastritis and/or enteritis. In another embodiment, the haemorrhage is profuse uterine bleeding, such as in placental abruption. In another embodiment, haemorrhage occurs in organs with a limited possibility for mechanical haemostasis, such as intracranially, intra-aurally or intraocularly. In another embodiment, haemorrhage is associated with anticoagulant therapy.

In a further embodiment, haemorrhage may be associated with thrombocytopaenia. In individuals with thrombocytopaenia, the bispecific antibodies described herein may be co-administered with platelets.

Routes of Administration

The bispecific antibodies described herein may be suitable for parenteral administration, preferably intravenous and/or subcutaneous administration. Subcutaneous administration is the preferred route of administration Dosing Regimens The bioavailability and half-life of the bispecific antibodies described herein renders them particularly attractive medicaments for the prophylactic, subcutaneous treatment of subjects that have an acquired and/or congenital coagulopathy. The bispecific antibodies described herein may be administered once weekly, such as once every two weeks, preferably once monthly, to subjects that have an acquired and/or congenital coagulopathy but that are not bleeding. The bispecific antibodies described herein may be administered pre-operatively to subjects that have a coagulopathy and that are due for an invasive procedure, such as surgery. The bispecific antibodies described herein may be administered to subjects that have a coagulopathy and that are undergoing an invasive procedure, such as surgery.

The bispecific antibodies described herein may also be co-administered with exogenous FVIIa, such as plasma-derived or recombinantly produced FVIIa, for on-demand or prophylactic treatment of subjects that have a coagulopathy or are experiencing a bleeding episode.

The dose administered to subjects that have a coagulopathy will depend upon the route of administration, whether it is administered prophylactically or on demand and individual variation. Subcutaneous administration will necessitate larger doses than intravenous administration.

In an embodiment of the invention, the bispecific antibody is administered subcutaneously, in a dose from 1.0 to 30.0 nmol/kg.

Unless otherwise indicated in the specification, terms presented in singular form also include the plural situation.

LIST OF EMBODIMENTS

The invention is further described by the following non-limiting list of embodiments of the present invention:

1. A bispecific antibody comprising
   (i) a first antigen binding site capable of binding Factor VII(a), and
   (ii) a second antigen binding site capable of binding TREM-like Transcript 1 (TLT-1).

2. The bispecific antibody according to embodiment 1, wherein the first antigen-binding site competes for binding to FVII(a) with any one of the anti-FVII(a) antibodies of Table 3:

TABLE 3

| Antibody | Target | VL SEQ ID NO | VH SEQ ID NO | Constant domain |
|---|---|---|---|---|
| mAb0522 | FVII(a) | 846 | 850 | B |
| Fab0883 | FVII(a) | 814 | 818 | G |
| mAb0005 | FVII(a) | 750 | 754 | M |
| mAb0004 | FVII(a) | 14 | 18 | M |
| mAb0013 | FVII(a) | 46 | 50 | M |
| mAb0018 | FVII(a) | 62 | 66 | M |
| mAb0544 | FVII(a) | 694 | 698 | M |
| mAb0552 | FVII(a) | 702 | 706 | M |
| mAb0001 | FVII(a) | 710 | 714 | M |

TABLE 3-continued

| Antibody | Target | VL SEQ ID NO | VH SEQ ID NO | Constant domain |
|---|---|---|---|---|
| mAb0007 | FVII(a) | 718 | 722 | M |
| mAb0578 | FVII(a) | 726 | 730 | M |
| mAb0701 | FVII(a) | 734 | 738 | M |
| mAb0587 | FVII(a) | 742 | 746 | M |

3. The bispecific antibody according to embodiment 1, wherein the antibody competes in a competitive ELISA assay as described in Example 7.

4. The bispecific antibody according to embodiment 1, wherein the first antigen-binding site is capable of binding an epitope comprising amino acid residues H115, T130, V131, and R392 of FVII(a) (SEQ ID NO: 1).

5. The bispecific antibody according to embodiment 1, wherein the first antigen-binding site is capable of binding an epitope comprising one or more of amino acid residues H115, T130, V131, and R392 of FVII(a) (SEQ ID NO: 1).

6. The bispecific antibody according to embodiment 1, wherein the first antigen-binding site is capable of binding an epitope comprising the following amino acid residues R113, C114, H115, E116, G117, Y118, S119, L120, T130, V131, N184, T185, P251, V252, V253, Q388, M391 and R392 of FVII(a) (SEQ ID NO: 1).

7. The bispecific antibody according to embodiment 1, wherein the first antigen-binding site is capable of binding an epitope comprising one or more of the following amino acid residues R113, C114, H115, E116, G117, Y118, S119, L120, T130, V131, N184, T185, P251, V252, V253, Q388, M391 and R392 of FVII(a) (SEQ ID NO: 1).

8. The bispecific antibody according to embodiment 1, wherein the first antigen-binding site comprises:
the CDRL1 represented by SEQ ID NO: 847, with 0, 1, 2 or 3 amino acid substitutions
the CDRL2 represented by SEQ ID NO: 848, with 0, 1, 2 or 3 amino acid substitutions
the CDRL3 represented by SEQ ID NO: 849, with 0, 1 or 2 amino acid substitutions
the CDRH1 represented by SEQ ID NO: 851, with 0 or 1 amino acid substitutions
the CDRH2 represented by SEQ ID NO: 852, with 0 or 1 amino acid substitutions
the CDRH3 represented by SEQ ID NO: 853, with 0, 1, 2 and 3 amino acid substitutions.

9. The bispecific antibody according to embodiment 1, wherein the first antigen-binding site comprises:
the CDRL1 represented by SEQ ID NO: 847,
the CDRL2 represented by SEQ ID NO: 848,
the CDRL3 represented by SEQ ID NO: 849,
the CDRH1 represented by SEQ ID NO: 851,
the CDRH2 represented by SEQ ID NO: 852, and
the CDRH3 represented by SEQ ID NO: 853.

10. The bispecific antibody according to embodiment 1, wherein the first antigen-binding site comprises variable heavy chain and variable light chain domain sequences according to an antibody listed in Table 13 or 14, where the affinity ($K_D$) is 1 nM or less.

11. The bispecific antibody according to embodiment 1, wherein the first antigen-binding site comprises variable heavy chain and variable light chain domain sequences according to an antibody listed in Table 13 or 14, where the affinity ($K_D$) is 5 nM or less.

12. The bispecific antibody according to embodiment 1, wherein the first antigen-binding site comprises variable heavy chain and variable light chain domain sequences according to an antibody listed in Table 13 or 14, where the affinity ($K_D$) is 10 nM or less.

13. The bispecific antibody according to embodiment 1, wherein the first antigen-binding site comprises variable heavy chain and variable light chain domain sequences according to an antibody listed in Table 13 or 14, where the affinity ($K_D$) is 25 nM or less.

14. The bispecific antibody according to any one of the preceding embodiments, wherein the antibody have an affinity ($K_D$) for FVII(a) of less than 1 pM, such as less than 10 pM, such as less than 100 pM, such as less than 200 pM, such as less than 400 pM, such as less than 600 pM, such as less than 1 nM, such as less than 5 nM, such as less than 10 nM, such as less than 20 nM, such as less than 50 nM, such as less than 100 nM, such as less than 200 nM, such as less than 400 nM, such as less than 600 nM, such as less than 800 nM.

15. The bispecific antibody according to embodiment 1, wherein the first antigen-binding site comprises a light chain variable domain identified by SEQ ID NO:846 and a heavy chain variable domain identified by SEQ ID NO:850.

16. The bispecific antibody according to embodiment 15, wherein the light chain variable domain and/or the heavy chain variable domain sequences have 1, 2, 3, 4, 5, 6, 7, 8, 9, 10, 11 or 12 amino acid substitutions.

17. The bispecific antibody according to embodiment 1, wherein the second antigen-binding site competes for binding to TLT-1 with any one of the anti-TLT-1 antibodies of Table 4:

TABLE 4

| Antibody | Target | VL SEQ ID NO | VH SEQ ID NO | Constant domain |
|---|---|---|---|---|
| mAb0524 | TLT-1 | 854 | 858 | H |
| mAb0012 | TLT-1 | 862 | 866 | A |
| mAb0023 | TLT-1 | 870 | 874 | A |
| mAb0051 | TLT-1 | 878 | 882 | A |
| mAb0062 | TLT-1 | 894 | 898 | A |

18. The bispecific antibody according to embodiment 17, wherein the antibody competes in a competitive ELISA assay as described in Example 32.

19. The bispecific antibody according to embodiment 1, wherein the second antigen-binding site is capable of binding an epitope comprising the following amino acid residues K8, 19, G10, S11, L12, A13, N15, A16, F17, S18, D19, P20, A21 of TLT-1 (SEQ ID NO: 13).

20. The bispecific antibody according to embodiment 1, wherein the second antigen-binding site comprises:
the CDRL1 represented by SEQ ID NO: 855, with 0, 1, 2 or 3 amino acid substitutions
the CDRL2 represented by SEQ ID NO: 856, with 0, 1 or 2 amino acid substitutions
the CDRL3 represented by SEQ ID NO: 857, with 0, 1 or 2 amino acid substitutions
the CDRH1 represented by SEQ ID NO: 859, with 0 or 1 amino acid substitutions
the CDRH2 represented by SEQ ID NO: 860, with 0, 1, 2 or 3 amino acid substitutions the CDRH3 represented by SEQ ID NO: 861. with 0 or 1 amino acid substitutions
21. The bispecific antibody according to embodiment 1, wherein the second antigen-binding site comprises:
the CDRL1 represented by SEQ ID NO: 855,
the CDRL2 represented by SEQ ID NO: 856,
the CDRL3 represented by SEQ ID NO: 857,
the CDRH1 represented by SEQ ID NO: 859,
the CDRH2 represented by SEQ ID NO: 860,
the CDRH3 represented by SEQ ID NO: 861.
22. The bispecific antibody according to embodiment 1, wherein the second antigen-binding site comprises:
the CDRL1 represented by SEQ ID NO: 871,
the CDRL2 represented by SEQ ID NO: 872,
the CDRL3 represented by SEQ ID NO: 873,
the CDRH1 represented by SEQ ID NO: 875,
the CDRH2 represented by SEQ ID NO: 876, and
the CDRH3 represented by SEQ ID NO: 877.
23. The bispecific antibody according to embodiment 1, wherein the second antigen-binding site comprises:
the CDRL1 represented by SEQ ID NO: 879,
the CDRL2 represented by SEQ ID NO: 880,
the CDRL3 represented by SEQ ID NO: 881,
the CDRH1 represented by SEQ ID NO: 883,
the CDRH2 represented by SEQ ID NO: 884, and
the CDRH3 represented by SEQ ID NO: 885.
24. The bispecific antibody according to embodiment 1, wherein the second antigen-binding site comprises:
the CDRL1 represented by SEQ ID NO: 895,
the CDRL2 represented by SEQ ID NO: 896,
the CDRL3 represented by SEQ ID NO: 897,
the CDRH1 represented by SEQ ID NO: 899,
the CDRH2 represented by SEQ ID NO: 900, and
the CDRH3 represented by SEQ ID NO: 901.
25. The bispecific antibody according to embodiment 1, wherein the second antigen-binding site is comprised by a light chain variable domain identified by SEQ ID NO:854 and a heavy chain variable domain identified by SEQ ID NO:858.
26. The bispecific antibody according to embodiment 25, wherein the light chain variable domain and/or the heavy chain variable domain sequences have 1, 2, 3, 4, 5, 6, 7, 8, 9, 10, 11 or 12 amino acid substitutions.
27. The bispecific antibody according to any one of the preceding embodiments, wherein the antibody have an affinity ($K_D$) for TLT-1 of less than 1 pM, such as less than 10 pM, such as less than 100 pM, such as less than 200 pM, such as less than 400 pM, such as less than 600 pM, such as less than 1 nM, such as less than 5 nM, such as less than 10 nM, such as less than 20 nM, such as less than 50 nM, such as less than 100 nM, such as less than 200 nM, such as less than 400 nM, such as less than 600 nM, such as less than 800 nM.
28. The bispecific antibody according to embodiment 1, wherein the first antigen-binding site comprises a light chain variable domain identified by SEQ ID NO:846 and a heavy chain variable domain identified by SEQ ID NO:850, and wherein the second antigen-binding site is comprised by a light chain variable domain identified by SEQ ID NO: 854 and a heavy chain variable domain identified by SEQ ID NO:858.
29. The bispecific antibody according to any one of the preceding embodiments, wherein the antibody comprises an Fc region.
30. The bispecific antibody according to embodiment 29, wherein the Fc region is an Fc variant of the Fc region of IgG1 comprising the substitutions L234A, L235E, G237A, A330S and P331S.
31. The bispecific antibody according to any one of the preceding embodiments, wherein the antibody is a fusion or conjugate of antigen binding fragments of antibodies.
32. The bispecific antibody according to embodiment 31, wherein one or more of the binding fragments are selected from the group of a Fab, a Fab', a Fab2, a Fab'2 and a scFv.
33. The bispecific antibody according to any one of the preceding embodiments, wherein the antibody is a multispecific antibody.
34. The bispecific antibody according to embodiment 1, wherein the first antigen-binding site comprises a first light chain variable domain identified by SEQ ID NO:846 and a first heavy chain variable domain identified by SEQ ID NO:850, and wherein the second antigen-binding site is comprised by a second light chain variable domain identified by SEQ ID NO: 854 and a second heavy chain variable domain identified by SEQ ID NO:858 and wherein the heavy chain constant domains attached to first and second heavy chain variable domain are identified by SEQ ID NO: 5 and 4, respectively and wherein the light chain constant domains attached to first and second light chain variable domain are both identified by SEQ ID No: 12.
35. The bispecific antibody according to embodiment 1, wherein the first antigen-binding site comprises a first light chain variable domain identified by SEQ ID NO:846 and a first heavy chain variable domain identified by SEQ ID NO:850, and wherein the second antigen-binding site is comprised by a second light chain variable domain identified by SEQ ID NO: 854 and a second heavy chain variable domain identified by SEQ ID NO:858 and wherein the heavy chain constant domains attached to first and second heavy chain variable domain are identified by SEQ ID NO: 943 and 942, respectively and wherein the light chain constant domains attached to first and second light chain variable domain are both identified by SEQ ID No: 12
36. The bispecific antibody according to embodiment 1, wherein the first antigen-binding site comprises a first light chain variable domain identified by SEQ ID NO:846 and a first heavy chain variable domain identified by SEQ ID NO:850, and wherein the second antigen-binding site is comprised by a second light chain variable domain identified by SEQ ID NO: 854 and a second heavy chain variable domain identified by SEQ ID NO:858 and wherein the heavy chain constant domains attached to first and second heavy chain variable domain are identified by SEQ ID NO: 7 and 6, respectively and wherein the light chain constant domains attached to first and second light chain variable domain are both identified by SEQ ID No: 12.
37. The bispecific antibody according to embodiment 1, wherein the first antigen-binding site comprises a first light chain variable domain identified by SEQ ID NO:846 and a first heavy chain variable domain identified by SEQ ID NO:850, and wherein the second antigen-binding site is comprised by a second light chain variable domain identified by SEQ ID NO: 854 and a second heavy chain variable domain identified by SEQ ID NO:858 and wherein the heavy chain constant domains attached to first and second heavy chain variable domain are identified by SEQ ID NO: 4 and 5, respectively and wherein the light chain constant domains attached to first and second light chain variable domain are both identified by SEQ ID NO: 12.

38. The bispecific antibody according to embodiment 1, wherein the first antigen-binding site comprises a first light chain variable domain identified by SEQ ID NO:846 and a first heavy chain variable domain identified by SEQ ID NO:850, and wherein the second antigen-binding site is comprised by a second light chain variable domain identified by SEQ ID NO: 854 and a second heavy chain variable domain identified by SEQ ID NO:858 and wherein the heavy chain constant domains attached to first and second heavy chain variable domain are identified by SEQ ID NO: 942 and 943, respectively and wherein the light chain constant domains attached to first and second light chain variable domain are both identified by SEQ ID NO: 12.

39. The bispecific antibody according to embodiment 1, wherein the first antigen-binding site comprises a first light chain variable domain identified by SEQ ID NO:846 and a first heavy chain variable domain identified by SEQ ID NO:850, and wherein the second antigen-binding site is comprised by a second light chain variable domain identified by SEQ ID NO: 854 and a second heavy chain variable domain identified by SEQ ID NO:858 and wherein the heavy chain constant domains attached to first and second heavy chain variable domain are identified by SEQ ID NO: 6 and 7, respectively and wherein the light chain constant domains attached to first and second light chain variable domain are both identified by SEQ ID NO: 12.

40. The bispecific antibody according to embodiment 1, wherein the antibody competes for binding to FVII(a) and competes for binding to TLT-1 with one or more of the bispecific antibodies as set forth in Table 5 (where constant domain abbreviation is defined according to table 2a):

TABLE 5

| biAb | anti-FVII(a) mAb | anti-TLT-1 mAb | Constant domain |
|---|---|---|---|
| biAb0001 | mAb0865 | mAb1076 | H |
| biAb0352 | mAb0350 | mAb0351 | I |
| biAb0015 | mAb0865 | mAb1038 | H |
| biAb0090 | mAb0865 | mAb1049 | H |
| biAb0095 | mAb0865 | mAb1047 | H |
| biAb0100 | mAb0522 | mAb0524 | L |
| biAb0241 | mAb0865 | mAb0023 | H |
| biAb0242 | mAb0865 | mAb0051 | H |
| biAb0243 | mAb0865 | mAb0062 | H |
| biAb0244 | mAb0864 | mAb1076 | H |
| biAb0245 | mAb0873 | mAb1076 | H |
| biAb0011 | mAb0875 | mAb1076 | H |
| biAb0016 | mAb0875 | mAb1038 | H |
| biAb0096 | mAb0875 | mAb1047 | H |
| biAb0091 | mAb0875 | mAb1049 | H |
| biAb0012 | mAb0872 | mAb1076 | H |
| biAb0017 | mAb0872 | mAb1038 | H |
| biAb0097 | mAb0872 | mAb1047 | H |
| biAb0092 | mAb0872 | mAb1049 | H |
| biAb0013 | mAb0874 | mAb1076 | H |
| biAb0018 | mAb0874 | mAb1038 | H |
| biAb0098 | mAb0874 | mAb1047 | H |
| biAb0093 | mAb0874 | mAb1049 | H |
| biAb0014 | mAb0873 | mAb1076 | H |
| biAb0019 | mAb0873 | mAb1047 | H |
| biAb0099 | mAb0873 | mAb1047 | H |
| biAb0094 | mAb0873 | mAb1049 | H |

41. The bispecific antibody according to embodiment 38, wherein the antibody competes for binding in a competitive ELISA to FVII(a) and competes for binding to TLT-1 with one or more of the bispecific antibodies as set forth in Table 5.

42. The bispecific antibody according to embodiment 38, wherein the antibody competes in a competitive ELISA assay as described in Example 7 and Example 32.

43. The bispecific antibody according to embodiment 1, wherein the first antigen-binding site is capable of binding an epitope comprising amino acid residues H115, T130, V131, and R392 of FVII(a) (SEQ ID NO: 1), and wherein the second antigen-binding site is capable of binding an epitope comprising the following amino acid residues K8, 19, G10, S11, L12, A13, N15, A16, F17, S18, D19, P20, A21 of TLT-1 (SEQ ID NO: 13).

44. The bispecific antibody according to embodiment 1, wherein the first antigen-binding site comprises:
the CDRL1 represented by amino acid residues (SEQ ID NO: 847), with 0, 1, 2 or 3 amino acid substitutions
the CDRL2 represented by amino acid residues (SEQ ID NO: 848), with 0, 1, 2 or 3 amino acid substitutions
the CDRL3 represented by amino acid residues (SEQ ID NO: 849), with 0, 1 or 2 amino acid substitutions
the CDRH1 represented by amino acid residues (SEQ ID NO: 851),
the CDRH2 represented by amino acid residues (SEQ ID NO: 852), with 0 or 1 amino acid substitutions
the CDRH3 represented by amino acid residues (SEQ ID NO: 853), with 0, 1, 2 and 3 amino acid substitutions, and
wherein the second antigen-binding site comprises:
the CDRL1 represented by SEQ ID NO: 855, with 0, 1, 2 or 3 amino acid substitutions
the CDRL2 represented by SEQ ID NO: 856, with 0, 1 or 2 amino acid substitutions
the CDRL3 represented by SEQ ID NO: 857, with 0, 1 or 2 amino acid substitutions
the CDRH1 represented by SEQ ID NO: 859, with 0 or 1 amino acid-substitutions
the CDRH2 represented by SEQ ID NO: 860, with 0, 1, 2 or 3 amino acid-substitutions
the CDRH3 represented by SEQ ID NO: 861. with 0 or 1 amino acid substitutions.

45. The bispecific antibody according to any one of the preceding embodiments, wherein the antibody increases the functional MRT of FVII(a), as measured with a FVIIa activity assay described in Example 8.

46. The bispecific antibody according to embodiment 41, wherein the antibody increases the functional MRT of FVII(a) by at least 2-fold, at least 3-fold, at least 5-fold, at least 10-fold, at least 20-fold, at least 30-fold, or at least 40-fold compared with administration of FVII(a) in the absence of the bispecific antibody of the invention.

47. The bispecific antibody according to any one of the preceding embodiments, wherein the antibody is capable of increasing the level of circulating endogenous functionally active FVIIa as determined according to Examples 27 and 28, compared to the level of circulating endogenous FVIIa in the absence of administered bispecific antibody.

48. The bispecific antibody according to embodiment 45, wherein the antibody increases the level of circulating endogenous functionally active FVIIa by at least 2-fold, at least 4-fold, at least 10-fold, at least 20-fold, at least 40-fold, at least 80-fold, at least 160-fold, at least 320-fold, at least 640-fold.
49. The bispecific antibody according to any one of the preceding embodiments, wherein the antibody is capable of increasing the ability of a FVIIa polypeptide to promote FX activation as determined by stimulatory activity assay as described in Example 21.
50. The bispecific antibody according to embodiment 43, wherein the stimulatory activities are at least 2-fold, at least 5-fold, at least 10-fold, at least 20-fold, at least 30-fold, at least 40-fold, at least 60-fold, at least 80-fold, at least 100-fold, or at least 150-fold.
51. A pharmaceutical formulation comprising the bispecific antibody according to any one of the preceding embodiments and a pharmaceutically acceptable carrier.
52. The bispecific antibody according to embodiments 1-48, wherein the pharmaceutical formulation according to embodiment 49 is administered by subcutaneous administration.
53. The bispecific antibody according to embodiments 1-48 or the pharmaceutical formulation according to embodiments 49 for use as a medicament.
54. The bispecific antibody according to any one of embodiments 1-48, and 50-51 or the pharmaceutical formulation according to embodiments 49 for use in the treatment of a coagulopathy, wherein said coagulopathy is congenital and/or acquired.
55. The bispecific antibody according to embodiment 52 wherein said coagulopathy is selected from the group consisting of haemophilia A, with or without inhibitors or haemophilia B, with or without inhibitors, FVII(a) deficiency and Glanzmann's thrombasthenia.
56. The bispecific antibody according to embodiments 1-48, and 50-51 for treatment of a bleeding, wherein the bleeding is associated with congenial or acquired haemophilia A, congenial or acquired haemophilia B, haemophilia A with inhibitors, haemophilia B with inhibitors or Factor VII(a) deficiency.
57. The use according to any one of embodiments 1-48, wherein said bispecific antibody or pharmaceutical formulation according to embodiment 49 is parenterally administered, such as intravenously, intramuscularly or subcutaneously administered.

Examples

Example 1: Generation of Anti-FVII(a) Mouse Monoclonal Antibodies Using Hybridoma Technology Monoclonal antibodies were prepared by immunisation of NMRCF1 mice (Charles River) with the FVIIa Q64C-sTF (1-219) G109C disulfide-linked complex described in the international patent application with publication number WO07/115953.
The mice were given an initial subcutaneous injection of 20 µg in FCA (Freund's complete adjuvant) followed by booster intraperitoneal injections in IFA (Freund's incomplete adjuvant) of 20 µg antigen. The spleens were removed aseptically and dispersed to a single cell suspension. Splenocytes were fused to X63Ag8.653 myeloma cells using electrofusion. Cells were seeded in microtiter plates and cultured at 37° C., 5% C02. The tissue culture medium (RPMI 1640+10% fetal calf serum), containing HAT (Sigma) for selection, was changed twice. Following 10 days growth, specific antibody-producing hybridoma clones were identified by ELISA screening using the following protocol. NUNC Maxisorb plates were coated with FVIIa Q64C-sTF(1-219) G109C disulfide-linked complex, or FVIIa (expressed and purified as described by Thim et al. (1988) Biochemistry 27:7785-7793 and Persson et al. (1996) FEBS Lett 385:241-243), 50 µl/well at 1 µg/ml (HEPES buffer containing 5 mM CaCl2), and incubated overnight at 4° C. The plates were washed 5 times and blocked in washing buffer for 15 min (HEPES buffer, 5 mM CaCl2, 0.05% TWEEN 20). 50 µl supernatant was transferred to each well and incubated for 1 hour. The plates were washed 5 times and 50 µl HRP-labelled goat-anti mouse was added (Fc gamma fragment specific; Jackson, working dilution 1/10000). The plates were incubated for 1 hour, washed 5 times, and developed with 50 µl TMB (TMB ONE ready to use; Kem-En-Tec) for 10 min. The reaction was stopped by adding 50 µl 4M H3PO4 and read in a FLUOStar Optima plate reader at 450 and 620 nm.

Hybridoma cells yielding positive results were subcloned at least twice by limiting dilution in order to secure monoclonality. Antibody purification was done using standard protein A purification.

Hybridoma cells producing antibodies for use in PK studies were up-scaled into T-flasks or shaker flasks, in RPM11640+10% FBS medium. Conditioned medium was harvested by centrifugation, and antibodies purified by protein A affinity chromatography followed by desalting.

Example 2: Cloning and Sequencing of Mouse Anti-FVII(a) Antibodies

This example describes cloning and sequencing of the murine heavy chain (HC) and light chain (LC) cDNA sequences encoding the variable domains of an anti-FVII(a) antibody. Total RNA was extracted from hybridoma cells using the RNeasy-Mini Kit from Qiagen and used as template for cDNA synthesis. cDNA was synthesized in a 5'-RACE reaction using the SMARTer RACE cDNA amplification kit from Clontech. Subsequent target amplification of the variable domain of the HC (designated VH) and of the variable domain of the LC (designated VL) sequences was performed by PCR using Phusion Hot Start polymerase (Finnzymes) and the universal primer mix (UPM) included in the SMARTer™ RACE kit as forward primer. The sequence of the reverse primer used for VH amplification was 5' agctgggaaggtgtgcacac 3'. The sequence of the reverse primer used for VL amplification was 5' gctctagactaacact-cattcctgttgaagctcttg 3'.

PCR products were separated by gel electrophoresis, extracted using the GFX PCR DNA & Gel Band Purification Kit from GE Healthcare Bio-Sciences and cloned for sequencing using a Zero Blunt TOPO PCR Cloning Kit and chemically competent TOP10 *E. coli* (Invitrogen). Sequencing was performed at MWG Biotech, Martinsried Germany using M13uni(–21)/M13rev(–29) sequencing primers. All kits and reagents were used according to the manufacturer's instructions.

Example 3: Recombinant Expression of Bivalent Antibodies, Monovalent Antibodies (OA Antibodies), and Antibody Fab Fragments Bivalent antibodies, monovalent antibodies (one-armed referred to as OA-antibodies) and antibody Fab fragments were expressed using transient transfection of HEK293 suspension cells (293Expi, Invitrogen) essentially following the manufacturer's instructions. 293Expi cells were subcultivated every 3-4 days in Expi293F expression medium (Invitrogen, catalogue number A1435104) supplemented with 1% P/S (GIBCO catalogue number 15140-122). Expi293F cells were transfected at a cell density of 2.5-3 million/ml using Expifectamine. For each litre of Expi293F cells, the transfection was performed by diluting a total of 1 mg of plasmid DNA into 50 ml Optimem (GIBCO, cat. no. 51985-026, dilution A) and by diluting 2.7 ml Expifectamine into 50 ml Optimem (dilution B). Bivalent antibodies were produced by co-transfecting VH-CH1-CH2-CH3 (HC) and VL-CL (LC) plasmid (1:1 ratio), and for Fab fragments plasmids were VH-CH1 and LC (1:1 ratio). For production of OA antibodies, the cells were transfected with three plasmids: the HC the LC plasmids, and a third plasmid encoding a truncated HC (trHC). The HC of the OA-antibodies contained the hole mutations (T366S, L368A, Y407V) and the trHC the knob (T366W) mutation, but knobs and holes can also be reversed. The knob/hole mutations are described in the international patent EP0979281 B1 and are introduced to optimize formation of the desired hetero-dimer, i.e. pairing of HC and trHC, and suppress unwanted formation of homodimers i.e. pairing of trHC with trHC and HC with HC. Dilution A and B were mixed and incubated at room temperature for 10-20 minutes. The transfection mix was hereafter added to the Expi293F cells and cells were incubated at 37° C. in a humidified incubator with orbital rotation (85-125 rpm). One-day post-transfection, transfected cells were supplemented with 5 ml of ExpiFectamine 293 Transfection Enhancer 1 and 50 ml of ExpiFectamine 293 Transfection Enhancer 2. Cell culture supernatants were harvested 4-5 days post-transfection by centrifugation followed by filtration.

Bivalent and monovalent antibodies were purified by standard protein A affinity chromatography known to a person skilled in the art and, where necessary, additional purification steps such as gel filtration or ion exchange chromatography. Fab fragments were purified by affinity chromatography using an affinity resin recognizing the kappa chain of the Fab.

Example 4: Preparation of Bispecific Antibodies and OA Antibodies by In Vitro Assembly Bispecific Antibodies Prepared by In Vitro Assembly Bispecific antibodies were generated by in vitro assembly of two parental antibodies by a method similar to that described in Labrijn et al. PNAS 2013, vol. 110, pp. 5145-5150, and known as the DuoBody® technology (Genmab). Instead of the IgG1 subtype used by Labrijn et al. IgG4 was used in the present invention. The exchange reaction was carried out at 30° C. for four hours in the presence of 75 mM 2-mercaptoethyl amine (2-MEA). The resulting bispecific antibody was purified by ion exchange chromatography to separate residual parental antibodies from the bispecific antibody. In the present example, the heavy chain constant region of the first parental antibody (anti-FVII(a)) was IgG4 S228P F405L R409K and the heavy chain constant region of the second parental antibody (anti-TLT-1) was IgG4 S228P (both using EU numbering). The light chain constant domains were human kappa. The two parental antibodies were produced as described in example 3. The bispecific anti-FVII(a)/anti-TLT-1 antibodies could also be assembled from a set of parental antibodies where the constant domain of the anti-FVII(a) antibody is IgG4 S228P and the constant domain of the anti-TLT-1 antibody is IgG4 S228P F405L R409K.

Monovalent Antibodies Prepared by In Vitro Assembly

Monovalent antibodies were generated by in vitro assembly as described above for bispecific antibodies with the exceptions that (1) instead of combining two antibodies to form a bispecific antibody, an antibody and a trHC dimer were combined to form the monovalent antibody. In the present example the trHC was IgG4 S228P F405L R409K and the HC was IgG4 S228P (both using EU-numbering). The light chain constant domain was human kappa. Typically arm-exchange reaction was carried out with the trHC dimer in 20-50% molar excess to minimize the amount of bivalent antibody in the reaction mixture. The monovalent antibody was purified by size-exclusion chromatography, optionally supplemented by additional purification steps, such as ion exchange chromatography, as desired.

Example 5: In Vitro Characterization of Anti-FVIIa(a) in Functional Assays

In order to facilitate accumulation of endogenous FVIIa and allow it to exert its procoagulant activity, anti-FVII(a) antibodies of the present invention should preferably not impair the activity of FVIIa and similarly preferably not promote the inactivation of FVIIa by its primary plasma inhibitor antithrombin (Agersø H, et al. (2011) J Thromb Haemost 9:333-338). To explore these aspects, the effect of anti-FVII(a) antibodies on the procoagulant activity of FVIIa and inactivation of FVIIa by antithrombin was determined in vitro using the assays described below.

Effect of Anti-FVII(a) Antibodies on Thrombin Generation in Hemophilia A-Induced Human Plasma The effect of bivalent or monovalent anti-FVII(a) antibodies on thrombin generation was measured in a kaolin-triggered thrombin generation assay (TGT) in a 96-well setup. In brief, hemophilia A-induced plasma was prepared by addition of an anti-hFVIII antibody 4F30 (described in the international patent application with publication number WO2012/035050) to a final conc. of 37.5 µg/ml. Phospholipids at a final concentration of 10 µM (Rossix) was added to the hemophilia A plasma and incubated at 37° C. for 15 min. Purified antibody (100 nM) and FVIIa (25 nM) were added to the mixture and incubated for 10 min at room temperature. The anti-FVII(a) antibodies were generated as described in examples 1, 2, and 3. Triggering was done by adding 10 µl Kaolin (Haemonetics) followed by addition of 10 al FIIa FluCa-kit (Thrombinoscope BV) and fluorescence (excitation at 390 nm and emission at 460 nm) was measured on an EnVision multi-label reader for two hours.

Thrombograms were calculated as the first derivative of the measured fluorescence. Peak thrombin height was calculated as the maximum value in the thrombogram. This was subsequently normalized and expressed as percentage by dividing the observed peak height with the peak height corresponding to that observed for 25 nM FVIIa in the absence of antibody. Based on this, antibodies were categorized as stimulatory (>120%), inhibitory (<90%) or neutral (90%-120%). As shown in Table 6, antibodies from all categories were identified. Preferred antibodies were stimulatory or neutral in the TGT assay.

Effect of Anti-FVII(a) Antibodies on FVIIa Inactivation by Plasma Derived Antithrombin Inhibition of FVIIa activity by plasma-derived antithrombin (AT) in the presence of bivalent or monovalent anti-FVII(a) antibody was measured by incubating FVIIa (200 nM) with low-molecular weight heparin (Enoxaparin, 12 pM) and the antibody (200-1000 nM) for 10 min in 50 mM HEPES, 100 mM NaCl, 10 mM CaCl2, 0.1% PEG8000, 1 mg/ml BSA, pH 7.3. AT (5 µM) was then added and at time points 10, 20, 30, 40, 60, and 80 min a sample was transferred to a new microtiter plate, where residual activity was measured in the presence of 1 mM S-2288 chromogenic substrate (Chromogenix), 200 nM soluble tissue factor (sTF; produced as described by Freskgard et al. (1996) Protein Sci 5:1531-1540) and polybrene (0.5 mg/ml) in a Spectramax instrument (Molecular Devices) at 405 nm for 5 min. Sample with buffer instead of AT provided the activity of uninhibited FVIIa.

Residual amidolytic activity was determined as a function of time relative to the activity in the absence of inhibitor. The inhibitory constant (kinh) was estimated by fitting the data to a one phase decay model. The value of kinh in the presence of FVII(a)-antibody in percent of that determined in the absence of antibody is termed kinh % and is reported for each antibody in Table 6.

Antibodies with an estimated kinh %<60% were classified as protecting FVIIa from AT inhibition. Antibodies with an estimated 60%≤kinh %≤150% were classified as neutral, while antibodies with an estimated kinh %>150% were classified as accelerating the inhibition of FVIIa by AT. As reported in Table 6, antibodies from all three categories were identified. Preferred antibodies were neutral or protected FVIIa from AT inhibition.

Among the tested antibodies, a subset of antibodies including 11F2 (mAb005 and mAb0048, corresponding to fully murine and murine/human chimera, respectively) were found to have desired in vitro properties as described above.

TABLE 6

Functional characterization of anti-FVII(a) antibodies in thrombin generation (TGT) and antithrombin (AT)-inhibition assays as described in Example 2.

| Anti-FVII(a) antibody | TGT activity (% FVIIa) | Ranking based on TGT activity | AT inhibition ($k_{inh}$ %) | Ranking based on AT inhibition |
|---|---|---|---|---|
| mAb0048 | n.d. | Neutral | 109 | Neutral |
| mAb0005 | 115 | | 133 | |
| mAb0007 | 113 | | 121 | |
| mAb0544 | 103 | | 111 | |
| mAb0552 | 104 | | 118 | |
| mAb0018 | 141 | Stimulatory | 525 | Accelerating |
| mAb0004 | 75 | Inhibitory | 24 | Protective |
| mAb0001 | 109 | Neutral | 82 | Neutral |
| mAb0578 | 91 | Neutral | 77 | Neutral |
| mAb0587 | 93 | Neutral | 103 | Neutral |
| mAb0013 | 128 | Stimulatory | 747 | Accelerating |
| mAb7250 | 91 | Neutral | 23 | Protective |
| mAb0701 | 88 | Inhibitory | 26 | Protective |

Example 6: SPR Analysis of Antibody Binding to FVIIa and the Effect of pH and Calcium Binding of antibodies from Example 5 to FVIIa was probed by surface plasmon resonance (Biacore T200). Anti-murine IgG (by GE Healthcare) was immobilised on a CM4 sensor chip using standard amine coupling chemistry kit (both supplied by GE Healthcare). Purified anti-FVII(a) antibodies according to Table 7 (0.25 nM) were injected at a flow rate of 10 µl/min for 1 min. Subsequently, 5, 15, 45 and 135 nM of FVIIa were injected at a flow rate of 30 µl/min for 7 min to allow for binding to the anti-FVII(a) antibody followed by a 9 min buffer injection allowing for dissociation from the anti-FVII(a) antibody. The running buffer was prepared by diluting 10-fold the 10×HBS-P buffer (supplied by GE Healthcare) and supplemented with 1 mg/ml BSA and 5 mM CaCl2, to give 10 mM HEPES, 150 mM NaCl, 0.05% v/v Polysorbate 20(P20), pH 7.4, 5 mM CaCl2, 1 mg/ml bovine serum albumin (BSA). The running buffer was also used for dilution of anti-FVII(a) antibody and FVII samples. Regeneration of the chip was achieved using regeneration buffer consisting of 10 mM Gly-HCl pH 1.7 (supplied by GE Healthcare). Binding data were analysed according to a 1:1 model using BiaEvaluation 4.1 supplied by the manufacturer (Biacore AB, Uppsala, Sweden). Analysis resulted in the binding constants reported in Table 7 demonstrating high-affinity binding of several antibodies to FVIIa including 11F2 (mAb005 and mAb0048, corresponding to fully murine and murine/human chimera, respectively).

TABLE 7

Estimated binding constants for the interaction of anti-FVII(a) antibodies with FVIIa as determined by surface plasmon resonance (SPR) analysis according to Example 6.

| Anti-FVII(a) antibody | $K_D$ (M) |
|---|---|
| mAb0001 | 1.7E−10 |
| mAb0007 | 2.5E−10 |
| mAb0544 | 2.7E−10 |
| mAb0552 | 7.6E−10 |
| mAb0578 | 5.8E−10 |
| mAb0587 | 4.9E−10 |
| mAb0005 | 1.4E−10 |
| mAb0004 | 1.6E−10 |
| mAb0018 | 9.3E−9 |
| mAb0048 | 2.9E−11 |

The effect of pH and CaCl2 on the binding of select antibodies from Example 5 to FVIIa and cFVIIa-chimera was probed by surface plasmon resonance (Biacore T200) at 37° C. cFVIIa-chimera sequence is indicated in the section titled detailed description of the invention and is expressed as outlined in examples 16 and 26. Anti-murine IgG (by GE Healthcare) was immobilised on a CM4 sensor chip using standard amine coupling chemistry kit (both supplied by GE Healthcare). A pre-equilibrated mixture of FVIIa at 1.2 nM and 4F9 (NN internal anti-FVII murine Ab binding to FVIIa EGF1 domain) at 0.5 nM was injected at a flow rate of 10 µl/min for 1 min. Subsequently, 540, 180, 60, 20, 6.66, 2.22, 0.74, 0.25 nM of anti-FVII(a) antibody were injected at a flow rate of 30 µl/min for 7 min to allow for binding to FVIIa followed by a 9 min buffer injection allowing for dissociation from FVIIa. Two running buffers were prepared. Buffer 1 was prepared by diluting 10-fold of the 10×HBS-P+ (supplied by GE Healthcare) and supplemented with 1 mg/ml BSA and 5 mM CaCl2 to give 10 mM HEPES, 150 mM NaCl, 0.05% v/v Polysorbate 20, pH 7.4, 5 mM CaCl2, 1 mg/ml bovine serum albumin (BSA). Buffer 2 was prepared by diluting 10-fold of the 10×HBS-P+ (supplied by GE Healthcare) and supplemented with 1 mg/ml BSA, 5 µM CaCl2, and adjusted pH to 6.0 (adjusted using 4M HCl) to give 10 mM HEPES, 150 mM NaCl, 0.05% v/v Polysorbate 20, pH 6.0, 5 µM CaCl2, 1 mg/ml bovine serum albumin (BSA). FVIIa, anti-FVII antibody 4F9, and anti-FVII(a) antibody were diluted in both the running buffers separately. Regeneration of the chip was achieved using regeneration buffer consisting of 10 mM Gly-HCl pH 1.7 (supplied by GE Healthcare). Binding data were analysed according to a 1:1 model using BiaEvaluation 4.1 supplied by the manufacturer (Biacore AB, Uppsala, Sweden). Analysis resulted in the binding constants reported in Table 7b demonstrating retained high-affinity binding between FVIIa and anti-FVII (a) antibody.

TABLE 7b

Estimated binding constants and fold-difference for the interaction of FVIIa and anti-FVII(a) antibodies in two different buffers as determined by surface plasmon resonance (SPR) analysis according to Example 6.

| mAb | Protein | $K_{D, 1}$ In Buffer 1, (M) | $K_{D, 2}$ In Buffer 2, (M) | Fold-difference, $(K_{D, 2}/K_{D, 1})$ |
|---|---|---|---|---|
| mAb0077(OA) | FVIIa | 304E-12 | 495E-12 | 1.6 |
|  | cFVIIa-chimera | 469E-12 | 652E-12 | 1.4 |
| mAb0842(OA) | FVIIa | 599E-12 | 2200E-12 | 3.7 |
|  | cFVIIa-chimera | 1020E-12 | 1600E-12 | 1.6 |

Example 7: Identification of Antibodies Competing with mAb0005 (11F2) for Binding to FVII(a) in a Competitive ELISA To determine if anti-FVII(a) antibodies with desired in vitro properties from Example 5 compete with mAb0005 (11F2), and antibodies derived thereof, for binding to FVIIa (a) competition studies were performed with the corresponding Fab fragment, Fab0076. FVIIa, H-D-Phe-Phe-Arg chloromethyl ketone (FFR-cmk; Bachem, Switzerland) active-site inhibited FVIIa (FVIIai; see Example 9) was immobilised on a NUNC maxisorp plate at a concentration of 125 ng/ml in dilution buffer (20 mM HEPES, 5 mM CaCl2, 150 mM NaCl, pH 7.2) over night at 4° C. The plates were washed and blocked in washing buffer (20 mM HEPES, 5 mM CaCl2, 150 mM NaCl, 0.5 mL/L Tween 20, pH 7.2) for 15 min. 11F2-Fab0076 was biotinylated using a standard biotinylation kit (EZ-Link, Thermo) used according to manufacturer's instructions. For the competition study, biotinylated Fab0076 at a final fixed concentration of 10 ng/ml was combined with a dilution series of anti-FVIIa (a) antibody to give final concentrations ranging from 100 mg/ml to 9.5 ng/ml in dilution buffer. The mixture was added to the wells of the plate and allowed to incubate for 1 hour. The plate was then washed and HRP-labelled streptavidin-HRPO (1:2000 in dilution buffer; Kirkegaard & Perry Labs) was added and incubated for 1 h. Finally, the plate was washed and developed with TMB ONE (KEMENTEC) for 10 min. The reaction was stopped by adding H3PO4 (4M) and the plate read in a FLUOStar Optima plate reader at 450 nm with subtraction of the background signal measured at 620 nm. Unless otherwise specified, all incubations were done at room temperature and plates were washed 5 times using washing buffer.

From the measured signals (OD units), competition at any given antibody concentration was calculated as % inhibition=(1−(OD units−100% inhibition)/(0% inhibition−100% inhibition))*100 where 0% inhibition was determined from the signal in wells without any competing anti-FVII(a) antibody, and 100% inhibition was determined as the signal from wells without biotinylated Fab0076 (i.e. corresponding to the assay background). Antibodies were considered to compete with 11F2 (mAb0005) for binding to FVII(a), if there was at least 50% observed inhibition (% inhibition) when the concentration of the antibody was tested in up to 10000-fold excess of the biotinylated Fab0076. Results are summarized in Table 8.

TABLE 8

Competition with 11F2-Fab0076 (mAb0005) for binding to FVII(a). As described in Example 7, a cutoff of 50% was used to categorize antibodies as competitors or non-competitors.

| Anti-FVII(a) antibody | % inhibition |
|---|---|
| mAb0765 | Yes |
| mAb0100 | No |
| mAb0047 | No |
| mAb0759 | Yes |
| mAb0762 | No |
| mAb0764 | No |

Example 8: FVIIa Activity Assay

FVIIa activity was measured using reagents from STAclot®VIIa-rTF kit (Diagnostica Stago) essentially as described in Morissey J H et al Blood, 1993; 81: 734-44. The assay was performed on an ACLTOP500 automated coagulation instrument from Instrumentation Laboratory. In the assay was 40 μl diluted animal plasma sample, calibrator (recombinant FVIIa (rFVIIa) reference material calibrated against the international WHO reference) or quality control (QC) sample mixed with 40 μl FVII-deficient plasma and 40 μl soluble tissue factor (sTF) with phospholipids. A volume of 40 μl 25 mM CaCl2 was added to start the reaction, and the clotting time measured by the instrument. Sample and QC clot times were compared to rFVIIa calibration curves with the same concentration of plasma as the diluted sample to mitigate interference of plasma. The calibrator curve range was 5-1000 mIU/mL and was fitted using a third degree polynomial equation. QC and sample results were calculated by the software on the ACLTOP500 instrument. Results in IU/mL were converted to nM using the specific activities (IU/pmol) of the dosed compounds.

Example 9: Pharmacokinetics in Rats of Recombinant FVIIa in Co-Formulation with Anti-FVII(a) Antibodies Monoclonal anti-FVII(a) antibodies with desired in vitro properties from Example 5 were dosed IV to male Sprague Dawley rats in a co-formulation with 20 nmol/kg human FVIIa. The molar ratio of FVIIa to antibody was 1:1 or 1:5 as indicated in Table 9. During the experiment, the animals were allowed free access to feed and water. FVIIa plasma activity was measured using the FVIIa activity assay as described in Example 8.

Pharmacokinetic analysis was carried out by non-compartmental methods using WinNonlin. From the data the mean residence time (MRT) was calculated. Results are given in Table 9.

Among the antibodies with desirable properties from Example 5, mAb0005 (11F2) and mAb0001 (11F26) endowed human FVIIa with the longest mean residence times of 7.9 and 7.5 hours, respectively, in comparison to a free mean residence time of 1.1 hour for free human FVIIa (see Table 9). mAb0005 and mAb0001 (mAb0759) are high affinity antibodies (Example 6) exhibiting competition for binding to FVIIa (Example 7).

TABLE 9

Mean residence time (MRT) of FVIIa plasma activity in sprague dawley rats following an IV dose of 20 nmol/kg FVIIa in either a 1:1 or 1:5 molar ratio with antibody as indicated. Vehicle indicates that FVIIa was administered in combination with buffer instead of antibody.

| Anti-FVII(a) antibody | Molar ratio FVIIa:antibody | MRT (h) |
|---|---|---|
| Vehicle | n.a. | 1.1 |
| mAb0005 | 1:5 | 7.9 |
| mAb0007 | 1:1 | 3.9 |
| mAb0018 | 1:5 | 1.1 |
| mAb0004 | 1:5 | 3.6 |
| mAb0001 | 1:1 | 7.5 |
| mAb0587 | 1:1 | 4.0 |
| mAb0578 | 1:1 | 4.2 |

Example 10: Effect of 11F2 Anti-FVII(a) Antibody on the Activation of FX by Free or TF-Complexed FVIIa Preferably, anti-FVII(a) antibodies of the invention should not interfere with the pharmacological action of FVIIa on the membrane surface or initiation of coagulation, i.e. the activation of FX by the FVIIa-TF complex. To explore these aspects, the effect of 11F2 on the TF-independent and TF-dependent proteolytic activity of FVIIa was determined in the absence or presence, respectively, of lipidated TF. A one-armed monovalent antibody format was used to avoid avidity effects arising from the simultaneous binding of two FVIIa molecules to a normal bivalent antibody.

Effect of 11F2 Antibody on FX Activation by FVIIa in the Presence of Phospholipid Membrane Activity measurements were performed in assay buffer (50 mM HEPES, 100 mM NaCl, 10 mM CaCl2, pH 7.3, 0.1% PEG8000 and 1 mg/ml BSA) containing 10 nM FVIIa, 0 or 200 nM antibody (see Table 10), and 25 µM 25:75 phosphatidyl serine:phosphatidyl choline vesicles (Haematologic Technologies Inc.). Reactions were initiated by addition of 0-300 nM human plasma-derived factor X (FX) and allowed to incubate for 20 min at room temperature in a total reaction volume of 100 µl in a 96-well plate (n=2). After incubation, reactions were quenched by addition of 50 µl quench buffer (50 mM HEPES, 100 mM NaCl, 10 mM CaCl2, 80 mM EDTA, pH 7.3) followed by 50 µl 1 mM S-2765 chromogenic substrate (Chromogenix) in water. Conversion of the chromogenic substrate by the generated FXa was measured as the slope of the linear absorbance increase at 405 nm for 10 min using a Spectramax microplate spectrophotometer. By relating the measured slopes to those generated under similar conditions with known amounts of plasma-derived human FXa, initial rates of FXa generation on a molar basis could be estimated. Enzyme kinetic parameters were estimated by non-linear curve-fitting of the data to the Michaelis-Menten equation ($v=k_{cat}*[FX]*[FVIIa\text{-}TF]/(K_m+[FX])$) using GraphPad Prism.

As shown in Table 10, the monovalent 11F2 did not affect the rate of FX activation by free FVIIa in the presence of phospolipid vesicles.

Effect of 11F2 Antibody on FX Activation by FVIIa in the Presence of TF

Activity measurements were performed in assay buffer (50 mM HEPES, 100 mM NaCl, 10 mM CaCl2, pH 7.3, 0.1% PEG8000 and 1 mg/ml BSA) containing 100 pM FVIIa, 0 or 200 nM antibody (see Table 10), and 2 pM *E. coli*-derived TF fragment 1-244 incorporated into 25:75 phosphatidylserine:phosphatidy choline (PS:PC) vesicles as described by Smith and Morrissey (2005) J. Thromb. Haemost., 2:1155-1162. Reactions were initiated by addition of 0-30 nM human plasma-derived factor X (FX) and allowed to incubate for 20 min at room temperature in a total reaction volume of 100 µl in a 96-well plate (n=2). After incubation, reactions were quenched and FXa quantified as described above.

As shown in Table 10, monovalent 11F2 (mAb0077(OA)) did not affect the rate of FX activation by the FVIIa/TF complex.

TABLE 10

Effect of 200 nM 11F2 in monovalent format on the kinetic parameters for activation of FX by the FVIIa-TF complex according to Example 10. Parameters shown as mean ± SD (n = 3) were estimated by fitting to the Michaelis-Menten equation. $k_{cat}/K_M$ is shown relative to the value determined in the absence of antibody.

| 11F2 antibody | Activator | $K_m$ (nM) | $k_{cat}$ ($s^{-1}$) | $k_{cat}/K_M$ (%) |
|---|---|---|---|---|
| None | TF-FVIIa | 3.9 ± 0.6 | 1.5 ± 0.1 | 100 |
| mAb0077(OA) | TF-FVIIa | 3.9 ± 0.7 | 1.7 ± 0.1 | 110 ± 29 |
| None | FVIIa/PS:PC | 137 ± 15 | (2.8 ± 0.1) × 10−4 | 100 |
| mAb0077(OA) | FVIIa/PS:PC | 89 ± 9 | (2.6 ± 0.1) × 10−4 | 147 ± 5 |

Example 11: Effect of 11F2 Antibody on the Inhibition of FVIIa by Plasma Inhibitors FVIIa exhibits a relatively short half-life in circulation in part due to its inactivation by the abundant plasma inhibitor antithrombin (AT). Similarly, animal studies have implicated another plasma inhibitor, alpha-2-macroglobulin, in the inactivation of FVIIa. Using purified plasma-derived inhibitors, the effect of monovalent 11F2 antibody on the inactivation of FVIIa by these inhibitors was studied.

Effect of 11F2 Antibody on the Inhibition of FVIIa by Antithrombin

The inhibition of FVIIa with human plasma-derived AT in the presence of monovalent 11F2 antibody (mAb0048, mAb0077(OA)) was performed under pseudo-first order conditions. The assay was conducted in a volume of 200 µl in assay buffer (50 mM HEPES, 100 mM Nacl, 10 mM CaCl2, 0.1% PEG8000, 1 mg/ml BSA, pH 7.3) at room temperature containing 200 nM FVIIa, 12 µM low molecular weight heparin (Enoxaparin, European Pharmacopeia Reference, Code E0180000, batch 5.0, Id 00CK18), and either 0 or 1000 nM antibody. Following 10 min pre-incubation, the reaction was initiated by addition of 5 µM AT (Antithrombin III, Baxter, Lot VNB1 M007; repurified on heparin-sepharose column to remove serum albumin in the formulation). At selected time points, 10 µl aliquots were transferred into a total volume of 200 µl containing 0.5 mg/ml polybrene (Hexadimethrine bromide, Sigma, catalog no H9268, lot SLBC8683V), 200 nM sTF, and 1 mM S-2288 (Chromogenix) to quench the reaction and saturate FVIIa with sTF, which allowed for measurement of the residual FVIIa activity from the hydrolysis of the chromogenic substrate monitored at 405 nm for 5 min. Residual amidolytic activities were determined as the slope of the linear progress curves after blank subtraction and these were subsequently fitted to a first-order exponential decay function using GraphPad Prism software to derive pseudo-first order rate constants (kapp) for the reaction. An apparent second order rate constant (kinh) was estimated as the kapp divided by the AT concentration.

From this analysis, the rate of inhibition of FVIIa in the presence of monovalent 11F2 (mAb0077(OA)) was found to be 133±10 M-1s-1 as compared to 124±7 M-1s-1 for the inhibition of free FVIIa.

Effect of 11F2 Antibody on the Inhibition of FVIIa by Alpha-2-Macroglobulin

The inhibition of FVIIa with human plasma-derived alpha-2-macroglobulin in the presence of 0 or 1000 nM monovalent 11F2 antibody (mAb0077(OA)) was performed under pseudo-first order conditions. The assay was conducted in a volume of 100 µl in assay buffer (50 mM HEPES, 100 mM NaCl, 5 mM CaCl2, 0.1% PEG8000, 0.01% Tween 80, pH 7.3) at room temperature containing 200 nM FVIIa and either 0 or 1000 nM antibody. The reaction was initiated by addition of 0 or 1000 nM alpha-2-macroglobulin purified from human plasma according to Banbula et al. (2005) J. Biochem., 138:527-537. At selected time points, 10 µl aliquots were transferred to 190 µl buffer (50 mM HEPES, 100 mM NaCl, 5 mM CaCl2, 0.1% PEG8000, 1 mg/ml BSA, pH 7.3) containing 200 nM sTF and 1 mM S-2288 (Chromogenix), which allowed for measurement of the residual FVIIa activity from the hydrolysis of the chromogenic substrate monitored at 405 nm for 5 min. Residual amidolytic activities were determined as the slope of the linear progress curves after blank subtraction and these were subsequently fitted to a first-order exponential decay function using GraphPad Prism software to derive pseudo-first order rate constants (kapp) for the reaction. An apparent second order rate constant (kinh) was estimated as the kapp divided by the alpha-2-macroglobulin concentration.

In the absence of antibody, the apparent second order rate constant for inhibition of FVIIa by alpha-2-macroglobulin was found to be 475±21 M-1s-1. However, in the presence of monovalent 11F2 antibody (mAb0077(OA)) no apparent inhibition of FVIIa was observed until the last time point at 125 min. From these studies, it can be concluded that 11F2 does not affect the inhibition of FVIIa by antithrombin, but protects FVIIa from inhibition by alpha-2-macroglobulin.

Example 12: Effect of 11F2 Antibody on FVII Auto-Activation

Upon vascular injury, endogenous FVII binds with high affinity to its cofactor tissue factor (TF), which is exposed on the cells surrounding the vascular endothelium. During this process FVII is converted to FVIIa by limited proteolysis. Activation is believed to occur as a result of TF-mediated FVIIa-FVII trans-activation, also referred to as auto-activation. To determine the effect of 11F2 antibody on FVII auto-activation, activation of FVII was measured in the presence of lipidated TF, FVII, a limiting concentration of FVIIa, and monovalent 11F2 antibody.

Activity measurements were performed in assay buffer (50 mM HEPES, 100 mM NaCl, 5 mM CaCl2, pH 7.3 containing 0.1% PEG8000 and 1 mg/ml BSA) containing 2 nM FVIIa, 145 nM FVII, 0 or 200 nM monovalent 11F2 antibody (mAb0077(OA)). Reactions were initiated by addition of 2 nM lipidated *E. coli*-derived TF fragment 1-244 incorporated into 25:75 PS:PC vesicles as described by Smith and Morrissey (2005) J. Thromb. Haemost., 2:1155-1162. The total reaction volume was 100 µl. At selected time points (typically 5, 10, 15, 20, 30, 40, 50 and 60 min) generated FVIIa was quantified according to the sub-sampling procedure described below.

Quantification of FVIIa by sub-sampling—at selected time points 10 µl samples were quenched by transfer to 140 µl 50 mM HEPES, 100 mM NaCl, 5 mM EDTA containing 0.1% PEG8000, 1 mg/ml BSA and 215 nM soluble tissue factor (sTF). Following collection of all samples, FVIIa chromogenic activity was measured by addition of 50 µl S-2288 (4 mM) in 60 mM CaCl2. Conversion of the chromogenic substrate by the generated FVIIa was measured as the slope of the linear absorbance increase at 405 nm for 10 min using a Spectramax plate reader. By relating the measured slopes to those generated under similar conditions with known amounts of FVIIa, molar concentrations of FVIIa could be estimated.

FVIIa auto-activation was found to be TF-dependent, and is shown from the measured FVIIa activities in Table 11 to not being impaired by the presence of monovalent 11F2 antibody.

TABLE 11

TF-mediated autoactivation of FVIIa according to Example 12 in the absence or presence of 200 nM monovalent 11F2 antibody mAb0077(OA)

| Time (min) | Activity no antibody | Activity mAb0077(OA) |
|---|---|---|
| 5 | 5.5 ± 0.1 | 6.0 ± 0.1 |
| 10 | 9.2 ± 0.1 | 11.2 ± 1.3 |
| 20 | 23.6 ± 1.1 | 27.6 ± 1.8 |
| 30 | 45.6 ± 1.6 | 52.7 ± 3.6 |
| 40 | 71.1 ± 2 | 78.2 ± 4.1 |
| 50 | 87.8 ± 1.4 | 100.0 ± 5.4 |

Example 13: Crystal Structure of 11F2-Fab0076 in Complex with Active-Site Inhibited FVIIa and Soluble Tissue Factor To determine the epitope recognized by the murine antibody 11F2 on FVII(a), the corresponding Fab fragment (Fab0076) was crystallized in complex with H-D-Phe-Phe-Arg chloromethyl ketone (FFR-cmk; Bachem, Switzerland) active-site inhibited FVIIa (FVIIai) and the soluble tissue factor fragment 1-219 (sTF) using the hanging-drop method in accordance with Kirchhofer. D., et al., Proteins Structure Function and Genetics. (1995), 22, 419-425.

Crystallisation

Crystals of Fab0076 mixed in a 1:1 molar ratio with FVIIai/sTF complex were grown using the hanging drop vapour diffusion technique at 18° C. A protein solution of 1 µl 4.6 mg/ml protein complex in 10 mM HEPES, 50 mM NaCl, 5 mM CaCl2, pH 7.0 was mixed with 0.5 µl 100 mM sodium citrate, pH 6.2 and 20% PEG 6000 as precipitant and incubated at a temperature of 18° C. over 1 ml of precipitant solution to obtain crystals of the complex.

Diffraction Data Collection

A crystal was cryo protected in a solution consisting of 75 mM sodium citrate, pH 6.2, 15% PEG 6000, 4% glycerol, 4% ethylene glycol, 4.5% sucrose, and 1% glucose prior to flash cooling in liquid nitrogen. Diffraction data were collected at 100K at the MAX-lab (Lund, Sweden) beamline 1911-3 using a marCCD225 detector from MAR Research. Autoindexing, integration and scaling of the data were performed with programmes from the XDS package (diffracting data statistics are summarised in Table 12).

Structure Determination and Refinement

The structure was determined by molecular replacement using Phaser as implemented in the programme suite Phenix with the chains A and B of protein data bank entry 1YY8 and protein data bank entry 3ELA. The asymmetric unit contains two Fab:FVIIai/sTF complexes. The model was refined using steps of Phenix refinement and manual rebuilding in COOT. The refinement statistics are found in Table 12.

TABLE 12

Data collection and refinement statistics from X-ray crystallographic structure determination of the complex between active-site inhibited FVIIa, soluble tissue factor (sTF) and Fab0076. Statistics for the highest-resolution shell are shown in parentheses.

| | Fab0076/FVIIai/sTF |
|---|---|
| Wavelength (Å) | 1.0000 |
| Resolution range | 47.88-3.02 (3.128-3.02) |
| Space group | P 2$_1$ 2$_1$ 2$_1$ |
| Unit cell | 101.02 149.02 179.86 90 90 90 |
| Total reflections | 842454 (26830) |
| Unique reflections | 53490 (5172) |
| Multiplicity | 15.7 (5.1) |
| Completeness (%) | 99 (99) |
| Mean I/sigma(I) | 4.45 (0.39) |
| Wilson B-factor | 65.28 |
| R-merge | 0.8138 (4.973) |
| R-meas | 0.8409 (5.535) |
| R-pim | 0.2063 (2.382) |
| CC1/2 | 0.967 (0.14) |
| CC* | 0.992 (0.496) |
| Reflections used in refinement | 53375 (5172) |
| Reflections used for R-free | 1995 (193) |
| R-work | 0.2820 (0.4497) |
| R-free | 0.3393 (0.4832) |
| CC(work) | 0.897 (0.319) |
| CC(free) | 0.846 (0.303) |
| Number of non-hydrogen atoms | 15284 |
| macromolecules | 15224 |
| ligands | 59 |
| solvent | 1 |
| Protein residues | 1966 |
| RMS(bonds) | 0.003 |
| RMS(angles) | 0.59 |
| Ramachandran favored (%) | 91 |
| Ramachandran allowed (%) | 7.3 |
| Ramachandran outliers (%) | 1.2 |
| Rotamer outliers (%) | 1.6 |
| Clashscore | 2.37 |
| Average B-factor | 102.32 |
| macromolecules | 102.32 |
| ligands | 104.51 |
| solvent | 0.00 |
| Number of TLS groups | 78 |

The epitope (defined as residues in FVIIai having a non-hydrogen atom positioned within a distance of less than or equal to 4 Å from a non-hydrogen atom in Fab0076) was found to include the following residues according to SEQ ID NO:1:

R113
C114
H115
E116
G117
Y118
S119
L120
T130
V131
N184
T185
I186
P251
V252
E265
M391
R392
E394

The paratope (defined as residues in Fab0076 having a non-hydrogen atom positioned within a distance of less than or equal to 4 Å from a non-hydrogen atom in FVIIai) was found to include the following light chain residues:

Q27
G28
S30
D31
Y32
K49
Y50
Q53
H92
S93
F94 according to SEQ ID NO: 64 and heavy chain residues:

D32
Y54
N59
N101
Y102

-continued

Y103

G104

N105 according to SEQ ID NO: 63.

Example 14: Humanization Murine 11F2

In order to humanize the murine antibody 11F2 (mAb0005) with VH and VL domain sequences corresponding to SEQ ID NO. 754 and SEQ ID NO. 750, respectively while conserving its high binding affinity for FVII(a), we combined information from sequence identity relative to human germlines, crystal structure of the complex between Fab0076 (Example 12) and active-site inhibited FVIIa (example 9) as well as in vitro binding data. Initially, we searched for human sequences of VH, VL, and VJ (for both heavy chain (HC) and light chain (LC)) with high sequence identity to the murine variable domain sequences of 11F2 in a database of human germlines using the blast algorithm. The sequences with highest sequence identity for VH of HC were: IGHV4-30-4*01, IGHV4-28*01, IGHV4-28*06, and IGHV459*01 and for the VJ-segment of HC the top germlines were: IGHJ5*01, IGHJ4*01. For the LC, the top sequences for VL were: IGKV6D-41*01 and IGKV3-11*01 and for the VJ-segment: IGKJ2*01 and IGKJ2*02 (Table 12). Next, the differences between the human germlines and the murine VH and VL sequences were mapped onto the crystal structure of the Fab0076/FVIIa complex. Residues in the murine variable domains separated by a distance of more than or equal to 10 Å from residues in the epitope were anticipated to have no or little impact on binding affinity and were exchanged to the corresponding human germline amino acid entity. In turn, residues constituting the paratope were considered more problematic to substitute without affecting affinity and here the murine amino acid entity was preserved. A subset of residues near the binding interface that potentially could affect the binding affinity was identified. Humanized variants were generated by mutating residues distal to the epitope to the human amino acid entity from the germline alignment. Furthermore, residues close to the paratope were mutated to the human entity in a subset to make the variants as close to human germline as possible. Included in the set were variants were the murine CDRs are grafted on to a fully human germ line of HC and LC. From the initial analysis 12 LCs and 13 HCs were generated and paired into 23 variants according to Table 13.

Affinities for binding to FVIIa (listed in Table 13) were measured for the humanized antibodies using Bio-Layer Interferometry (Fortebio). All steps were performed in running buffer (20 mM HEPES buffer (pH 7.4), 150 mM NaCl, 5 mM CaCl2, 0.03% Tween 20, 1 mg/ml IgG-free BSA) at 30 Antibodies were captured on anti-human tips (AHC, Fortebio) for 3 min at a concentration of 10 ug/ml. This was followed by a 3 min incubation to establish a baseline. Following this, association was monitored for 3 min using four different concentrations of VIIa (25 nm, 50 nM, 100 nM, and 200 nM), followed by a 3 mi dissociation. Sensorgrams were analysed using Fortebio data analysis software. The Fortebio data were used for ranking, and absolute affinity values may deviate from values determined by SPR (Example 6, Table 7).

TABLE 12

Human germline sequences used for humanization of murine 11F2. Numbers in parenthesis reflect identity ((n/m) denotes n identical positions out of a total of m positions) between the murine variable domains of Fab0076 and the specified human germline sequence

| VH-LC | VJ-LC | VH-HC | VJ-HC |
|---|---|---|---|
| IGKV3-11*01 (81/95) | IGKJ2*01 (11/11) | IGHV4-28*06 (87/98) | IGHJ5*02(12/12) |
| IGKV3D-11*01 (80/89) | IGKJ2*012 (H/11) | IGHV4-61*01 (90/99) | IGHJ1*01(11/11) |
|  |  | IGHV4-30-4*01 (91/99) |  |

TABLE 13

Pairing of VH and VL in first round of humanization of the murine 11F2-mAb0048 with measured affinities of corresponding antibodies for FVIIa (determined as described herein). For some variants no binding (nb) was measured.

| Antibody | SEQID No (VH) | SEQID No (VL) | $K_D$ (nM) |
|---|---|---|---|
| mAb0108 | 74 | 70 | nb |
| mAb0109 | 82 | 78 | 11 |
| mAb0110 | 90 | 86 | 4.2E+4 |
| mAb0111 | 98 | 94 | nb |
| mAb0112 | 106 | 102 | 13 |
| mAb0113 | 114 | 110 | 1.8 |
| mAb0114 | 122 | 118 | 1.5 |
| mAb0115 | 130 | 126 | 1.5 |
| mAb0116 | 138 | 134 | 32 |
| mAb0117 | 146 | 142 | 1.4 |
| mAb0118 | 154 | 150 | 1.7 |
| mAb0119 | 162 | 158 | 1.0 |
| mAb0120 | 170 | 166 | 1.7 |
| mAb0121 | 178 | 174 | 2.0 |
| mAb0122 | 186 | 182 | 1.7 |
| mAb0123 | 194 | 190 | 5.8 |
| mAb0124 | 202 | 198 | 1.8 |
| mAb0125 | 210 | 206 | 1.7 |
| mAb0126 | 218 | 214 | 2.5 |
| mAb0127 | 226 | 222 | nb |
| mAb0128 | 234 | 230 | 1.7 |
| mAb0129 | 242 | 238 | 2.2 |
| mAb0130 | 250 | 246 | 1.8 |

Variants from the first round of humanization having an affinity on par or higher than the parental murine antibody were identified and those mutations that were found to preserve or improve binding affinity were used to design the second round of variants. From this set of mutations, the second round of variants were generated by inserting as many of these mutations on top of the humanised HC and LC already having the desired affinity. From the analysis 19 VH sequences (corresponding to SEQ ID No: 314, 514, 522, 530, 538, 546, 554, 562, 570, 578, 586, 594, 602, 610, 618, 626, 634, 642 and 650) and 25 VL sequences (corresponding to SEQ ID No: 310, 318, 326, 334, 342, 350, 358, 366, 374, 382, 390, 398, 406, 414, 422, 430, 438, 446, 454, 462, 470, 478, 486, 494 and 502) were designed and were experimentally tested by combining all VL with VL resulting in a total of 475 combinations. Dissociation constant (KD) values for binding to FVIIa were measured for the resulting 475 humanized antibodies using Bio-Layer Interferometry (Fortebio), as described above. Measured KD-values are listed in Table 14.

TABLE 14

Dissociation constant values (M, nb for no binding) for humanized variants of the murine 11F2 anti-FVII(a) antibody. Antibodies are defined by their respective VH and VL SEQID Nos.

| | VL | | | | | | | |
|---|---|---|---|---|---|---|---|---|
| VH | 310 | 318 | 326 | 334 | 342 | 350 | 358 | 366 |
| 314 | nb | 1.7E−08 | 1.5E−08 | 2.1E−08 | 2.8E−08 | 1.9E−08 | 1.8E−08 | nb |
| 514 | 3.1E−09 | 9.9E−10 | 7.5E−10 | 1.1E−09 | 1.3E−09 | 9.4E−10 | 8.7E−10 | 1.4E−09 |
| 522 | 8.3E−09 | 9.7E−10 | 8.1E−10 | 1.2E−09 | 1.4E−09 | 1.3E−09 | 1.3E−09 | 1.4E−08 |
| 530 | 2.5E−09 | 1.2E−09 | 1.1E−09 | 1.2E−09 | 1.2E−09 | 9.6E−10 | 1.0E−09 | 3.2E−09 |
| 538 | 2.5E−09 | 6.4E−10 | 5.8E−10 | 9.7E−10 | 1.2E−09 | 1.0E−09 | 8.9E−10 | 6.2E−09 |
| 546 | 3.2E−09 | 8.6E−10 | 8.1E−10 | 1.1E−09 | 1.2E−09 | 9.6E−10 | 9.9E−10 | 5.7E−09 |
| 554 | nb | 1.5E−08 | 1.4E−08 | 1.8E−08 | 2.3E−08 | 1.9E−08 | 1.6E−08 | nb |
| 562 | 6.4E−09 | 9.2E−10 | 7.8E−10 | 1.2E−09 | 1.3E−09 | 9.3E−10 | 9.5E−10 | 8.3E−09 |
| 570 | 1.3E−08 | 8.3E−10 | 5.5E−10 | 9.2E−10 | 1.5E−09 | 1.0E−09 | 8.5E−10 | 1.4E−08 |
| 578 | nb | 1.7E−08 | 1.6E−08 | 2.2E−08 | 4.3E−08 | 2.1E−08 | 1.9E−08 | nb |
| 586 | 1.5E−06 | 9.8E−09 | 9.9E−09 | 1.3E−08 | 1.8E−08 | 1.2E−08 | 1.1E−08 | 2.1E−08 |
| 594 | nb | 2.3E−08 | 2.2E−08 | 3.2E−08 | 1.2E−07 | 3.4E−08 | 2.4E−08 | nb |
| 602 | 4.8E−08 | 9.0E−09 | 8.8E−09 | 1.0E−08 | 1.4E−08 | 1.0E−08 | 9.2E−09 | 5.1E−08 |
| 610 | 8.0E−08 | 1.0E−08 | 1.1E−08 | 1.3E−08 | 1.6E−08 | 1.1E−08 | 1.1E−08 | 3.3E−07 |
| 618 | 1.2E−08 | 1.1E−09 | 1.1E−09 | 1.3E−09 | 1.2E−09 | 1.0E−09 | 9.5E−10 | 2.1E−08 |
| 626 | 9.2E−09 | 7.1E−10 | 7.9E−10 | 9.5E−10 | 8.5E−10 | 6.5E−10 | 7.2E−10 | 8.7E−08 |
| 634 | 2.1E−09 | 8.6E−10 | 9.0E−10 | 1.0E−09 | 1.0E−09 | 1.2E−09 | 8.2E−10 | 3.1E−09 |
| 642 | 1.6E−06 | 8.1E−08 | 2.3E−08 | 1.0E−06 | 4.0E−08 | 1.2E−07 | 3.2E−07 | nb |
| 650 | 1.6E−08 | 1.2E−09 | 1.1E−09 | 1.5E−09 | 1.6E−09 | 9.9E−10 | 1.1E−09 | 3.5E−08 |

| | VL | | | | | | | |
|---|---|---|---|---|---|---|---|---|
| VH | 374 | 382 | 390 | 398 | 406 | 414 | 422 | 430 |
| 314 | nb | 2.7E−08 | nb | nb | nb | nb | nb | nb |
| 514 | nb | 1.2E−09 | 4.7E−09 | 7.9E−09 | 5.3E−09 | 4.6E−09 | 6.8E−08 | 7.1E−09 |
| 522 | 1.4E−08 | 1.3E−09 | 1.5E−08 | 3.2E−07 | 1.7E−08 | 3.1E−08 | 1.1E−07 | 1.2E−08 |
| 530 | 4.2E−09 | 1.1E−09 | 4.1E−09 | 7.1E−09 | 4.3E−09 | 4.5E−09 | 2.6E−08 | 4.9E−09 |
| 538 | 7.4E−09 | 1.2E−09 | 7.0E−09 | 1.1E−08 | 6.1E−09 | 6.9E−09 | 2.1E−08 | 8.3E−09 |
| 546 | 6.8E−09 | 1.3E−09 | 7.0E−09 | 1.1E−08 | 6.7E−09 | 7.1E−09 | 2.4E−08 | 8.1E−09 |
| 554 | nb | 2.1E−08 | nb | nb | nb | nb | nb | nb |
| 562 | nb | 1.2E−09 | 1.0E−08 | nb | 7.7E−09 | 8.8E−09 | 1.8E−08 | 7.9E−09 |
| 570 | nb | 1.3E−09 | 4.8E−08 | 2.9E−08 | 2.0E−08 | 2.1E−08 | 2.4E−06 | 1.6E−08 |
| 578 | nb | 3.0E−08 | nb | nb | nb | nb | nb | 8.2E−07 |
| 586 | nb | 1.7E−08 | 3.8E−08 | nb | 1.9E−08 | 2.5E−08 | nb | 1.3E−08 |
| 594 | nb | 1.4E−07 | nb | nb | nb | nb | nb | nb |
| 602 | nb | 1.4E−08 | 3.7E−07 | nb | 9.0E−08 | 3.1E−07 | nb | 5.9E−07 |
| 610 | nb | 1.7E−08 | 3.8E−07 | nb | 4.8E−07 | 7.8E−07 | nb | 1.5E−06 |
| 618 | nb | 1.1E−08 | 3.3E−08 | 1.8E−07 | 2.4E−08 | 2.4E−08 | 5.8E−06 | 1.1E−07 |
| 626 | nb | 1.1E−09 | 2.7E−08 | 8.2E−07 | 8.7E−08 | 1.8E−08 | 2.4E−06 | 5.3E−08 |
| 634 | 4.5E−09 | 1.2E−09 | 4.3E−09 | 8.2E−09 | 4.2E−09 | 4.6E−09 | 2.6E−08 | 4.9E−09 |
| 642 | nb | 6.0E−07 | nb | nb | nb | nb | nb | 5.4E−07 |
| 650 | 4.6E−08 | 1.9E−09 | 9.9E−08 | 5.5E−08 | 1.8E−07 | 8.4E−08 | 2.6E−06 | 2.8E−08 |

| | VL | | | | | | | | |
|---|---|---|---|---|---|---|---|---|---|
| VH | 438 | 446 | 454 | 462 | 470 | 478 | 486 | 494 | 502 |
| 314 | nb | nb | 3.2E−08 | 2.6E−08 | 2.0E−08 | 6.4E−08 | 2.2E−08 | 2.8E−08 | 2.5E−08 |
| 514 | 5.4E−09 | 7.7E−09 | 1.3E−09 | 1.2E−09 | 1.2E−09 | 1.9E−09 | 9.5E−10 | 1.4E−09 | 9.2E−10 |
| 522 | 5.7E−08 | 1.7E−07 | 1.0E−09 | 1.2E−09 | 9.6E−10 | 1.6E−09 | 1.5E−09 | 1.7E−09 | 1.4E−09 |
| 530 | 4.6E−09 | 7.9E−09 | 1.1E−09 | 1.0E−09 | 9.6E−10 | 1.4E−09 | 9.9E−10 | 1.0E−09 | 9.4E−10 |
| 538 | 8.3E−09 | 1.2E−08 | 1.2E−09 | 1.3E−09 | 1.0E−09 | 1.8E−09 | 1.0E−09 | 1.1E−09 | 8.8E−10 |
| 546 | 8.0E−09 | 1.0E−08 | 1.1E−09 | 1.1E−09 | 1.2E−09 | 2.0E−09 | 1.1E−09 | 1.2E−09 | 1.1E−09 |
| 554 | nb | nb | 1.9E−08 | 2.0E−08 | 1.9E−08 | 2.1E−08 | 1.9E−08 | 2.2E−08 | 1.8E−08 |
| 562 | 1.1E−08 | nb | 1.4E−09 | 1.4E−09 | 1.4E−09 | 2.6E−09 | 1.3E−09 | 1.6E−09 | 1.1E−09 |
| 570 | 2.1E−07 | 2.4E−08 | 1.1E−09 | 1.1E−09 | 1.1E−09 | 1.9E−09 | 9.9E−10 | 1.1E−09 | 9.2E−10 |
| 578 | nb | nb | 2.5E−08 | 2.7E−08 | 2.5E−08 | 3.1E−07 | 2.3E−08 | 2.8E−08 | 2.4E−08 |
| 586 | 2.3E−08 | nb | 1.6E−08 | 1.8E−08 | 1.5E−08 | 2.7E−08 | 1.8E−08 | 1.7E−08 | 1.5E−08 |
| 594 | nb | nb | 3.2E−08 | 3.9E−08 | 3.5E−08 | 2.0E−07 | 3.3E−08 | 4.3E−08 | 3.0E−08 |
| 602 | 6.0E−07 | nb | 1.3E−08 | 1.5E−08 | 1.3E−08 | 2.4E−08 | 1.5E−08 | 1.4E−08 | 1.4E−08 |
| 610 | 6.2E−07 | 4.9E−08 | 1.6E−08 | 1.7E−08 | 1.6E−08 | 3.3E−08 | 1.7E−08 | 1.7E−08 | 1.7E−08 |
| 618 | 3.4E−08 | 2.0E−07 | 1.3E−09 | 1.4E−09 | 1.2E−09 | 2.0E−09 | 1.2E−09 | 1.4E−09 | 1.2E−09 |
| 626 | 7.7E−08 | 8.8E−07 | 1.4E−09 | 1.4E−09 | 1.1E−09 | 2.5E−09 | 1.6E−09 | 1.8E−09 | 1.8E−09 |
| 634 | 4.8E−09 | 7.7E−09 | 1.2E−09 | 1.2E−09 | 1.0E−09 | 1.4E−09 | 1.4E−09 | 1.3E−09 | 1.3E−09 |
| 642 | 3.3E−08 | nb | 2.5E−08 | 5.2E−08 | 4.7E−08 | 1.1E−08 | 7.7E−09 | 1.0E−08 | 4.6E−09 |
| 650 | 2.8E−08 | 3.9E−08 | 1.4E−09 | 1.6E−09 | 1.6E−09 | 3.0E−09 | 1.3E−09 | 1.6E−09 | 1.3E−09 |

SPR Analysis of Humanized 11F2 Variants

The affinity of selected humanized 11F2 variants were determined by SPR analysis as detailed in Example 6. Measured dissociation constants are listed in Table 15 and show retained high-affinity binding of the variants to human FVIIa.

TABLE 15

Estimated binding constants ($K_D$) for the interaction of humanized 11F2 antibodies in monovalent format and biAbs with FVIIa as determined by surface plasmon resonance (SPR) analysis according to Example 6.

| Anti-FVII(a) antibody | $K_D$ (M) |
|---|---|
| mAb0077(OA) | 4.1E−11 |
| mAb0099(OA) | 1.2E−10 |
| mAb0138(OA) | 1.3E−10 |
| mAb0140(OA) | 8.3E−11 |
| mAb0141(OA) | 7.8E−11 |
| mAb0142(OA) | 1.0E−09 |
| mAb0143(OA) | 7.9E−11 |
| mAb0705(OA) | 5.05E−11 |
| mAb0706(OA) | 5.42E−11 |
| mAb0707(OA) | 1.06E−10 |
| mAb0709(OA) | 1.04E−10 |
| mAb0710(OA) | 1.28E−10 |
| biAb0001 | 0.06E−09 |
| biAb0245 | 600E−09 |

Functional Characterization of Humanized 11F2 Variants

The effect of selected humanized 11F2 variants on the activity of FVIIa and susceptibility to inhibition by antithrombin was determined as detailed in Example 5. Results are listed in Table 16 and show that the humanized variants retain desirable properties with respect to these parameters.

TABLE 16

Functional characterization of anti-FVII(a) antibodies in thrombin generation (TGT) and antithrombin (AT)-inhibition assays as described in Example 5.

| Anti-FVII(a) antibody | TGT activity (% FVIIa) | AT inhibition ($k_{inh}$ %) |
|---|---|---|
| mAb0077(OA) | 103 | 119 |
| mAb0099(OA) | 98 | 117 |
| mAb0137(OA) | 102 | 105 |
| mAb0138(OA) | 99 | 105 |
| mAb0139(OA) | 100 | 110 |
| mAb0140(OA) | 100 | 106 |
| mAb0141(OA) | 103 | 109 |
| mAb0142(OA) | 106 | 114 |
| mAb0143(OA) | 107 | 109 |
| mAb0705(OA) | 100 | 129 |
| mAb0706(OA) | 101 | 132 |
| mAb0707(OA) | 102 | 129 |
| mAb0709(OA) | 103 | 137 |
| mAb0710(OA) | 102 | 136 |

Pharmacokinetics in Rats of FVIIa in Co-Formulation with Humanized 11F2 Variants Humanized 11F2 variants family were dosed IV to male Sprague Dawley rats in a co-formulation with 20 nmol/kg FVIIa and as detailed in Example 9.

Results are given in Table 17 and show that several of the humanized 11F2 variants endow FVIIa with the same long half-life as the parental antibody.

TABLE 17

Mean residence time (MRT) of FVIIa plasma activity in Sprague Dawley rats following an IV dose of 20 nmol/kg FVIIa in different molar ratios with antibody. Values are mean ± SD, n = 3. n.a.: Not applicable

| Anti-FVII(a) antibody | Molar ratio FVIIa:antibody | MRT (h) |
|---|---|---|
| Vehicle | n.a. | 1.1 |
| mAb0005 | 1:5 | 7.9 |
| mAb0077(OA) | 1:1 | 11 ± 0.2 |
| mAb0099(OA) | 1:1 | 7.7 ± 0.4 |
| mAb0137(OA) | 1:1 | 7.0 |
| mAb0139(OA) | 1:1 | 2.7 |
| mAb0140(OA) | 1:1 | 7.7 |
| mAb0141(OA) | 1:1 | 7.7 |
| mAb0705(OA) | 1:1 | 7.7 ± 0.4 |
| mAb0706(OA) | 1:1 | 7.3 ± 0.3 |
| mAb0707(OA) | 1:1 | 6.4 ± 1.0 |
| mAb0709(OA) | 1:1 | 5.9 ± 0.4 |
| mAb0710(OA) | 1:1 | 5.7 ± 0.3 |

Example 15: Crystallisation and Epitope Mapping of 11F2 Fab0883 in Complex with Active-Site Inhibited FVIIa and Soluble Tissue Factor To determine the epitope on FVII(a) recognized by humanized 11F2, i.e. mAb0705(OA) and mAb0842(OA), the corresponding Fab fragment Fab0883, was crystallized in complex with H-D-Phe-Phe-Arg chloromethyl ketone (FFR-cmk; Bachem, Switzerland) active-site inhibited FVIIa (FVIIai) and the soluble tissue factor fragment 1-219 (sTF) using the hanging-drop method in accordance with [Kirchhofer. D., et al., Proteins Structure Function and Genetics. (1995), 22, 419-425.

Crystallisation

Crystals of a SEC purified complex of the Fab in complex with FVIIai/sTF were grown using the sitting drop vapour diffusion technique at 18° C. A protein solution of 360 nl protein complex (4.5 mg/ml) in 20 mM HEPES, 150 mM NaCl, 0.1 mM CaCl2, pH 7.4 was mixed with 360 nl of a precipitant solution containing 0.15 M CsCl and 15% (w/v) Polyethylen glycol 3350 and 360 nl water and equilibrated against 80 µl precipitant solution. Crystals grew within 6 weeks.

Diffraction Data Collection

The crystal was cryo-protected in a solution consisting of 0.15M CsCl, 15% (w/v) Polyethylen glycol 3350 and 20% (v/v) glycerol prior to flash cooling in liquid nitrogen. Diffraction data were collected at 100K at a Rigaku FRX rotating anode generator equipped with a Dectris Pilatus 1 M detector. Data reduction was performed with programmes from the XDS package (diffraction data statistics are summarised in Table 18).

Structure Determination and Refinement

All crystallographic calculations were performed using the Phenix suite of crystallographic programs. The structure was determined by molecular replacement using the program Phaser with the coordinates of the complex structure obtained as described in example 13 as a search model. The asymmetric unit contains four Fab:FVIIai/sTF complexes. Iterative cycles of manual rebuilding using COOT and Phenix refinement yielded the final model (Table 18)

TABLE 18

Data collection and refinement statistics from X-ray structure determination of the complex between active-site inhibited FVIIa, soluble tissue factor (sTF) and Fab0883. Statistics for the highest-resolution shell are shown in parentheses.

| | Fab0883 |
|---|---|
| Wavelength | 1.542 |
| Resolution range | 46.66-3.4 (3.52-3.4) |
| Space group | P 1 21 1 (No. 4) |
| Unit cell | 144.78 100.79 181.74 90 101.23 90 |
| Total reflections | 340556 (24056) |
| Unique reflections | 69058 (6446) |
| Multiplicity | 4.9 (3.7) |
| Completeness (%) | 96.4 (91.4) |
| Mean I/sigma(I) | 3.59 (0.86) |
| Wilson B-factor | 63.67 |
| R-merge | 0.31 (1.05) |
| R-meas | 0.3465 (1.22) |
| R-pim | 0.151 (0.603) |
| CC1/2 | 0.98 (0.697) |
| CC* | 0.995 (0.906) |
| Reflections used in refinement | 68475 (6424) |
| Reflections used for R-free | 1960 (180) |
| R-work | 0.2968 (0.4173) |
| R-free | 0.3323 (0.4271) |
| CC(work) | 0.855 (0.660) |
| CC(free) | 0.822 (0.503) |
| Number of non-hydrogen atoms | 29262 |
| macromolecules | 29251 |
| ligands | 11 |
| Protein residues | 3791 |
| RMS(bonds) | 0.016 |
| RMS(angles) | 1.74 |
| Ramachandran favored (%) | 90.11 |
| Ramachandran allowed (%) | 7.73 |
| Ramachandran outliers (%) | 2.16 |
| Rotamer outliers (%) | 0.12 |
| Clashscore | 30.81 |
| Average B-factor | 57.11 |
| macromolecules | 57.11 |
| ligands | 68.66 |

Epitope Mapping

A residue is considered to be part of the epitope, if all of the four independently determined FVIIa molecules in the crystal are having a non-hydrogen atom of said residue positioned within a distance of less than or equal to 4 Å from a non-hydrogen atom in the Fab. Thus, the epitope was found to comprise the following residues according to SEQ ID NO:1:

R113
C114
H115
E116
G117
Y118
S119
L120
T130
V131
N184
T185
P251
V252
V253
Q388
M391
R392

Paratope Determination

A residue is considered to be part of the paratope, if all of the four independently determined Fab molecules in the crystal are having a non-hydrogen atom of said residue positioned within a distance of less than or equal to 4 Å from a non-hydrogen atom in FVIIa). The paratope was found to comprise the following light chain residues (according to SEQ ID NO: 814):

Q27
G28
Y32
Y50
H92
S93
F94 and heavy chain residues (according to SEQ ID NO: 818):

D32
Y54
Y103
N105

Example 16: Hot-Spot Analysis of 11F2 mAb0842(OA) Using SPR

Expression of Alanine Variants of FVIIa hFVII alanine variants were generated with the QMCF Technology, a stable episomal expression system (Icosagen). CHOEBNALT85 cells were cultivated in Qmix1 medium (1 L=1:1 CD-CHO and SFM II (NVO11514701)+10 ml Pen/Strep (Gibco, 15140-122)+2 ml Puromycin (Gibco, A11138-03)) in E125 flasks in a C02 shaking incubator. On the day of transfection 1×10e7 CHOEBNALT85 cells were transfected with 2 µg hFVII variant-encoding plasmid and 50 µg salmon sperm DNA using electroporation (Bio-Rad Gene Pulser Xcell Electroporation System, 300 V, 900 µF, 4 mm cuvette). One day after transfection G418 selection was started by shifting cells to the Qmix2 medium (1 L=1:1 CD-CHO and SFM II (NV011514701)+10 ml Pen/Strep (Gibco, 15140-122)+1 ml K-Vitamin (K.vit 13A 01311)+14 ml G418 (Gibco, 10131-027)). After 10-14d of G418 selection cells reached >95% viability (Vi-Cell XR cell counter). Cells were split to 0.4×10e6 cells/ml to 2×250 ml Qmix2 in 2×E1000 flasks. After 3-4 days cells reached a density of approx. 4-5×10e6 cells/ml. Expression was initiated by adding 20% CHO CD Efficient Feed B (Gibco A10240)+6 mM GlutaMax (Gibco, 35050). After 4 days initiation another 10% CHO CD Efficient Feed B+6 mM GlutaMAX was added. On day 6 after initiation cultures were harvest and spun down (200 g, 5 min). Supernatants were collected and 15 mM HEPES (Gibco, 15630) and 5 mM CaCl2 (Sigma, 21115) were added. Supernatants were sterile-filtered using a 0.22 μm bottle top filter (Corning, CLS430049).

Expression and Purification of cFVIIa-Chimera (22017-051)

cFVIIa-chimera was generated using a similar expression system as outlined above. The zymogen cFVII-chimera was purified from the medium using an affinity column prepared by coupling an in-house anti-FVII(a) antibody (F1A2) to sepharose beads as described in example 26. The anti-FVII (a) antibody F1A2 binds to the Gla domain of FVII(a) in a Ca++ dependent manner. The zymogen cFVII-chimera was activated using human FIXa and re-purified using the F1A2 affinity purification to obtain the final cFVIIa-chimera.

Hot Spot Analysis

Hot-spot analysis using monovalent humanized antibody mAb0842(OA) was carried out by binding studies with a panel of 19 FVII(a) variants using surface plasmon resonance (Biacore T200) at 25° C. Anti-FVII(a) antibody (NN internal Ab 4F6 (Nielsen A L et al, PNAS 114 (47) 12454-12459, 2017)), targeting the FVII(a) gla domain, at 25 μg/ml was immobilized on a CM4 sensor chip using standard amine coupling chemistry kit (both supplied by GE Healthcare). FVII(a) variants, according to Table 19, in cell culture supernatants (as described above) were diluted in running buffer and injected at a flow rate of 10 al/min for 1 min to achieve a capture level of 5-55 RU. Each FVII(a) variant was captured by the immobilized anti-FVII(a) gla Ab. Subsequently, 540 nM (with 3× dilution) of mAb0842(OA) was injected at a flow rate of 30 μl/min for 7 min to allow for binding to captured FVII(a) variant followed by a 9 min buffer injection allowing dissociation of the one-armed anti-FVII(a) antibody. The running buffer was prepared by diluting 10-fold the 10×HBS-P buffer (supplied by GE Healthcare) and supplemented with 1 mg/ml BSA and 5 mM CaCl2 to give 10 mM HEPES, 150 mM NaCl, 0.05% v/v Polysorbate 20, pH 7.4, 5 mM CaCl2, 1 mg/ml bovine serum albumin (BSA). The running buffer was also used for dilution of anti-FVII(a) antibody and FVII(a) samples. Regeneration of the chip was achieved using 10 mM HEPES, 150 mM NaCl, 20 mM EDTA, 0.05 v/v Polysorbate 20, pH 7.4. Binding data were analysed according to a 1:1 Kinetic model and steady state analysis using BiaEvaluation 4.1 supplied by the manufacturer (Biacore AB, Uppsala, Sweden). Wherever possible, ka, kd and KD values from 1:1 kinetic fitting model are reported. For 4 FVII(a) variants, KD values using the steady state fitting model was reported. In addition, capture signal are reported for all FVII(a) variants. An amino acid residue is considered a hot-spot residue if substitution of that amino acid residue with alanine results in an affinity reduction of ten (10) fold or more relative to the wild type. Based on the data presented in Table 19 it is concluded that the amino acid residues H115, T130, V131, and R392 are hot-spots.

TABLE 19

FVII(a) variants binding interaction with the monovalent humanized antibody mAb0842(OA) as determined by surface plasmon resonance (SPR) analysis according to Example 16.

| FVII(a) variant | Capture (RU) | $K_D$ (nM) | Fold diff (Variant/WT) |
|---|---|---|---|
| WT | 19.2 | 0.31 | 1.0 |
| R113A | 17.7 | 0.29 | 1.0 |
| H115A | 19.3 | 8.16 | 26.8 |
| G117A | 9.5 | 0.31 | 1.0 |
| Y118A | 54.8 | 1.48 | 4.9 |
| L120A | 15.2 | 0.60 | 2.0 |
| T130A | 16.9 | 32.10 | 105.2 |
| V131A | 18 | 5.22 | 17.1 |
| N184A | 8.4 | 1.91 | 6.3 |
| T185A | 15.4 | 1.01 | 3.3 |
| I186A | 28.2 | 0.39 | 1.3 |
| P251A | 9 | 0.85 | 2.8 |
| V252A | 15.6 | 0.28 | 0.9 |
| E265A | 8.3 | 0.98 | 3.2 |
| M391A | 5.5 | 0.25 | 0.8 |
| R392A | 14.1 | 43.40 | 142.3 |
| E394A | 26.9 | 0.79 | 2.6 |
| E116A | 9.5 | 0.50 | 1.6 |
| S119A | 51.6 | 0.31 | 1.0 |

Example 18: Pharmacokinetics of Recombinant FVIIa in Co-Formulation with Humanized 11F2 Antibody in Cynomolgus Monkeys FVIIa plasma activity-time profiles were estimated in cynomolgus monkey studies following IV or SC administration of either recombinant FVIIa (rFVIIa) alone or in a 1:3 molar ratio co-formulation with monovalent one-arm 11F2 mAb0705(OA). The formulations were administered as a single dose of 5.4 nmol/kg FVIIa (including 16.2 nmol/kg mAb0705(OA) for the co-formulation) with blood samples drawn over a three weeks period.

During the experiment the animals were kept and handled according to standard procedures of local health authorities and were allowed free access to feed and water. FVIIa plasma activity was measured using the FVIIa activity assay as described in example 8. Endogenous cynomolgus FVIIa was below LLOQ (0.1 nM) prior to administration and consequently disregarded.

Pharmacokinetic analysis of FVIIa plasma activity-time profiles was carried out by non-compartmental methods using Phoenix WinNonlin 6.4. From the data the following parameters were estimated: clearance (CL), mean residence time (MRT) and SC bioavailability (F). Parameters are listed in Table 20 and shows a substantial protraction of FVIIa activity by co-formulation with mAb0705(OA), both after IV and SC administration, compared to FVIIa in the absence of antibody.

TABLE 20

Clearance (CL), mean residence time (MRT) and SC bioavailability (F) of FVIIa plasma activity in cynomolgus monkey studies following an IV or SC dose of 5.4 nmol/kg FVIIa alone or in 1:3 molar ratio co-formulation with mAb0705(OA). Values are mean (SD), n = 3.

| Formulation | CL (mL/h/kg) | MRT (h) | F (%) |
|---|---|---|---|
| FVIIa | 39 (5.2) | 2.0 (0.2) | 22 |
| FVIIa | 43.8 (2.2) | 2.15 (0.08) | Not determined |
| FVIIa:mAb0705(OA) | 2.7 (0.07) | 53.5 (15.3) | 61.4 |

Example 19: Humanization and Optimization of the Murine Anti-TLT-1 Antibody mAb0012

Humanization

The murine anti-human TLT-1 antibody mAb0082 disclosed in WO2012/117091 was used as the starting point for the humanization process. mAb0082 is derived from mAb0012, by incorporating two point mutations, C41A in VL and T61A in VH, to remove an unpaired cysteine in FR1 of VL and a N-glycosylation site in CDR2 of VH, respectively. The humanization process was based on standard molecular biology methods known to the person skilled in the art.

In brief, mAb0082 CDRH1, CDRH2 and CDRH3 sequences were grafted onto a human germline sequence based on the VH3_74/JH1 sequence as defined in the IMGT databases. Furthermore, three VH3_74/JH1 human amino acid substitutions were introduced into the grafted CDRH2 sequence in order to further humanize this CDR sequence: P62D, L64V and D66G. In order to obtain binding affinities comparable to that of mAb0082 three back mutations were introduced into the VL sequence at positions S49G, D62P and R98S. With respect to humanization of VL, mAb0082 CDRL1, CDRL2 and CDRL3 sequences were grafted onto a human germline sequence based on the VKII_A23/JK2 sequence as defined in the IMGT database. The VL sequence contains a potential deamidation hot-spot (NG motif) in CDR1. Using saturating mutagenesis at this position it was found that the NG motif could be eliminated by the N33Q substitution without compromising affinity for TLT-1.

The final humanized and optimized variant of mAb0082 is referred to as mAb1076 corresponding to SEQ ID NO:934 (VL) and 938 (VH).

SPR Analysis of Humanized TLT1 Variants

Binding of sTLT1 (corresponding to SEQ ID No: 3 with six histidine residues added at the C-terminus) to biAb from (Example 4) was probed by surface plasmon resonance (Biacore T200) at 25° C. Anti-human IgG was immobilised on a CM5 sensor chip (both supplied by GE Healthcare) using standard amine coupling chemistry. Purified biAbs according to Table 21 (1 nM) were injected at a flow rate of 10 µl/min for 1 min. Subsequently, sTLT1, between 0 and 60 µM, were injected at a flow rate of 30 al/min for 3 min to allow for binding to the biAb followed by a 3 min buffer injection allowing for dissociation from the biAb. The running buffer was prepared by diluting 10-fold the 10×HBS-P buffer (supplied by GE Healthcare) and supplemented with 1 mg/ml BSA and 5 mM CaCl2 to give 10 mM HEPES, 150 mM NaCl, 0.05% v/v Polysorbate 20, pH 7.4, 5 mM CaCl2, 1 mg/ml bovine serum albumin (BSA). The running buffer was also used for dilution of biAb and sTLT1 samples. Regeneration of the chip was achieved using recommended regeneration buffer consisted of 3M MgCl2 (supplied by GE Healthcare). Binding data were analysed according to a 1:1 model using BiaEvaluation 4.1 supplied by the manufacturer (Biacore AB, Uppsala, Sweden). Analysis resulted in the binding constants reported in Table 21 demonstrating a range of affinity, from 2.9 nM to 320 nM, for sTLT1 binding by the biAbs.

TABLE 21

Estimated binding constants for the interaction of sTLT1 with biAbs as determined by surface plasmon resonance (SPR) analysis according to Example X.

| biAb | Parental anti-FVII(a) | Parental Anti-TLT-1 | $K_D$ (M) |
| --- | --- | --- | --- |
| biAb0001 | mAb0865 | mAb1076 | 2.9E−9 |
| biAb0015 | mAb0865 | mAb1038 | 1.9E−8 |
| biAb0090 | mAb0865 | mAb1049 | 3.2E−7 |
| biAb0095 | mAb0865 | mAb1047 | 7.5E−8 |

Example 20: Crystal Structure of Hz-TLT1 and TLT-1 Peptide Complex Preparation The Fab fragment used for crystallization in complex with the TLT-1 stalk peptide comprised the VL and VH domain sequences corresponding to mAb1076 (SEQ ID NO: 854 and 858, respectively), a human IgG4 CH1 domain, and a human kappa CL with a single point mutation (G157C). The G to C substitution is in the constant domain of the Fab fragment, i.e. far from the antigen binding site, and has no influence on the binding to TLT-1. The 37-mer stalk peptide, EEEEETHKIGSLAENAFSDPAGSANPLEPSQDEKSIP (SEQ ID NO: 13), corresponding to residues 111-147 of SEQ ID No: 2, was prepared by standard peptide synthesis methods known to the person skilled in the art. The Fab and the stalk peptide were mixed at a 1:2 molar ratio in hepes buffer (20 mM Hepes (pH 7.3), 150 mM of NaCl). The 1:1 Fab:peptide complex was isolated using gelfiltration on a superdex 200 column eluted with hepes buffer and was subsequently concentrated to ~11 mg/mL and used for crystallization.

Crystallisation

Crystals of the gel filtrated 1:1 molar Fab/peptide complex were grown using the sitting drop vapour diffusion technique at 18° C. A protein solution of 150 nl 10.8 mg/ml Fab:peptide complex in 20 mM Hepes, pH 7.3 and 150 mM NaCl was mixed with 50 nl of 1M LiCl, 0.1 M NaCitrate-citrid acid, pH 4 and 20% (w/v) PEG 6000 as precipitant and incubated over 60 µl precipitant.

Diffraction Data Collection

The crystal was cryo protected by addition of 1 µl of precipitant added 20% of ethylene glycol to the crystallisation drop prior to flash cooling in liquid nitrogen. Diffraction data were collected at 100K at the BioMAX beamline at the MAX IV synchrotron (Lund, Sweden), using an Eiger 16M Hybrid-pixel detector from Dectris. Autoindexing, integration and scaling of the data were performed with programmes from the XDS package (diffraction data statistics are summarised in Table 22).

Structure Determination and Refinement

The asymmetric unit contains two Fab:peptide complexes as judged from Matthews coefficient analysis. The structure was determined by molecular replacement. Phaser as implemented in the programme suite Phenix was used with the chains H and L of protein data bank entry 5KMV as search model localising two Fabs. These were model built with the correct amino acid sequence using COOT and thereafter refined using Phenix refinement. Amino acids 7 to 21 from the peptide were clearly seen in the difference electron density maps and could be model built manually using COOT. The model was further refined using steps of Phenix refinement and manual rebuilding in COOT. The refinement statistics are found in Table 22.

TABLE 22

| Data collection and refinement statistics. | |
| --- | --- |
| Wavelength (Å) | 0.9799 |
| Resolution range (Å) | 29.42-1.49 (1.543-1.49) |
| Space group | P 1 |
| Unit cell (Å, deg) | 53.23 65.38 67.15 |
| | 91.88 91.72 92.89 |
| Total reflections | 260187 (25653) |
| Unique reflections | 140071 (9127) |
| Multiplicity | 1.9 (1.9) |
| Completeness (%) | 91.03 (62.11) |
| Mean I/sigma(I) | 9.03 (1.37) |
| Wilson B-factor | 18.72 |
| R-merge | 0.05225 (0.593) |
| R-meas | 0.07387 (0.8385) |
| R-pim | 0.05222 (0.5928) |
| CC1/2 | 0.994 (0.0683) |
| CC* | 0.999 (0.358) |
| Reflections used in refinement | 134361 (9125) |
| Reflections used for R-free | 1784 (123) |
| R-work | 0.1582 (0.2655) |
| R-free | 0.1779 (0.2932) |
| CC(work) | 0.966 (0.671) |
| CC(free) | 0.962 (0.632) |
| Number of non-hydrogen atoms | 8094 |
| macromolecules | 7042 |
| Solvent | 1052 |
| Protein residues | 897 |
| RMS(bonds) | 0.009 |
| RMS(angles) | 1.36 |
| Ramachandran favored (%) | 97.06 |
| Ramachandran allowed (%) | 2.83 |
| Ramachandran outliers (%) | 0.11 |
| Rotamer outliers (%) | 1.35 |
| Clashscore | 4.17 |
| Average B-factor (Å$^2$) | 25.71 |
| macromolecules | 24.26 |
| Solvent | 35.47 |
| Number of TLS groups | 1 |

Statistics for the highest-resolution shell are shown in parentheses.

The Epitope and Paratope of the Fab/Peptide Complex

The epitope is defined as residues in the TLT-1 stalk-peptide characterized by having a heavy atom (i.e. a non-hydrogen atom) within a distance of 4.0 Å from a heavy atom in the Fab in both of the complexes in the asymmetric unit. Similarly, the paratope is defined as residues in the Fab fragment characterized by having a heavy atom within a distance of 4.0 Å from a heavy atom in the TLT-1 stalk-peptide in both of the complexes in the asymmetric unit the epitope was found to comprise the following residues from the 37aa TLT-1 peptide according to SEQ ID NO: 13:

K8
I9
G10
S11
L12
A13
N15
A16
F17
S18
D19
P20
A21 corresponding to K118, I119, G120, S121, L122, A123, N125, A126, F127, S128, D129, P130 and A131 of SEQ ID No:2 and 3).

The paratope comprises the following residues from the heavy chain variable domain (SEQ ID NO: 938):

V2
F27
R31
Y32
W33
E50
T57
N59
S98
G99
V100
T102
S103 and from the light chain variable domain (SEQ ID NO: 934):

H31
Y37
H39
Y54
F60
S61
S96
T97
V99
Y101

Example 21: Effect of Affinity on Anti-FVII(a)/Anti-TLT-1 Bispecific Antibody Stimulatory Activity To determine the effect of affinity on bispecific antibody activity, a number of anti-FVII(a) and anti-TLT-1 mAbs from the humanization of 11F2 mAb0005 (see Example 14) and mAb0012 (see Example 19) and with varying affinities for FVIIa and TLT-1, respectively, were tested in a bispecific format in a FXa generation assay using lipidated TLT-1 as described in WO2011/023785.

In a first step, FX activation was measured in the presence of 4 nM recombinant TLT-1 incorporated into 10:90 phosphatidyl serine:phosphatidyl choline vesicles (WO2011023785), 2.5 nM FVIIa, and bispecific antibody (biAb) in a concentration series from 0 to 300 nM. Following 10-min preincubation in assay buffer (50 mM HEPES, 100 mM NaCl, 10 mM CaCl2, pH 7.3+1 mg/ml BSA and 0.1% PEG8000) at room temperature, 150 nM plasma-derived FX (Haematologic Technologies) were added to give a total volume of 50 μl and activation allowed to proceed for 20 min. Activation was then terminated by addition of 25 μl quench buffer (50 mM HEPES, 100 mM NaCl, 80 mM EDTA, pH 7.3) and generated FXa quantified from its ability hydrolyze 0.5 mM S-2765 (Chromogenix) chromogenic substrate (added as 2 mM stock in 25 μl volume), which was followed at 405 nm for 5 min in a SPECTRAmax Plus384 plate reader. From the slope of the linear absorbance increases, the normalized activity ($A_{biAb}$) was calculated for each biAb at a concentration of 100 nM by subtraction of the background activity in the absence of biAb and division by the FVIIa concentration in the assay.

In a second step, the same assay was run with biAb replaced by assay buffer and a concentration series of FVIIa from 0 to 80 nM. The slope of the linear relationship between background-subtracted FXa generation and the concentration of FVIIa in the assay provided a measure of the specific activity of free FVIIa ($A_{FVIIa}$) under the assay conditions employed.

Based on the measured activities, the stimulatory activity of each biAb at 100 nM was calculated as the ratio $A_{biAb}/A_{FVIIa}$. The stimulatory activity provides a measure of the fold increase in generated FXa by FVIIa upon addition of 100 nM biAb.

Stimulatory activities are provided in Table 23 and shows a dependence of the biAb stimulation on the strengths (expressed as dissociation constant ($K_D$) values) by which FVIIa and TLT-1 are bound, respectively. Among the biAbs tested, biAb0001 exhibit the highest stimulatory activity.

TABLE 23

Stimulatory activities of bispecific antibodies in the presence FX, FVIIa, and lipidated TLT-1 as described in Example 21. For each bispecific antibody, the measured stimulatory activity is listed (mean ± SD, n = 2) together with dissociation constants for the interaction with FVIIa and TLT-1, respectively.

| Bispecific antibody | Anti-FVIIa arm | Anti-TLT-1 arm | $K_D$ (FVIIa) [nM] | $K_D$ (TLT-1) [nM] | Stimulation (fold) |
|---|---|---|---|---|---|
| biAb0001 | mAb0865 | mAb1076 | 0.06 | 2.9 | 29.2 ± 1.7 |
| biAb0015 | mAb0865 | mAb1038 | 0.06 | 19 | 18.7 ± 1.5 |
| biAb0095 | mAb0865 | mAb1047 | 0.06 | 75 | 13.9 ± 1.1 |
| biAb0090 | mAb0865 | mAb1049 | 0.06 | 320 | 11.1 ± 1 |
| biAb0011 | mAb0875 | mAb1076 | 0.28 | 2.9 | 20.3 ± 1.3 |
| biAb0016 | mAb0875 | mAb1038 | 0.28 | 19 | 17.3 ± 1.6 |
| biAb0096 | mAb0875 | mAb1047 | 0.28 | 75 | 12.4 ± 1.1 |
| biAb0091 | mAb0875 | mAb1049 | 0.28 | 320 | 11.3 ± 1.3 |
| biAb0012 | mAb0872 | mAb1076 | 2.2 | 2.9 | 22.1 ± 0.4 |
| biAb0017 | mAb0872 | mAb1038 | 2.2 | 19 | 13.6 ± 0.1 |
| biAb0097 | mAb0872 | mAb1047 | 2.2 | 75 | 17.4 ± 0.1 |
| biAb0092 | mAb0872 | mAb1049 | 2.2 | 320 | 11.2 ± 0.2 |
| biAb0013 | mAb0874 | mAb1076 | 16.2 | 2.9 | 16 ± 0.1 |
| biAb0018 | mAb0874 | mAb1038 | 16.2 | 19 | 12.8 ± 0.2 |
| biAb0098 | mAb0874 | mAb1047 | 16.2 | 75 | 15.3 ± 0.1 |
| biAb0093 | mAb0874 | mAb1049 | 16.2 | 320 | 9.6 ± 0.2 |
| biAb0014 | mAb0873 | mAb1076 | 600 | 2.9 | 8 ± 0.2 |
| biAb0019 | mAb0873 | mAb1038 | 600 | 19 | 9.4 ± 0.5 |
| biAb0099 | mAb0873 | mAb1047 | 600 | 75 | 5.8 ± 0.5 |
| biAb0094 | mAb0873 | mAb1049 | 600 | 320 | 5.4 ± 0.5 |

Example 22: Effect of Epitope Location on Anti-FVII(a)/Anti-TLT-1 Bispecific Antibody Stimulatory Activity To determine the effect of epitope location on bispecific antibody activity, a number of anti-TLT-1 and anti-FVIIa mAbs binding to different epitopes on TLT-1 and FVIIa, respectively, were tested in a bispecific format in a FXa generation assay as done in Example 21.

Results are provided in Table 24 and shows a dependence of the biAb stimulatory activity on epitope location. In particular, anti-TLT-1 mAbs mAb1076, mAb0023, mAb0051, and mAb0062 in combination with anti-FVIIa mAb mAb0865 exhibit comparable stimulatory activity.

TABLE 24

Stimulatory activities of bispecific antibodies in the presence FX, FVIIa, and lipidated TLT-1 as described in Example 22. For each bispecific antibody, the measured stimulatory activity activity is listed (mean ± SD, n = 2) together dissociation constants for the interaction with FVIIa and TLT-1, respectively.

| biAb | Anti-FVIIa arm | Anti-TLT-1 arm | Stimulation (fold) |
|---|---|---|---|
| biAb0001 | mAb0865 | mAb1076 | 29.2 ± 1.7 |
| biAb0241 | mAb0865 | mAb0023 | 35.3 ± 2.4 |
| biAb0242 | mAb0865 | mAb0051 | 21.8 ± 0.9 |
| biAb0243 | mAb0865 | mAb0062 | 25.5 ± 2.0 |
| biAb0244 | mAb0864 | mAb1076 | 2.7 ± 0.2 |

Example 23: Antigen Assay for Human IgG (LOCI)

The presence of human IgG (hIgG) in cynomolgus plasma was measured by Luminescent Oxygen Channeling Immunoassay (LOCI). In brief, the LOCI reagents included two latex bead reagents (donor and acceptor beads) and a biotinylated monoclonal antibody against hIgG (Biosite, cat. no. AFC4249). The donor bead reagent, containing a photosensitive dye, was coated with streptavidin. The second bead reagent, the acceptor beads, was conjugated with an in-house monoclonal antibody (0421) against hIgG, which made up the sandwich. During the assay, the three reactants were combined with hIgG in the plasma to form a bead-aggregate immuno complex. Excitations of the complex released singlet oxygen molecules from the donor beads, which were channeled into the acceptor beads and triggered a chemiluminescence response. This was then measured in the EnVision plate reader. The amount of light generated, reported as counts per second (cps), was proportional to the concentration of hIgG. Samples were diluted at least 100× in assay buffer and a calibration curve was prepared based on hIgG added to 1% cynomolgus plasma.

Example 24: Antigen Assay for FVII(a) (LOCI)

FVII(a) antigen including FVII zymogen, FVIIa, and FVIIa:antithrombin (FVIIa:AT) complexes was measured by a LOCI assay as described in example 23, except that the assay for FVII(a) consisted of acceptor beads coated with an in-house anti-FVII(a) antibody (4F9) and an in-house biotinylated anti-FVII(a) monoclonal antibody (4F7). Samples were diluted at least 100× in assay buffer and a calibration curve was prepared by adding known amounts of human rFVIIa to assay buffer.

Example 25: Antigen Assay for FVIIa:AT (Antithrombin) (EIA)

FVIIa:AT (antithrombin) complexes were measured by use of an enzyme immuno assay (EIA) as described in Agersø H et al, J Thromb Haemost 2011; 9: 333-8. A monoclonal anti-FVIIa antibody (Dako Denmark A/S, Glostrup, Denmark, product code 09572) that binds to the N-terminal EGF-domain and does not block antithrombin binding was used for capture of the FVIIa:AT complex. A preformed complex of human FVIIa and cynomolgus antithrombin (FVIIa:AT) was prepared by incubation of FVIIa with 2-fold molar excess of antithrombin in the presence of 10 µM low-molecular weight heparin (Enoxaparin). The residual amidolytic activity of FVIIa (see Example 11) after overnight incubation at room temperature was verified to be below 10% of the initial FVIIa activity. The complex was used to construct EIA calibration curves. A polyclonal anti-human antithrombin antibody peroxidase conjugate was used for detection (Siemens Healthcare Diagnostics ApS, Ballerup, Denmark, product code OWMG15). TMB was added, colour development allowed to proceed until sufficient colour was developed, stopped by adding H2SO4 and the absorbance at 450 nm with 650 nm as reference measured on an absorbance plate reader (BioTek). The colour intensity is proportional to the concentration of FVIIa:AT.

Example 26: Preparation of Human FVIIa, FVII (Zymogen), and FVIIa:AT (Antithrombin) Complex Preparation of Human FVIIa (Activated FVII)

Unless otherwise noted, recombinant human activated FVII (FVIIa) was prepared as described in Thim et al. (1988) Biochemistry 27:7785-7793 and Persson et al. (1996) FEBS Lett 385:241-243.

Preparation of Human FVII (Zymogen FVII)

Recombinant human FVII produced in CHO cells were purified by single-step calcium-dependent affinity chromatography as described by Thim et al. (1988) Biochemistry 27:7785-7793. Following purification, zymogen FVII was dialyzed into 10 mM MES, 100 mM NaCl, 10 mM CaCl2, pH 6.0 buffer. The level of activated FVII (FVIIa) in the preparation was determined by measuring the amidolytic activity in the presence of 1 mM chromogenic substrate S-2288 and 200 nM sTF (see Example 11). By relating this to a standard curve prepared with known concentration of FVIIa, the measured activity could be converted to a molar concentration of FVIIa in the zymogen FVII preparation.

Preparation of Human FVIIa:AT (Antithrombin) Complex

FVIIa:AT (antithrombin) complex was prepared by incubating equimolar concentrations of human recombinant FVIIa, human plasma-derived AT (Baxter), and low-molecular weight heparin (Enoxaparin sodium) for 16 hours at 4° C. To remove contaminating excipients, AT was re-purified before use on heparin sepharose 6 fast flow (GE healthcare) column by applying a sodium chloride gradient. Eluted AT was up-concentrated by ultrafiltration to give a final preparation in 10 mM HEPES, 25 mM NaCl, pH 7.3 containing 50% glycerol. The FVIIa:AT complex was purified by SEC chromatography at 4° C. in 20 mM MES, 100 mM NaCl, 1 mM EDTA, pH 5.5 to maximize complex stability. Residual levels of FVIIa in the preparation were determined as described above. To minimize complex breakdown, preparations were stored in aliquots at −80° C. and immediately thawed and kept on ice before use.

Example 27: Single Dose Pharmacokinetics of Anti-FVII(a)/Anti-TLT-1 biAb in Cynomolgus Monkeys biAb0001 and the corresponding YTE-variant, biAb0352, where additional three half-life extending substitutions (M252Y, S254T and T256E) were introduced in to the constant heavy chain domain, were dosed intravenously (iv) at 3.0, 9.49 or 30 nmol/kg or subcutaneously (sc) at 9.49 nmol/kg to cynomolgus monkeys. Each group consisted of two monkeys (one male and one female). Sodium citrate-stabilised blood samples of 1 mL were taken prior to dosing and for the iv groups at 0.5 h; 2.5 h; 6 h; 12 h; 24 h; 48 h; 72 h and at day 8; 10 and 15 after dosing. For the sc groups blood samples were taken pre-dose and at 0.5 h; 3 h; 6 h; 12 h; 16 h; 24 h; 30 h, 38 h; 48 h; 54 h; 72 h; 78 h; 96 h; 120 h; and at day 8, 10 and 15 after dosing. Blood samples were centrifuged 10 min at 2000 g, the plasma removed, divided into aliquots and stored at −80° C. until analysis for hIgG (see example 23), total FVII(a) antigen (see example 24), FVIIa activity (see example 8) and FVIIa:AT complexes (example 25). Pharmacokinetic (PK) analysis of concentration versus time profiles of hIgG was carried out by non-compartmental methods using Phoenix WinNonlin 6.4. The following PK parameters are shown in Table 24: half-life (t½/), clearance (Cl), volume of distribution (Vz), mean residence time (MRT) and SC bioavailability (F).

TABLE 24

PK parameters of biAb with and without YTE mutation analysed based on plasma samples from cynomolgus monkeys.*

| Compound | Dose (nmol/kg) | Route | $t_{1/2}$ (h) | Cl or Cl/F** (mL/h × kg) | $V_z$ (mL/kg) | MRT (h) | AUC (h × nM) |
|---|---|---|---|---|---|---|---|
| biAb0001 | 3.0 | iv | 80 | 0.64 | 73.6 | 106 | 4084 |
|  |  |  | 100 | 0.47 | 67.7 | 132 | 5325 |
|  | 9.49 | iv | 127 | 0.43 | 78.3 | 177 | 16269 |
|  |  |  | 121 | 0.33 | 58.1 | 161 | 21647 |
|  | 30 | iv | 207 | 0.48 | 143.4 | 305 | 33046 |
|  |  |  | 207 | 0.36 | 106.9 | 277 | 49476 |
|  | 9.49 | sc | 127 | 0.70 | — | 193 | 9672 |
|  |  |  | 138 | 0.43 | — | 205 | 15059 |
| biAb0352 | 3.0 | iv | 98 | 0.27 | 37.9 | 133 | 8445 |
|  |  |  | 212 | 0.21 | 65.7 | 285 | 8040 |
|  | 9.49 | iv | 218 | 0.20 | 63.5 | 296 | 26397 |
|  |  |  | 201 | 0.26 | 75.0 | 267 | 21870 |
|  | 30 | iv | 206 | 0.26 | 78.2 | 282 | 65712 |
|  |  |  | 226 | 0.27 | 87.4 | 304 | 62075 |
|  | 9.49 | sc | 249 | 0.31 | — | 376 | 13966 |
|  |  |  | 218 | 0.33 | — | 342 | 13932 |

*each line represents data from one cynomolgus monkey,
**Cl is noted for the iv dosed groups, and Cl/F for the sc groups. F corresponds to sc bioavailability.

Accumulation of endogenous FVII(a) was observed in the monkeys dosed with BiAb0001 or the corresponding YTE-variant, biAb0352. Table 25 shows pre-dose levels of FVII (a) antigen, FVIIa activity and FVII:AT together with mean accumulated levels measured between 72 and 240 h after administration. An antibody dose-dependent accumulation of FVII(a) antigen, FVIIa activity and FVIIa:AT was observed. FVII(a) antigen was increased up to 3-fold relative to the pre-dose level, and FVIIa and FVIIa:AT up to 5-fold. The data demonstrate that iv or sc administration of a single dose of biAb0001 or biAb0352 with YTE mutation lead to accumulation of endogenous FVII(a) antigen, FVIIa activity and FVIIa:AT complexes in vivo.

TABLE 25

Accumulation of FVII(a) antigen, FVIIa and FVIIa:AT after single iv or sc administration of biAb with or without YTE mutations to cynomolgus monkeys.

| | | | Level achieved between 72 and 240 h after dosing* | | |
|---|---|---|---|---|---|
| Compound | Route of administration | Dose (nmol/kg) | FVII(a) antigen (nM) | FVIIa activity (nM) | FVIIa:AT (nM) |
| biAb0001 | iv | 3 | 11.2 ± 2.7 | 0.21 ± 0.05 | 1.98 ± 0.44 |
| biAb0001 | iv | 9.49 | 15.9 ± 2.4 | 0.59 ± 0.20 | 4.67 ± 1.15 |
| biAb0001 | iv | 30 | 19.7 ± 4.8 | 0.91 ± 0.56 | 8.50 ± 0.62 |
| biAb0001 | sc | 9.49 | 14.6 ± 3.4 | 0.43 ± 0.13 | 3.36 ± 0.68 |
| biAb0352 | iv | 3 | 8.9 ± 2.6 | 0.37 ± 0.16 | 3.21 ± 1.42 |
| biAb0352 | iv | 9.49 | 17.6 ± 4.5 | 0.66 ± 0.12 | 4.62 ± 0.64 |
| biAb0352 | iv | 30 | 17.6 ± 4.5 | 2.04 ± 1.19 | 8.05 ± 1.15 |
| biAb0352 | sc | 9.49 | 20.4 ± 3.0 | 0.81 ± 0.15 | 3.88 ± 0.27 |
| Pre-dose | | | 6.2 ± 1.4 | 0.16 ± 0.04 | 1.63 ± 0.37 |

*data are mean and SD of measurements from n = 2 animals per group and 3 time points from the iv groups and 6 time points from the sc groups. The pre-dose values are based on one time-point (pre-dose) for all 16 animals.

Example 28: Single and Multiple Dose Pharmacokinetics of Monovalent 11F2 Anti-FVII(a) Antibody mAb0705(OA) in Cynomolgus Monkeys In vivo accumulation of FVII, FVIIa and FVIIa:AT was analysed by administration of the monovalent 11F2 anti-FVII(a) antibody mAb0705(OA) to cynomolgus monkeys, followed by measurement of FVII antigen, FVIIa activity and FVIIa:AT in plasma samples. Two male cynomolgus monkeys of approx. 2.5 kg were dosed iv in the saphenous, cephalic or lateral caudal veins of the tail with 40 nmol/kg mAb0705(OA), and 3 male cynomolgus monkeys were dosed every other day for two weeks subcutaneously (sc) in the thigh (alternating between left and right thigh) with 20 nmol/kg of the one-armed anti-FVIIa antibody (i.e. the antibody was dosed on day 1, 3, 5, 7, 9, 11, 13, and 15). Blood was sampled in 3.8% trisodium citrate from the cephalic vein or the femoral vein at time points up to 21 days after dosing.

The blood was centrifuged 10 min at 2300 g and plasma aliquoted and stored at −80° C. until analysis for hIgG (see example 23), total FVII(a) antigen (see example 24), FVIIa activity (see example 8) and FVIIa:AT complexes (see example 25). PK analysis of concentration versus time profiles was carried out by non-compartmental methods using Phoenix WinNonlin 6.4. The PK parameters for iv administration are shown in Table 26. The half-life (t½) of the one-armed antibody was on the average 116 h (4.8 days) after single iv administration. The estimated half-life for the sc administered antibody was 181±20 h (mean and SD of n=3). The antibody accumulated during the two weeks of dosing resulting in a maximal level of 1179±140 nM at time points between 336 and 366 h after initial dosing (mean and SD of data from n=3 animals and 3 time points).

TABLE 26

PK parameters of mAb0705(OA) administered iv in cynomolgus monkeys at 40 nmol/kg.

| Animal | $t_{1/2}$ (h) | Cl (mL/h × kg) | $V_z$ (mL/kg) | MRT (h) | AUC (h × nM) |
|---|---|---|---|---|---|
| #1 | 113 | 0.487 | 79.5 | 167 | 82207 |
| #2 | 119 | 0.417 | 71.4 | 175 | 95894 |

Single iv or repeated sc dosing of mAb0705(OA) resulted in accumulation of endogenous FVII(a). Total FVII(a) antigen, FVIIa:AT and FVIIa after single iv dose of 40 nmol/kg are shown in Table 27. The total FVII antigen increased from 7.0 nM pre-dose to 35.0±4.7 nM at day 7-14. Likewise, FVIIa increased from below detection limit (0.009 nM) to 2.3±0.7 nM and FVIIa:AT increased from 1.0 to 6.3±0.8 nM at day 7-14. The zymogen FVII level after administration of 40 nmol/kh one-armed antibody was 26.4 nM as calculated by subtracting FVIIa and FVIIa:AT from total FVII(a) antigen.

TABLE 27

Levels of FVII(a) after a single iv dose of 40 nmol/kg mAb0705(OA) measured at day 7-14 after dosing.

| FVII(a) | Pre-dose level (nM) | Steady state concentration (nM) |
|---|---|---|
| Total FVII(a) antigen | 7.0 | 35.0 ± 4.7 |
| FVIIa:AT | 1.0 | 6.3 ± 0.8 |
| FVIIa | <0.009 | 2.3 ± 0.7 |

The steady state level of total FVII(a), FVIIa and FVIIa:AT after multiple sc dosing are shown in table 28. The total FVII(a) antigen increased from 6.5±1.5 nM pre-dose to 36.9±9.8 nM at day 12-21. Likewise, FVIIa increased from below detection limit (0.009 nM) to 3.9±1.6 nM at day 12-21 and FVIIa:AT increased from 1.0±0.3 to 9.1±0.6 nM at day 12-21. The steady state zymogen FVII level calculated by subtracting FVIIa and FVIIa:AT from total FVII(a) antigen was 24 nM.

The data demonstrates that administration of the one-armed anti-FVII(a) antibody mAb0705(OA) resulted in accumulation of endogenous FVII(a), FVIIa and FVIIa:AT in vivo. The clearance of the one-armed anti-FVII(a) antibody (0.42-0.49 mL/kg×kg, Table 26) was comparable with the clearance of the biAb0001 after i.v. administration (0.33-0.64 mL/kg×kg, Example 27, Table 24). Therefore, the steady-state levels of FVII(a) antigen, FVIIa and FVIIa:AT measured after repeated administration of the one-armed anti-FVII(a) antibody is expected to be representative of the levels that would be achieved at steady state after repeated administration of the biAb with the same FVII(a) binding arm.

TABLE 28

Steady state levels of FVII(a) after repeated sc dosing of 20 nmol/kg mAb0705(OA) measured at day 12-21 after initial dosing.

| FVII(a) | Pre-dose level (nM) | Steady state concentration (nM) |
|---|---|---|
| Total FVII(a) antigen | 6.5 ± 1.5 | 36.9 ± 9.8 |
| FVIIa:AT | 1.0 ± 0.3 | 9.1 ± 0.6 |
| FVIIa | <0.009 | 3.9 ± 1.6 |

Example 29: Thromboelastography at Haemophilia A-Like Conditions in Human Whole Blood Added Anti-FVII(a)/Anti-TLT-1 biAb0001 and Steady State Levels of Zymogen FVII, FVIIa and FVIIa:AT The effect of the bispecific anti-FVII(a)/anti-TLT-1 antibody biAb0001 (where the parental anti-FVII(a) is mAb0865 and the parental anti-TLT-1 antibody is mAb1076) and accumulated levels of zymogen FVII, FVIIa and FVIIa:AT from Example 28 were evaluated by thromboelastography in human whole blood at haemophilia A-like conditions and compared with the effect of rFVIIa added to the blood. The thromboelastography analysis was carried out using TEG® instruments (Thrombelastograph Coagulation Analyzer, Haemoscope Corp.) in principle as described in Viuff D, et al. Thromb Res 2010; 126: 144-9. Citrate-stabilised whole blood from healthy donors was incubated 30 min with 0.1 mg/mL neutralising anti-FVIII sheep polyclonal antibody (Haematological Technologies Inc, cat no PAHFVIII-S-C) and 5 µg/mL neutralising anti-TF mouse monoclonal antibody (1F44, prepared in house). biAb0001 at a final plasma concentration of 100 nM in HBS/BSA buffer (20 mM Hepes, 140 mM NaCl, pH 7.4, 2% BSA) was mixed with rFVIIa (Novo Seven®, Novo Nordisk, final plasma concentration 3.9 nM), zymogen FVII (as prepared in Example 26), final plasma concentration 24 nM) and FVIIa:AT complexes (as prepared in Example 26), final plasma concentration 9 nM) and added to a sample of the blood. Predilutions of FVIIa:AT were made in cold 20 mM MES, 100 mM NaCl, 1 mM EDTA, pH 5.5+2% BSA, and added to the remaining proteins immediately prior to initiating the assay. The FVII zymogen and FVIIa:AT preparations contained trace amounts of FVIIa, hence corresponding lower amount of FVIIa was added to compensate for this and an expected plasma concentration of FVIIa in the donor blood (0.1 nM, Morissey J H et al Blood, 1993; 81: 734-44). Likewise was the amount of added zymogen FVII compensated for an expected plasma concentration of 10 nM zymogen FVIIa in the donor blood. A separate sample contained 25 nM rFVIIa corresponding to the theoretical maximal plasma concentration after administration of 90 µg/kg rFVIIa (NovoSeven®) to human subjects with haemophilia A (Lindley C M et al. Clin Pharmacol Ther 1994; 55: 638-48). Controls included biAb alone and FVII/FVIIa/FVIIa:AT mixture without biAb. Platelets were maximally activated by adding PAR1 agonist peptide SFLLRN (Tocris Biosciences cat no 3497) to a final concentration of 30 µM and GPVI agonist convulxin (5-Diagnostics, cat no 5D-1192-50UG) to a final concentration of 10 ng/mL. A volume of 20 µL 0.2 M CaCl2 in 20 mM Hepes, pH 7.4, was added to the TEG cup followed by 340 µL of blood samples and the analysis immediately initiated. Clot time (R-time) defined as time to 2 mm amplitude of the TEG-trace was calculated by the software (TEG® Analytical Software, version 4.1.73). Data from 4 donors are shown in Table 29. The clot time was delayed from 290±12 s in normal blood to 3506±1561 s after inducing haemophilia A-like conditions by neutralising FVIII. Adding 25 nM rFVIIa resulted in shortening of the clot time of the mimicked haemophilia A blood to 694±158 s. Adding 100 nM biAb to the blood resulted in a modest reduction of clot time to 2198±712 s, most likely due to a potentiation of the effect of the endogenous FVIIa in the blood. Adding steady state levels of FVII/FVIIa/FVIIa:AT reduced the clot time to 1440±275 s. Combining 100 nM biAb and steady state levels of FVII/FVIIa/FVIIa:AT reduced the clot time to 495±39 s, i.e. to a level comparable to or slightly lower than the clot time after adding 25 nM FVIIa. The data demonstrates that the biAb potentiate the effect of the accumulated level of FVII/FVIIa/FVIIa:AT resulting in a clot time reduction similar to or slightly better than the clot time reduction achieved with a therapeutic effective concentration of rFVIIa.

TABLE 29

Thromboelastography analysis of the effect of biAb0001 (100 nM) in human whole blood with or without steady state levels of FVII/FVIIa/FVIIa:AT.

| | Clot time (R-time, s) | | | | | |
|---|---|---|---|---|---|---|
| Date of experiment | Normal | Haemophilia A (HA) | HA + FVIIa at 25 nM | HA + BiAb | HA + FVII/FVIIa/FVIIa:AT | HA + biab + FVII/FVIIa/FVIIa:AT |
| 2018 Mar. 14 | 295 | 3160 | 615 | 2460 | 1690 | 445 |
| 2018 Mar. 15 | 280 | 1660 | 540 | 1145 | 1065 | 495 |
| 2018 Mar. 22 | 280 | 3770 | 715 | 2720 | 1415 | 500 |
| 2018 Mar. 21 | 305 | 5433 | 905 | 2465 | 1590 | 540 |
| mean | 290 | 3506 | 694 | 2198 | 1440 | 495 |
| SD | 12 | 1561 | 158 | 712 | 275 | 39 |

Example 30: Thromboelastography at Haemophilia A-Like Conditions in Human Whole Blood Added Bispecific Anti-FVII(a)/Anti-TLT-1 Antibodies with Different TLT-1 Affinities and Steady State Levels of Zymogen FVII, FVIIa and FVIIa:AT In the present example the following bispecific anti-FVII (a)/anti-TLT-1 antibodies with different affinities for TLT-1 were tested:

| biAb | Anti-FVII(a) | Anti-TLT-1 | $K_D$ (TLT-1) [nM] |
|---|---|---|---|
| biAb0001 | mAb0865 | mAb1076 | 2.9 |
| biAb0015 | mAb0865 | mAb1038 | 19 |
| biAb0090 | mAb0865 | mAb1049 | 320 |
| biAb0095 | mAb0865 | mAb1047 | 75 |

Bispecific antibodies at a concentration of 100 nM were evaluated by thromboelastography as described in Example 29. Clot times (R-time) are listed in Table 30. The clot time was delayed from 340 s to 5433 s upon induction of haemophilia A (HA) by adding anti-FVIII antibodies. The presence of the biAb with for the highest affinity for TLT-1(biAb0001) reduced the clot time to 2465 s i.e. more than the clot time reduction observed for the three other biAbs alone: biAb0015 reduced the clot time to 3645 s; –biAb0090 to 4335 s and biAb0095 to 4110 s. Likewise, combination of biAb with steady state levels of FVII, FVIIa, and FVII:AT resulted in a more pronounced reduction of the clot time for biAb0001 (to 540 s) than for the three other biAbs; i.e. to 1100 s for biAb0015, to 1040 s for biAb0090 and to 815 s for biAb0095 The data demonstrate that biAb0001 with the highest affinity (i.e. lowest $K_D$) for TLT-1 was the most effective in clot time reduction.

TABLE 30

Thromboelastography analysis of the effect of biAb0001, biAb0015 or biAb0090 (each 100 nM) in human whole blood with or without steady state levels of FVII/FVIIa/FVIIa:AT.

| Sample | Clot time (R-time, s) |
|---|---|
| Normal | 340 |
| Haemophilia A (HA) | 5433 |
| Haemophilia A (HA) + 25 nM FVIIa | 905 |
| HA + FVII/FVIIa/FVIIa:AT | 1590 |
| HA + biAb0001 | 2465 |
| HA + FVII/FVIIa/FVIIa:AT + biAb0001 | 540 |
| HA + biAb0015 | 3645 |
| HA + FVII/FVIIa/FVIIa:AT + biAb0015 | 1100 |
| HA + biAb0090 | 4335 |
| HA + FVII/FVIIa/FVIIa:AT + biAb0090 | 1040 |
| HA + biAb0095 | 4110 |
| HA + FVII/FVIIa/FVIIa:AT + biAb0095 | 815 |

Example 31: In Vivo Effect of Anti-FVII(a)/Anti-TLT-1 Bispecific Antibody biAb0001 in Tail Vein Transection Model in FVIII-Deficient Transgenic Human TLT-1 Mice In vivo efficacy of the anti-FVII(a)/anti-TLT-1 bispecific antibody biAb0001 was determined using a Tail Vein Transection (TVT) model in transgenic FVIII knock-out (i.e. haemophilia A), murine TLT-1 knock-out, human knock-in mice. Since the anti-FVII(a) does not recognize murine FVII(a), the biAb was co-administered with human FVIIa, FVII, FVII:AT to give target plasma levels of these components in the mouse (3.8, 26.2 and 9.0 nM, respectively) mimicking their expected clinical steady-state plasma levels according to Example 28. The concentration of biAb was either 40 or 100 nM. In short, the mice were anaesthetized with isoflurane and placed on a heating pad, set to keep animal body temperature at 37° C., with their tails immersed in saline (37° C.). Dosing was performed in the right lateral tail vein 5 minutes prior to the injury. In the present TVT model (Johansen et al., Haemophilia, 2016, 625-31) the lateral vein was transected. If the bleeding stopped at 10, 20, or 30 min, the tail was taken up from the saline, and the wound was gently wiped with a saline wetted gauze swab. Total blood loss was determined after 40 min by quantifying the amount of haemoglobin in the saline. At 40 min after administration, a blood sample was collected in 3.8% trisodium citrate from the orbital plexus. The blood was centrifuged 5 min at 4000 g and plasma aliquoted and stored at −80° C. until analysis for hIgG (see example 23), total FVII(a) antigen (see example 24), and FVIIa activity (see example 8).

As shown in Table 31, all combinations of FVIIa and biAb led to a significant reduction in blood loss compared with biAb alone or FVII(a) dosed without biAb. For all combinations, platelet count measured 45 min after treatment was comparable to that observed for a vehicle group.

In conclusion, these data demonstrate a significant in vivo haemostatic effect of biAb0001 in the presence of expected steady-state levels of FVIIa, FVII, and FVII:AT.

TABLE 31

Blood loss following tail-vein transection (TVT) in FVIII knock-out/ murine TLT-1 knock-out/human TLT-1 knock-in mice administered combinations of biAb0001, FVIIa, FVII, and FVIIa:AT as indicated. Administered doses, expected and measured plasma concentrations, and determined blood loss are shown as mean ± SEM (n = 10). Using a One-Way ANOVA followed by a Dunnett's multiplecomparison test, the blood loss of group 3-5 were found to be significantly different from group 1 and 2. Total FVII(a) antigen concentrations (measured according to Example 23) are listed in the rows labelled 'FVII' and values are marked by asterisks.

| Group | Co-adm. compound | Dose (nmol/ kg) | Expected plasma conc (nM) | Measured plasma conc (nM) | Blood loss (nmol haem.) |
|---|---|---|---|---|---|
| 1 | biAb0001 | 0.5 | 4 | 7.1 ± 0.4 | 3935 ± 711 |
|   | FVIIa |   |   |   |   |
|   | FVII |   |   |   |   |
|   | FVIIa:AT |   |   |   |   |
| 2 | biAb0001 |   |   |   | 3225 ± 731 |
|   | FVIIa | 0.5 | 3.8 | 1.8 ± 0.2 |   |
|   | FVII | 3.45 | 26.2 | 37.2 ± 1.9* |   |
|   | FVIIa:AT | 1.18 | 9.0 |   |   |
| 3 | biAb0001 | 0.5 | 4 | 5.5 ± 0.6 | 820 ± 187 |
|   | FVIIa | 0.5 | 3.8 | 3.9 ± 0.1 |   |
|   | FVII |   |   | 3.8 ± 0.2* |   |
|   | FVIIa:AT |   |   |   |   |
| 4 | biAb0001 | 5.13 | 40 | 126.3 ± 11.1 | 381 ± 63 |
|   | FVIIa | 0.5 | 3.8 | 6.3 ± 0.5 |   |
|   | FVII | 3.45 | 26.2 | 72.4 ± 5.5* |   |
|   | FVIIa:AT | 1.18 | 9.0 |   |   |
| 5 | biAb0001 | 12.83 | 100 | 586.0 ± 115.9 | 598 ± 150 |
|   | FVIIa | 0.5 | 3.8 | 5.9 ± 0.4 |   |
|   | FVII | 3.45 | 26.2 | 124 ± 14.2* |   |
|   | FVIIa:AT | 1.18 | 9.0 |   |   |

While certain features of the invention have been illustrated and described herein, many modifications, substitutions, changes and equivalents will now occur to those of ordinary skill in the art. It is, therefore, to be understood that

Example 32: Identification of Antibodies Competing with Anti-TLT-1 mAb1076 for Binding to TLT-1 in a Competitive ELISA The Fab fragment (anti-TLT-1 Fab) to be used for competition experiments comprises the VH and VL domain sequences corresponding to mAb1076 (SEQ ID NO: 938 and 934, respectively), a human IgG4 CH1 domain, and a human kappa CL with a single point mutation (G157C). The G to C substitution is in the constant domain of the Fab fragment, i.e. far from the antigen binding site, and has no influence on the binding to TLT-1 (see Example 20). Recombinant is produced as TLT-1 as described in WO2011/023785. The anti-TLT-1 Fab is biotinylated using standard methods including application of the biotinylation kit (EZ-link, Thermo) according to manufacturer's instructions.

To determine if anti-TLT-1 antibodies compete with the anti-TLT-1 Fab, and antibodies derived thereof, for binding to TLT-1 competition studies were performed. Recombinant TLT-1 is immobilised in a NUNC maxisorp plate over night at 4° C. in dilution buffer (20 mM HEPES, 5 mM CaCl2, 150 mM NaCl, pH 7.2). The plates are washed and blocked in washing buffer (20 mM HEPES, 5 mM CaCl2, 150 mM NaCl, 0.5 mL/L Tween 20, pH 7.2) for 15 min. For the competition study, biotinylated anti-TLT-1 Fab at a final fixed concentration is combined with a dilution series of anti-TLT-1 antibody to give final concentrations ranging from 0 and up to 100 mg/ml in dilution buffer. The mixture is added to the wells of the plate and allowed to incubate for 1 hour. The plate is then washed and HRP-labelled streptavidin-HRPO (1:2000 in dilution buffer; Kirkegaard & Perry Labs) is added and incubated for 1 h. Finally, the plate is washed and developed with TMB ONE (KEMENTEC) for 10 min. The reaction is stopped by adding H3PO4 (4M) and the plate read in a FLUOStar Optima plate reader at 450 nm with subtraction of the background signal measured at 620 nm. Unless otherwise specified, all incubations are done at room temperature and plates are washed 5 times using washing buffer.

The concentration of recombinant TLT-1 to be immobilized in the NUNC maxisorp plate as well as the fixed concentration of biotinylated anti-TLT-1 Fab to be mixed with competitor antibody for the competition study are determined by individual titrations of the two components with the aim to give a sufficient signal to allow for detection of competition (i.e. decrease in signal) by competitor antibodies. The concentration of TLT-1 for immobilization is typically in the range from 0-1 mg/ml, such as 125 ng/ml. The concentration of biotinylated anti-TLT-1 Fab is typically in the range from 0-1 mg/ml, such as 10 ng/ml.

From the measured signals (OD units), competition at any given antibody concentration is calculated as $$\% \text{ inhibition} = (1 - (\text{OD units} - 100\% \text{ inhibition}) / (0\% \text{ inhibition} - 100\% \text{ inhibition})) * 100$$

where 0% inhibition is determined from the signal in wells without any competing anti-TLT-1 antibody, and 100% inhibition is determined as the signal from wells without biotinylated anti-TLT-1 Fab (i.e. corresponding to the assay background). Antibodies are considered to compete with anti-TLT-1 Fab for binding to TLT-1, if there is at least 50% observed inhibition (% inhibition) when the concentration of the antibody is tested in up to 10000-fold excess of the biotinylated anti-TLT-1 Fab.

---

The invention claimed is:

1. A bispecific antibody comprising
   (i) a first antigen binding site capable of binding Factor VII(a), and
   (ii) a second antigen binding site capable of binding TREM-like Transcript 1 (TLT-1);
   wherein the first antigen-binding site comprises:
   a CDRL1 represented by SEQ ID NO: 847,
   a CDRL2 represented by SEQ ID NO: 848,
   a CDRL3 represented by SEQ ID NO: 849,
   a CDRH1 represented by SEQ ID NO: 851,
   a CDRH2 represented by SEQ ID NO: 852, and
   a CDRH3 represented by SEQ ID NO: 853;
   wherein the second antigen-binding site comprises:
   a CDRL1 represented by SEQ ID NO: 855,
   a CDRL2 represented by SEQ ID NO: 856,
   a CDRL3 represented by SEQ ID NO: 857,
   a CDRH1 represented by SEQ ID NO: 859,
   a CDRH2 represented by SEQ ID NO: 860, and
   a CDRH3 represented by SEQ ID NO: 861; and
   wherein the antibody comprises an Fc region.

2. The bispecific antibody according to claim 1, wherein the first antigen-binding site comprises a light chain variable domain identified by SEQ ID NO:846 and a heavy chain variable domain identified by SEQ ID NO:850, and wherein the second antigen-binding site is comprised by a light chain variable domain identified by SEQ ID NO: 854 and a heavy chain variable domain identified by SEQ ID NO:858.

3. The bispecific antibody according to claim 1, wherein the first antigen-binding site comprises a first light chain variable domain identified by SEQ ID NO:846 and a first heavy chain variable domain identified by SEQ ID NO:850, wherein the second antigen-binding site is comprised by a second light chain variable domain identified by SEQ ID NO: 854 and a second heavy chain variable domain identified by SEQ ID NO:858, wherein the heavy chain constant domains attached to the first and second heavy chain variable domains are identified by SEQ ID NO: 943 and 942, respectively, and wherein the light chain constant domains attached to the first and second light chain variable domains are both identified by SEQ ID NO: 12.

4. A pharmaceutical formulation comprising the bispecific antibody according to claim 1 and a pharmaceutically acceptable carrier.

5. The pharmaceutical formulation according to claim 4, wherein the first antigen-binding site comprises a light chain variable domain identified by SEQ ID NO:846 and a heavy chain variable domain identified by SEQ ID NO:850, and wherein the second antigen-binding site is comprised by a light chain variable domain identified by SEQ ID NO: 854 and a heavy chain variable domain identified by SEQ ID NO:858.

6. The pharmaceutical formulation according to claim 4, wherein the first antigen-binding site comprises a first light chain variable domain identified by SEQ ID NO:846 and a first heavy chain variable domain identified by SEQ ID NO:850, wherein the second antigen-binding site is comprised by a second light chain variable domain identified by SEQ ID NO: 854 and a second heavy chain variable domain identified by SEQ ID NO:858, wherein the heavy chain constant domains attached to the first and second heavy chain variable domains are identified by SEQ ID NO: 943 and 942, respectively, and wherein the light chain constant domains attached to the first and second light chain variable domains are both identified by SEQ ID NO: 12.

7. A method for treating a coagulopathy in an individual, comprising administering an effective amount of a bispecific antibody to the individual;
   wherein the bispecific antibody comprises:
   (i) a first antigen binding site capable of binding Factor VII(a); and
   (ii) a second antigen binding site capable of binding TREM-like Transcript 1 (TLT-1);
   wherein the first antigen-binding site comprises:
   a CDRL1 represented by SEQ ID NO: 847,
   a CDRL2 represented by SEQ ID NO: 848,
   a CDRL3 represented by SEQ ID NO: 849,
   a CDRH1 represented by SEQ ID NO: 851,
   a CDRH2 represented by SEQ ID NO: 852, and
   a CDRH3 represented by SEQ ID NO: 853;
   wherein the second antigen-binding site comprises:
   a CDRL1 represented by SEQ ID NO: 855,
   a CDRL2 represented by SEQ ID NO: 856,
   a CDRL3 represented by SEQ ID NO: 857,
   a CDRH1 represented by SEQ ID NO: 859,
   a CDRH2 represented by SEQ ID NO: 860, and
   a CDRH3 represented by SEQ ID NO: 861;
   wherein the coagulopathy is selected from the group consisting of hemophilia A, with or without inhibitors; hemophilia B, with or without inhibitors; FVII(a) deficiency; and Glanzmann's thrombasthenia.

8. The method according to claim 7, wherein the first antigen-binding site comprises a light chain variable domain identified by SEQ ID NO:846 and a heavy chain variable domain identified by SEQ ID NO:850, and wherein the second antigen-binding site is comprised by a light chain variable domain identified by SEQ ID NO: 854 and a heavy chain variable domain identified by SEQ ID NO:858.

9. The method according to claim 7, wherein the first antigen-binding site comprises a first light chain variable domain identified by SEQ ID NO:846 and a first heavy chain variable domain identified by SEQ ID NO:850, wherein the second antigen-binding site is comprised by a second light chain variable domain identified by SEQ ID NO: 854 and a second heavy chain variable domain identified by SEQ ID NO:858, wherein the heavy chain constant domains attached to the first and second heavy chain variable domains are identified by SEQ ID NO: 943 and 942, respectively, and wherein the light chain constant domains attached to the first and second light chain variable domains are both identified by SEQ ID NO: 12.

* * * * *

SEQUENCE LISTING

```
<160> NUMBER OF SEQ ID NOS: 943

<210> SEQ ID NO 1
<211> LENGTH: 406
<212> TYPE: PRT
<213> ORGANISM: Artificial Sequence
<220> FEATURE:
<223> OTHER INFORMATION: Recombinant protein

<400> SEQUENCE: 1

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125
```

-continued

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 2
<211> LENGTH: 296
<212> TYPE: PRT
<213> ORGANISM: Homo sapiens

<400> SEQUENCE: 2

Gln Gly Ile Val Gly Ser Leu Pro Glu Val Leu Gln Ala Pro Val Gly
1               5                   10                  15

Ser Ser Ile Leu Val Gln Cys His Tyr Arg Leu Gln Asp Val Lys Ala
            20                  25                  30

Gln Lys Val Trp Cys Arg Phe Leu Pro Glu Gly Cys Gln Pro Leu Val
        35                  40                  45

Ser Ser Ala Val Asp Arg Arg Ala Pro Ala Gly Arg Arg Thr Phe Leu
    50                  55                  60

Thr Asp Leu Gly Gly Gly Leu Leu Gln Val Glu Met Val Thr Leu Gln
65                  70                  75                  80

Glu Glu Asp Ala Gly Glu Tyr Gly Cys Met Val Asp Gly Ala Arg Gly
                85                  90                  95

```
Pro Gln Ile Leu His Arg Val Ser Leu Asn Ile Leu Pro Glu Glu
            100                 105                 110

Glu Glu Glu Thr His Lys Ile Gly Ser Leu Ala Glu Asn Ala Phe Ser
        115                 120                 125

Asp Pro Ala Gly Ser Ala Asn Pro Leu Glu Pro Ser Gln Asp Glu Lys
    130                 135                 140

Ser Ile Pro Leu Ile Trp Gly Ala Val Leu Leu Val Gly Leu Leu Val
145                 150                 155                 160

Ala Ala Val Val Leu Phe Ala Val Met Ala Lys Arg Lys Gln Gly Asn
                165                 170                 175

Arg Leu Gly Val Cys Gly Arg Phe Leu Ser Ser Arg Val Ser Gly Met
                180                 185                 190

Asn Pro Ser Ser Val Val His His Val Ser Asp Ser Gly Pro Ala Ala
            195                 200                 205

Glu Leu Pro Leu Asp Val Pro His Ile Arg Leu Asp Ser Pro Pro Ser
    210                 215                 220

Phe Asp Asn Thr Thr Tyr Thr Ser Leu Pro Leu Asp Ser Pro Ser Gly
225                 230                 235                 240

Lys Pro Ser Leu Pro Ala Pro Ser Ser Leu Pro Pro Leu Pro Pro Lys
                245                 250                 255

Val Leu Val Cys Ser Lys Pro Val Thr Tyr Ala Thr Val Ile Phe Pro
                260                 265                 270

Gly Gly Asn Lys Gly Gly Gly Thr Ser Cys Gly Pro Ala Gln Asn Pro
            275                 280                 285

Pro Asn Asn Gln Thr Pro Ser Ser
    290                 295

<210> SEQ ID NO 3
<211> LENGTH: 147
<212> TYPE: PRT
<213> ORGANISM: Homo sapiens

<400> SEQUENCE: 3

Gln Gly Ile Val Gly Ser Leu Pro Glu Val Leu Gln Ala Pro Val Gly
1               5                   10                  15

Ser Ser Ile Leu Val Gln Cys His Tyr Arg Leu Gln Asp Val Lys Ala
            20                  25                  30

Gln Lys Val Trp Cys Arg Phe Leu Pro Glu Gly Cys Gln Pro Leu Val
        35                  40                  45

Ser Ser Ala Val Asp Arg Arg Ala Pro Ala Gly Arg Arg Thr Phe Leu
    50                  55                  60

Thr Asp Leu Gly Gly Gly Leu Leu Gln Val Glu Met Val Thr Leu Gln
65                  70                  75                  80

Glu Glu Asp Ala Gly Glu Tyr Gly Cys Met Val Asp Gly Ala Arg Gly
                85                  90                  95

Pro Gln Ile Leu His Arg Val Ser Leu Asn Ile Leu Pro Pro Glu Glu
            100                 105                 110

Glu Glu Glu Thr His Lys Ile Gly Ser Leu Ala Glu Asn Ala Phe Ser
        115                 120                 125

Asp Pro Ala Gly Ser Ala Asn Pro Leu Glu Pro Ser Gln Asp Glu Lys
    130                 135                 140

Ser Ile Pro
145
```

```
<210> SEQ ID NO 4
<211> LENGTH: 327
<212> TYPE: PRT
<213> ORGANISM: Artificial Sequence
<220> FEATURE:
<223> OTHER INFORMATION: Recombinant protein

<400> SEQUENCE: 4
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

```
<210> SEQ ID NO 5
<211> LENGTH: 327
<212> TYPE: PRT
<213> ORGANISM: Artificial Sequence
<220> FEATURE:
<223> OTHER INFORMATION: Recombinant protein
```

<400> SEQUENCE: 5

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Leu Leu Tyr Ser
        275                 280                 285

Lys Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 6
<211> LENGTH: 327
<212> TYPE: PRT
<213> ORGANISM: Artificial Sequence
<220> FEATURE:
<223> OTHER INFORMATION: Recombinant protein

<400> SEQUENCE: 6

```
Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 7
<211> LENGTH: 327
<212> TYPE: PRT
<213> ORGANISM: Artificial Sequence
<220> FEATURE:
<223> OTHER INFORMATION: Recombinant protein

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

```
Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Tyr Ile Thr Arg Glu Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Leu Leu Tyr Ser
            275                 280                 285

Lys Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 8
<211> LENGTH: 230
<212> TYPE: PRT
<213> ORGANISM: Artificial Sequence
<220> FEATURE:
<223> OTHER INFORMATION: Recombinant protein

<400> SEQUENCE: 8

Val Glu Ser Lys Tyr Gly Pro Pro Cys Pro Pro Cys Pro Ala Pro Glu
 1               5                  10                  15

Phe Leu Gly Gly Pro Ser Val Phe Leu Phe Pro Pro Lys Pro Lys Asp
                20                  25                  30

Thr Leu Met Ile Ser Arg Thr Pro Glu Val Thr Cys Val Val Val Asp
            35                  40                  45

Val Ser Gln Glu Asp Pro Glu Val Gln Phe Asn Trp Tyr Val Asp Gly
        50                  55                  60

Val Glu Val His Asn Ala Lys Thr Lys Pro Arg Glu Glu Gln Phe Asn
65                  70                  75                  80
```

```
Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Leu Leu Tyr Ser Lys
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly Lys
225                 230

<210> SEQ ID NO 9
<211> LENGTH: 327
<212> TYPE: PRT
<213> ORGANISM: Artificial Sequence
<220> FEATURE:
<223> OTHER INFORMATION: Recombinant protein

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

```
Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Ser Cys Ala Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Val Ser
                275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 10
<211> LENGTH: 229
<212> TYPE: PRT
<213> ORGANISM: Artificial Sequence
<220> FEATURE:
<223> OTHER INFORMATION: Recombinant protein

<400> SEQUENCE: 10

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

```
<210> SEQ ID NO 11
<211> LENGTH: 98
<212> TYPE: PRT
<213> ORGANISM: Artificial Sequence
<220> FEATURE:
<223> OTHER INFORMATION: Recombinant protein

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 12
<211> LENGTH: 107
<212> TYPE: PRT
<213> ORGANISM: Artificial Sequence
<220> FEATURE:
<223> OTHER INFORMATION: Recombinant protein

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 37
<212> TYPE: PRT
<213> ORGANISM: Artificial Sequence
<220> FEATURE:
<223> OTHER INFORMATION: Recombinant protein

<400> SEQUENCE: 13

Glu Glu Glu Glu Glu Thr His Lys Ile Gly Ser Leu Ala Glu Asn Ala
1               5                   10                  15

Phe Ser Asp Pro Ala Gly Ser Ala Asn Pro Leu Glu Pro Ser Gln Asp
                20                  25                  30

Glu Lys Ser Ile Pro
            35
```

<210> SEQ ID NO 14
<211> LENGTH: 107
<212> TYPE: PRT
<213> ORGANISM: Mus musculus

<400> SEQUENCE: 14

Asp Ile Val Met Thr Gln Ser His Lys Ile Met Ser Thr Leu Val Gly
1               5                   10                  15

Asp Arg Val Ser Ile Thr Cys Lys Ala Ser Gln Asp Val Asp Pro Ala
            20                  25                  30

Val Ala Trp Tyr Gln Gln Lys Pro Gly Gln Tyr Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Lys Tyr Pro Tyr
                85                  90                  95

Thr Phe Gly Gly Gly Thr Lys Leu Glu Ile Lys
            100                 105

<210> SEQ ID NO 15
<211> LENGTH: 11
<212> TYPE: PRT
<213> ORGANISM: Mus musculus

<400> SEQUENCE: 15

Lys Ala Ser Gln Asp Val Asp Pro Ala Val Ala
1               5                   10

<210> SEQ ID NO 16
<211> LENGTH: 7
<212> TYPE: PRT
<213> ORGANISM: Mus musculus

<400> SEQUENCE: 16

Trp Ala Ser Thr Arg His Thr
1               5

<210> SEQ ID NO 17
<211> LENGTH: 9
<212> TYPE: PRT
<213> ORGANISM: Mus musculus

<400> SEQUENCE: 17

Gln Gln Tyr Ser Lys Tyr Pro Tyr Thr
1               5

<210> SEQ ID NO 18
<211> LENGTH: 118
<212> TYPE: PRT
<213> ORGANISM: Mus musculus

<400> SEQUENCE: 18

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Ser Trp Ile Arg Gln Pro Pro Gly Lys Gly Leu Glu Trp Leu
        35                  40                  45

Gly Val Ile Trp Gly Gly Asn Thr Tyr Asn Asn Ser Ala Leu Lys
            50                  55                  60

Ser Arg Leu Ser Ile Ser Lys Asp Asn Ser Lys Ser Gln Val Phe Leu
 65                  70                  75                  80

Lys Met Asn Ser Leu Gln Ala Asp Asp Thr Ala Met Tyr Phe Cys Ala
                 85                  90                  95

Lys His Gly Tyr Tyr Gly Tyr Val Met Asp Tyr Trp Gly Gln Gly Thr
            100                 105                 110

Ser Val Thr Val Ser Ser
            115

<210> SEQ ID NO 19
<211> LENGTH: 5
<212> TYPE: PRT
<213> ORGANISM: Mus musculus

<400> SEQUENCE: 19

Asp Tyr Gly Val Ser
 1               5

<210> SEQ ID NO 20
<211> LENGTH: 16
<212> TYPE: PRT
<213> ORGANISM: Mus musculus

<400> SEQUENCE: 20

Val Ile Trp Gly Gly Gly Asn Thr Tyr Asn Asn Ser Ala Leu Lys Ser
 1               5                  10                  15

<210> SEQ ID NO 21
<211> LENGTH: 10
<212> TYPE: PRT
<213> ORGANISM: Mus musculus

<400> SEQUENCE: 21

His Gly Tyr Tyr Gly Tyr Val Met Asp Tyr
 1               5                  10

<210> SEQ ID NO 22
<211> LENGTH: 107
<212> TYPE: PRT
<213> ORGANISM: Artificial Sequence
<220> FEATURE:
<223> OTHER INFORMATION: Recombinant protein

<400> SEQUENCE: 22

Asp Ile Val Met Thr Gln Ser Pro Ala Thr Leu Ser Val Thr Ala Gly
 1               5                  10                  15

Asp Arg Val Ser Leu Ser Cys Arg Ala Ser Gln Gly Ile Ser Asp Tyr
                20                  25                  30

Leu His Trp Tyr Gln Gln Lys Ser His Glu Ser Pro Arg Leu Leu Ile
             35                  40                  45

Lys Tyr Thr Ser Gln Pro Val Ser Gly Ile Pro Ser Arg Phe Ser Gly
         50                  55                  60

Ser Gly Ser Gly Ser Glu Phe Thr Leu Ser Ile Asn Ser Val Glu Pro
 65                  70                  75                  80

Glu Asp Val Gly Val Tyr Tyr Cys Gln Asn Gly His Ser Phe Pro Leu
                 85                  90                  95

Thr Phe Gly Ala Gly Thr Lys Leu Glu Leu Lys
            100                 105

<210> SEQ ID NO 23
<211> LENGTH: 11
<212> TYPE: PRT
<213> ORGANISM: Artificial Sequence
<220> FEATURE:
<223> OTHER INFORMATION: Recombinant protein

<400> SEQUENCE: 23

Arg Ala Ser Gln Gly Ile Ser Asp Tyr Leu His
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Recombinant protein

<400> SEQUENCE: 24

Tyr Thr Ser Gln Pro Val Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Recombinant protein

<400> SEQUENCE: 25

Gln Asn Gly His Ser Phe Pro Leu Thr
1               5

<210> SEQ ID NO 26
<211> LENGTH: 122
<212> TYPE: PRT
<213> ORGANISM: Artificial Sequence
<220> FEATURE:
<223> OTHER INFORMATION: Recombinant protein

<400> SEQUENCE: 26

Asp Val Gln Leu Gln Glu Ser Gly Pro Gly Leu Val Glu Pro Ser Gln
1               5                   10                  15

Ser Leu Ser Leu Thr Cys Thr Val Thr Gly Tyr Ser Ile Thr Ser Asp
            20                  25                  30

Cys Ala Trp Ser Trp Ile Arg Gln Phe Pro Gly Asn Lys Leu Glu Trp
        35                  40                  45

Met Gly Tyr Ile Asn Tyr Ser Gly Ser Thr Asn Tyr Asn Pro Ser Leu
    50                  55                  60

Lys Ser Arg Ile Ser Val Thr Arg Asp Thr Ser Lys Asn Gln Phe Phe
65                  70                  75                  80

Leu Arg Leu Ser Ser Val Thr Ala Glu Asp Thr Ala Thr Tyr Tyr Cys
                85                  90                  95

Thr Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 27
<211> LENGTH: 6
<212> TYPE: PRT
<213> ORGANISM: Artificial Sequence

```
<220> FEATURE:
<223> OTHER INFORMATION: Recombinant protein

<400> SEQUENCE: 27

Ser Asp Cys Ala Trp Ser
1               5

<210> SEQ ID NO 28
<211> LENGTH: 16
<212> TYPE: PRT
<213> ORGANISM: Artificial Sequence
<220> FEATURE:
<223> OTHER INFORMATION: Recombinant protein

<400> SEQUENCE: 28

Tyr Ile Asn Tyr Ser Gly Ser Thr Asn Tyr Asn Pro Ser Leu Lys Ser
1               5                   10                  15

<210> SEQ ID NO 29
<211> LENGTH: 13
<212> TYPE: PRT
<213> ORGANISM: Artificial Sequence
<220> FEATURE:
<223> OTHER INFORMATION: Recombinant protein

<400> SEQUENCE: 29

Ser Val Asn Tyr Tyr Gly Asn Ser Phe Ala Val Gly Tyr
1               5                   10

<210> SEQ ID NO 30
<211> LENGTH: 107
<212> TYPE: PRT
<213> ORGANISM: Artificial Sequence
<220> FEATURE:
<223> OTHER INFORMATION: Recombinant protein

<400> SEQUENCE: 30

Asp Ile Val Met Thr Gln Ser Pro Ala Thr Leu Ser Val Thr Ala Gly
1               5                   10                  15

Asp Arg Val Ser Leu Ser Cys Arg Ala Ser Gln Gly Ile Ser Asp Tyr
                20                  25                  30

Leu His Trp Tyr Gln Gln Lys Ser His Glu Ser Pro Arg Leu Leu Ile
            35                  40                  45

Lys Tyr Thr Ser Gln Pro Val Ser Gly Ile Pro Ser Arg Phe Ser Gly
        50                  55                  60

Ser Gly Ser Gly Ser Glu Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 31
<211> LENGTH: 11
<212> TYPE: PRT
<213> ORGANISM: Artificial Sequence
<220> FEATURE:
<223> OTHER INFORMATION: Recombinant protein

<400> SEQUENCE: 31

Arg Ala Ser Gln Gly Ile Ser Asp Tyr Leu His
1               5                   10
```

```
<210> SEQ ID NO 32
<211> LENGTH: 7
<212> TYPE: PRT
<213> ORGANISM: Artificial Sequence
<220> FEATURE:
<223> OTHER INFORMATION: Recombinant protein

<400> SEQUENCE: 32

Tyr Thr Ser Gln Pro Val Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Recombinant protein

<400> SEQUENCE: 33

Gln Asn Gly His Ser Phe Pro Leu Thr
1               5

<210> SEQ ID NO 34
<211> LENGTH: 122
<212> TYPE: PRT
<213> ORGANISM: Artificial Sequence
<220> FEATURE:
<223> OTHER INFORMATION: Recombinant protein

<400> SEQUENCE: 34

Asp Val Gln Leu Gln Glu Ser Gly Pro Gly Leu Val Glu Pro Ser Gln
1               5                   10                  15

Ser Leu Ser Leu Thr Cys Thr Val Thr Gly Tyr Ser Ile Thr Ser Asp
                20                  25                  30

Cys Ala Trp Ser Trp Ile Arg Gln Phe Pro Gly Asn Lys Leu Glu Trp
            35                  40                  45

Met Gly Tyr Ile Asn Tyr Ser Gly Ser Thr Asn Tyr Asn Pro Ser Leu
        50                  55                  60

Lys Ser Arg Ile Ser Val Thr Arg Asp Thr Ser Lys Asn Gln Phe Phe
65                  70                  75                  80

Leu Arg Leu Ser Ser Val Thr Ala Glu Asp Thr Ala Thr Tyr Tyr Cys
                85                  90                  95

Thr Arg Ser Val Asn Tyr Gly Asn Ser Phe Ala Val Gly Tyr Trp
            100                 105                 110

Gly Gln Gly Thr Ser Val Thr Val Ser Ser
        115                 120

<210> SEQ ID NO 35
<211> LENGTH: 6
<212> TYPE: PRT
<213> ORGANISM: Artificial Sequence
<220> FEATURE:
<223> OTHER INFORMATION: Recombinant protein

<400> SEQUENCE: 35

Ser Asp Cys Ala Trp Ser
1               5

<210> SEQ ID NO 36
<211> LENGTH: 16
<212> TYPE: PRT
<213> ORGANISM: Artificial Sequence
<220> FEATURE:
<223> OTHER INFORMATION: Recombinant protein
```

```
<400> SEQUENCE: 36

Tyr Ile Asn Tyr Ser Gly Ser Thr Asn Tyr Asn Pro Ser Leu Lys Ser
1               5                   10                  15

<210> SEQ ID NO 37
<211> LENGTH: 13
<212> TYPE: PRT
<213> ORGANISM: Artificial Sequence
<220> FEATURE:
<223> OTHER INFORMATION: Recombinant protein

<400> SEQUENCE: 37

Ser Val Asn Tyr Tyr Gly Asn Ser Phe Ala Val Gly Tyr
1               5                   10

<210> SEQ ID NO 38
<211> LENGTH: 107
<212> TYPE: PRT
<213> ORGANISM: Artificial Sequence
<220> FEATURE:
<223> OTHER INFORMATION: Recombinant protein

<400> SEQUENCE: 38

Asp Ile Val Met Thr Gln Ser Pro Ala Thr Leu Ser Val Thr Ala Gly
1               5                   10                  15

Asp Arg Val Ser Leu Ser Cys Arg Ala Ser Gln Gly Ile Ser Asp Tyr
            20                  25                  30

Leu His Trp Tyr Gln Gln Lys Ser His Glu Ser Pro Arg Leu Leu Ile
        35                  40                  45

Lys Tyr Thr Ser Gln Pro Val Ser Gly Ile Pro Ser Arg Phe Ser Gly
    50                  55                  60

Ser Gly Ser Gly Ser Glu Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 39
<211> LENGTH: 11
<212> TYPE: PRT
<213> ORGANISM: Artificial Sequence
<220> FEATURE:
<223> OTHER INFORMATION: Recombinant protein

<400> SEQUENCE: 39

Arg Ala Ser Gln Gly Ile Ser Asp Tyr Leu His
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Recombinant protein

<400> SEQUENCE: 40

Tyr Thr Ser Gln Pro Val Ser
1               5

<210> SEQ ID NO 41
<211> LENGTH: 9
```

```
<212> TYPE: PRT
<213> ORGANISM: Artificial Sequence
<220> FEATURE:
<223> OTHER INFORMATION: Recombinant protein

<400> SEQUENCE: 41

Gln Asn Gly His Ser Phe Pro Leu Thr
1               5

<210> SEQ ID NO 42
<211> LENGTH: 122
<212> TYPE: PRT
<213> ORGANISM: Artificial Sequence
<220> FEATURE:
<223> OTHER INFORMATION: Recombinant protein

<400> SEQUENCE: 42

Asp Val Gln Leu Gln Glu Ser Gly Pro Gly Leu Val Glu Pro Ser Gln
1               5                   10                  15

Ser Leu Ser Leu Thr Cys Thr Val Thr Gly Tyr Ser Ile Thr Ser Asp
            20                  25                  30

Cys Ala Trp Ser Trp Ile Arg Gln Phe Pro Gly Asn Lys Leu Glu Trp
        35                  40                  45

Met Gly Tyr Ile Asn Tyr Ser Gly Ser Thr Asn Tyr Asn Pro Ser Leu
    50                  55                  60

Lys Ser Arg Ile Ser Val Thr Arg Asp Thr Ser Lys Asn Gln Phe Phe
65                  70                  75                  80

Leu Arg Leu Ser Ser Val Thr Ala Glu Asp Thr Ala Thr Tyr Tyr Cys
                85                  90                  95

Thr Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 43
<211> LENGTH: 6
<212> TYPE: PRT
<213> ORGANISM: Artificial Sequence
<220> FEATURE:
<223> OTHER INFORMATION: Recombinant protein

<400> SEQUENCE: 43

Ser Asp Cys Ala Trp Ser
1               5

<210> SEQ ID NO 44
<211> LENGTH: 16
<212> TYPE: PRT
<213> ORGANISM: Artificial Sequence
<220> FEATURE:
<223> OTHER INFORMATION: Recombinant protein

<400> SEQUENCE: 44

Tyr Ile Asn Tyr Ser Gly Ser Thr Asn Tyr Asn Pro Ser Leu Lys Ser
1               5                   10                  15

<210> SEQ ID NO 45
<211> LENGTH: 13
<212> TYPE: PRT
<213> ORGANISM: Artificial Sequence
<220> FEATURE:
<223> OTHER INFORMATION: Recombinant protein

<400> SEQUENCE: 45
```

```
Ser Val Asn Tyr Tyr Gly Asn Ser Phe Ala Val Gly Tyr
1               5                   10

<210> SEQ ID NO 46
<211> LENGTH: 113
<212> TYPE: PRT
<213> ORGANISM: Mus musculus

<400> SEQUENCE: 46

Asp Ile Val Met Thr Gln Ser Pro Ser Ser Leu Thr Val Thr Ala Gly
1               5                   10                  15

Glu Lys Val Thr Val Ser Cys Lys Ser Ser Gln Ser Leu Leu Asn Ser
                20                  25                  30

Gly Asp Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Phe Ser Tyr Pro Tyr Thr Phe Gly Gly Gly Thr Lys Leu Glu Ile
            100                 105                 110

Lys

<210> SEQ ID NO 47
<211> LENGTH: 17
<212> TYPE: PRT
<213> ORGANISM: Mus musculus

<400> SEQUENCE: 47

Lys Ser Ser Gln Ser Leu Leu Asn Ser Gly Asp Gln Lys Asn Tyr Leu
1               5                   10                  15

Thr

<210> SEQ ID NO 48
<211> LENGTH: 7
<212> TYPE: PRT
<213> ORGANISM: Mus musculus

<400> SEQUENCE: 48

Trp Ala Ser Thr Arg Glu Ser
1               5

<210> SEQ ID NO 49
<211> LENGTH: 9
<212> TYPE: PRT
<213> ORGANISM: Mus musculus

<400> SEQUENCE: 49

Gln Asn Asp Phe Ser Tyr Pro Tyr Thr
1               5

<210> SEQ ID NO 50
<211> LENGTH: 118
<212> TYPE: PRT
<213> ORGANISM: Mus musculus

<400> SEQUENCE: 50

Gln Ile Gln Leu Val Gln Ser Gly Pro Glu Leu Lys Lys Pro Gly Glu
```

```
1               5                   10                  15
Thr Val Lys Ile Ser Cys Lys Ala Ser Gly Tyr Thr Phe Thr Asp Tyr
                20                  25                  30

Ser Ile Gln Trp Val Lys Gln Ala Pro Gly Lys Gly Leu Lys Trp Met
            35                  40                  45

Gly Trp Ile Asn Thr Glu Thr Gly Lys Pro Ser Tyr Ala Asp Asp Leu
        50                  55                  60

Lys Gly Arg Ser Ala Phe Ser Leu Glu Thr Ser Gly Ser Thr Ala Tyr
65                  70                  75                  80

Leu Gln Ile Ser Asn Leu Lys Asn Glu Asp Met Ala Thr Tyr Phe Cys
                85                  90                  95

Val Arg Asp Asp Tyr Tyr Gly Arg Glu Asp Tyr Trp Gly Gln Gly Thr
                100                 105                 110

Thr Leu Thr Val Ser Ser
            115
```

<210> SEQ ID NO 51
<211> LENGTH: 5
<212> TYPE: PRT
<213> ORGANISM: Mus musculus

<400> SEQUENCE: 51

```
Asp Tyr Ser Ile Gln
1               5
```

<210> SEQ ID NO 52
<211> LENGTH: 17
<212> TYPE: PRT
<213> ORGANISM: Mus musculus

<400> SEQUENCE: 52

```
Trp Ile Asn Thr Glu Thr Gly Lys Pro Ser Tyr Ala Asp Asp Leu Lys
1               5                   10                  15

Gly
```

<210> SEQ ID NO 53
<211> LENGTH: 9
<212> TYPE: PRT
<213> ORGANISM: Mus musculus

<400> SEQUENCE: 53

```
Asp Asp Tyr Tyr Gly Arg Glu Asp Tyr
1               5
```

<210> SEQ ID NO 54
<211> LENGTH: 107
<212> TYPE: PRT
<213> ORGANISM: Artificial Sequence
<220> FEATURE:
<223> OTHER INFORMATION: Recombinant protein

<400> SEQUENCE: 54

```
Asp Ile Val Met Thr Gln Ser Pro Ala Thr Leu Ser Val Thr Ala Gly
1               5                   10                  15

Asp Arg Val Ser Leu Ser Cys Arg Ala Ser Gln Gly Ile Ser Asp Tyr
                20                  25                  30

Leu His Trp Tyr Gln Gln Lys Ser His Glu Ser Pro Arg Leu Leu Ile
            35                  40                  45

Lys Tyr Thr Ser Gln Pro Val Ser Gly Ile Pro Ser Arg Phe Ser Gly
        50                  55                  60
```

Ser Gly Ser Gly Ser Glu Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 55
<211> LENGTH: 11
<212> TYPE: PRT
<213> ORGANISM: Artificial Sequence
<220> FEATURE:
<223> OTHER INFORMATION: Recombinant protein

<400> SEQUENCE: 55

Arg Ala Ser Gln Gly Ile Ser Asp Tyr Leu His
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Recombinant protein

<400> SEQUENCE: 56

Tyr Thr Ser Gln Pro Val Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Recombinant protein

<400> SEQUENCE: 57

Gln Asn Gly His Ser Phe Pro Leu Thr
1               5

<210> SEQ ID NO 58
<211> LENGTH: 122
<212> TYPE: PRT
<213> ORGANISM: Artificial Sequence
<220> FEATURE:
<223> OTHER INFORMATION: Recombinant protein

<400> SEQUENCE: 58

Asp Val Gln Leu Gln Glu Ser Gly Pro Gly Leu Val Glu Pro Ser Gln
1               5                   10                  15

Ser Leu Ser Leu Thr Cys Thr Val Thr Gly Tyr Ser Ile Thr Ser Asp
                20                  25                  30

Ser Ala Trp Ser Trp Ile Arg Gln Phe Pro Gly Asn Lys Leu Glu Trp
            35                  40                  45

Met Gly Tyr Ile Gln Tyr Ser Gly Ser Thr Asn Tyr Asn Pro Ser Leu
        50                  55                  60

Lys Ser Arg Ile Ser Val Thr Arg Asp Thr Ser Lys Asn Gln Phe Phe
65                  70                  75                  80

Leu Arg Leu Ser Ser Val Thr Ala Glu Asp Thr Ala Thr Tyr Tyr Cys
                85                  90                  95

Thr Arg Ser Val Asn Tyr Gly Asn Ser Phe Ala Val Gly Tyr Trp
            100                 105                 110

```
Gly Gln Gly Thr Ser Val Thr Val Ser Ser
        115                 120

<210> SEQ ID NO 59
<211> LENGTH: 6
<212> TYPE: PRT
<213> ORGANISM: Artificial Sequence
<220> FEATURE:
<223> OTHER INFORMATION: Recombinant protein

<400> SEQUENCE: 59

Ser Asp Ser Ala Trp Ser
1               5

<210> SEQ ID NO 60
<211> LENGTH: 16
<212> TYPE: PRT
<213> ORGANISM: Artificial Sequence
<220> FEATURE:
<223> OTHER INFORMATION: Recombinant protein

<400> SEQUENCE: 60

Tyr Ile Gln Tyr Ser Gly Ser Thr Asn Tyr Asn Pro Ser Leu Lys Ser
1               5                   10                  15

<210> SEQ ID NO 61
<211> LENGTH: 13
<212> TYPE: PRT
<213> ORGANISM: Artificial Sequence
<220> FEATURE:
<223> OTHER INFORMATION: Recombinant protein

<400> SEQUENCE: 61

Ser Val Asn Tyr Tyr Gly Asn Ser Phe Ala Val Gly Tyr
1               5                   10

<210> SEQ ID NO 62
<211> LENGTH: 113
<212> TYPE: PRT
<213> ORGANISM: Mus musculus

<400> SEQUENCE: 62

Asp Ile Val Leu Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Ser Leu Ala Trp Tyr Gln His Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Asn Val Lys Ala Glu Asp Leu Ala Val Tyr Tyr Cys His Gln
                85                  90                  95

Tyr Tyr Asn Tyr Leu Leu Thr Phe Gly Pro Gly Thr Lys Leu Glu Leu
            100                 105                 110

Lys

<210> SEQ ID NO 63
<211> LENGTH: 17
<212> TYPE: PRT
<213> ORGANISM: Mus musculus
```

<400> SEQUENCE: 63

Lys Ser Ser Gln Ser Leu Leu Tyr Ser Ser Asn Gln Lys Asn Ser Leu
1               5                   10                  15

Ala

<210> SEQ ID NO 64
<211> LENGTH: 7
<212> TYPE: PRT
<213> ORGANISM: Mus musculus

<400> SEQUENCE: 64

Trp Ala Ser Thr Arg Glu Ser
1               5

<210> SEQ ID NO 65
<211> LENGTH: 9
<212> TYPE: PRT
<213> ORGANISM: Mus musculus

<400> SEQUENCE: 65

His Gln Tyr Tyr Asn Tyr Leu Leu Thr
1               5

<210> SEQ ID NO 66
<211> LENGTH: 123
<212> TYPE: PRT
<213> ORGANISM: Mus musculus

<400> SEQUENCE: 66

Gln Ile Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Leu Gly Val Gly Trp Ile Arg Gln Thr Ser Gly Lys Gly Leu Glu
        35                  40                  45

Trp Leu Ala His Ile Trp Trp Asp Asp Lys Tyr Tyr Tyr Pro Pro
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Ala Phe Tyr Asp Gly Tyr Tyr Gly Pro Met Glu Tyr
            100                 105                 110

Trp Gly Gln Gly Thr Ser Val Thr Val Ser Ser
        115                 120

<210> SEQ ID NO 67
<211> LENGTH: 7
<212> TYPE: PRT
<213> ORGANISM: Mus musculus

<400> SEQUENCE: 67

Thr Ser Gly Leu Gly Val Gly
1               5

<210> SEQ ID NO 68
<211> LENGTH: 16
<212> TYPE: PRT
<213> ORGANISM: Mus musculus

```
<400> SEQUENCE: 68

His Ile Trp Trp Asp Asp Asp Lys Tyr Tyr Pro Pro Leu Lys Ser
1               5                   10                  15

<210> SEQ ID NO 69
<211> LENGTH: 13
<212> TYPE: PRT
<213> ORGANISM: Mus musculus

<400> SEQUENCE: 69

Arg Ala Phe Tyr Asp Gly Tyr Tyr Gly Pro Met Glu Tyr
1               5                   10

<210> SEQ ID NO 70
<211> LENGTH: 107
<212> TYPE: PRT
<213> ORGANISM: Artificial Sequence
<220> FEATURE:
<223> OTHER INFORMATION: Recombinant protein

<400> SEQUENCE: 70

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu His Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Ser Gly His Ser Phe Pro Tyr
                85                  90                  95

Thr Phe Gly Gln Gly Thr Lys Leu Glu Ile Lys
            100                 105

<210> SEQ ID NO 71
<211> LENGTH: 11
<212> TYPE: PRT
<213> ORGANISM: Artificial Sequence
<220> FEATURE:
<223> OTHER INFORMATION: Recombinant protein

<400> SEQUENCE: 71

Arg Ala Ser Gln Gly Val Ser Ser Tyr Leu His
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Recombinant protein

<400> SEQUENCE: 72

Tyr Ala Ser Gln Pro Ala Thr
1               5

<210> SEQ ID NO 73
<211> LENGTH: 9
<212> TYPE: PRT
<213> ORGANISM: Artificial Sequence
<220> FEATURE:
```

<223> OTHER INFORMATION: Recombinant protein

<400> SEQUENCE: 73

Gln Ser Gly His Ser Phe Pro Tyr Thr
1               5

<210> SEQ ID NO 74
<211> LENGTH: 122
<212> TYPE: PRT
<213> ORGANISM: Artificial Sequence
<220> FEATURE:
<223> OTHER INFORMATION: Recombinant protein

<400> SEQUENCE: 74

Asp Val Gln Leu Gln Glu Ser Gly Pro Gly Leu Val Glu Pro Ser Gln
1               5                   10                  15

Ser Leu Ser Leu Thr Cys Thr Val Thr Gly Tyr Ser Ile Thr Ser Asp
            20                  25                  30

Ser Ala Trp Ser Trp Ile Arg Gln Phe Pro Gly Asn Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Ile Ser Val Thr Arg Asp Thr Ser Lys Asn Gln Phe Phe
65                  70                  75                  80

Leu Arg Leu Ser Ser Val Thr Ala Glu Asp Thr Ala Thr Tyr Tyr Cys
                85                  90                  95

Thr Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 75
<211> LENGTH: 6
<212> TYPE: PRT
<213> ORGANISM: Artificial Sequence
<220> FEATURE:
<223> OTHER INFORMATION: Recombinant protein

<400> SEQUENCE: 75

Ser Asp Ser Ala Trp Ser
1               5

<210> SEQ ID NO 76
<211> LENGTH: 16
<212> TYPE: PRT
<213> ORGANISM: Artificial Sequence
<220> FEATURE:
<223> OTHER INFORMATION: Recombinant protein

<400> SEQUENCE: 76

Tyr Ile Gln Tyr Ser Gly Ser Thr Asn Tyr Asn Pro Ser Leu Lys Ser
1               5                   10                  15

<210> SEQ ID NO 77
<211> LENGTH: 13
<212> TYPE: PRT
<213> ORGANISM: Artificial Sequence
<220> FEATURE:
<223> OTHER INFORMATION: Recombinant protein

<400> SEQUENCE: 77

Ser Val Asn Tyr Tyr Gly Asn Ser Phe Ala Val Gly Tyr
1               5                   10

<210> SEQ ID NO 78
<211> LENGTH: 107
<212> TYPE: PRT
<213> ORGANISM: Artificial Sequence
<220> FEATURE:
<223> OTHER INFORMATION: Recombinant protein

<400> SEQUENCE: 78

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Ser Gly His Ser Phe Pro Leu
                85                  90                  95

Thr Phe Gly Ala Gly Thr Lys Leu Glu Leu Lys
            100                 105

<210> SEQ ID NO 79
<211> LENGTH: 11
<212> TYPE: PRT
<213> ORGANISM: Artificial Sequence
<220> FEATURE:
<223> OTHER INFORMATION: Recombinant protein

<400> SEQUENCE: 79

Arg Ala Ser Gln Gly Ile Ser Asp Tyr Leu His
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Recombinant protein

<400> SEQUENCE: 80

Tyr Thr Ser Gln Pro Ala Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Recombinant protein

<400> SEQUENCE: 81

Gln Ser Gly His Ser Phe Pro Leu Thr
1               5

<210> SEQ ID NO 82
<211> LENGTH: 122
<212> TYPE: PRT
<213> ORGANISM: Artificial Sequence
<220> FEATURE:
<223> OTHER INFORMATION: Recombinant protein

<400> SEQUENCE: 82

Asp Val Gln Leu Gln Glu Ser Gly Pro Gly Leu Val Glu Pro Ser Gln
1               5                   10                  15

Ser Leu Ser Leu Thr Cys Thr Val Thr Gly Tyr Ser Ile Thr Ser Asp
            20                  25                  30

Ser Ala Trp Ser Trp Ile Arg Gln Phe Pro Gly Asn Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Ile Ser Val Thr Arg Asp Thr Ser Lys Asn Gln Phe Phe
65                  70                  75                  80

Leu Arg Leu Ser Ser Val Thr Ala Glu Asp Thr Ala Thr Tyr Tyr Cys
                85                  90                  95

Thr Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 83
<211> LENGTH: 6
<212> TYPE: PRT
<213> ORGANISM: Artificial Sequence
<220> FEATURE:
<223> OTHER INFORMATION: Recombinant protein

<400> SEQUENCE: 83

Ser Asp Ser Ala Trp Ser
1               5

<210> SEQ ID NO 84
<211> LENGTH: 16
<212> TYPE: PRT
<213> ORGANISM: Artificial Sequence
<220> FEATURE:
<223> OTHER INFORMATION: Recombinant protein

<400> SEQUENCE: 84

Tyr Ile Gln Tyr Ser Gly Ser Thr Asn Tyr Asn Pro Ser Leu Lys Ser
1               5                   10                  15

<210> SEQ ID NO 85
<211> LENGTH: 13
<212> TYPE: PRT
<213> ORGANISM: Artificial Sequence
<220> FEATURE:
<223> OTHER INFORMATION: Recombinant protein

<400> SEQUENCE: 85

Ser Val Asn Tyr Tyr Gly Asn Ser Phe Ala Val Gly Tyr
1               5                   10

<210> SEQ ID NO 86
<211> LENGTH: 107
<212> TYPE: PRT
<213> ORGANISM: Artificial Sequence
<220> FEATURE:
<223> OTHER INFORMATION: Recombinant protein

<400> SEQUENCE: 86

Asp Ile Val Met Thr Gln Ser Pro Ala Thr Leu Ser Val Thr Ala Gly
1               5                   10                  15

Asp Arg Val Ser Leu Ser Cys Arg Ala Ser Gln Gly Ile Ser Asp Tyr

```
            20                  25                  30
Leu His Trp Tyr Gln Gln Lys Ser His Glu Ser Pro Arg Leu Leu Ile
            35                  40                  45

Lys Tyr Thr Ser Gln Pro Val Ser Gly Ile Pro Ser Arg Phe Ser Gly
        50                  55                  60

Ser Gly Ser Gly Ser Glu Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
                100                 105

<210> SEQ ID NO 87
<211> LENGTH: 11
<212> TYPE: PRT
<213> ORGANISM: Artificial Sequence
<220> FEATURE:
<223> OTHER INFORMATION: Recombinant protein

<400> SEQUENCE: 87

Arg Ala Ser Gln Gly Ile Ser Asp Tyr Leu His
1               5                   10

<210> SEQ ID NO 88
<211> LENGTH: 7
<212> TYPE: PRT
<213> ORGANISM: Artificial Sequence
<220> FEATURE:
<223> OTHER INFORMATION: Recombinant protein

<400> SEQUENCE: 88

Tyr Thr Ser Gln Pro Val Ser
1               5

<210> SEQ ID NO 89
<211> LENGTH: 9
<212> TYPE: PRT
<213> ORGANISM: Artificial Sequence
<220> FEATURE:
<223> OTHER INFORMATION: Recombinant protein

<400> SEQUENCE: 89

Gln Asn Gly His Ser Phe Pro Leu Thr
1               5

<210> SEQ ID NO 90
<211> LENGTH: 122
<212> TYPE: PRT
<213> ORGANISM: Artificial Sequence
<220> FEATURE:
<223> OTHER INFORMATION: Recombinant protein

<400> SEQUENCE: 90

Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
            35                  40                  45

Ile Gly Tyr Ile Gln Tyr Ser Gly Ser Thr Asn Tyr Asn Pro Ser Leu
        50                  55                  60

Lys Ser Arg Val Thr Ile Ser Arg Asp Thr Ser Lys Asn Gln Phe Ser
```

```
                65                  70                  75                  80
Leu Lys Leu Ser Ser Val Thr Ala Ala Asp Thr Ala Val Tyr Tyr Cys
                    85                  90                  95

Ala Arg Ser Val Asn Tyr Tyr Gly Asn Ser Phe Trp Val Asp Pro Trp
                100                 105                 110

Gly Gln Gly Thr Leu Val Thr Val Ser Ser
        115                 120

<210> SEQ ID NO 91
<211> LENGTH: 6
<212> TYPE: PRT
<213> ORGANISM: Artificial Sequence
<220> FEATURE:
<223> OTHER INFORMATION: Recombinant protein

<400> SEQUENCE: 91

Ser Asp Ser Ala Trp Ser
1               5

<210> SEQ ID NO 92
<211> LENGTH: 16
<212> TYPE: PRT
<213> ORGANISM: Artificial Sequence
<220> FEATURE:
<223> OTHER INFORMATION: Recombinant protein

<400> SEQUENCE: 92

Tyr Ile Gln Tyr Ser Gly Ser Thr Asn Tyr Asn Pro Ser Leu Lys Ser
1               5                   10                  15

<210> SEQ ID NO 93
<211> LENGTH: 13
<212> TYPE: PRT
<213> ORGANISM: Artificial Sequence
<220> FEATURE:
<223> OTHER INFORMATION: Recombinant protein

<400> SEQUENCE: 93

Ser Val Asn Tyr Tyr Gly Asn Ser Phe Trp Val Asp Pro
1               5                   10

<210> SEQ ID NO 94
<211> LENGTH: 107
<212> TYPE: PRT
<213> ORGANISM: Artificial Sequence
<220> FEATURE:
<223> OTHER INFORMATION: Recombinant protein

<400> SEQUENCE: 94

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
                20                  25                  30

Leu His Trp Tyr Gln Gln Lys Pro Gly Gln Ala Pro Arg Leu Leu Ile
            35                  40                  45

Lys Tyr Ala Ser Gln Pro Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Ser Gly His Ser Phe Pro Tyr
                85                  90                  95

Thr Phe Gly Gln Gly Thr Lys Leu Glu Ile Lys
```

<210> SEQ ID NO 95
<211> LENGTH: 11
<212> TYPE: PRT
<213> ORGANISM: Artificial Sequence
<220> FEATURE:
<223> OTHER INFORMATION: Recombinant protein

<400> SEQUENCE: 95

Arg Ala Ser Gln Gly Val Ser Ser Tyr Leu His
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Recombinant protein

<400> SEQUENCE: 96

Tyr Ala Ser Gln Pro Ala Thr
1               5

<210> SEQ ID NO 97
<211> LENGTH: 9
<212> TYPE: PRT
<213> ORGANISM: Artificial Sequence
<220> FEATURE:
<223> OTHER INFORMATION: Recombinant protein

<400> SEQUENCE: 97

Gln Ser Gly His Ser Phe Pro Tyr Thr
1               5

<210> SEQ ID NO 98
<211> LENGTH: 122
<212> TYPE: PRT
<213> ORGANISM: Artificial Sequence
<220> FEATURE:
<223> OTHER INFORMATION: Recombinant protein

<400> SEQUENCE: 98

Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
                20                  25                  30

Ser Ala Trp Ser Trp Ile Arg Gln Pro Pro Gly Lys Gly Leu Glu Trp
            35                  40                  45

Ile Gly Tyr Ile Gln Tyr Ser Gly Ser Thr Asn Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Trp Val Asp Pro Trp
                100                 105                 110

Gly Gln Gly Thr Leu Val Thr Val Ser Ser
            115                 120

<210> SEQ ID NO 99
<211> LENGTH: 6
<212> TYPE: PRT

<213> ORGANISM: Artificial Sequence
<220> FEATURE:
<223> OTHER INFORMATION: Recombinant protein

<400> SEQUENCE: 99

Ser Asp Ser Ala Trp Ser
1               5

<210> SEQ ID NO 100
<211> LENGTH: 16
<212> TYPE: PRT
<213> ORGANISM: Artificial Sequence
<220> FEATURE:
<223> OTHER INFORMATION: Recombinant protein

<400> SEQUENCE: 100

Tyr Ile Gln Tyr Ser Gly Ser Thr Asn Tyr Asn Pro Ser Leu Lys Ser
1               5                   10                  15

<210> SEQ ID NO 101
<211> LENGTH: 13
<212> TYPE: PRT
<213> ORGANISM: Artificial Sequence
<220> FEATURE:
<223> OTHER INFORMATION: Recombinant protein

<400> SEQUENCE: 101

Ser Val Asn Tyr Tyr Gly Asn Ser Phe Trp Val Asp Pro
1               5                   10

<210> SEQ ID NO 102
<211> LENGTH: 107
<212> TYPE: PRT
<213> ORGANISM: Artificial Sequence
<220> FEATURE:
<223> OTHER INFORMATION: Recombinant protein

<400> SEQUENCE: 102

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 103
<211> LENGTH: 11
<212> TYPE: PRT
<213> ORGANISM: Artificial Sequence
<220> FEATURE:
<223> OTHER INFORMATION: Recombinant protein

<400> SEQUENCE: 103

Arg Ala Ser Gln Gly Ile Ser Asp Tyr Leu His
1               5                   10

```
<210> SEQ ID NO 104
<211> LENGTH: 7
<212> TYPE: PRT
<213> ORGANISM: Artificial Sequence
<220> FEATURE:
<223> OTHER INFORMATION: Recombinant protein

<400> SEQUENCE: 104

Tyr Thr Ser Gln Pro Ala Thr
1               5

<210> SEQ ID NO 105
<211> LENGTH: 9
<212> TYPE: PRT
<213> ORGANISM: Artificial Sequence
<220> FEATURE:
<223> OTHER INFORMATION: Recombinant protein

<400> SEQUENCE: 105

Gln Asn Gly His Ser Phe Pro Leu Thr
1               5

<210> SEQ ID NO 106
<211> LENGTH: 122
<212> TYPE: PRT
<213> ORGANISM: Artificial Sequence
<220> FEATURE:
<223> OTHER INFORMATION: Recombinant protein

<400> SEQUENCE: 106

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Trp Val Gly Tyr Trp
            100                 105                 110

Gly Gln Gly Thr Ser Val Thr Val Ser Ser
        115                 120

<210> SEQ ID NO 107
<211> LENGTH: 6
<212> TYPE: PRT
<213> ORGANISM: Artificial Sequence
<220> FEATURE:
<223> OTHER INFORMATION: Recombinant protein

<400> SEQUENCE: 107

Ser Asp Ser Ala Trp Ser
1               5

<210> SEQ ID NO 108
<211> LENGTH: 16
<212> TYPE: PRT
<213> ORGANISM: Artificial Sequence
<220> FEATURE:
```

<223> OTHER INFORMATION: Recombinant protein

<400> SEQUENCE: 108

Tyr Ile Gln Tyr Ser Gly Ser Thr Asn Tyr Asn Pro Ser Leu Lys Ser
1               5                   10                  15

<210> SEQ ID NO 109
<211> LENGTH: 13
<212> TYPE: PRT
<213> ORGANISM: Artificial Sequence
<220> FEATURE:
<223> OTHER INFORMATION: Recombinant protein

<400> SEQUENCE: 109

Ser Val Asn Tyr Tyr Gly Asn Ser Phe Trp Val Gly Tyr
1               5                   10

<210> SEQ ID NO 110
<211> LENGTH: 107
<212> TYPE: PRT
<213> ORGANISM: Artificial Sequence
<220> FEATURE:
<223> OTHER INFORMATION: Recombinant protein

<400> SEQUENCE: 110

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
                20                  25                  30

Leu His Trp Tyr Gln Gln Lys Pro Gly Glu Ala Pro Arg Leu Leu Ile
            35                  40                  45

Lys Tyr Thr Ser Gln Pro Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 111
<211> LENGTH: 11
<212> TYPE: PRT
<213> ORGANISM: Artificial Sequence
<220> FEATURE:
<223> OTHER INFORMATION: Recombinant protein

<400> SEQUENCE: 111

Arg Ala Ser Gln Gly Ile Ser Asp Tyr Leu His
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Recombinant protein

<400> SEQUENCE: 112

Tyr Thr Ser Gln Pro Ala Thr
1               5

<210> SEQ ID NO 113

```
<211> LENGTH: 9
<212> TYPE: PRT
<213> ORGANISM: Artificial Sequence
<220> FEATURE:
<223> OTHER INFORMATION: Recombinant protein

<400> SEQUENCE: 113

Gln Asn Gly His Ser Phe Pro Leu Thr
 1               5

<210> SEQ ID NO 114
<211> LENGTH: 122
<212> TYPE: PRT
<213> ORGANISM: Artificial Sequence
<220> FEATURE:
<223> OTHER INFORMATION: Recombinant protein

<400> SEQUENCE: 114

Asp Val Gln Leu Gln Glu Ser Gly Pro Gly Leu Val Lys Pro Ser Gln
 1               5                  10                  15

Thr Leu Ser Leu Thr Cys Thr Val Ser Gly Tyr Ser Ile Thr Ser Asp
             20                  25                  30

Ser Ala Trp Ser Trp Ile Arg Gln Phe Pro Gly Lys Lys Leu Glu Trp
         35                  40                  45

Met Gly Tyr Ile Gln Tyr Ser Gly Ser Thr Asn Tyr Asn Pro Ser Leu
     50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Glu Asp Thr Ala Val Tyr Tyr Cys
                 85                  90                  95

Ala Arg Ser Val Asn Tyr Tyr Gly Asn Ser Phe Ala Val Gly Tyr Trp
             100                 105                 110

Gly Gln Gly Thr Ser Val Thr Val Ser Ser
            115                 120

<210> SEQ ID NO 115
<211> LENGTH: 6
<212> TYPE: PRT
<213> ORGANISM: Artificial Sequence
<220> FEATURE:
<223> OTHER INFORMATION: Recombinant protein

<400> SEQUENCE: 115

Ser Asp Ser Ala Trp Ser
 1               5

<210> SEQ ID NO 116
<211> LENGTH: 16
<212> TYPE: PRT
<213> ORGANISM: Artificial Sequence
<220> FEATURE:
<223> OTHER INFORMATION: Recombinant protein

<400> SEQUENCE: 116

Tyr Ile Gln Tyr Ser Gly Ser Thr Asn Tyr Asn Pro Ser Leu Lys Ser
 1               5                  10                  15

<210> SEQ ID NO 117
<211> LENGTH: 13
<212> TYPE: PRT
<213> ORGANISM: Artificial Sequence
<220> FEATURE:
<223> OTHER INFORMATION: Recombinant protein
```

```
<400> SEQUENCE: 117

Ser Val Asn Tyr Tyr Gly Asn Ser Phe Ala Val Gly Tyr
1               5                   10

<210> SEQ ID NO 118
<211> LENGTH: 107
<212> TYPE: PRT
<213> ORGANISM: Artificial Sequence
<220> FEATURE:
<223> OTHER INFORMATION: Recombinant protein

<400> SEQUENCE: 118

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 119
<211> LENGTH: 11
<212> TYPE: PRT
<213> ORGANISM: Artificial Sequence
<220> FEATURE:
<223> OTHER INFORMATION: Recombinant protein

<400> SEQUENCE: 119

Arg Ala Ser Gln Gly Ile Ser Asp Tyr Leu His
1               5                   10

<210> SEQ ID NO 120
<211> LENGTH: 7
<212> TYPE: PRT
<213> ORGANISM: Artificial Sequence
<220> FEATURE:
<223> OTHER INFORMATION: Recombinant protein

<400> SEQUENCE: 120

Tyr Thr Ser Gln Pro Ala Thr
1               5

<210> SEQ ID NO 121
<211> LENGTH: 9
<212> TYPE: PRT
<213> ORGANISM: Artificial Sequence
<220> FEATURE:
<223> OTHER INFORMATION: Recombinant protein

<400> SEQUENCE: 121

Gln Asn Gly His Ser Phe Pro Leu Thr
1               5

<210> SEQ ID NO 122
<211> LENGTH: 122
<212> TYPE: PRT
```

<213> ORGANISM: Artificial Sequence
<220> FEATURE:
<223> OTHER INFORMATION: Recombinant protein

<400> SEQUENCE: 122

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 123
<211> LENGTH: 6
<212> TYPE: PRT
<213> ORGANISM: Artificial Sequence
<220> FEATURE:
<223> OTHER INFORMATION: Recombinant protein

<400> SEQUENCE: 123

Ser Asp Ser Ala Trp Ser
1               5

<210> SEQ ID NO 124
<211> LENGTH: 16
<212> TYPE: PRT
<213> ORGANISM: Artificial Sequence
<220> FEATURE:
<223> OTHER INFORMATION: Recombinant protein

<400> SEQUENCE: 124

Tyr Ile Gln Tyr Ser Gly Ser Thr Asn Tyr Asn Pro Ser Leu Lys Ser
1               5                   10                  15

<210> SEQ ID NO 125
<211> LENGTH: 13
<212> TYPE: PRT
<213> ORGANISM: Artificial Sequence
<220> FEATURE:
<223> OTHER INFORMATION: Recombinant protein

<400> SEQUENCE: 125

Ser Val Asn Tyr Tyr Gly Asn Ser Phe Ala Val Gly Tyr
1               5                   10

<210> SEQ ID NO 126
<211> LENGTH: 107
<212> TYPE: PRT
<213> ORGANISM: Artificial Sequence
<220> FEATURE:
<223> OTHER INFORMATION: Recombinant protein

<400> SEQUENCE: 126

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105
```

<210> SEQ ID NO 127
<211> LENGTH: 11
<212> TYPE: PRT
<213> ORGANISM: Artificial Sequence
<220> FEATURE:
<223> OTHER INFORMATION: Recombinant protein

<400> SEQUENCE: 127

```
Arg Ala Ser Gln Gly Ile Ser Asp Tyr Leu His
1               5                   10
```

<210> SEQ ID NO 128
<211> LENGTH: 7
<212> TYPE: PRT
<213> ORGANISM: Artificial Sequence
<220> FEATURE:
<223> OTHER INFORMATION: Recombinant protein

<400> SEQUENCE: 128

```
Tyr Thr Ser Gln Pro Ala Thr
1               5
```

<210> SEQ ID NO 129
<211> LENGTH: 9
<212> TYPE: PRT
<213> ORGANISM: Artificial Sequence
<220> FEATURE:
<223> OTHER INFORMATION: Recombinant protein

<400> SEQUENCE: 129

```
Gln Asn Gly His Ser Phe Pro Leu Thr
1               5
```

<210> SEQ ID NO 130
<211> LENGTH: 122
<212> TYPE: PRT
<213> ORGANISM: Artificial Sequence
<220> FEATURE:
<223> OTHER INFORMATION: Recombinant protein

<400> SEQUENCE: 130

```
Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Pro Pro Gly Lys Lys Leu Glu Trp
        35                  40                  45
```

```
Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120
```

<210> SEQ ID NO 131
<211> LENGTH: 6
<212> TYPE: PRT
<213> ORGANISM: Artificial Sequence
<220> FEATURE:
<223> OTHER INFORMATION: Recombinant protein

<400> SEQUENCE: 131

```
Ser Asp Ser Ala Trp Ser
1               5
```

<210> SEQ ID NO 132
<211> LENGTH: 16
<212> TYPE: PRT
<213> ORGANISM: Artificial Sequence
<220> FEATURE:
<223> OTHER INFORMATION: Recombinant protein

<400> SEQUENCE: 132

```
Tyr Ile Gln Tyr Ser Gly Ser Thr Asn Tyr Asn Pro Ser Leu Lys Ser
1               5                   10                  15
```

<210> SEQ ID NO 133
<211> LENGTH: 13
<212> TYPE: PRT
<213> ORGANISM: Artificial Sequence
<220> FEATURE:
<223> OTHER INFORMATION: Recombinant protein

<400> SEQUENCE: 133

```
Ser Val Asn Tyr Tyr Gly Asn Ser Phe Ala Val Gly Tyr
1               5                   10
```

<210> SEQ ID NO 134
<211> LENGTH: 107
<212> TYPE: PRT
<213> ORGANISM: Artificial Sequence
<220> FEATURE:
<223> OTHER INFORMATION: Recombinant protein

<400> SEQUENCE: 134

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
                20                  25                  30

Leu His Trp Tyr Gln Gln Lys Pro Gly Glu Ala Pro Arg Leu Leu Ile
            35                  40                  45

Lys Tyr Thr Ser Gln Pro Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80
```

```
Glu Asp Val Gly Val Tyr Tyr Cys Gln Asn Gly His Ser Phe Pro Leu
                85                  90                  95
Thr Phe Gly Ala Gly Thr Lys Leu Glu Leu Lys
            100                 105

<210> SEQ ID NO 135
<211> LENGTH: 11
<212> TYPE: PRT
<213> ORGANISM: Artificial Sequence
<220> FEATURE:
<223> OTHER INFORMATION: Recombinant protein

<400> SEQUENCE: 135

Arg Ala Ser Gln Gly Ile Ser Asp Tyr Leu His
1               5                   10

<210> SEQ ID NO 136
<211> LENGTH: 7
<212> TYPE: PRT
<213> ORGANISM: Artificial Sequence
<220> FEATURE:
<223> OTHER INFORMATION: Recombinant protein

<400> SEQUENCE: 136

Tyr Thr Ser Gln Pro Ala Thr
1               5

<210> SEQ ID NO 137
<211> LENGTH: 9
<212> TYPE: PRT
<213> ORGANISM: Artificial Sequence
<220> FEATURE:
<223> OTHER INFORMATION: Recombinant protein

<400> SEQUENCE: 137

Gln Asn Gly His Ser Phe Pro Leu Thr
1               5

<210> SEQ ID NO 138
<211> LENGTH: 122
<212> TYPE: PRT
<213> ORGANISM: Artificial Sequence
<220> FEATURE:
<223> OTHER INFORMATION: Recombinant protein

<400> SEQUENCE: 138

Asp Val Gln Leu Gln Glu Ser Gly Pro Gly Leu Val Glu Pro Ser Gln
1               5                   10                  15
Thr Leu Ser Leu Thr Cys Thr Val Ser Gly Tyr Ser Ile Thr Ser Asp
            20                  25                  30
Ser Ala Trp Ser Trp Ile Arg Gln Phe Pro Gly Lys Lys Leu Glu Trp
        35                  40                  45
Met Gly Tyr Ile Gln Tyr Ser Gly Ser Thr Asn Tyr Asn Pro Ser Leu
    50                  55                  60
Lys Ser Arg Val Thr Ile Ser Arg Asp Thr Ser Lys Asn Gln Phe Ser
65                  70                  75                  80
Leu Lys Leu Ser Ser Val Thr Ala Glu Asp Thr Ala Val Tyr Tyr Cys
                85                  90                  95
Ala Arg Ser Val Asn Tyr Tyr Gly Asn Ser Phe Ala Val Asp Tyr Trp
            100                 105                 110
Gly Gln Gly Thr Ser Val Thr Val Ser Ser
        115                 120
```

<210> SEQ ID NO 139
<211> LENGTH: 6
<212> TYPE: PRT
<213> ORGANISM: Artificial Sequence
<220> FEATURE:
<223> OTHER INFORMATION: Recombinant protein

<400> SEQUENCE: 139

Ser Asp Ser Ala Trp Ser
1               5

<210> SEQ ID NO 140
<211> LENGTH: 16
<212> TYPE: PRT
<213> ORGANISM: Artificial Sequence
<220> FEATURE:
<223> OTHER INFORMATION: Recombinant protein

<400> SEQUENCE: 140

Tyr Ile Gln Tyr Ser Gly Ser Thr Asn Tyr Asn Pro Ser Leu Lys Ser
1               5                   10                  15

<210> SEQ ID NO 141
<211> LENGTH: 13
<212> TYPE: PRT
<213> ORGANISM: Artificial Sequence
<220> FEATURE:
<223> OTHER INFORMATION: Recombinant protein

<400> SEQUENCE: 141

Ser Val Asn Tyr Tyr Gly Asn Ser Phe Ala Val Asp Tyr
1               5                   10

<210> SEQ ID NO 142
<211> LENGTH: 107
<212> TYPE: PRT
<213> ORGANISM: Artificial Sequence
<220> FEATURE:
<223> OTHER INFORMATION: Recombinant protein

<400> SEQUENCE: 142

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 143
<211> LENGTH: 11
<212> TYPE: PRT
<213> ORGANISM: Artificial Sequence
<220> FEATURE:
<223> OTHER INFORMATION: Recombinant protein

<400> SEQUENCE: 143

Arg Ala Ser Gln Gly Ile Ser Asp Tyr Leu His
1               5                   10

<210> SEQ ID NO 144
<211> LENGTH: 7
<212> TYPE: PRT
<213> ORGANISM: Artificial Sequence
<220> FEATURE:
<223> OTHER INFORMATION: Recombinant protein

<400> SEQUENCE: 144

Tyr Thr Ser Gln Pro Ala Thr
1               5

<210> SEQ ID NO 145
<211> LENGTH: 9
<212> TYPE: PRT
<213> ORGANISM: Artificial Sequence
<220> FEATURE:
<223> OTHER INFORMATION: Recombinant protein

<400> SEQUENCE: 145

Gln Asn Gly His Ser Phe Pro Leu Thr
1               5

<210> SEQ ID NO 146
<211> LENGTH: 122
<212> TYPE: PRT
<213> ORGANISM: Artificial Sequence
<220> FEATURE:
<223> OTHER INFORMATION: Recombinant protein

<400> SEQUENCE: 146

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
                20                  25                  30

Ser Ala Trp Ser Trp Ile Arg Gln Phe Pro Gly Lys Gly Leu Glu Trp
            35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
                100                 105                 110

Gly Gln Gly Thr Ser Val Thr Val Ser Ser
            115                 120

<210> SEQ ID NO 147
<211> LENGTH: 6
<212> TYPE: PRT
<213> ORGANISM: Artificial Sequence
<220> FEATURE:
<223> OTHER INFORMATION: Recombinant protein

<400> SEQUENCE: 147

Ser Asp Ser Ala Trp Ser
1               5

<210> SEQ ID NO 148

```
<211> LENGTH: 16
<212> TYPE: PRT
<213> ORGANISM: Artificial Sequence
<220> FEATURE:
<223> OTHER INFORMATION: Recombinant protein

<400> SEQUENCE: 148

Tyr Ile Gln Tyr Ser Gly Ser Thr Asn Tyr Asn Pro Ser Leu Lys Ser
1               5                   10                  15

<210> SEQ ID NO 149
<211> LENGTH: 13
<212> TYPE: PRT
<213> ORGANISM: Artificial Sequence
<220> FEATURE:
<223> OTHER INFORMATION: Recombinant protein

<400> SEQUENCE: 149

Ser Val Asn Tyr Tyr Gly Asn Ser Phe Ala Val Gly Tyr
1               5                   10

<210> SEQ ID NO 150
<211> LENGTH: 107
<212> TYPE: PRT
<213> ORGANISM: Artificial Sequence
<220> FEATURE:
<223> OTHER INFORMATION: Recombinant protein

<400> SEQUENCE: 150

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 151
<211> LENGTH: 11
<212> TYPE: PRT
<213> ORGANISM: Artificial Sequence
<220> FEATURE:
<223> OTHER INFORMATION: Recombinant protein

<400> SEQUENCE: 151

Arg Ala Ser Gln Gly Ile Ser Asp Tyr Leu His
1               5                   10

<210> SEQ ID NO 152
<211> LENGTH: 7
<212> TYPE: PRT
<213> ORGANISM: Artificial Sequence
<220> FEATURE:
<223> OTHER INFORMATION: Recombinant protein

<400> SEQUENCE: 152

Tyr Thr Ser Gln Pro Ala Thr
1               5
```

```
1               5

<210> SEQ ID NO 153
<211> LENGTH: 9
<212> TYPE: PRT
<213> ORGANISM: Artificial Sequence
<220> FEATURE:
<223> OTHER INFORMATION: Recombinant protein

<400> SEQUENCE: 153

Gln Asn Gly His Ser Phe Pro Leu Thr
1               5

<210> SEQ ID NO 154
<211> LENGTH: 122
<212> TYPE: PRT
<213> ORGANISM: Artificial Sequence
<220> FEATURE:
<223> OTHER INFORMATION: Recombinant protein

<400> SEQUENCE: 154

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 155
<211> LENGTH: 6
<212> TYPE: PRT
<213> ORGANISM: Artificial Sequence
<220> FEATURE:
<223> OTHER INFORMATION: Recombinant protein

<400> SEQUENCE: 155

Ser Asp Ser Ala Trp Ser
1               5

<210> SEQ ID NO 156
<211> LENGTH: 16
<212> TYPE: PRT
<213> ORGANISM: Artificial Sequence
<220> FEATURE:
<223> OTHER INFORMATION: Recombinant protein

<400> SEQUENCE: 156

Tyr Ile Gln Tyr Ser Gly Ser Thr Asn Tyr Asn Pro Ser Leu Lys Ser
1               5                   10                  15

<210> SEQ ID NO 157
<211> LENGTH: 13
<212> TYPE: PRT
```

```
<213> ORGANISM: Artificial Sequence
<220> FEATURE:
<223> OTHER INFORMATION: Recombinant protein

<400> SEQUENCE: 157

Ser Val Asn Tyr Tyr Gly Asn Ser Phe Ala Val Gly Tyr
1               5                   10

<210> SEQ ID NO 158
<211> LENGTH: 107
<212> TYPE: PRT
<213> ORGANISM: Artificial Sequence
<220> FEATURE:
<223> OTHER INFORMATION: Recombinant protein

<400> SEQUENCE: 158

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 159
<211> LENGTH: 11
<212> TYPE: PRT
<213> ORGANISM: Artificial Sequence
<220> FEATURE:
<223> OTHER INFORMATION: Recombinant protein

<400> SEQUENCE: 159

Arg Ala Ser Gln Gly Ile Ser Asp Tyr Leu His
1               5                   10

<210> SEQ ID NO 160
<211> LENGTH: 7
<212> TYPE: PRT
<213> ORGANISM: Artificial Sequence
<220> FEATURE:
<223> OTHER INFORMATION: Recombinant protein

<400> SEQUENCE: 160

Tyr Thr Ser Gln Pro Ala Thr
1               5

<210> SEQ ID NO 161
<211> LENGTH: 9
<212> TYPE: PRT
<213> ORGANISM: Artificial Sequence
<220> FEATURE:
<223> OTHER INFORMATION: Recombinant protein

<400> SEQUENCE: 161

Gln Asn Gly His Ser Phe Pro Leu Thr
1               5
```

```
<210> SEQ ID NO 162
<211> LENGTH: 122
<212> TYPE: PRT
<213> ORGANISM: Artificial Sequence
<220> FEATURE:
<223> OTHER INFORMATION: Recombinant protein

<400> SEQUENCE: 162

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120

<210> SEQ ID NO 163
<211> LENGTH: 6
<212> TYPE: PRT
<213> ORGANISM: Artificial Sequence
<220> FEATURE:
<223> OTHER INFORMATION: Recombinant protein

<400> SEQUENCE: 163

Ser Asp Ser Ala Trp Ser
1               5

<210> SEQ ID NO 164
<211> LENGTH: 16
<212> TYPE: PRT
<213> ORGANISM: Artificial Sequence
<220> FEATURE:
<223> OTHER INFORMATION: Recombinant protein

<400> SEQUENCE: 164

Tyr Ile Gln Tyr Ser Gly Ser Thr Asn Tyr Asn Pro Ser Leu Lys Ser
1               5                   10                  15

<210> SEQ ID NO 165
<211> LENGTH: 13
<212> TYPE: PRT
<213> ORGANISM: Artificial Sequence
<220> FEATURE:
<223> OTHER INFORMATION: Recombinant protein

<400> SEQUENCE: 165

Ser Val Asn Tyr Tyr Gly Asn Ser Phe Ala Val Gly Tyr
1               5                   10

<210> SEQ ID NO 166
<211> LENGTH: 107
<212> TYPE: PRT
<213> ORGANISM: Artificial Sequence
<220> FEATURE:
```

<223> OTHER INFORMATION: Recombinant protein

<400> SEQUENCE: 166

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Gly Ile Ser Asp Tyr
            20                  25                  30
Leu His Trp Tyr Gln Gln Lys Pro Gly Glu Ala Pro Arg Leu Leu Ile
        35                  40                  45
Lys Tyr Thr Ser Gln Pro Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Val Gly Val Tyr Tyr Cys Gln Asn Gly His Ser Phe Pro Leu
                85                  90                  95
Thr Phe Gly Ala Gly Thr Lys Leu Glu Leu Lys
            100                 105
```

<210> SEQ ID NO 167
<211> LENGTH: 11
<212> TYPE: PRT
<213> ORGANISM: Artificial Sequence
<220> FEATURE:
<223> OTHER INFORMATION: Recombinant protein

<400> SEQUENCE: 167

```
Arg Ala Ser Gln Gly Ile Ser Asp Tyr Leu His
1               5                   10
```

<210> SEQ ID NO 168
<211> LENGTH: 7
<212> TYPE: PRT
<213> ORGANISM: Artificial Sequence
<220> FEATURE:
<223> OTHER INFORMATION: Recombinant protein

<400> SEQUENCE: 168

```
Tyr Thr Ser Gln Pro Ala Thr
1               5
```

<210> SEQ ID NO 169
<211> LENGTH: 9
<212> TYPE: PRT
<213> ORGANISM: Artificial Sequence
<220> FEATURE:
<223> OTHER INFORMATION: Recombinant protein

<400> SEQUENCE: 169

```
Gln Asn Gly His Ser Phe Pro Leu Thr
1               5
```

<210> SEQ ID NO 170
<211> LENGTH: 122
<212> TYPE: PRT
<213> ORGANISM: Artificial Sequence
<220> FEATURE:
<223> OTHER INFORMATION: Recombinant protein

<400> SEQUENCE: 170

```
Asp Val Gln Leu Gln Glu Ser Gly Pro Gly Leu Val Glu Pro Ser Gln
1               5                   10                  15
Thr Leu Ser Leu Thr Cys Thr Val Ser Gly Tyr Ser Ile Ser Ser Asp
            20                  25                  30
```

```
Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
 50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Glu Asp Thr Ala Val Tyr Tyr Cys
                 85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
            115                 120

<210> SEQ ID NO 171
<211> LENGTH: 6
<212> TYPE: PRT
<213> ORGANISM: Artificial Sequence
<220> FEATURE:
<223> OTHER INFORMATION: Recombinant protein

<400> SEQUENCE: 171

Ser Asp Ser Ala Trp Ser
1               5

<210> SEQ ID NO 172
<211> LENGTH: 16
<212> TYPE: PRT
<213> ORGANISM: Artificial Sequence
<220> FEATURE:
<223> OTHER INFORMATION: Recombinant protein

<400> SEQUENCE: 172

Tyr Ile Gln Tyr Ser Gly Ser Thr Asn Tyr Asn Pro Ser Leu Lys Ser
1               5                   10                  15

<210> SEQ ID NO 173
<211> LENGTH: 13
<212> TYPE: PRT
<213> ORGANISM: Artificial Sequence
<220> FEATURE:
<223> OTHER INFORMATION: Recombinant protein

<400> SEQUENCE: 173

Ser Val Asn Tyr Tyr Gly Asn Ser Phe Ala Val Gly Tyr
1               5                   10

<210> SEQ ID NO 174
<211> LENGTH: 107
<212> TYPE: PRT
<213> ORGANISM: Artificial Sequence
<220> FEATURE:
<223> OTHER INFORMATION: Recombinant protein

<400> SEQUENCE: 174

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
             20                  25                  30

Leu His Trp Tyr Gln Gln Lys Pro Gly Glu Ala Pro Arg Leu Leu Ile
         35                  40                  45

Lys Tyr Thr Ser Gln Pro Ala Thr Gly Ile Pro Ala Arg Phe Ser Gly
 50                  55                  60
```

```
Ser Gly Ser Gly Thr Asp Phe Thr Leu Thr Ile Ser Ser Leu Glu Pro
 65                  70                  75                  80

Glu Asp Val Gly Val Tyr Tyr Cys Gln Asn Gly His Ser Phe Pro Leu
                 85                  90                  95

Thr Phe Gly Ala Gly Thr Lys Leu Glu Leu Lys
            100                 105

<210> SEQ ID NO 175
<211> LENGTH: 11
<212> TYPE: PRT
<213> ORGANISM: Artificial Sequence
<220> FEATURE:
<223> OTHER INFORMATION: Recombinant protein

<400> SEQUENCE: 175

Arg Ala Ser Gln Gly Ile Ser Asp Tyr Leu His
 1               5                  10

<210> SEQ ID NO 176
<211> LENGTH: 7
<212> TYPE: PRT
<213> ORGANISM: Artificial Sequence
<220> FEATURE:
<223> OTHER INFORMATION: Recombinant protein

<400> SEQUENCE: 176

Tyr Thr Ser Gln Pro Ala Thr
 1               5

<210> SEQ ID NO 177
<211> LENGTH: 9
<212> TYPE: PRT
<213> ORGANISM: Artificial Sequence
<220> FEATURE:
<223> OTHER INFORMATION: Recombinant protein

<400> SEQUENCE: 177

Gln Asn Gly His Ser Phe Pro Leu Thr
 1               5

<210> SEQ ID NO 178
<211> LENGTH: 122
<212> TYPE: PRT
<213> ORGANISM: Artificial Sequence
<220> FEATURE:
<223> OTHER INFORMATION: Recombinant protein

<400> SEQUENCE: 178

Asp Val Gln Leu Gln Glu Ser Gly Pro Gly Leu Val Glu Pro Ser Gln
 1               5                  10                  15

Thr Leu Ser Leu Thr Cys Thr Val Ser Gly Tyr Ser Ile Thr Ser Asp
                 20                  25                  30

Ser Ala Trp Ser Trp Ile Arg Gln Phe Pro Gly Lys Lys Leu Glu Trp
             35                  40                  45

Met Gly Tyr Ile Gln Tyr Ser Gly Ser Thr Asn Tyr Asn Pro Ser Leu
         50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Glu Asp Thr Ala Val Tyr Tyr Cys
                 85                  90                  95

Ala Arg Ser Val Asn Tyr Tyr Gly Asn Ser Phe Ala Val Gly Pro Trp
                100                 105                 110
```

```
Gly Gln Gly Thr Ser Val Thr Val Ser Ser
        115                 120

<210> SEQ ID NO 179
<211> LENGTH: 6
<212> TYPE: PRT
<213> ORGANISM: Artificial Sequence
<220> FEATURE:
<223> OTHER INFORMATION: Recombinant protein

<400> SEQUENCE: 179

Ser Asp Ser Ala Trp Ser
1               5

<210> SEQ ID NO 180
<211> LENGTH: 16
<212> TYPE: PRT
<213> ORGANISM: Artificial Sequence
<220> FEATURE:
<223> OTHER INFORMATION: Recombinant protein

<400> SEQUENCE: 180

Tyr Ile Gln Tyr Ser Gly Ser Thr Asn Tyr Asn Pro Ser Leu Lys Ser
1               5                   10                  15

<210> SEQ ID NO 181
<211> LENGTH: 13
<212> TYPE: PRT
<213> ORGANISM: Artificial Sequence
<220> FEATURE:
<223> OTHER INFORMATION: Recombinant protein

<400> SEQUENCE: 181

Ser Val Asn Tyr Tyr Gly Asn Ser Phe Ala Val Gly Pro
1               5                   10

<210> SEQ ID NO 182
<211> LENGTH: 107
<212> TYPE: PRT
<213> ORGANISM: Artificial Sequence
<220> FEATURE:
<223> OTHER INFORMATION: Recombinant protein

<400> SEQUENCE: 182

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Gln Gly Thr Lys Leu Glu Leu Lys
            100                 105

<210> SEQ ID NO 183
<211> LENGTH: 11
<212> TYPE: PRT
<213> ORGANISM: Artificial Sequence
```

```
<220> FEATURE:
<223> OTHER INFORMATION: Recombinant protein

<400> SEQUENCE: 183

Arg Ala Ser Gln Gly Ile Ser Asp Tyr Leu His
1               5                   10

<210> SEQ ID NO 184
<211> LENGTH: 7
<212> TYPE: PRT
<213> ORGANISM: Artificial Sequence
<220> FEATURE:
<223> OTHER INFORMATION: Recombinant protein

<400> SEQUENCE: 184

Tyr Thr Ser Gln Pro Ala Thr
1               5

<210> SEQ ID NO 185
<211> LENGTH: 9
<212> TYPE: PRT
<213> ORGANISM: Artificial Sequence
<220> FEATURE:
<223> OTHER INFORMATION: Recombinant protein

<400> SEQUENCE: 185

Gln Asn Gly His Ser Phe Pro Leu Thr
1               5

<210> SEQ ID NO 186
<211> LENGTH: 122
<212> TYPE: PRT
<213> ORGANISM: Artificial Sequence
<220> FEATURE:
<223> OTHER INFORMATION: Recombinant protein

<400> SEQUENCE: 186

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 187
<211> LENGTH: 6
<212> TYPE: PRT
<213> ORGANISM: Artificial Sequence
<220> FEATURE:
<223> OTHER INFORMATION: Recombinant protein

<400> SEQUENCE: 187

Ser Asp Ser Ala Trp Ser
```

```
<210> SEQ ID NO 188
<211> LENGTH: 16
<212> TYPE: PRT
<213> ORGANISM: Artificial Sequence
<220> FEATURE:
<223> OTHER INFORMATION: Recombinant protein

<400> SEQUENCE: 188

Tyr Ile Gln Tyr Ser Gly Ser Thr Asn Tyr Asn Pro Ser Leu Lys Ser
1               5                   10                  15

<210> SEQ ID NO 189
<211> LENGTH: 13
<212> TYPE: PRT
<213> ORGANISM: Artificial Sequence
<220> FEATURE:
<223> OTHER INFORMATION: Recombinant protein

<400> SEQUENCE: 189

Ser Val Asn Tyr Tyr Gly Asn Ser Phe Ala Val Gly Tyr
1               5                   10

<210> SEQ ID NO 190
<211> LENGTH: 107
<212> TYPE: PRT
<213> ORGANISM: Artificial Sequence
<220> FEATURE:
<223> OTHER INFORMATION: Recombinant protein

<400> SEQUENCE: 190

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Ser Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 191
<211> LENGTH: 11
<212> TYPE: PRT
<213> ORGANISM: Artificial Sequence
<220> FEATURE:
<223> OTHER INFORMATION: Recombinant protein

<400> SEQUENCE: 191

Arg Ala Ser Gln Gly Ile Ser Ser Tyr Leu His
1               5                   10

<210> SEQ ID NO 192
<211> LENGTH: 7
<212> TYPE: PRT
<213> ORGANISM: Artificial Sequence
<220> FEATURE:
<223> OTHER INFORMATION: Recombinant protein
```

<400> SEQUENCE: 192

Tyr Thr Ser Gln Pro Ala Thr
1               5

<210> SEQ ID NO 193
<211> LENGTH: 9
<212> TYPE: PRT
<213> ORGANISM: Artificial Sequence
<220> FEATURE:
<223> OTHER INFORMATION: Recombinant protein

<400> SEQUENCE: 193

Gln Asn Gly His Ser Phe Pro Leu Thr
1               5

<210> SEQ ID NO 194
<211> LENGTH: 122
<212> TYPE: PRT
<213> ORGANISM: Artificial Sequence
<220> FEATURE:
<223> OTHER INFORMATION: Recombinant protein

<400> SEQUENCE: 194

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 195
<211> LENGTH: 6
<212> TYPE: PRT
<213> ORGANISM: Artificial Sequence
<220> FEATURE:
<223> OTHER INFORMATION: Recombinant protein

<400> SEQUENCE: 195

Ser Asp Ser Ala Trp Ser
1               5

<210> SEQ ID NO 196
<211> LENGTH: 16
<212> TYPE: PRT
<213> ORGANISM: Artificial Sequence
<220> FEATURE:
<223> OTHER INFORMATION: Recombinant protein

<400> SEQUENCE: 196

Tyr Ile Gln Tyr Ser Gly Ser Thr Asn Tyr Asn Pro Ser Leu Lys Ser
1               5                   10                  15

-continued

```
<210> SEQ ID NO 197
<211> LENGTH: 13
<212> TYPE: PRT
<213> ORGANISM: Artificial Sequence
<220> FEATURE:
<223> OTHER INFORMATION: Recombinant protein

<400> SEQUENCE: 197

Ser Val Asn Tyr Tyr Gly Asn Ser Phe Ala Val Gly Tyr
1               5                   10

<210> SEQ ID NO 198
<211> LENGTH: 107
<212> TYPE: PRT
<213> ORGANISM: Artificial Sequence
<220> FEATURE:
<223> OTHER INFORMATION: Recombinant protein

<400> SEQUENCE: 198

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Gln Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 199
<211> LENGTH: 11
<212> TYPE: PRT
<213> ORGANISM: Artificial Sequence
<220> FEATURE:
<223> OTHER INFORMATION: Recombinant protein

<400> SEQUENCE: 199

Arg Ala Ser Gln Gly Ile Ser Asp Tyr Leu His
1               5                   10

<210> SEQ ID NO 200
<211> LENGTH: 7
<212> TYPE: PRT
<213> ORGANISM: Artificial Sequence
<220> FEATURE:
<223> OTHER INFORMATION: Recombinant protein

<400> SEQUENCE: 200

Tyr Thr Ser Gln Pro Ala Thr
1               5

<210> SEQ ID NO 201
<211> LENGTH: 9
<212> TYPE: PRT
<213> ORGANISM: Artificial Sequence
<220> FEATURE:
<223> OTHER INFORMATION: Recombinant protein

<400> SEQUENCE: 201
```

```
<210> SEQ ID NO 202
<211> LENGTH: 122
<212> TYPE: PRT
<213> ORGANISM: Artificial Sequence
<220> FEATURE:
<223> OTHER INFORMATION: Recombinant protein

<400> SEQUENCE: 202

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 203
<211> LENGTH: 6
<212> TYPE: PRT
<213> ORGANISM: Artificial Sequence
<220> FEATURE:
<223> OTHER INFORMATION: Recombinant protein

<400> SEQUENCE: 203

Ser Asp Ser Ala Trp Ser
1               5

<210> SEQ ID NO 204
<211> LENGTH: 16
<212> TYPE: PRT
<213> ORGANISM: Artificial Sequence
<220> FEATURE:
<223> OTHER INFORMATION: Recombinant protein

<400> SEQUENCE: 204

Tyr Ile Gln Tyr Ser Gly Ser Thr Asn Tyr Asn Pro Ser Leu Lys Ser
1               5                   10                  15

<210> SEQ ID NO 205
<211> LENGTH: 13
<212> TYPE: PRT
<213> ORGANISM: Artificial Sequence
<220> FEATURE:
<223> OTHER INFORMATION: Recombinant protein

<400> SEQUENCE: 205

Ser Val Asn Tyr Tyr Gly Asn Ser Phe Ala Val Gly Tyr
1               5                   10

<210> SEQ ID NO 206
```

(Preceding sequence fragment)

```
Gln Asn Gly His Ser Phe Pro Leu Thr
1               5
```

```
<211> LENGTH: 107
<212> TYPE: PRT
<213> ORGANISM: Artificial Sequence
<220> FEATURE:
<223> OTHER INFORMATION: Recombinant protein

<400> SEQUENCE: 206

Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Ala Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 207
<211> LENGTH: 11
<212> TYPE: PRT
<213> ORGANISM: Artificial Sequence
<220> FEATURE:
<223> OTHER INFORMATION: Recombinant protein

<400> SEQUENCE: 207

Arg Ala Ser Gln Gly Ile Ser Asp Tyr Leu His
1               5                  10

<210> SEQ ID NO 208
<211> LENGTH: 7
<212> TYPE: PRT
<213> ORGANISM: Artificial Sequence
<220> FEATURE:
<223> OTHER INFORMATION: Recombinant protein

<400> SEQUENCE: 208

Tyr Thr Ser Gln Pro Ala Thr
1               5

<210> SEQ ID NO 209
<211> LENGTH: 9
<212> TYPE: PRT
<213> ORGANISM: Artificial Sequence
<220> FEATURE:
<223> OTHER INFORMATION: Recombinant protein

<400> SEQUENCE: 209

Gln Asn Gly His Ser Phe Pro Leu Thr
1               5

<210> SEQ ID NO 210
<211> LENGTH: 122
<212> TYPE: PRT
<213> ORGANISM: Artificial Sequence
<220> FEATURE:
<223> OTHER INFORMATION: Recombinant protein

<400> SEQUENCE: 210

Asp Val Gln Leu Gln Glu Ser Gly Pro Gly Leu Val Glu Pro Ser Gln
```

```
                1               5                   10                  15
            Thr Leu Ser Leu Thr Cys Thr Val Ser Gly Tyr Ser Ile Thr Ser Asp
                            20                  25                  30

Ser Ala Trp Ser Trp Ile Arg Gln Phe Pro Gly Lys Lys Leu Glu Trp
                        35                  40                  45

Met Gly Tyr Ile Gln Tyr Ser Gly Ser Thr Asn Tyr Asn Pro Ser Leu
                    50                  55                  60

Lys Ser Arg Val Thr Ile Ser Arg Asp Thr Ser Lys Asn Gln Phe Ser
            65                  70                  75                  80

Leu Lys Leu Ser Ser Val Thr Ala Glu Asp Thr Ala Val Tyr Tyr Cys
                            85                  90                  95

Ala Arg Ser Val Asn Tyr Tyr Gly Asn Ser Phe Ala Val Gly Tyr Trp
                        100                 105                 110

Gly Gln Gly Thr Ser Val Thr Val Ser Ser
                    115                 120
```

<210> SEQ ID NO 211
<211> LENGTH: 6
<212> TYPE: PRT
<213> ORGANISM: Artificial Sequence
<220> FEATURE:
<223> OTHER INFORMATION: Recombinant protein

<400> SEQUENCE: 211

```
            Ser Asp Ser Ala Trp Ser
            1               5
```

<210> SEQ ID NO 212
<211> LENGTH: 16
<212> TYPE: PRT
<213> ORGANISM: Artificial Sequence
<220> FEATURE:
<223> OTHER INFORMATION: Recombinant protein

<400> SEQUENCE: 212

```
            Tyr Ile Gln Tyr Ser Gly Ser Thr Asn Tyr Asn Pro Ser Leu Lys Ser
            1               5                   10                  15
```

<210> SEQ ID NO 213
<211> LENGTH: 13
<212> TYPE: PRT
<213> ORGANISM: Artificial Sequence
<220> FEATURE:
<223> OTHER INFORMATION: Recombinant protein

<400> SEQUENCE: 213

```
            Ser Val Asn Tyr Tyr Gly Asn Ser Phe Ala Val Gly Tyr
            1               5                   10
```

<210> SEQ ID NO 214
<211> LENGTH: 107
<212> TYPE: PRT
<213> ORGANISM: Artificial Sequence
<220> FEATURE:
<223> OTHER INFORMATION: Recombinant protein

<400> SEQUENCE: 214

```
            Glu Ile Val Leu Thr Gln Ser Pro Ala Thr Leu Ser Leu Ser Pro Gly
            1               5                   10                  15

Glu Arg Ala Thr Leu Ser Cys Arg Ala Ser Gln Gly Val Ser Asp Tyr
                            20                  25                  30

Leu His Trp Tyr Gln Gln Lys Pro Gly Glu Ala Pro Arg Leu Leu Ile
```

```
                35                  40                  45
Lys Tyr Thr Ser Gln Pro Ala Thr Gly Ile Pro Ala Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Val Gly Val Tyr Tyr Cys Gln Asn Gly His Ser Phe Pro Leu
                 85                  90                  95
Thr Phe Gly Ala Gly Thr Lys Leu Glu Leu Lys
            100                 105

<210> SEQ ID NO 215
<211> LENGTH: 11
<212> TYPE: PRT
<213> ORGANISM: Artificial Sequence
<220> FEATURE:
<223> OTHER INFORMATION: Recombinant protein

<400> SEQUENCE: 215

Arg Ala Ser Gln Gly Val Ser Asp Tyr Leu His
 1               5                  10

<210> SEQ ID NO 216
<211> LENGTH: 7
<212> TYPE: PRT
<213> ORGANISM: Artificial Sequence
<220> FEATURE:
<223> OTHER INFORMATION: Recombinant protein

<400> SEQUENCE: 216

Tyr Thr Ser Gln Pro Ala Thr
 1               5

<210> SEQ ID NO 217
<211> LENGTH: 9
<212> TYPE: PRT
<213> ORGANISM: Artificial Sequence
<220> FEATURE:
<223> OTHER INFORMATION: Recombinant protein

<400> SEQUENCE: 217

Gln Asn Gly His Ser Phe Pro Leu Thr
 1               5

<210> SEQ ID NO 218
<211> LENGTH: 122
<212> TYPE: PRT
<213> ORGANISM: Artificial Sequence
<220> FEATURE:
<223> OTHER INFORMATION: Recombinant protein

<400> SEQUENCE: 218

Asp Val Gln Leu Gln Glu Ser Gly Pro Gly Leu Val Glu Pro Ser Gln
 1               5                  10                  15
Thr Leu Ser Leu Thr Cys Thr Val Ser Gly Tyr Ser Ile Thr Ser Asp
                 20                  25                  30
Ser Ala Trp Ser Trp Ile Arg Gln Phe Pro Gly Lys Lys Leu Glu Trp
             35                  40                  45
Met Gly Tyr Ile Gln Tyr Ser Gly Ser Thr Asn Tyr Asn Pro Ser Leu
         50                  55                  60
Lys Ser Arg Val Thr Ile Ser Arg Asp Thr Ser Lys Asn Gln Phe Ser
 65                  70                  75                  80
Leu Lys Leu Ser Ser Val Thr Ala Glu Asp Thr Ala Val Tyr Tyr Cys
```

```
                        85                  90                  95
Ala Arg Ser Val Asn Tyr Tyr Gly Asn Ser Phe Ala Val Gly Tyr Trp
                100                 105                 110

Gly Gln Gly Thr Ser Val Thr Val Ser Ser
        115                 120
```

<210> SEQ ID NO 219
<211> LENGTH: 6
<212> TYPE: PRT
<213> ORGANISM: Artificial Sequence
<220> FEATURE:
<223> OTHER INFORMATION: Recombinant protein

<400> SEQUENCE: 219

```
Ser Asp Ser Ala Trp Ser
1               5
```

<210> SEQ ID NO 220
<211> LENGTH: 16
<212> TYPE: PRT
<213> ORGANISM: Artificial Sequence
<220> FEATURE:
<223> OTHER INFORMATION: Recombinant protein

<400> SEQUENCE: 220

```
Tyr Ile Gln Tyr Ser Gly Ser Thr Asn Tyr Asn Pro Ser Leu Lys Ser
1               5                   10                  15
```

<210> SEQ ID NO 221
<211> LENGTH: 13
<212> TYPE: PRT
<213> ORGANISM: Artificial Sequence
<220> FEATURE:
<223> OTHER INFORMATION: Recombinant protein

<400> SEQUENCE: 221

```
Ser Val Asn Tyr Tyr Gly Asn Ser Phe Ala Val Gly Tyr
1               5                   10
```

<210> SEQ ID NO 222
<211> LENGTH: 107
<212> TYPE: PRT
<213> ORGANISM: Artificial Sequence
<220> FEATURE:
<223> OTHER INFORMATION: Recombinant protein

<400> SEQUENCE: 222

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Tyr
                85                  90                  95

Thr Phe Gly Ala Gly Thr Lys Leu Glu Leu Lys
                100                 105
```

<210> SEQ ID NO 223
<211> LENGTH: 11
<212> TYPE: PRT
<213> ORGANISM: Artificial Sequence
<220> FEATURE:
<223> OTHER INFORMATION: Recombinant protein

<400> SEQUENCE: 223

Arg Ala Ser Gln Gly Ile Ser Asp Tyr Leu His
1               5                   10

<210> SEQ ID NO 224
<211> LENGTH: 7
<212> TYPE: PRT
<213> ORGANISM: Artificial Sequence
<220> FEATURE:
<223> OTHER INFORMATION: Recombinant protein

<400> SEQUENCE: 224

Tyr Thr Ser Gln Pro Ala Thr
1               5

<210> SEQ ID NO 225
<211> LENGTH: 9
<212> TYPE: PRT
<213> ORGANISM: Artificial Sequence
<220> FEATURE:
<223> OTHER INFORMATION: Recombinant protein

<400> SEQUENCE: 225

Gln Asn Gly His Ser Phe Pro Tyr Thr
1               5

<210> SEQ ID NO 226
<211> LENGTH: 122
<212> TYPE: PRT
<213> ORGANISM: Artificial Sequence
<220> FEATURE:
<223> OTHER INFORMATION: Recombinant protein

<400> SEQUENCE: 226

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
                20                  25                  30

Ser Ala Trp Ser Trp Ile Arg Gln Phe Pro Gly Lys Lys Leu Glu Trp
            35                  40                  45

Met Gly Tyr Ile Gln Tyr Ser Gly Ser Thr Asn Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
                100                 105                 110

Gly Gln Gly Thr Ser Val Thr Val Ser Ser
            115                 120

<210> SEQ ID NO 227
<211> LENGTH: 6
<212> TYPE: PRT
<213> ORGANISM: Artificial Sequence
<220> FEATURE:
<223> OTHER INFORMATION: Recombinant protein -continued

<400> SEQUENCE: 227

Ser Asp Ser Ala Trp Ser
1               5

<210> SEQ ID NO 228
<211> LENGTH: 16
<212> TYPE: PRT
<213> ORGANISM: Artificial Sequence
<220> FEATURE:
<223> OTHER INFORMATION: Recombinant protein

<400> SEQUENCE: 228

Tyr Ile Gln Tyr Ser Gly Ser Thr Asn Tyr Asn Pro Ser Leu Lys Ser
1               5                   10                  15

<210> SEQ ID NO 229
<211> LENGTH: 13
<212> TYPE: PRT
<213> ORGANISM: Artificial Sequence
<220> FEATURE:
<223> OTHER INFORMATION: Recombinant protein

<400> SEQUENCE: 229

Ser Val Asn Tyr Tyr Gly Asn Ser Phe Ala Val Gly Tyr
1               5                   10

<210> SEQ ID NO 230
<211> LENGTH: 107
<212> TYPE: PRT
<213> ORGANISM: Artificial Sequence
<220> FEATURE:
<223> OTHER INFORMATION: Recombinant protein

<400> SEQUENCE: 230

Glu Ile Val Leu Thr Gln Ser Pro Ala Thr Leu Ser Leu Ser Ala Gly
1               5                   10                  15

Glu Arg Ala Thr Leu Ser Cys Arg Ala Ser Gln Gly Ile Ser Asp Tyr
                20                  25                  30

Leu His Trp Tyr Gln Gln Lys Ser Gly Glu Ala Pro Arg Leu Leu Ile
            35                  40                  45

Lys Tyr Thr Ser Gln Pro Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 231
<211> LENGTH: 11
<212> TYPE: PRT
<213> ORGANISM: Artificial Sequence
<220> FEATURE:
<223> OTHER INFORMATION: Recombinant protein

<400> SEQUENCE: 231

Arg Ala Ser Gln Gly Ile Ser Asp Tyr Leu His
1               5                   10

<210> SEQ ID NO 232
<211> LENGTH: 7

```
<212> TYPE: PRT
<213> ORGANISM: Artificial Sequence
<220> FEATURE:
<223> OTHER INFORMATION: Recombinant protein

<400> SEQUENCE: 232

Tyr Thr Ser Gln Pro Ala Thr
1               5

<210> SEQ ID NO 233
<211> LENGTH: 9
<212> TYPE: PRT
<213> ORGANISM: Artificial Sequence
<220> FEATURE:
<223> OTHER INFORMATION: Recombinant protein

<400> SEQUENCE: 233

Gln Asn Gly His Ser Phe Pro Leu Thr
1               5

<210> SEQ ID NO 234
<211> LENGTH: 122
<212> TYPE: PRT
<213> ORGANISM: Artificial Sequence
<220> FEATURE:
<223> OTHER INFORMATION: Recombinant protein

<400> SEQUENCE: 234

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 235
<211> LENGTH: 6
<212> TYPE: PRT
<213> ORGANISM: Artificial Sequence
<220> FEATURE:
<223> OTHER INFORMATION: Recombinant protein

<400> SEQUENCE: 235

Ser Asp Ser Ala Trp Ser
1               5

<210> SEQ ID NO 236
<211> LENGTH: 16
<212> TYPE: PRT
<213> ORGANISM: Artificial Sequence
<220> FEATURE:
<223> OTHER INFORMATION: Recombinant protein

<400> SEQUENCE: 236
```

```
Tyr Ile Gln Tyr Ser Gly Ser Thr Asn Tyr Asn Pro Ser Leu Lys Ser
1               5                   10                  15
```

<210> SEQ ID NO 237
<211> LENGTH: 13
<212> TYPE: PRT
<213> ORGANISM: Artificial Sequence
<220> FEATURE:
<223> OTHER INFORMATION: Recombinant protein

<400> SEQUENCE: 237

```
Ser Val Asn Tyr Tyr Gly Asn Ser Phe Ala Val Gly Tyr
1               5                   10
```

<210> SEQ ID NO 238
<211> LENGTH: 107
<212> TYPE: PRT
<213> ORGANISM: Artificial Sequence
<220> FEATURE:
<223> OTHER INFORMATION: Recombinant protein

<400> SEQUENCE: 238

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Ala Ser Gln Pro Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105
```

<210> SEQ ID NO 239
<211> LENGTH: 11
<212> TYPE: PRT
<213> ORGANISM: Artificial Sequence
<220> FEATURE:
<223> OTHER INFORMATION: Recombinant protein

<400> SEQUENCE: 239

```
Arg Ala Ser Gln Gly Ile Ser Asp Tyr Leu His
1               5                   10
```

<210> SEQ ID NO 240
<211> LENGTH: 7
<212> TYPE: PRT
<213> ORGANISM: Artificial Sequence
<220> FEATURE:
<223> OTHER INFORMATION: Recombinant protein

<400> SEQUENCE: 240

```
Tyr Ala Ser Gln Pro Ala Thr
1               5
```

<210> SEQ ID NO 241
<211> LENGTH: 9
<212> TYPE: PRT
<213> ORGANISM: Artificial Sequence

```
<220> FEATURE:
<223> OTHER INFORMATION: Recombinant protein

<400> SEQUENCE: 241

Gln Asn Gly His Ser Phe Pro Leu Thr
1               5

<210> SEQ ID NO 242
<211> LENGTH: 122
<212> TYPE: PRT
<213> ORGANISM: Artificial Sequence
<220> FEATURE:
<223> OTHER INFORMATION: Recombinant protein

<400> SEQUENCE: 242

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 243
<211> LENGTH: 6
<212> TYPE: PRT
<213> ORGANISM: Artificial Sequence
<220> FEATURE:
<223> OTHER INFORMATION: Recombinant protein

<400> SEQUENCE: 243

Ser Asp Ser Ala Trp Ser
1               5

<210> SEQ ID NO 244
<211> LENGTH: 16
<212> TYPE: PRT
<213> ORGANISM: Artificial Sequence
<220> FEATURE:
<223> OTHER INFORMATION: Recombinant protein

<400> SEQUENCE: 244

Tyr Ile Gln Tyr Ser Gly Ser Thr Asn Tyr Asn Pro Ser Leu Lys Ser
1               5                   10                  15

<210> SEQ ID NO 245
<211> LENGTH: 13
<212> TYPE: PRT
<213> ORGANISM: Artificial Sequence
<220> FEATURE:
<223> OTHER INFORMATION: Recombinant protein

<400> SEQUENCE: 245

Ser Val Asn Tyr Tyr Gly Asn Ser Phe Ala Val Gly Tyr
```

<210> SEQ ID NO 246
<211> LENGTH: 107
<212> TYPE: PRT
<213> ORGANISM: Artificial Sequence
<220> FEATURE:
<223> OTHER INFORMATION: Recombinant protein

<400> SEQUENCE: 246

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Gly Ile Ser Asp Tyr
            20                  25                  30
Leu His Trp Tyr Gln Gln Lys Pro Gly Glu Ala Pro Arg Leu Leu Ile
        35                  40                  45
Lys Tyr Thr Ser Gln Pro Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Gly Val Tyr Tyr Cys Gln Asn Gly His Ser Phe Pro Leu
                85                  90                  95
Thr Phe Gly Ala Gly Thr Lys Leu Glu Leu Lys
            100                 105
```

<210> SEQ ID NO 247
<211> LENGTH: 11
<212> TYPE: PRT
<213> ORGANISM: Artificial Sequence
<220> FEATURE:
<223> OTHER INFORMATION: Recombinant protein

<400> SEQUENCE: 247

```
Arg Ala Ser Gln Gly Ile Ser Asp Tyr Leu His
1               5                   10
```

<210> SEQ ID NO 248
<211> LENGTH: 7
<212> TYPE: PRT
<213> ORGANISM: Artificial Sequence
<220> FEATURE:
<223> OTHER INFORMATION: Recombinant protein

<400> SEQUENCE: 248

```
Tyr Thr Ser Gln Pro Ala Thr
1               5
```

<210> SEQ ID NO 249
<211> LENGTH: 9
<212> TYPE: PRT
<213> ORGANISM: Artificial Sequence
<220> FEATURE:
<223> OTHER INFORMATION: Recombinant protein

<400> SEQUENCE: 249

```
Gln Asn Gly His Ser Phe Pro Leu Thr
1               5
```

<210> SEQ ID NO 250
<211> LENGTH: 122
<212> TYPE: PRT
<213> ORGANISM: Artificial Sequence
<220> FEATURE:
<223> OTHER INFORMATION: Recombinant protein

<400> SEQUENCE: 250

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 251
<211> LENGTH: 6
<212> TYPE: PRT
<213> ORGANISM: Artificial Sequence
<220> FEATURE:
<223> OTHER INFORMATION: Recombinant protein

<400> SEQUENCE: 251

Ser Asp Ser Ala Trp Ser
1               5

<210> SEQ ID NO 252
<211> LENGTH: 16
<212> TYPE: PRT
<213> ORGANISM: Artificial Sequence
<220> FEATURE:
<223> OTHER INFORMATION: Recombinant protein

<400> SEQUENCE: 252

Tyr Ile Gln Tyr Ser Gly Ser Thr Asn Tyr Asn Pro Ser Leu Lys Ser
1               5                   10                  15

<210> SEQ ID NO 253
<211> LENGTH: 13
<212> TYPE: PRT
<213> ORGANISM: Artificial Sequence
<220> FEATURE:
<223> OTHER INFORMATION: Recombinant protein

<400> SEQUENCE: 253

Ser Val Asn Tyr Tyr Gly Asn Ser Phe Ala Val Gly Tyr
1               5                   10

<210> SEQ ID NO 254
<211> LENGTH: 107
<212> TYPE: PRT
<213> ORGANISM: Artificial Sequence
<220> FEATURE:
<223> OTHER INFORMATION: Recombinant protein

<400> SEQUENCE: 254

Glu Ile Val Leu Thr Gln Ser Pro Ala Thr Leu Ser Leu Ser Pro Gly
1               5                   10                  15

```
Glu Arg Ala Thr Leu Ser Cys Arg Ala Ser Gln Gly Ile Ser Asp Tyr
             20                  25                  30

Leu His Trp Tyr Gln Gln Lys Pro Gly Glu Ala Pro Arg Leu Leu Ile
         35                  40                  45

Lys Tyr Thr Ser Gln Pro Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Val Gly Val Tyr Tyr Cys Gln Asn Gly His Ser Phe Pro Leu
                 85                  90                  95

Thr Phe Gly Ala Gly Thr Lys Leu Glu Leu Lys
            100                 105
```

<210> SEQ ID NO 255
<211> LENGTH: 11
<212> TYPE: PRT
<213> ORGANISM: Artificial Sequence
<220> FEATURE:
<223> OTHER INFORMATION: Recombinant protein

<400> SEQUENCE: 255

```
Arg Ala Ser Gln Gly Ile Ser Asp Tyr Leu His
 1               5                  10
```

<210> SEQ ID NO 256
<211> LENGTH: 7
<212> TYPE: PRT
<213> ORGANISM: Artificial Sequence
<220> FEATURE:
<223> OTHER INFORMATION: Recombinant protein

<400> SEQUENCE: 256

```
Tyr Thr Ser Gln Pro Ala Thr
 1               5
```

<210> SEQ ID NO 257
<211> LENGTH: 9
<212> TYPE: PRT
<213> ORGANISM: Artificial Sequence
<220> FEATURE:
<223> OTHER INFORMATION: Recombinant protein

<400> SEQUENCE: 257

```
Gln Asn Gly His Ser Phe Pro Leu Thr
 1               5
```

<210> SEQ ID NO 258
<211> LENGTH: 122
<212> TYPE: PRT
<213> ORGANISM: Artificial Sequence
<220> FEATURE:
<223> OTHER INFORMATION: Recombinant protein

<400> SEQUENCE: 258

```
Asp Val Gln Leu Gln Glu Ser Gly Pro Gly Leu Val Glu Pro Ser Gln
 1               5                  10                  15

Thr Leu Ser Leu Thr Cys Thr Val Ser Gly Tyr Ser Ile Thr Ser Asp
             20                  25                  30

Ser Ala Trp Ser Trp Ile Arg Gln Phe Pro Gly Lys Lys Leu Glu Trp
         35                  40                  45

Met Gly Tyr Ile Gln Tyr Ser Gly Ser Thr Asn Tyr Asn Pro Ser Leu
 50                  55                  60
```

```
Lys Ser Arg Val Thr Ile Ser Arg Asp Thr Ser Lys Asn Gln Phe Ser
 65                 70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120
```

<210> SEQ ID NO 259
<211> LENGTH: 6
<212> TYPE: PRT
<213> ORGANISM: Artificial Sequence
<220> FEATURE:
<223> OTHER INFORMATION: Recombinant protein

<400> SEQUENCE: 259

```
Ser Asp Ser Ala Trp Ser
1               5
```

<210> SEQ ID NO 260
<211> LENGTH: 16
<212> TYPE: PRT
<213> ORGANISM: Artificial Sequence
<220> FEATURE:
<223> OTHER INFORMATION: Recombinant protein

<400> SEQUENCE: 260

```
Tyr Ile Gln Tyr Ser Gly Ser Thr Asn Tyr Asn Pro Ser Leu Lys Ser
1               5                   10                  15
```

<210> SEQ ID NO 261
<211> LENGTH: 13
<212> TYPE: PRT
<213> ORGANISM: Artificial Sequence
<220> FEATURE:
<223> OTHER INFORMATION: Recombinant protein

<400> SEQUENCE: 261

```
Ser Val Asn Tyr Tyr Gly Asn Ser Phe Ala Val Gly Tyr
1               5                   10
```

<210> SEQ ID NO 262
<211> LENGTH: 107
<212> TYPE: PRT
<213> ORGANISM: Artificial Sequence
<220> FEATURE:
<223> OTHER INFORMATION: Recombinant protein

<400> SEQUENCE: 262

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95
```

Thr Phe Gly Ala Gly Thr Lys Leu Glu Leu Lys
            100                 105

<210> SEQ ID NO 263
<211> LENGTH: 11
<212> TYPE: PRT
<213> ORGANISM: Artificial Sequence
<220> FEATURE:
<223> OTHER INFORMATION: Recombinant protein

<400> SEQUENCE: 263

Arg Ala Ser Gln Gly Ile Ser Asp Tyr Leu His
1               5                   10

<210> SEQ ID NO 264
<211> LENGTH: 7
<212> TYPE: PRT
<213> ORGANISM: Artificial Sequence
<220> FEATURE:
<223> OTHER INFORMATION: Recombinant protein

<400> SEQUENCE: 264

Tyr Thr Ser Gln Pro Ala Thr
1               5

<210> SEQ ID NO 265
<211> LENGTH: 9
<212> TYPE: PRT
<213> ORGANISM: Artificial Sequence
<220> FEATURE:
<223> OTHER INFORMATION: Recombinant protein

<400> SEQUENCE: 265

Gln Asn Gly His Ser Phe Pro Leu Thr
1               5

<210> SEQ ID NO 266
<211> LENGTH: 122
<212> TYPE: PRT
<213> ORGANISM: Artificial Sequence
<220> FEATURE:
<223> OTHER INFORMATION: Recombinant protein

<400> SEQUENCE: 266

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Pro Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 267
<211> LENGTH: 6

```
<212> TYPE: PRT
<213> ORGANISM: Artificial Sequence
<220> FEATURE:
<223> OTHER INFORMATION: Recombinant protein

<400> SEQUENCE: 267

Ser Asp Ser Ala Trp Ser
1               5

<210> SEQ ID NO 268
<211> LENGTH: 16
<212> TYPE: PRT
<213> ORGANISM: Artificial Sequence
<220> FEATURE:
<223> OTHER INFORMATION: Recombinant protein

<400> SEQUENCE: 268

Tyr Ile Gln Tyr Ser Gly Ser Thr Asn Tyr Asn Pro Ser Leu Lys Ser
1               5                   10                  15

<210> SEQ ID NO 269
<211> LENGTH: 13
<212> TYPE: PRT
<213> ORGANISM: Artificial Sequence
<220> FEATURE:
<223> OTHER INFORMATION: Recombinant protein

<400> SEQUENCE: 269

Ser Val Asn Tyr Tyr Gly Asn Ser Phe Ala Val Gly Tyr
1               5                   10

<210> SEQ ID NO 270
<211> LENGTH: 107
<212> TYPE: PRT
<213> ORGANISM: Artificial Sequence
<220> FEATURE:
<223> OTHER INFORMATION: Recombinant protein

<400> SEQUENCE: 270

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
                20                  25                  30

Leu His Trp Tyr Gln Gln Lys Pro Gly Glu Ala Pro Arg Leu Leu Ile
            35                  40                  45

Lys Tyr Thr Ser Gln Pro Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 271
<211> LENGTH: 11
<212> TYPE: PRT
<213> ORGANISM: Artificial Sequence
<220> FEATURE:
<223> OTHER INFORMATION: Recombinant protein

<400> SEQUENCE: 271

Arg Ala Ser Gln Gly Ile Ser Asp Tyr Leu His
1               5                   10
```

<210> SEQ ID NO 272
<211> LENGTH: 7
<212> TYPE: PRT
<213> ORGANISM: Artificial Sequence
<220> FEATURE:
<223> OTHER INFORMATION: Recombinant protein

<400> SEQUENCE: 272

Tyr Thr Ser Gln Pro Ala Thr
1               5

<210> SEQ ID NO 273
<211> LENGTH: 9
<212> TYPE: PRT
<213> ORGANISM: Artificial Sequence
<220> FEATURE:
<223> OTHER INFORMATION: Recombinant protein

<400> SEQUENCE: 273

Gln Asn Gly His Ser Phe Pro Leu Thr
1               5

<210> SEQ ID NO 274
<211> LENGTH: 122
<212> TYPE: PRT
<213> ORGANISM: Artificial Sequence
<220> FEATURE:
<223> OTHER INFORMATION: Recombinant protein

<400> SEQUENCE: 274

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Asp Tyr Trp
            100                 105                 110

Gly Gln Gly Thr Ser Val Thr Val Ser Ser
        115                 120

<210> SEQ ID NO 275
<211> LENGTH: 6
<212> TYPE: PRT
<213> ORGANISM: Artificial Sequence
<220> FEATURE:
<223> OTHER INFORMATION: Recombinant protein

<400> SEQUENCE: 275

Ser Asp Ser Ala Trp Ser
1               5

<210> SEQ ID NO 276
<211> LENGTH: 16
<212> TYPE: PRT
<213> ORGANISM: Artificial Sequence

```
<220> FEATURE:
<223> OTHER INFORMATION: Recombinant protein

<400> SEQUENCE: 276

Tyr Ile Gln Tyr Ser Gly Ser Thr Asn Tyr Asn Pro Ser Leu Lys Ser
1               5                   10                  15

<210> SEQ ID NO 277
<211> LENGTH: 13
<212> TYPE: PRT
<213> ORGANISM: Artificial Sequence
<220> FEATURE:
<223> OTHER INFORMATION: Recombinant protein

<400> SEQUENCE: 277

Ser Val Asn Tyr Tyr Gly Asn Ser Phe Ala Val Asp Tyr
1               5                   10

<210> SEQ ID NO 278
<211> LENGTH: 107
<212> TYPE: PRT
<213> ORGANISM: Artificial Sequence
<220> FEATURE:
<223> OTHER INFORMATION: Recombinant protein

<400> SEQUENCE: 278

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 279
<211> LENGTH: 11
<212> TYPE: PRT
<213> ORGANISM: Artificial Sequence
<220> FEATURE:
<223> OTHER INFORMATION: Recombinant protein

<400> SEQUENCE: 279

Arg Ala Ser Gln Gly Ile Ser Asp Tyr Leu His
1               5                   10

<210> SEQ ID NO 280
<211> LENGTH: 7
<212> TYPE: PRT
<213> ORGANISM: Artificial Sequence
<220> FEATURE:
<223> OTHER INFORMATION: Recombinant protein

<400> SEQUENCE: 280

Tyr Thr Ser Gln Pro Ala Thr
1               5
```

<210> SEQ ID NO 281
<211> LENGTH: 9
<212> TYPE: PRT
<213> ORGANISM: Artificial Sequence
<220> FEATURE:
<223> OTHER INFORMATION: Recombinant protein

<400> SEQUENCE: 281

Gln Asn Gly His Ser Phe Pro Leu Thr
1               5

<210> SEQ ID NO 282
<211> LENGTH: 122
<212> TYPE: PRT
<213> ORGANISM: Artificial Sequence
<220> FEATURE:
<223> OTHER INFORMATION: Recombinant protein

<400> SEQUENCE: 282

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 283
<211> LENGTH: 6
<212> TYPE: PRT
<213> ORGANISM: Artificial Sequence
<220> FEATURE:
<223> OTHER INFORMATION: Recombinant protein

<400> SEQUENCE: 283

Ser Asp Ser Ala Trp Ser
1               5

<210> SEQ ID NO 284
<211> LENGTH: 16
<212> TYPE: PRT
<213> ORGANISM: Artificial Sequence
<220> FEATURE:
<223> OTHER INFORMATION: Recombinant protein

<400> SEQUENCE: 284

Tyr Ile Gln Tyr Ser Gly Ser Thr Asn Tyr Asn Pro Ser Leu Lys Ser
1               5                   10                  15

<210> SEQ ID NO 285
<211> LENGTH: 13
<212> TYPE: PRT
<213> ORGANISM: Artificial Sequence
<220> FEATURE:
<223> OTHER INFORMATION: Recombinant protein

<400> SEQUENCE: 285

Ser Val Asn Tyr Tyr Gly Asn Ser Phe Ala Val Gly Tyr
1               5                   10

<210> SEQ ID NO 286
<211> LENGTH: 107
<212> TYPE: PRT
<213> ORGANISM: Artificial Sequence
<220> FEATURE:
<223> OTHER INFORMATION: Recombinant protein

<400> SEQUENCE: 286

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 287
<211> LENGTH: 11
<212> TYPE: PRT
<213> ORGANISM: Artificial Sequence
<220> FEATURE:
<223> OTHER INFORMATION: Recombinant protein

<400> SEQUENCE: 287

Arg Ala Ser Gln Gly Ile Ser Asp Tyr Leu His
1               5                   10

<210> SEQ ID NO 288
<211> LENGTH: 7
<212> TYPE: PRT
<213> ORGANISM: Artificial Sequence
<220> FEATURE:
<223> OTHER INFORMATION: Recombinant protein

<400> SEQUENCE: 288

Tyr Thr Ser Gln Pro Ala Thr
1               5

<210> SEQ ID NO 289
<211> LENGTH: 9
<212> TYPE: PRT
<213> ORGANISM: Artificial Sequence
<220> FEATURE:
<223> OTHER INFORMATION: Recombinant protein

<400> SEQUENCE: 289

Gln Asn Gly His Ser Phe Pro Leu Thr
1               5

<210> SEQ ID NO 290
<211> LENGTH: 122

```
<212> TYPE: PRT
<213> ORGANISM: Artificial Sequence
<220> FEATURE:
<223> OTHER INFORMATION: Recombinant protein

<400> SEQUENCE: 290

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120

<210> SEQ ID NO 291
<211> LENGTH: 6
<212> TYPE: PRT
<213> ORGANISM: Artificial Sequence
<220> FEATURE:
<223> OTHER INFORMATION: Recombinant protein

<400> SEQUENCE: 291

Ser Asp Ser Ala Trp Ser
1               5

<210> SEQ ID NO 292
<211> LENGTH: 16
<212> TYPE: PRT
<213> ORGANISM: Artificial Sequence
<220> FEATURE:
<223> OTHER INFORMATION: Recombinant protein

<400> SEQUENCE: 292

Tyr Ile Gln Tyr Ser Gly Ser Thr Asn Tyr Asn Pro Ser Leu Lys Ser
1               5                   10                  15

<210> SEQ ID NO 293
<211> LENGTH: 13
<212> TYPE: PRT
<213> ORGANISM: Artificial Sequence
<220> FEATURE:
<223> OTHER INFORMATION: Recombinant protein

<400> SEQUENCE: 293

Ser Val Asn Tyr Tyr Gly Asn Ser Phe Ala Val Gly Tyr
1               5                   10

<210> SEQ ID NO 294
<211> LENGTH: 107
<212> TYPE: PRT
<213> ORGANISM: Artificial Sequence
<220> FEATURE:
<223> OTHER INFORMATION: Recombinant protein

<400> SEQUENCE: 294
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Ser Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 295
<211> LENGTH: 11
<212> TYPE: PRT
<213> ORGANISM: Artificial Sequence
<220> FEATURE:
<223> OTHER INFORMATION: Recombinant protein

<400> SEQUENCE: 295

Arg Ala Ser Gln Gly Ile Ser Ser Tyr Leu His
1               5                   10

<210> SEQ ID NO 296
<211> LENGTH: 7
<212> TYPE: PRT
<213> ORGANISM: Artificial Sequence
<220> FEATURE:
<223> OTHER INFORMATION: Recombinant protein

<400> SEQUENCE: 296

Tyr Thr Ser Gln Pro Ala Thr
1               5

<210> SEQ ID NO 297
<211> LENGTH: 9
<212> TYPE: PRT
<213> ORGANISM: Artificial Sequence
<220> FEATURE:
<223> OTHER INFORMATION: Recombinant protein

<400> SEQUENCE: 297

Gln Asn Gly His Ser Phe Pro Leu Thr
1               5

<210> SEQ ID NO 298
<211> LENGTH: 122
<212> TYPE: PRT
<213> ORGANISM: Artificial Sequence
<220> FEATURE:
<223> OTHER INFORMATION: Recombinant protein

<400> SEQUENCE: 298

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

```
Met Gly Tyr Ile Gln Tyr Ser Gly Ser Thr Asn Tyr Asn Pro Ser Leu
     50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Glu Asp Thr Ala Val Tyr Tyr Cys
                 85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
            115                 120

<210> SEQ ID NO 299
<211> LENGTH: 6
<212> TYPE: PRT
<213> ORGANISM: Artificial Sequence
<220> FEATURE:
<223> OTHER INFORMATION: Recombinant protein

<400> SEQUENCE: 299

Ser Asp Ser Ala Trp Ser
1               5

<210> SEQ ID NO 300
<211> LENGTH: 16
<212> TYPE: PRT
<213> ORGANISM: Artificial Sequence
<220> FEATURE:
<223> OTHER INFORMATION: Recombinant protein

<400> SEQUENCE: 300

Tyr Ile Gln Tyr Ser Gly Ser Thr Asn Tyr Asn Pro Ser Leu Lys Ser
1               5                   10                  15

<210> SEQ ID NO 301
<211> LENGTH: 13
<212> TYPE: PRT
<213> ORGANISM: Artificial Sequence
<220> FEATURE:
<223> OTHER INFORMATION: Recombinant protein

<400> SEQUENCE: 301

Ser Val Asn Tyr Tyr Gly Asn Ser Phe Ala Val Gly Tyr
1               5                   10

<210> SEQ ID NO 302
<211> LENGTH: 107
<212> TYPE: PRT
<213> ORGANISM: Artificial Sequence
<220> FEATURE:
<223> OTHER INFORMATION: Recombinant protein

<400> SEQUENCE: 302

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80
```

Glu Asp Phe Gly Val Tyr Tyr Cys Gln Asn Gly His Ser Phe Pro Leu
            85                  90                  95

Thr Phe Gly Ala Gly Thr Lys Leu Glu Leu Lys
            100                 105

<210> SEQ ID NO 303
<211> LENGTH: 11
<212> TYPE: PRT
<213> ORGANISM: Artificial Sequence
<220> FEATURE:
<223> OTHER INFORMATION: Recombinant protein

<400> SEQUENCE: 303

Arg Ala Ser Gln Gly Ile Ser Asp Tyr Leu His
1               5                   10

<210> SEQ ID NO 304
<211> LENGTH: 7
<212> TYPE: PRT
<213> ORGANISM: Artificial Sequence
<220> FEATURE:
<223> OTHER INFORMATION: Recombinant protein

<400> SEQUENCE: 304

Tyr Thr Ser Gln Pro Ala Thr
1               5

<210> SEQ ID NO 305
<211> LENGTH: 9
<212> TYPE: PRT
<213> ORGANISM: Artificial Sequence
<220> FEATURE:
<223> OTHER INFORMATION: Recombinant protein

<400> SEQUENCE: 305

Gln Asn Gly His Ser Phe Pro Leu Thr
1               5

<210> SEQ ID NO 306
<211> LENGTH: 122
<212> TYPE: PRT
<213> ORGANISM: Artificial Sequence
<220> FEATURE:
<223> OTHER INFORMATION: Recombinant protein

<400> SEQUENCE: 306

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
            85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
            115                 120

<210> SEQ ID NO 307
<211> LENGTH: 6
<212> TYPE: PRT
<213> ORGANISM: Artificial Sequence
<220> FEATURE:
<223> OTHER INFORMATION: Recombinant protein

<400> SEQUENCE: 307

Ser Asp Ser Ala Trp Ser
1               5

<210> SEQ ID NO 308
<211> LENGTH: 16
<212> TYPE: PRT
<213> ORGANISM: Artificial Sequence
<220> FEATURE:
<223> OTHER INFORMATION: Recombinant protein

<400> SEQUENCE: 308

Tyr Ile Gln Tyr Ser Gly Ser Thr Asn Tyr Asn Pro Ser Leu Lys Ser
1               5                   10                  15

<210> SEQ ID NO 309
<211> LENGTH: 13
<212> TYPE: PRT
<213> ORGANISM: Artificial Sequence
<220> FEATURE:
<223> OTHER INFORMATION: Recombinant protein

<400> SEQUENCE: 309

Ser Val Asn Tyr Tyr Gly Asn Ser Phe Ala Val Gly Tyr
1               5                   10

<210> SEQ ID NO 310
<211> LENGTH: 107
<212> TYPE: PRT
<213> ORGANISM: Artificial Sequence
<220> FEATURE:
<223> OTHER INFORMATION: Recombinant protein

<400> SEQUENCE: 310

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
                20                  25                  30

Leu Ala Trp Tyr Gln Gln Lys Pro Gly Gln Ala Pro Arg Leu Leu Ile
            35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 311
<211> LENGTH: 11
<212> TYPE: PRT
<213> ORGANISM: Artificial Sequence
<220> FEATURE:
<223> OTHER INFORMATION: Recombinant protein

```
<400> SEQUENCE: 311

Arg Ala Ser Gln Gly Ile Ser Asp Tyr Leu Ala
1               5                   10

<210> SEQ ID NO 312
<211> LENGTH: 7
<212> TYPE: PRT
<213> ORGANISM: Artificial Sequence
<220> FEATURE:
<223> OTHER INFORMATION: Recombinant protein

<400> SEQUENCE: 312

Tyr Ala Ser Gln Pro Ala Thr
1               5

<210> SEQ ID NO 313
<211> LENGTH: 9
<212> TYPE: PRT
<213> ORGANISM: Artificial Sequence
<220> FEATURE:
<223> OTHER INFORMATION: Recombinant protein

<400> SEQUENCE: 313

Gln Asn Gly His Ser Phe Pro Leu Thr
1               5

<210> SEQ ID NO 314
<211> LENGTH: 122
<212> TYPE: PRT
<213> ORGANISM: Artificial Sequence
<220> FEATURE:
<223> OTHER INFORMATION: Recombinant protein

<400> SEQUENCE: 314

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
                20                  25                  30

Ser Ala Trp Ser Trp Ile Arg Gln Pro Pro Gly Lys Gly Leu Glu Trp
            35                  40                  45

Ile Gly Tyr Ile Gln Tyr Ser Gly Ser Thr Asn Tyr Asn Pro Ser Leu
        50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
                100                 105                 110

Gly Gln Gly Thr Leu Val Thr Val Ser Ser
            115                 120

<210> SEQ ID NO 315
<211> LENGTH: 6
<212> TYPE: PRT
<213> ORGANISM: Artificial Sequence
<220> FEATURE:
<223> OTHER INFORMATION: Recombinant protein

<400> SEQUENCE: 315

Ser Asp Ser Ala Trp Ser
1               5
```

```
<210> SEQ ID NO 316
<211> LENGTH: 16
<212> TYPE: PRT
<213> ORGANISM: Artificial Sequence
<220> FEATURE:
<223> OTHER INFORMATION: Recombinant protein

<400> SEQUENCE: 316

Tyr Ile Gln Tyr Ser Gly Ser Thr Asn Tyr Asn Pro Ser Leu Lys Ser
1               5                   10                  15

<210> SEQ ID NO 317
<211> LENGTH: 13
<212> TYPE: PRT
<213> ORGANISM: Artificial Sequence
<220> FEATURE:
<223> OTHER INFORMATION: Recombinant protein

<400> SEQUENCE: 317

Ser Val Asn Tyr Tyr Gly Asn Ser Phe Ala Val Gly Pro
1               5                   10

<210> SEQ ID NO 318
<211> LENGTH: 107
<212> TYPE: PRT
<213> ORGANISM: Artificial Sequence
<220> FEATURE:
<223> OTHER INFORMATION: Recombinant protein

<400> SEQUENCE: 318

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
                20                  25                  30

Leu His Trp Tyr Gln Gln Lys Pro Gly Glu Ala Pro Arg Leu Leu Ile
            35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 319
<211> LENGTH: 11
<212> TYPE: PRT
<213> ORGANISM: Artificial Sequence
<220> FEATURE:
<223> OTHER INFORMATION: Recombinant protein

<400> SEQUENCE: 319

Arg Ala Ser Gln Gly Ile Ser Asp Tyr Leu His
1               5                   10

<210> SEQ ID NO 320
<211> LENGTH: 7
<212> TYPE: PRT
<213> ORGANISM: Artificial Sequence
<220> FEATURE:
<223> OTHER INFORMATION: Recombinant protein

<400> SEQUENCE: 320
```

```
Tyr Thr Ser Gln Pro Ala Thr
1               5

<210> SEQ ID NO 321
<211> LENGTH: 9
<212> TYPE: PRT
<213> ORGANISM: Artificial Sequence
<220> FEATURE:
<223> OTHER INFORMATION: Recombinant protein

<400> SEQUENCE: 321

Gln Asn Gly His Ser Phe Pro Leu Thr
1               5

<210> SEQ ID NO 322
<211> LENGTH: 122
<212> TYPE: PRT
<213> ORGANISM: Artificial Sequence
<220> FEATURE:
<223> OTHER INFORMATION: Recombinant protein

<400> SEQUENCE: 322

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 323
<211> LENGTH: 6
<212> TYPE: PRT
<213> ORGANISM: Artificial Sequence
<220> FEATURE:
<223> OTHER INFORMATION: Recombinant protein

<400> SEQUENCE: 323

Ser Asp Ser Ala Trp Ser
1               5

<210> SEQ ID NO 324
<211> LENGTH: 16
<212> TYPE: PRT
<213> ORGANISM: Artificial Sequence
<220> FEATURE:
<223> OTHER INFORMATION: Recombinant protein

<400> SEQUENCE: 324

Tyr Ile Gln Tyr Ser Gly Ser Thr Asn Tyr Asn Pro Ser Leu Lys Ser
1               5                   10                  15

<210> SEQ ID NO 325
<211> LENGTH: 13
```

```
<212> TYPE: PRT
<213> ORGANISM: Artificial Sequence
<220> FEATURE:
<223> OTHER INFORMATION: Recombinant protein

<400> SEQUENCE: 325

Ser Val Asn Tyr Tyr Gly Asn Ser Phe Ala Val Gly Pro
1               5                   10

<210> SEQ ID NO 326
<211> LENGTH: 107
<212> TYPE: PRT
<213> ORGANISM: Artificial Sequence
<220> FEATURE:
<223> OTHER INFORMATION: Recombinant protein

<400> SEQUENCE: 326

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
                20                  25                  30

Leu His Trp Tyr Gln Gln Lys Pro Gly Glu Ala Pro Arg Leu Leu Ile
            35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Gly Val Tyr Tyr Cys Gln Asn Gly His Ser Phe Pro Leu
                85                  90                  95

Thr Phe Gly Ala Gly Thr Lys Leu Glu Leu Lys
                100                 105

<210> SEQ ID NO 327
<211> LENGTH: 11
<212> TYPE: PRT
<213> ORGANISM: Artificial Sequence
<220> FEATURE:
<223> OTHER INFORMATION: Recombinant protein

<400> SEQUENCE: 327

Arg Ala Ser Gln Gly Ile Ser Asp Tyr Leu His
1               5                   10

<210> SEQ ID NO 328
<211> LENGTH: 7
<212> TYPE: PRT
<213> ORGANISM: Artificial Sequence
<220> FEATURE:
<223> OTHER INFORMATION: Recombinant protein

<400> SEQUENCE: 328

Tyr Thr Ser Gln Pro Ala Thr
1               5

<210> SEQ ID NO 329
<211> LENGTH: 9
<212> TYPE: PRT
<213> ORGANISM: Artificial Sequence
<220> FEATURE:
<223> OTHER INFORMATION: Recombinant protein

<400> SEQUENCE: 329

Gln Asn Gly His Ser Phe Pro Leu Thr
1               5
```

<210> SEQ ID NO 330
<211> LENGTH: 122
<212> TYPE: PRT
<213> ORGANISM: Artificial Sequence
<220> FEATURE:
<223> OTHER INFORMATION: Recombinant protein

<400> SEQUENCE: 330

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 331
<211> LENGTH: 6
<212> TYPE: PRT
<213> ORGANISM: Artificial Sequence
<220> FEATURE:
<223> OTHER INFORMATION: Recombinant protein

<400> SEQUENCE: 331

Ser Asp Ser Ala Trp Ser
1               5

<210> SEQ ID NO 332
<211> LENGTH: 16
<212> TYPE: PRT
<213> ORGANISM: Artificial Sequence
<220> FEATURE:
<223> OTHER INFORMATION: Recombinant protein

<400> SEQUENCE: 332

Tyr Ile Gln Tyr Ser Gly Ser Thr Asn Tyr Asn Pro Ser Leu Lys Ser
1               5                   10                  15

<210> SEQ ID NO 333
<211> LENGTH: 13
<212> TYPE: PRT
<213> ORGANISM: Artificial Sequence
<220> FEATURE:
<223> OTHER INFORMATION: Recombinant protein

<400> SEQUENCE: 333

Ser Val Asn Tyr Tyr Gly Asn Ser Phe Ala Val Gly Pro
1               5                   10

<210> SEQ ID NO 334
<211> LENGTH: 107
<212> TYPE: PRT
<213> ORGANISM: Artificial Sequence
<220> FEATURE:
<223> OTHER INFORMATION: Recombinant protein

<400> SEQUENCE: 334

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 335
<211> LENGTH: 11
<212> TYPE: PRT
<213> ORGANISM: Artificial Sequence
<220> FEATURE:
<223> OTHER INFORMATION: Recombinant protein

<400> SEQUENCE: 335

Arg Ala Ser Gln Gly Ile Ser Asp Tyr Leu His
1               5                   10

<210> SEQ ID NO 336
<211> LENGTH: 7
<212> TYPE: PRT
<213> ORGANISM: Artificial Sequence
<220> FEATURE:
<223> OTHER INFORMATION: Recombinant protein

<400> SEQUENCE: 336

Tyr Ala Ser Gln Pro Ala Thr
1               5

<210> SEQ ID NO 337
<211> LENGTH: 9
<212> TYPE: PRT
<213> ORGANISM: Artificial Sequence
<220> FEATURE:
<223> OTHER INFORMATION: Recombinant protein

<400> SEQUENCE: 337

Gln Asn Gly His Ser Phe Pro Leu Thr
1               5

<210> SEQ ID NO 338
<211> LENGTH: 122
<212> TYPE: PRT
<213> ORGANISM: Artificial Sequence
<220> FEATURE:
<223> OTHER INFORMATION: Recombinant protein

<400> SEQUENCE: 338

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp

```
            20                  25                  30
Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 339
<211> LENGTH: 6
<212> TYPE: PRT
<213> ORGANISM: Artificial Sequence
<220> FEATURE:
<223> OTHER INFORMATION: Recombinant protein

<400> SEQUENCE: 339

Ser Asp Ser Ala Trp Ser
1               5

<210> SEQ ID NO 340
<211> LENGTH: 16
<212> TYPE: PRT
<213> ORGANISM: Artificial Sequence
<220> FEATURE:
<223> OTHER INFORMATION: Recombinant protein

<400> SEQUENCE: 340

Tyr Ile Gln Tyr Ser Gly Ser Thr Asn Tyr Asn Pro Ser Leu Lys Ser
1               5                   10                  15

<210> SEQ ID NO 341
<211> LENGTH: 13
<212> TYPE: PRT
<213> ORGANISM: Artificial Sequence
<220> FEATURE:
<223> OTHER INFORMATION: Recombinant protein

<400> SEQUENCE: 341

Ser Val Asn Tyr Tyr Gly Asn Ser Phe Ala Val Gly Pro
1               5                   10

<210> SEQ ID NO 342
<211> LENGTH: 107
<212> TYPE: PRT
<213> ORGANISM: Artificial Sequence
<220> FEATURE:
<223> OTHER INFORMATION: Recombinant protein

<400> SEQUENCE: 342

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Gln Ala Pro Arg Leu Leu Ile
        35                  40                  45

Lys Tyr Thr Ser Gln Pro Ala Thr Gly Ile Pro Ala Arg Phe Ser Gly
```

```
                50                  55                  60
Ser Gly Ser Gly Arg Asp Phe Thr Leu Thr Ile Ser Ser Leu Glu Pro
 65                  70                  75                  80

Glu Asp Phe Ala Val Tyr Tyr Cys Gln Asn Gly His Ser Phe Pro Leu
                 85                  90                  95

Thr Phe Gly Ala Gly Thr Lys Leu Glu Leu Lys
            100                 105
```

<210> SEQ ID NO 343
<211> LENGTH: 11
<212> TYPE: PRT
<213> ORGANISM: Artificial Sequence
<220> FEATURE:
<223> OTHER INFORMATION: Recombinant protein

<400> SEQUENCE: 343

```
Arg Ala Ser Gln Gly Ile Ser Asp Tyr Leu His
 1               5                  10
```

<210> SEQ ID NO 344
<211> LENGTH: 7
<212> TYPE: PRT
<213> ORGANISM: Artificial Sequence
<220> FEATURE:
<223> OTHER INFORMATION: Recombinant protein

<400> SEQUENCE: 344

```
Tyr Thr Ser Gln Pro Ala Thr
 1               5
```

<210> SEQ ID NO 345
<211> LENGTH: 9
<212> TYPE: PRT
<213> ORGANISM: Artificial Sequence
<220> FEATURE:
<223> OTHER INFORMATION: Recombinant protein

<400> SEQUENCE: 345

```
Gln Asn Gly His Ser Phe Pro Leu Thr
 1               5
```

<210> SEQ ID NO 346
<211> LENGTH: 122
<212> TYPE: PRT
<213> ORGANISM: Artificial Sequence
<220> FEATURE:
<223> OTHER INFORMATION: Recombinant protein

<400> SEQUENCE: 346

```
Gln Val Gln Leu Gln Glu Ser Gly Pro Gly Leu Val Glu Pro Ser Asp
 1               5                  10                  15

Thr Leu Ser Leu Thr Cys Ala Val Ser Gly Tyr Ser Ile Ser Ser Asp
                 20                  25                  30

Ser Ala Trp Ser Trp Ile Arg Gln Pro Pro Gly Lys Gly Leu Glu Trp
             35                  40                  45

Ile Gly Tyr Ile Gln Tyr Ser Gly Ser Thr Asn Tyr Asn Pro Ser Leu
         50                  55                  60

Lys Ser Arg Val Thr Met Ser Val Asp Thr Ser Lys Asn Gln Phe Ser
 65                  70                  75                  80

Leu Lys Leu Ser Ser Val Thr Ala Leu Asp Thr Ala Val Tyr Tyr Cys
                 85                  90                  95

Ala Arg Ser Val Asn Tyr Tyr Gly Asn Ser Phe Ala Val Gly Pro Trp
```

```
              100                 105                 110

Gly Gln Gly Thr Leu Val Thr Val Ser Ser
        115                 120

<210> SEQ ID NO 347
<211> LENGTH: 6
<212> TYPE: PRT
<213> ORGANISM: Artificial Sequence
<220> FEATURE:
<223> OTHER INFORMATION: Recombinant protein

<400> SEQUENCE: 347

Ser Asp Ser Ala Trp Ser
1               5

<210> SEQ ID NO 348
<211> LENGTH: 16
<212> TYPE: PRT
<213> ORGANISM: Artificial Sequence
<220> FEATURE:
<223> OTHER INFORMATION: Recombinant protein

<400> SEQUENCE: 348

Tyr Ile Gln Tyr Ser Gly Ser Thr Asn Tyr Asn Pro Ser Leu Lys Ser
1               5                   10                  15

<210> SEQ ID NO 349
<211> LENGTH: 13
<212> TYPE: PRT
<213> ORGANISM: Artificial Sequence
<220> FEATURE:
<223> OTHER INFORMATION: Recombinant protein

<400> SEQUENCE: 349

Ser Val Asn Tyr Tyr Gly Asn Ser Phe Ala Val Gly Pro
1               5                   10

<210> SEQ ID NO 350
<211> LENGTH: 107
<212> TYPE: PRT
<213> ORGANISM: Artificial Sequence
<220> FEATURE:
<223> OTHER INFORMATION: Recombinant protein

<400> SEQUENCE: 350

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Gln Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 351
<211> LENGTH: 11
<212> TYPE: PRT
```

<213> ORGANISM: Artificial Sequence
<220> FEATURE:
<223> OTHER INFORMATION: Recombinant protein

<400> SEQUENCE: 351

Arg Ala Ser Gln Gly Ile Ser Asp Tyr Leu His
1               5                   10

<210> SEQ ID NO 352
<211> LENGTH: 7
<212> TYPE: PRT
<213> ORGANISM: Artificial Sequence
<220> FEATURE:
<223> OTHER INFORMATION: Recombinant protein

<400> SEQUENCE: 352

Tyr Thr Ser Gln Pro Ala Thr
1               5

<210> SEQ ID NO 353
<211> LENGTH: 9
<212> TYPE: PRT
<213> ORGANISM: Artificial Sequence
<220> FEATURE:
<223> OTHER INFORMATION: Recombinant protein

<400> SEQUENCE: 353

Gln Asn Gly His Ser Phe Pro Leu Thr
1               5

<210> SEQ ID NO 354
<211> LENGTH: 122
<212> TYPE: PRT
<213> ORGANISM: Artificial Sequence
<220> FEATURE:
<223> OTHER INFORMATION: Recombinant protein

<400> SEQUENCE: 354

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 355
<211> LENGTH: 6
<212> TYPE: PRT
<213> ORGANISM: Artificial Sequence
<220> FEATURE:
<223> OTHER INFORMATION: Recombinant protein

<400> SEQUENCE: 355
```
Ser Asp Ser Ala Trp Ser
1               5
```

<210> SEQ ID NO 356
<211> LENGTH: 16
<212> TYPE: PRT
<213> ORGANISM: Artificial Sequence
<220> FEATURE:
<223> OTHER INFORMATION: Recombinant protein

<400> SEQUENCE: 356

```
Tyr Ile Gln Tyr Ser Gly Ser Thr Asn Tyr Asn Pro Ser Leu Lys Ser
1               5                   10                  15
```

<210> SEQ ID NO 357
<211> LENGTH: 13
<212> TYPE: PRT
<213> ORGANISM: Artificial Sequence
<220> FEATURE:
<223> OTHER INFORMATION: Recombinant protein

<400> SEQUENCE: 357

```
Ser Val Asn Tyr Tyr Gly Asn Ser Phe Ala Val Gly Pro
1               5                   10
```

<210> SEQ ID NO 358
<211> LENGTH: 107
<212> TYPE: PRT
<213> ORGANISM: Artificial Sequence
<220> FEATURE:
<223> OTHER INFORMATION: Recombinant protein

<400> SEQUENCE: 358

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Gln Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105
```

<210> SEQ ID NO 359
<211> LENGTH: 11
<212> TYPE: PRT
<213> ORGANISM: Artificial Sequence
<220> FEATURE:
<223> OTHER INFORMATION: Recombinant protein

<400> SEQUENCE: 359

```
Arg Ala Ser Gln Gly Ile Ser Asp Tyr Leu His
1               5                   10
```

<210> SEQ ID NO 360
<211> LENGTH: 7
<212> TYPE: PRT
<213> ORGANISM: Artificial Sequence
<220> FEATURE:

<223> OTHER INFORMATION: Recombinant protein

<400> SEQUENCE: 360

Tyr Thr Ser Gln Pro Ala Thr
1               5

<210> SEQ ID NO 361
<211> LENGTH: 9
<212> TYPE: PRT
<213> ORGANISM: Artificial Sequence
<220> FEATURE:
<223> OTHER INFORMATION: Recombinant protein

<400> SEQUENCE: 361

Gln Asn Gly His Ser Phe Pro Leu Thr
1               5

<210> SEQ ID NO 362
<211> LENGTH: 122
<212> TYPE: PRT
<213> ORGANISM: Artificial Sequence
<220> FEATURE:
<223> OTHER INFORMATION: Recombinant protein

<400> SEQUENCE: 362

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 363
<211> LENGTH: 6
<212> TYPE: PRT
<213> ORGANISM: Artificial Sequence
<220> FEATURE:
<223> OTHER INFORMATION: Recombinant protein

<400> SEQUENCE: 363

Ser Asp Ser Ala Trp Ser
1               5

<210> SEQ ID NO 364
<211> LENGTH: 16
<212> TYPE: PRT
<213> ORGANISM: Artificial Sequence
<220> FEATURE:
<223> OTHER INFORMATION: Recombinant protein

<400> SEQUENCE: 364

Tyr Ile Gln Tyr Ser Gly Ser Thr Asn Tyr Asn Pro Ser Leu Lys Ser
1               5                   10                  15

<210> SEQ ID NO 365
<211> LENGTH: 13
<212> TYPE: PRT
<213> ORGANISM: Artificial Sequence
<220> FEATURE:
<223> OTHER INFORMATION: Recombinant protein

<400> SEQUENCE: 365

Ser Val Asn Tyr Tyr Gly Asn Ser Phe Ala Val Gly Pro
1               5                   10

<210> SEQ ID NO 366
<211> LENGTH: 107
<212> TYPE: PRT
<213> ORGANISM: Artificial Sequence
<220> FEATURE:
<223> OTHER INFORMATION: Recombinant protein

<400> SEQUENCE: 366

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Leu Ser Asp Tyr
            20                  25                  30

Leu Ala Trp Tyr Gln Gln Lys Pro Gly Glu Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 367
<211> LENGTH: 11
<212> TYPE: PRT
<213> ORGANISM: Artificial Sequence
<220> FEATURE:
<223> OTHER INFORMATION: Recombinant protein

<400> SEQUENCE: 367

Arg Ala Ser Gln Gly Leu Ser Asp Tyr Leu Ala
1               5                   10

<210> SEQ ID NO 368
<211> LENGTH: 7
<212> TYPE: PRT
<213> ORGANISM: Artificial Sequence
<220> FEATURE:
<223> OTHER INFORMATION: Recombinant protein

<400> SEQUENCE: 368

Tyr Ala Ser Gln Pro Ala Thr
1               5

<210> SEQ ID NO 369
<211> LENGTH: 9
<212> TYPE: PRT
<213> ORGANISM: Artificial Sequence
<220> FEATURE:
<223> OTHER INFORMATION: Recombinant protein

<400> SEQUENCE: 369

Gln Asn Gly His Ser Phe Pro Leu Thr
1               5

<210> SEQ ID NO 370
<211> LENGTH: 122
<212> TYPE: PRT
<213> ORGANISM: Artificial Sequence
<220> FEATURE:
<223> OTHER INFORMATION: Recombinant protein

<400> SEQUENCE: 370

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 371
<211> LENGTH: 6
<212> TYPE: PRT
<213> ORGANISM: Artificial Sequence
<220> FEATURE:
<223> OTHER INFORMATION: Recombinant protein

<400> SEQUENCE: 371

Ser Asp Ser Ala Trp Ser
1               5

<210> SEQ ID NO 372
<211> LENGTH: 16
<212> TYPE: PRT
<213> ORGANISM: Artificial Sequence
<220> FEATURE:
<223> OTHER INFORMATION: Recombinant protein

<400> SEQUENCE: 372

Tyr Ile Gln Tyr Ser Gly Ser Thr Asn Tyr Asn Pro Ser Leu Lys Ser
1               5                   10                  15

<210> SEQ ID NO 373
<211> LENGTH: 13
<212> TYPE: PRT
<213> ORGANISM: Artificial Sequence
<220> FEATURE:
<223> OTHER INFORMATION: Recombinant protein

<400> SEQUENCE: 373

Ser Val Asn Tyr Tyr Gly Asn Ser Phe Ala Val Gly Pro
1               5                   10

-continued

<210> SEQ ID NO 374
<211> LENGTH: 107
<212> TYPE: PRT
<213> ORGANISM: Artificial Sequence
<220> FEATURE:
<223> OTHER INFORMATION: Recombinant protein

<400> SEQUENCE: 374

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Leu Ser Asp Tyr
            20                  25                  30

Leu Ala Trp Tyr Gln Gln Lys Pro Gly Gln Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 375
<211> LENGTH: 11
<212> TYPE: PRT
<213> ORGANISM: Artificial Sequence
<220> FEATURE:
<223> OTHER INFORMATION: Recombinant protein

<400> SEQUENCE: 375

Arg Ala Ser Gln Gly Leu Ser Asp Tyr Leu Ala
1               5                   10

<210> SEQ ID NO 376
<211> LENGTH: 7
<212> TYPE: PRT
<213> ORGANISM: Artificial Sequence
<220> FEATURE:
<223> OTHER INFORMATION: Recombinant protein

<400> SEQUENCE: 376

Tyr Thr Ser Gln Pro Ala Thr
1               5

<210> SEQ ID NO 377
<211> LENGTH: 9
<212> TYPE: PRT
<213> ORGANISM: Artificial Sequence
<220> FEATURE:
<223> OTHER INFORMATION: Recombinant protein

<400> SEQUENCE: 377

Gln Asn Gly His Ser Phe Pro Leu Thr
1               5

<210> SEQ ID NO 378
<211> LENGTH: 122
<212> TYPE: PRT
<213> ORGANISM: Artificial Sequence
<220> FEATURE:
<223> OTHER INFORMATION: Recombinant protein

<400> SEQUENCE: 378

```
Gln Val Gln Leu Gln Glu Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
            115                 120
```

<210> SEQ ID NO 379
<211> LENGTH: 6
<212> TYPE: PRT
<213> ORGANISM: Artificial Sequence
<220> FEATURE:
<223> OTHER INFORMATION: Recombinant protein

<400> SEQUENCE: 379

```
Ser Asp Ser Ala Trp Ser
1               5
```

<210> SEQ ID NO 380
<211> LENGTH: 16
<212> TYPE: PRT
<213> ORGANISM: Artificial Sequence
<220> FEATURE:
<223> OTHER INFORMATION: Recombinant protein

<400> SEQUENCE: 380

```
Tyr Ile Gln Tyr Ser Gly Ser Thr Asn Tyr Asn Pro Ser Leu Lys Ser
1               5                   10                  15
```

<210> SEQ ID NO 381
<211> LENGTH: 13
<212> TYPE: PRT
<213> ORGANISM: Artificial Sequence
<220> FEATURE:
<223> OTHER INFORMATION: Recombinant protein

<400> SEQUENCE: 381

```
Ser Val Asn Tyr Tyr Gly Asn Ser Phe Ala Val Gly Pro
1               5                   10
```

<210> SEQ ID NO 382
<211> LENGTH: 107
<212> TYPE: PRT
<213> ORGANISM: Artificial Sequence
<220> FEATURE:
<223> OTHER INFORMATION: Recombinant protein

<400> SEQUENCE: 382

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Leu Ser Asp Tyr
            20                  25                  30
```

```
Leu His Trp Tyr Gln Gln Lys Pro Gly Glu Ala Pro Arg Leu Leu Ile
         35                  40                  45

Lys Tyr Ala Ser Gln Pro Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Asn Gly His Ser Phe Pro Leu
                 85                  90                  95

Thr Phe Gly Gln Gly Thr Lys Leu Glu Ile Lys
            100                 105
```

<210> SEQ ID NO 383
<211> LENGTH: 11
<212> TYPE: PRT
<213> ORGANISM: Artificial Sequence
<220> FEATURE:
<223> OTHER INFORMATION: Recombinant protein

<400> SEQUENCE: 383

```
Arg Ala Ser Gln Gly Leu Ser Asp Tyr Leu His
 1               5                  10
```

<210> SEQ ID NO 384
<211> LENGTH: 7
<212> TYPE: PRT
<213> ORGANISM: Artificial Sequence
<220> FEATURE:
<223> OTHER INFORMATION: Recombinant protein

<400> SEQUENCE: 384

```
Tyr Ala Ser Gln Pro Ala Thr
 1               5
```

<210> SEQ ID NO 385
<211> LENGTH: 9
<212> TYPE: PRT
<213> ORGANISM: Artificial Sequence
<220> FEATURE:
<223> OTHER INFORMATION: Recombinant protein

<400> SEQUENCE: 385

```
Gln Asn Gly His Ser Phe Pro Leu Thr
 1               5
```

<210> SEQ ID NO 386
<211> LENGTH: 122
<212> TYPE: PRT
<213> ORGANISM: Artificial Sequence
<220> FEATURE:
<223> OTHER INFORMATION: Recombinant protein

<400> SEQUENCE: 386

```
Gln Val Gln Leu Gln Glu Ser Gly Pro Gly Leu Val Glu Pro Ser Asp
 1               5                  10                  15

Thr Leu Ser Leu Thr Cys Ala Val Ser Gly Tyr Ser Ile Ser Ser Asp
                 20                  25                  30

Ser Ala Trp Ser Trp Ile Arg Gln Pro Pro Gly Lys Gly Leu Glu Trp
             35                  40                  45

Ile Gly Tyr Ile Gln Tyr Ser Gly Ser Thr Asn Tyr Asn Pro Ser Leu
 50                  55                  60

Lys Ser Arg Val Thr Met Ser Val Asp Thr Ser Lys Asn Gln Phe Ser
 65                  70                  75                  80
```

```
Leu Lys Leu Ser Ser Val Thr Ala Leu Asp Thr Ala Val Tyr Tyr Cys
            85                  90                  95

Ala Arg Ser Val Asn Tyr Tyr Gly Asn Ser Phe Ala Val Gly Pro Trp
        100                 105                 110

Gly Gln Gly Thr Leu Val Thr Val Ser Ser
        115                 120
```

<210> SEQ ID NO 387
<211> LENGTH: 6
<212> TYPE: PRT
<213> ORGANISM: Artificial Sequence
<220> FEATURE:
<223> OTHER INFORMATION: Recombinant protein

<400> SEQUENCE: 387

```
Ser Asp Ser Ala Trp Ser
1               5
```

<210> SEQ ID NO 388
<211> LENGTH: 16
<212> TYPE: PRT
<213> ORGANISM: Artificial Sequence
<220> FEATURE:
<223> OTHER INFORMATION: Recombinant protein

<400> SEQUENCE: 388

```
Tyr Ile Gln Tyr Ser Gly Ser Thr Asn Tyr Asn Pro Ser Leu Lys Ser
1               5                   10                  15
```

<210> SEQ ID NO 389
<211> LENGTH: 13
<212> TYPE: PRT
<213> ORGANISM: Artificial Sequence
<220> FEATURE:
<223> OTHER INFORMATION: Recombinant protein

<400> SEQUENCE: 389

```
Ser Val Asn Tyr Tyr Gly Asn Ser Phe Ala Val Gly Pro
1               5                   10
```

<210> SEQ ID NO 390
<211> LENGTH: 107
<212> TYPE: PRT
<213> ORGANISM: Artificial Sequence
<220> FEATURE:
<223> OTHER INFORMATION: Recombinant protein

<400> SEQUENCE: 390

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
            20                  25                  30

Leu Ala Trp Tyr Gln Gln Lys Pro Gly Glu Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105
```

<210> SEQ ID NO 391
<211> LENGTH: 11
<212> TYPE: PRT
<213> ORGANISM: Artificial Sequence
<220> FEATURE:
<223> OTHER INFORMATION: Recombinant protein

<400> SEQUENCE: 391

Arg Ala Ser Gln Gly Val Ser Asp Tyr Leu Ala
1               5                   10

<210> SEQ ID NO 392
<211> LENGTH: 7
<212> TYPE: PRT
<213> ORGANISM: Artificial Sequence
<220> FEATURE:
<223> OTHER INFORMATION: Recombinant protein

<400> SEQUENCE: 392

Tyr Ala Ser Gln Pro Ala Thr
1               5

<210> SEQ ID NO 393
<211> LENGTH: 9
<212> TYPE: PRT
<213> ORGANISM: Artificial Sequence
<220> FEATURE:
<223> OTHER INFORMATION: Recombinant protein

<400> SEQUENCE: 393

Gln Asn Gly His Ser Phe Pro Leu Thr
1               5

<210> SEQ ID NO 394
<211> LENGTH: 122
<212> TYPE: PRT
<213> ORGANISM: Artificial Sequence
<220> FEATURE:
<223> OTHER INFORMATION: Recombinant protein

<400> SEQUENCE: 394

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
                20                  25                  30

Ser Ala Trp Ser Trp Ile Arg Gln Pro Pro Gly Lys Gly Leu Glu Trp
            35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
                100                 105                 110

Gly Gln Gly Thr Leu Val Thr Val Ser Ser
        115                 120

<210> SEQ ID NO 395
<211> LENGTH: 6
<212> TYPE: PRT
<213> ORGANISM: Artificial Sequence
<220> FEATURE:

```
<223> OTHER INFORMATION: Recombinant protein

<400> SEQUENCE: 395

Ser Asp Ser Ala Trp Ser
1               5

<210> SEQ ID NO 396
<211> LENGTH: 16
<212> TYPE: PRT
<213> ORGANISM: Artificial Sequence
<220> FEATURE:
<223> OTHER INFORMATION: Recombinant protein

<400> SEQUENCE: 396

Tyr Ile Gln Tyr Ser Gly Ser Thr Asn Tyr Asn Pro Ser Leu Lys Ser
1               5                   10                  15

<210> SEQ ID NO 397
<211> LENGTH: 13
<212> TYPE: PRT
<213> ORGANISM: Artificial Sequence
<220> FEATURE:
<223> OTHER INFORMATION: Recombinant protein

<400> SEQUENCE: 397

Ser Val Asn Tyr Tyr Gly Asn Ser Phe Ala Val Gly Pro
1               5                   10

<210> SEQ ID NO 398
<211> LENGTH: 107
<212> TYPE: PRT
<213> ORGANISM: Artificial Sequence
<220> FEATURE:
<223> OTHER INFORMATION: Recombinant protein

<400> SEQUENCE: 398

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
                20                  25                  30

Leu Ala Trp Tyr Gln Gln Lys Pro Gly Glu Ala Pro Arg Leu Leu Ile
            35                  40                  45

Lys Tyr Thr Ser Gln Pro Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 399
<211> LENGTH: 11
<212> TYPE: PRT
<213> ORGANISM: Artificial Sequence
<220> FEATURE:
<223> OTHER INFORMATION: Recombinant protein

<400> SEQUENCE: 399

Arg Ala Ser Gln Gly Val Ser Asp Tyr Leu Ala
1               5                   10

<210> SEQ ID NO 400
```

```
<211> LENGTH: 7
<212> TYPE: PRT
<213> ORGANISM: Artificial Sequence
<220> FEATURE:
<223> OTHER INFORMATION: Recombinant protein

<400> SEQUENCE: 400

Tyr Thr Ser Gln Pro Ala Thr
1               5

<210> SEQ ID NO 401
<211> LENGTH: 9
<212> TYPE: PRT
<213> ORGANISM: Artificial Sequence
<220> FEATURE:
<223> OTHER INFORMATION: Recombinant protein

<400> SEQUENCE: 401

Gln Asn Gly His Ser Phe Pro Leu Thr
1               5

<210> SEQ ID NO 402
<211> LENGTH: 122
<212> TYPE: PRT
<213> ORGANISM: Artificial Sequence
<220> FEATURE:
<223> OTHER INFORMATION: Recombinant protein

<400> SEQUENCE: 402

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 403
<211> LENGTH: 6
<212> TYPE: PRT
<213> ORGANISM: Artificial Sequence
<220> FEATURE:
<223> OTHER INFORMATION: Recombinant protein

<400> SEQUENCE: 403

Ser Asp Ser Ala Trp Ser
1               5

<210> SEQ ID NO 404
<211> LENGTH: 16
<212> TYPE: PRT
<213> ORGANISM: Artificial Sequence
<220> FEATURE:
<223> OTHER INFORMATION: Recombinant protein
```

```
<400> SEQUENCE: 404

Tyr Ile Gln Tyr Ser Gly Ser Thr Asn Tyr Asn Pro Ser Leu Lys Ser
1               5                   10                  15

<210> SEQ ID NO 405
<211> LENGTH: 13
<212> TYPE: PRT
<213> ORGANISM: Artificial Sequence
<220> FEATURE:
<223> OTHER INFORMATION: Recombinant protein

<400> SEQUENCE: 405

Ser Val Asn Tyr Tyr Gly Asn Ser Phe Ala Val Gly Pro
1               5                   10

<210> SEQ ID NO 406
<211> LENGTH: 107
<212> TYPE: PRT
<213> ORGANISM: Artificial Sequence
<220> FEATURE:
<223> OTHER INFORMATION: Recombinant protein

<400> SEQUENCE: 406

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Ala Gly Thr Lys Leu Glu Ile Lys
            100                 105

<210> SEQ ID NO 407
<211> LENGTH: 11
<212> TYPE: PRT
<213> ORGANISM: Artificial Sequence
<220> FEATURE:
<223> OTHER INFORMATION: Recombinant protein

<400> SEQUENCE: 407

Arg Ala Ser Gln Gly Val Ser Asp Tyr Leu Ala
1               5                   10

<210> SEQ ID NO 408
<211> LENGTH: 7
<212> TYPE: PRT
<213> ORGANISM: Artificial Sequence
<220> FEATURE:
<223> OTHER INFORMATION: Recombinant protein

<400> SEQUENCE: 408

Tyr Ala Ser Gln Pro Ala Thr
1               5

<210> SEQ ID NO 409
<211> LENGTH: 9
<212> TYPE: PRT
```

<213> ORGANISM: Artificial Sequence
<220> FEATURE:
<223> OTHER INFORMATION: Recombinant protein

<400> SEQUENCE: 409

Gln Asn Gly His Ser Phe Pro Leu Thr
1               5

<210> SEQ ID NO 410
<211> LENGTH: 122
<212> TYPE: PRT
<213> ORGANISM: Artificial Sequence
<220> FEATURE:
<223> OTHER INFORMATION: Recombinant protein

<400> SEQUENCE: 410

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 411
<211> LENGTH: 6
<212> TYPE: PRT
<213> ORGANISM: Artificial Sequence
<220> FEATURE:
<223> OTHER INFORMATION: Recombinant protein

<400> SEQUENCE: 411

Ser Asp Ser Ala Trp Ser
1               5

<210> SEQ ID NO 412
<211> LENGTH: 16
<212> TYPE: PRT
<213> ORGANISM: Artificial Sequence
<220> FEATURE:
<223> OTHER INFORMATION: Recombinant protein

<400> SEQUENCE: 412

Tyr Ile Gln Tyr Ser Gly Ser Thr Asn Tyr Asn Pro Ser Leu Lys Ser
1               5                   10                  15

<210> SEQ ID NO 413
<211> LENGTH: 13
<212> TYPE: PRT
<213> ORGANISM: Artificial Sequence
<220> FEATURE:
<223> OTHER INFORMATION: Recombinant protein

<400> SEQUENCE: 413

```
Ser Val Asn Tyr Tyr Gly Asn Ser Phe Ala Val Gly Pro
1               5                   10
```

<210> SEQ ID NO 414
<211> LENGTH: 107
<212> TYPE: PRT
<213> ORGANISM: Artificial Sequence
<220> FEATURE:
<223> OTHER INFORMATION: Recombinant protein

<400> SEQUENCE: 414

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105
```

<210> SEQ ID NO 415
<211> LENGTH: 11
<212> TYPE: PRT
<213> ORGANISM: Artificial Sequence
<220> FEATURE:
<223> OTHER INFORMATION: Recombinant protein

<400> SEQUENCE: 415

```
Arg Ala Ser Gln Gly Val Ser Asp Tyr Leu Ala
1               5                   10
```

<210> SEQ ID NO 416
<211> LENGTH: 7
<212> TYPE: PRT
<213> ORGANISM: Artificial Sequence
<220> FEATURE:
<223> OTHER INFORMATION: Recombinant protein

<400> SEQUENCE: 416

```
Tyr Ala Ser Gln Pro Ala Thr
1               5
```

<210> SEQ ID NO 417
<211> LENGTH: 9
<212> TYPE: PRT
<213> ORGANISM: Artificial Sequence
<220> FEATURE:
<223> OTHER INFORMATION: Recombinant protein

<400> SEQUENCE: 417

```
Gln Asn Gly His Ser Phe Pro Leu Thr
1               5
```

<210> SEQ ID NO 418
<211> LENGTH: 122
<212> TYPE: PRT
<213> ORGANISM: Artificial Sequence
<220> FEATURE:

<223> OTHER INFORMATION: Recombinant protein

<400> SEQUENCE: 418

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
            115                 120

<210> SEQ ID NO 419
<211> LENGTH: 6
<212> TYPE: PRT
<213> ORGANISM: Artificial Sequence
<220> FEATURE:
<223> OTHER INFORMATION: Recombinant protein

<400> SEQUENCE: 419

Ser Asp Ser Ala Trp Ser
1               5

<210> SEQ ID NO 420
<211> LENGTH: 16
<212> TYPE: PRT
<213> ORGANISM: Artificial Sequence
<220> FEATURE:
<223> OTHER INFORMATION: Recombinant protein

<400> SEQUENCE: 420

Tyr Ile Gln Tyr Ser Gly Ser Thr Asn Tyr Asn Pro Ser Leu Lys Ser
1               5                   10                  15

<210> SEQ ID NO 421
<211> LENGTH: 13
<212> TYPE: PRT
<213> ORGANISM: Artificial Sequence
<220> FEATURE:
<223> OTHER INFORMATION: Recombinant protein

<400> SEQUENCE: 421

Ser Val Asn Tyr Tyr Gly Asn Ser Phe Ala Val Gly Pro
1               5                   10

<210> SEQ ID NO 422
<211> LENGTH: 107
<212> TYPE: PRT
<213> ORGANISM: Artificial Sequence
<220> FEATURE:
<223> OTHER INFORMATION: Recombinant protein

<400> SEQUENCE: 422

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly His Ser Phe Pro Leu
                85                  90                  95

Thr Phe Gly Gln Gly Thr Lys Leu Glu Ile Lys
            100                 105

<210> SEQ ID NO 423
<211> LENGTH: 11
<212> TYPE: PRT
<213> ORGANISM: Artificial Sequence
<220> FEATURE:
<223> OTHER INFORMATION: Recombinant protein

<400> SEQUENCE: 423

Arg Ala Ser Gln Gly Val Ser Asp Tyr Leu Ala
1               5                   10

<210> SEQ ID NO 424
<211> LENGTH: 7
<212> TYPE: PRT
<213> ORGANISM: Artificial Sequence
<220> FEATURE:
<223> OTHER INFORMATION: Recombinant protein

<400> SEQUENCE: 424

Tyr Ala Ser Gln Pro Ala Thr
1               5

<210> SEQ ID NO 425
<211> LENGTH: 9
<212> TYPE: PRT
<213> ORGANISM: Artificial Sequence
<220> FEATURE:
<223> OTHER INFORMATION: Recombinant protein

<400> SEQUENCE: 425

Gln Gln Gly His Ser Phe Pro Leu Thr
1               5

<210> SEQ ID NO 426
<211> LENGTH: 122
<212> TYPE: PRT
<213> ORGANISM: Artificial Sequence
<220> FEATURE:
<223> OTHER INFORMATION: Recombinant protein

<400> SEQUENCE: 426

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
50                  55                  60

```
Lys Ser Arg Val Thr Met Ser Val Asp Thr Ser Lys Asn Gln Phe Ser
 65                  70                  75                  80

Leu Lys Leu Ser Ser Val Thr Ala Leu Asp Thr Ala Val Tyr Tyr Cys
                 85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 427
<211> LENGTH: 6
<212> TYPE: PRT
<213> ORGANISM: Artificial Sequence
<220> FEATURE:
<223> OTHER INFORMATION: Recombinant protein

<400> SEQUENCE: 427

Ser Asp Ser Ala Trp Ser
1               5

<210> SEQ ID NO 428
<211> LENGTH: 16
<212> TYPE: PRT
<213> ORGANISM: Artificial Sequence
<220> FEATURE:
<223> OTHER INFORMATION: Recombinant protein

<400> SEQUENCE: 428

Tyr Ile Gln Tyr Ser Gly Ser Thr Asn Tyr Asn Pro Ser Leu Lys Ser
1               5                   10                  15

<210> SEQ ID NO 429
<211> LENGTH: 13
<212> TYPE: PRT
<213> ORGANISM: Artificial Sequence
<220> FEATURE:
<223> OTHER INFORMATION: Recombinant protein

<400> SEQUENCE: 429

Ser Val Asn Tyr Tyr Gly Asn Ser Phe Ala Val Gly Pro
1               5                   10

<210> SEQ ID NO 430
<211> LENGTH: 107
<212> TYPE: PRT
<213> ORGANISM: Artificial Sequence
<220> FEATURE:
<223> OTHER INFORMATION: Recombinant protein

<400> SEQUENCE: 430

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
                20                  25                  30

Leu Ala Trp Tyr Gln Gln Lys Pro Gly Gln Ala Pro Arg Leu Leu Ile
            35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Gly Val Tyr Tyr Cys Gln Asn Gly His Ser Phe Pro Leu
                85                  90                  95
```

Thr Phe Gly Gln Gly Thr Lys Leu Glu Ile Lys
            100                 105

<210> SEQ ID NO 431
<211> LENGTH: 11
<212> TYPE: PRT
<213> ORGANISM: Artificial Sequence
<220> FEATURE:
<223> OTHER INFORMATION: Recombinant protein

<400> SEQUENCE: 431

Arg Ala Ser Gln Gly Val Ser Asp Tyr Leu Ala
1               5                   10

<210> SEQ ID NO 432
<211> LENGTH: 7
<212> TYPE: PRT
<213> ORGANISM: Artificial Sequence
<220> FEATURE:
<223> OTHER INFORMATION: Recombinant protein

<400> SEQUENCE: 432

Tyr Ala Ser Gln Pro Ala Thr
1               5

<210> SEQ ID NO 433
<211> LENGTH: 9
<212> TYPE: PRT
<213> ORGANISM: Artificial Sequence
<220> FEATURE:
<223> OTHER INFORMATION: Recombinant protein

<400> SEQUENCE: 433

Gln Asn Gly His Ser Phe Pro Leu Thr
1               5

<210> SEQ ID NO 434
<211> LENGTH: 122
<212> TYPE: PRT
<213> ORGANISM: Artificial Sequence
<220> FEATURE:
<223> OTHER INFORMATION: Recombinant protein

<400> SEQUENCE: 434

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 435

```
<211> LENGTH: 6
<212> TYPE: PRT
<213> ORGANISM: Artificial Sequence
<220> FEATURE:
<223> OTHER INFORMATION: Recombinant protein

<400> SEQUENCE: 435

Ser Asp Ser Ala Trp Ser
1               5

<210> SEQ ID NO 436
<211> LENGTH: 16
<212> TYPE: PRT
<213> ORGANISM: Artificial Sequence
<220> FEATURE:
<223> OTHER INFORMATION: Recombinant protein

<400> SEQUENCE: 436

Tyr Ile Gln Tyr Ser Gly Ser Thr Asn Tyr Asn Pro Ser Leu Lys Ser
1               5                   10                  15

<210> SEQ ID NO 437
<211> LENGTH: 13
<212> TYPE: PRT
<213> ORGANISM: Artificial Sequence
<220> FEATURE:
<223> OTHER INFORMATION: Recombinant protein

<400> SEQUENCE: 437

Ser Val Asn Tyr Tyr Gly Asn Ser Phe Ala Val Gly Pro
1               5                   10

<210> SEQ ID NO 438
<211> LENGTH: 107
<212> TYPE: PRT
<213> ORGANISM: Artificial Sequence
<220> FEATURE:
<223> OTHER INFORMATION: Recombinant protein

<400> SEQUENCE: 438

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
                20                  25                  30

Leu Ala Trp Tyr Gln Gln Lys Pro Gly Gln Ala Pro Arg Leu Leu Ile
            35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 439
<211> LENGTH: 11
<212> TYPE: PRT
<213> ORGANISM: Artificial Sequence
<220> FEATURE:
<223> OTHER INFORMATION: Recombinant protein

<400> SEQUENCE: 439

Arg Ala Ser Gln Gly Val Ser Asp Tyr Leu Ala
1               5                   10
```

```
1               5                   10
```

<210> SEQ ID NO 440
<211> LENGTH: 7
<212> TYPE: PRT
<213> ORGANISM: Artificial Sequence
<220> FEATURE:
<223> OTHER INFORMATION: Recombinant protein

<400> SEQUENCE: 440

Tyr Ala Ser Gln Pro Ala Thr
1               5

<210> SEQ ID NO 441
<211> LENGTH: 9
<212> TYPE: PRT
<213> ORGANISM: Artificial Sequence
<220> FEATURE:
<223> OTHER INFORMATION: Recombinant protein

<400> SEQUENCE: 441

Gln Asn Gly His Ser Phe Pro Leu Thr
1               5

<210> SEQ ID NO 442
<211> LENGTH: 122
<212> TYPE: PRT
<213> ORGANISM: Artificial Sequence
<220> FEATURE:
<223> OTHER INFORMATION: Recombinant protein

<400> SEQUENCE: 442

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 443
<211> LENGTH: 6
<212> TYPE: PRT
<213> ORGANISM: Artificial Sequence
<220> FEATURE:
<223> OTHER INFORMATION: Recombinant protein

<400> SEQUENCE: 443

Ser Asp Ser Ala Trp Ser
1               5

<210> SEQ ID NO 444
<211> LENGTH: 16
<212> TYPE: PRT

```
<213> ORGANISM: Artificial Sequence
<220> FEATURE:
<223> OTHER INFORMATION: Recombinant protein

<400> SEQUENCE: 444

Tyr Ile Gln Tyr Ser Gly Ser Thr Asn Tyr Asn Pro Ser Leu Lys Ser
1               5                   10                  15

<210> SEQ ID NO 445
<211> LENGTH: 13
<212> TYPE: PRT
<213> ORGANISM: Artificial Sequence
<220> FEATURE:
<223> OTHER INFORMATION: Recombinant protein

<400> SEQUENCE: 445

Ser Val Asn Tyr Tyr Gly Asn Ser Phe Ala Val Gly Pro
1               5                   10

<210> SEQ ID NO 446
<211> LENGTH: 107
<212> TYPE: PRT
<213> ORGANISM: Artificial Sequence
<220> FEATURE:
<223> OTHER INFORMATION: Recombinant protein

<400> SEQUENCE: 446

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
            20                  25                  30

Leu Ala Trp Tyr Gln Gln Lys Pro Gly Gln Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 447
<211> LENGTH: 11
<212> TYPE: PRT
<213> ORGANISM: Artificial Sequence
<220> FEATURE:
<223> OTHER INFORMATION: Recombinant protein

<400> SEQUENCE: 447

Arg Ala Ser Gln Gly Val Ser Asp Tyr Leu Ala
1               5                   10

<210> SEQ ID NO 448
<211> LENGTH: 7
<212> TYPE: PRT
<213> ORGANISM: Artificial Sequence
<220> FEATURE:
<223> OTHER INFORMATION: Recombinant protein

<400> SEQUENCE: 448

Tyr Thr Ser Gln Pro Ala Thr
1               5
```

```
<210> SEQ ID NO 449
<211> LENGTH: 9
<212> TYPE: PRT
<213> ORGANISM: Artificial Sequence
<220> FEATURE:
<223> OTHER INFORMATION: Recombinant protein

<400> SEQUENCE: 449

Gln Asn Gly His Ser Phe Pro Leu Thr
1               5

<210> SEQ ID NO 450
<211> LENGTH: 122
<212> TYPE: PRT
<213> ORGANISM: Artificial Sequence
<220> FEATURE:
<223> OTHER INFORMATION: Recombinant protein

<400> SEQUENCE: 450

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 451
<211> LENGTH: 6
<212> TYPE: PRT
<213> ORGANISM: Artificial Sequence
<220> FEATURE:
<223> OTHER INFORMATION: Recombinant protein

<400> SEQUENCE: 451

Ser Asp Ser Ala Trp Ser
1               5

<210> SEQ ID NO 452
<211> LENGTH: 16
<212> TYPE: PRT
<213> ORGANISM: Artificial Sequence
<220> FEATURE:
<223> OTHER INFORMATION: Recombinant protein

<400> SEQUENCE: 452

Tyr Ile Gln Tyr Ser Gly Ser Thr Asn Tyr Asn Pro Ser Leu Lys Ser
1               5                   10                  15

<210> SEQ ID NO 453
<211> LENGTH: 13
<212> TYPE: PRT
<213> ORGANISM: Artificial Sequence
<220> FEATURE:
```

<223> OTHER INFORMATION: Recombinant protein

<400> SEQUENCE: 453

Ser Val Asn Tyr Tyr Gly Asn Ser Phe Ala Val Gly Pro
1               5                   10

<210> SEQ ID NO 454
<211> LENGTH: 107
<212> TYPE: PRT
<213> ORGANISM: Artificial Sequence
<220> FEATURE:
<223> OTHER INFORMATION: Recombinant protein

<400> SEQUENCE: 454

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
            20                  25                  30

Leu His Trp Tyr Gln Gln Lys Pro Gly Glu Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 455
<211> LENGTH: 11
<212> TYPE: PRT
<213> ORGANISM: Artificial Sequence
<220> FEATURE:
<223> OTHER INFORMATION: Recombinant protein

<400> SEQUENCE: 455

Arg Ala Ser Gln Gly Val Ser Asp Tyr Leu His
1               5                   10

<210> SEQ ID NO 456
<211> LENGTH: 7
<212> TYPE: PRT
<213> ORGANISM: Artificial Sequence
<220> FEATURE:
<223> OTHER INFORMATION: Recombinant protein

<400> SEQUENCE: 456

Tyr Ala Ser Gln Pro Ala Thr
1               5

<210> SEQ ID NO 457
<211> LENGTH: 9
<212> TYPE: PRT
<213> ORGANISM: Artificial Sequence
<220> FEATURE:
<223> OTHER INFORMATION: Recombinant protein

<400> SEQUENCE: 457

Gln Asn Gly His Ser Phe Pro Leu Thr
1               5

<210> SEQ ID NO 458

```
<211> LENGTH: 122
<212> TYPE: PRT
<213> ORGANISM: Artificial Sequence
<220> FEATURE:
<223> OTHER INFORMATION: Recombinant protein

<400> SEQUENCE: 458

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 459
<211> LENGTH: 6
<212> TYPE: PRT
<213> ORGANISM: Artificial Sequence
<220> FEATURE:
<223> OTHER INFORMATION: Recombinant protein

<400> SEQUENCE: 459

Ser Asp Ser Ala Trp Ser
1               5

<210> SEQ ID NO 460
<211> LENGTH: 16
<212> TYPE: PRT
<213> ORGANISM: Artificial Sequence
<220> FEATURE:
<223> OTHER INFORMATION: Recombinant protein

<400> SEQUENCE: 460

Tyr Ile Gln Tyr Ser Gly Ser Thr Asn Tyr Asn Pro Ser Leu Lys Ser
1               5                   10                  15

<210> SEQ ID NO 461
<211> LENGTH: 13
<212> TYPE: PRT
<213> ORGANISM: Artificial Sequence
<220> FEATURE:
<223> OTHER INFORMATION: Recombinant protein

<400> SEQUENCE: 461

Ser Val Asn Tyr Tyr Gly Asn Ser Phe Ala Val Gly Pro
1               5                   10

<210> SEQ ID NO 462
<211> LENGTH: 107
<212> TYPE: PRT
<213> ORGANISM: Artificial Sequence
<220> FEATURE:
<223> OTHER INFORMATION: Recombinant protein
```

<400> SEQUENCE: 462

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Ala Gly Thr Lys Leu Glu Ile Lys
            100                 105

<210> SEQ ID NO 463
<211> LENGTH: 11
<212> TYPE: PRT
<213> ORGANISM: Artificial Sequence
<220> FEATURE:
<223> OTHER INFORMATION: Recombinant protein

<400> SEQUENCE: 463

Arg Ala Ser Gln Gly Val Ser Asp Tyr Leu His
1               5                   10

<210> SEQ ID NO 464
<211> LENGTH: 7
<212> TYPE: PRT
<213> ORGANISM: Artificial Sequence
<220> FEATURE:
<223> OTHER INFORMATION: Recombinant protein

<400> SEQUENCE: 464

Tyr Ala Ser Gln Pro Ala Thr
1               5

<210> SEQ ID NO 465
<211> LENGTH: 9
<212> TYPE: PRT
<213> ORGANISM: Artificial Sequence
<220> FEATURE:
<223> OTHER INFORMATION: Recombinant protein

<400> SEQUENCE: 465

Gln Asn Gly His Ser Phe Pro Leu Thr
1               5

<210> SEQ ID NO 466
<211> LENGTH: 122
<212> TYPE: PRT
<213> ORGANISM: Artificial Sequence
<220> FEATURE:
<223> OTHER INFORMATION: Recombinant protein

<400> SEQUENCE: 466

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp

```
            35                  40                  45
Ile Gly Tyr Ile Gln Tyr Ser Gly Ser Thr Asn Tyr Asn Pro Ser Leu
 50                  55                  60

Lys Ser Arg Val Thr Met Ser Val Asp Thr Ser Lys Asn Gln Phe Ser
 65                  70                  75                  80

Leu Lys Leu Ser Ser Val Thr Ala Leu Asp Thr Ala Val Tyr Tyr Cys
                 85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120
```

<210> SEQ ID NO 467
<211> LENGTH: 6
<212> TYPE: PRT
<213> ORGANISM: Artificial Sequence
<220> FEATURE:
<223> OTHER INFORMATION: Recombinant protein

<400> SEQUENCE: 467

```
Ser Asp Ser Ala Trp Ser
 1               5
```

<210> SEQ ID NO 468
<211> LENGTH: 16
<212> TYPE: PRT
<213> ORGANISM: Artificial Sequence
<220> FEATURE:
<223> OTHER INFORMATION: Recombinant protein

<400> SEQUENCE: 468

```
Tyr Ile Gln Tyr Ser Gly Ser Thr Asn Tyr Asn Pro Ser Leu Lys Ser
 1               5                  10                  15
```

<210> SEQ ID NO 469
<211> LENGTH: 13
<212> TYPE: PRT
<213> ORGANISM: Artificial Sequence
<220> FEATURE:
<223> OTHER INFORMATION: Recombinant protein

<400> SEQUENCE: 469

```
Ser Val Asn Tyr Tyr Gly Asn Ser Phe Ala Val Gly Pro
 1               5                  10
```

<210> SEQ ID NO 470
<211> LENGTH: 107
<212> TYPE: PRT
<213> ORGANISM: Artificial Sequence
<220> FEATURE:
<223> OTHER INFORMATION: Recombinant protein

<400> SEQUENCE: 470

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Gly Val Ser Asp Tyr
             20                  25                  30

Leu His Trp Tyr Gln Gln Lys Pro Gly Gln Ala Pro Arg Leu Leu Ile
         35                  40                  45

Lys Tyr Ala Ser Gln Pro Ala Thr Gly Ile Pro Ala Arg Phe Ser Gly
 50                  55                  60

Ser Gly Ser Gly Thr Asp Phe Thr Leu Thr Ile Ser Ser Leu Glu Pro
```

```
                 65                  70                  75                  80
Glu Asp Phe Ala Val Tyr Tyr Cys Gln Asn Gly His Ser Phe Pro Leu
                 85                  90                  95
Thr Phe Gly Gln Gly Thr Lys Leu Glu Ile Lys
                100                 105
```

<210> SEQ ID NO 471
<211> LENGTH: 11
<212> TYPE: PRT
<213> ORGANISM: Artificial Sequence
<220> FEATURE:
<223> OTHER INFORMATION: Recombinant protein

<400> SEQUENCE: 471

```
Arg Ala Ser Gln Gly Val Ser Asp Tyr Leu His
1               5                   10
```

<210> SEQ ID NO 472
<211> LENGTH: 7
<212> TYPE: PRT
<213> ORGANISM: Artificial Sequence
<220> FEATURE:
<223> OTHER INFORMATION: Recombinant protein

<400> SEQUENCE: 472

```
Tyr Ala Ser Gln Pro Ala Thr
1               5
```

<210> SEQ ID NO 473
<211> LENGTH: 9
<212> TYPE: PRT
<213> ORGANISM: Artificial Sequence
<220> FEATURE:
<223> OTHER INFORMATION: Recombinant protein

<400> SEQUENCE: 473

```
Gln Asn Gly His Ser Phe Pro Leu Thr
1               5
```

<210> SEQ ID NO 474
<211> LENGTH: 122
<212> TYPE: PRT
<213> ORGANISM: Artificial Sequence
<220> FEATURE:
<223> OTHER INFORMATION: Recombinant protein

<400> SEQUENCE: 474

```
Gln Val Gln Leu Gln Glu Ser Gly Pro Gly Leu Val Glu Pro Ser Asp
1               5                   10                  15
Thr Leu Ser Leu Thr Cys Ala Val Ser Gly Tyr Ser Ile Ser Ser Asp
                20                  25                  30
Ser Ala Trp Ser Trp Ile Arg Gln Pro Pro Gly Lys Gly Leu Glu Trp
            35                  40                  45
Ile Gly Tyr Ile Gln Tyr Ser Gly Ser Thr Asn Tyr Asn Pro Ser Leu
        50                  55                  60
Lys Ser Arg Val Thr Met Ser Val Asp Thr Ser Lys Asn Gln Phe Ser
65                  70                  75                  80
Leu Lys Leu Ser Ser Val Thr Ala Leu Asp Thr Ala Val Tyr Tyr Cys
                85                  90                  95
Ala Arg Ser Val Asn Tyr Tyr Gly Asn Ser Phe Ala Val Gly Pro Trp
                100                 105                 110
Gly Gln Gly Thr Leu Val Thr Val Ser Ser
```

<210> SEQ ID NO 475
<211> LENGTH: 6
<212> TYPE: PRT
<213> ORGANISM: Artificial Sequence
<220> FEATURE:
<223> OTHER INFORMATION: Recombinant protein

<400> SEQUENCE: 475

Ser Asp Ser Ala Trp Ser
1               5

<210> SEQ ID NO 476
<211> LENGTH: 16
<212> TYPE: PRT
<213> ORGANISM: Artificial Sequence
<220> FEATURE:
<223> OTHER INFORMATION: Recombinant protein

<400> SEQUENCE: 476

Tyr Ile Gln Tyr Ser Gly Ser Thr Asn Tyr Asn Pro Ser Leu Lys Ser
1               5                   10                  15

<210> SEQ ID NO 477
<211> LENGTH: 13
<212> TYPE: PRT
<213> ORGANISM: Artificial Sequence
<220> FEATURE:
<223> OTHER INFORMATION: Recombinant protein

<400> SEQUENCE: 477

Ser Val Asn Tyr Tyr Gly Asn Ser Phe Ala Val Gly Pro
1               5                   10

<210> SEQ ID NO 478
<211> LENGTH: 107
<212> TYPE: PRT
<213> ORGANISM: Artificial Sequence
<220> FEATURE:
<223> OTHER INFORMATION: Recombinant protein

<400> SEQUENCE: 478

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly His Ser Phe Pro Leu
                85                  90                  95

Thr Phe Gly Gln Gly Thr Lys Leu Glu Ile Lys
            100                 105

<210> SEQ ID NO 479
<211> LENGTH: 11
<212> TYPE: PRT
<213> ORGANISM: Artificial Sequence
<220> FEATURE:
<223> OTHER INFORMATION: Recombinant protein

```
<400> SEQUENCE: 479

Arg Ala Ser Gln Gly Val Ser Asp Tyr Leu His
1               5                   10

<210> SEQ ID NO 480
<211> LENGTH: 7
<212> TYPE: PRT
<213> ORGANISM: Artificial Sequence
<220> FEATURE:
<223> OTHER INFORMATION: Recombinant protein

<400> SEQUENCE: 480

Tyr Ala Ser Gln Pro Ala Thr
1               5

<210> SEQ ID NO 481
<211> LENGTH: 9
<212> TYPE: PRT
<213> ORGANISM: Artificial Sequence
<220> FEATURE:
<223> OTHER INFORMATION: Recombinant protein

<400> SEQUENCE: 481

Gln Gln Gly His Ser Phe Pro Leu Thr
1               5

<210> SEQ ID NO 482
<211> LENGTH: 122
<212> TYPE: PRT
<213> ORGANISM: Artificial Sequence
<220> FEATURE:
<223> OTHER INFORMATION: Recombinant protein

<400> SEQUENCE: 482

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 483
<211> LENGTH: 6
<212> TYPE: PRT
<213> ORGANISM: Artificial Sequence
<220> FEATURE:
<223> OTHER INFORMATION: Recombinant protein

<400> SEQUENCE: 483

Ser Asp Ser Ala Trp Ser
1               5
```

```
<210> SEQ ID NO 484
<211> LENGTH: 16
<212> TYPE: PRT
<213> ORGANISM: Artificial Sequence
<220> FEATURE:
<223> OTHER INFORMATION: Recombinant protein

<400> SEQUENCE: 484

Tyr Ile Gln Tyr Ser Gly Ser Thr Asn Tyr Asn Pro Ser Leu Lys Ser
1               5                   10                  15

<210> SEQ ID NO 485
<211> LENGTH: 13
<212> TYPE: PRT
<213> ORGANISM: Artificial Sequence
<220> FEATURE:
<223> OTHER INFORMATION: Recombinant protein

<400> SEQUENCE: 485

Ser Val Asn Tyr Tyr Gly Asn Ser Phe Ala Val Gly Pro
1               5                   10

<210> SEQ ID NO 486
<211> LENGTH: 107
<212> TYPE: PRT
<213> ORGANISM: Artificial Sequence
<220> FEATURE:
<223> OTHER INFORMATION: Recombinant protein

<400> SEQUENCE: 486

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Gly Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 487
<211> LENGTH: 11
<212> TYPE: PRT
<213> ORGANISM: Artificial Sequence
<220> FEATURE:
<223> OTHER INFORMATION: Recombinant protein

<400> SEQUENCE: 487

Arg Ala Ser Gln Gly Val Ser Asp Tyr Leu His
1               5                   10

<210> SEQ ID NO 488
<211> LENGTH: 7
<212> TYPE: PRT
<213> ORGANISM: Artificial Sequence
<220> FEATURE:
<223> OTHER INFORMATION: Recombinant protein

<400> SEQUENCE: 488
```

```
Tyr Ala Ser Gln Pro Ala Thr
1               5

<210> SEQ ID NO 489
<211> LENGTH: 9
<212> TYPE: PRT
<213> ORGANISM: Artificial Sequence
<220> FEATURE:
<223> OTHER INFORMATION: Recombinant protein

<400> SEQUENCE: 489

Gln Asn Gly His Ser Phe Pro Leu Thr
1               5

<210> SEQ ID NO 490
<211> LENGTH: 122
<212> TYPE: PRT
<213> ORGANISM: Artificial Sequence
<220> FEATURE:
<223> OTHER INFORMATION: Recombinant protein

<400> SEQUENCE: 490

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 491
<211> LENGTH: 6
<212> TYPE: PRT
<213> ORGANISM: Artificial Sequence
<220> FEATURE:
<223> OTHER INFORMATION: Recombinant protein

<400> SEQUENCE: 491

Ser Asp Ser Ala Trp Ser
1               5

<210> SEQ ID NO 492
<211> LENGTH: 16
<212> TYPE: PRT
<213> ORGANISM: Artificial Sequence
<220> FEATURE:
<223> OTHER INFORMATION: Recombinant protein

<400> SEQUENCE: 492

Tyr Ile Gln Tyr Ser Gly Ser Thr Asn Tyr Asn Pro Ser Leu Lys Ser
1               5                   10                  15

<210> SEQ ID NO 493
```

```
<211> LENGTH: 13
<212> TYPE: PRT
<213> ORGANISM: Artificial Sequence
<220> FEATURE:
<223> OTHER INFORMATION: Recombinant protein

<400> SEQUENCE: 493

Ser Val Asn Tyr Tyr Gly Asn Ser Phe Ala Val Gly Pro
1               5                   10

<210> SEQ ID NO 494
<211> LENGTH: 107
<212> TYPE: PRT
<213> ORGANISM: Artificial Sequence
<220> FEATURE:
<223> OTHER INFORMATION: Recombinant protein

<400> SEQUENCE: 494

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 495
<211> LENGTH: 11
<212> TYPE: PRT
<213> ORGANISM: Artificial Sequence
<220> FEATURE:
<223> OTHER INFORMATION: Recombinant protein

<400> SEQUENCE: 495

Arg Ala Ser Gln Gly Val Ser Asp Tyr Leu His
1               5                   10

<210> SEQ ID NO 496
<211> LENGTH: 7
<212> TYPE: PRT
<213> ORGANISM: Artificial Sequence
<220> FEATURE:
<223> OTHER INFORMATION: Recombinant protein

<400> SEQUENCE: 496

Tyr Ala Ser Gln Pro Ala Thr
1               5

<210> SEQ ID NO 497
<211> LENGTH: 9
<212> TYPE: PRT
<213> ORGANISM: Artificial Sequence
<220> FEATURE:
<223> OTHER INFORMATION: Recombinant protein

<400> SEQUENCE: 497

Gln Asn Gly His Ser Phe Pro Leu Thr
```

1               5

<210> SEQ ID NO 498
<211> LENGTH: 122
<212> TYPE: PRT
<213> ORGANISM: Artificial Sequence
<220> FEATURE:
<223> OTHER INFORMATION: Recombinant protein

<400> SEQUENCE: 498

Gln Val Gln Leu Gln Glu Ser Gly Pro Gly Leu Val Glu Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 499
<211> LENGTH: 6
<212> TYPE: PRT
<213> ORGANISM: Artificial Sequence
<220> FEATURE:
<223> OTHER INFORMATION: Recombinant protein

<400> SEQUENCE: 499

Ser Asp Ser Ala Trp Ser
1               5

<210> SEQ ID NO 500
<211> LENGTH: 16
<212> TYPE: PRT
<213> ORGANISM: Artificial Sequence
<220> FEATURE:
<223> OTHER INFORMATION: Recombinant protein

<400> SEQUENCE: 500

Tyr Ile Gln Tyr Ser Gly Ser Thr Asn Tyr Asn Pro Ser Leu Lys Ser
1               5                   10                  15

<210> SEQ ID NO 501
<211> LENGTH: 13
<212> TYPE: PRT
<213> ORGANISM: Artificial Sequence
<220> FEATURE:
<223> OTHER INFORMATION: Recombinant protein

<400> SEQUENCE: 501

Ser Val Asn Tyr Tyr Gly Asn Ser Phe Ala Val Gly Pro
1               5                   10

<210> SEQ ID NO 502
<211> LENGTH: 107
<212> TYPE: PRT

<213> ORGANISM: Artificial Sequence
<220> FEATURE:
<223> OTHER INFORMATION: Recombinant protein

<400> SEQUENCE: 502

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
            20                  25                  30

Leu His Trp Tyr Gln Gln Lys Pro Gly Gln Ala Pro Arg Leu Leu Ile
        35                  40                  45

Lys Tyr Thr Ser Gln Pro Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 503
<211> LENGTH: 11
<212> TYPE: PRT
<213> ORGANISM: Artificial Sequence
<220> FEATURE:
<223> OTHER INFORMATION: Recombinant protein

<400> SEQUENCE: 503

Arg Ala Ser Gln Gly Val Ser Asp Tyr Leu His
1               5                   10

<210> SEQ ID NO 504
<211> LENGTH: 7
<212> TYPE: PRT
<213> ORGANISM: Artificial Sequence
<220> FEATURE:
<223> OTHER INFORMATION: Recombinant protein

<400> SEQUENCE: 504

Tyr Thr Ser Gln Pro Ala Thr
1               5

<210> SEQ ID NO 505
<211> LENGTH: 9
<212> TYPE: PRT
<213> ORGANISM: Artificial Sequence
<220> FEATURE:
<223> OTHER INFORMATION: Recombinant protein

<400> SEQUENCE: 505

Gln Asn Gly His Ser Phe Pro Leu Thr
1               5

<210> SEQ ID NO 506
<211> LENGTH: 122
<212> TYPE: PRT
<213> ORGANISM: Artificial Sequence
<220> FEATURE:
<223> OTHER INFORMATION: Recombinant protein

<400> SEQUENCE: 506

Gln Val Gln Leu Gln Glu Ser Gly Pro Gly Leu Val Glu Pro Ser Asp
1               5                   10                  15

```
Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 507
<211> LENGTH: 6
<212> TYPE: PRT
<213> ORGANISM: Artificial Sequence
<220> FEATURE:
<223> OTHER INFORMATION: Recombinant protein

<400> SEQUENCE: 507

Ser Asp Ser Ala Trp Ser
1               5

<210> SEQ ID NO 508
<211> LENGTH: 16
<212> TYPE: PRT
<213> ORGANISM: Artificial Sequence
<220> FEATURE:
<223> OTHER INFORMATION: Recombinant protein

<400> SEQUENCE: 508

Tyr Ile Gln Tyr Ser Gly Ser Thr Asn Tyr Asn Pro Ser Leu Lys Ser
1               5                   10                  15

<210> SEQ ID NO 509
<211> LENGTH: 13
<212> TYPE: PRT
<213> ORGANISM: Artificial Sequence
<220> FEATURE:
<223> OTHER INFORMATION: Recombinant protein

<400> SEQUENCE: 509

Ser Val Asn Tyr Tyr Gly Asn Ser Phe Ala Val Gly Pro
1               5                   10

<210> SEQ ID NO 510
<211> LENGTH: 107
<212> TYPE: PRT
<213> ORGANISM: Artificial Sequence
<220> FEATURE:
<223> OTHER INFORMATION: Recombinant protein

<400> SEQUENCE: 510

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45
```

```
Lys Tyr Ala Ser Gln Pro Ala Thr Gly Ile Pro Ala Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Asn Gly His Ser Phe Pro Leu
                 85                  90                  95
Thr Phe Gly Gln Gly Thr Lys Leu Glu Ile Lys
            100                 105
```

<210> SEQ ID NO 511
<211> LENGTH: 11
<212> TYPE: PRT
<213> ORGANISM: Artificial Sequence
<220> FEATURE:
<223> OTHER INFORMATION: Recombinant protein

<400> SEQUENCE: 511

```
Arg Ala Ser Gln Gly Ile Ser Asp Tyr Leu Ala
 1               5                  10
```

<210> SEQ ID NO 512
<211> LENGTH: 7
<212> TYPE: PRT
<213> ORGANISM: Artificial Sequence
<220> FEATURE:
<223> OTHER INFORMATION: Recombinant protein

<400> SEQUENCE: 512

```
Tyr Ala Ser Gln Pro Ala Thr
 1               5
```

<210> SEQ ID NO 513
<211> LENGTH: 9
<212> TYPE: PRT
<213> ORGANISM: Artificial Sequence
<220> FEATURE:
<223> OTHER INFORMATION: Recombinant protein

<400> SEQUENCE: 513

```
Gln Asn Gly His Ser Phe Pro Leu Thr
 1               5
```

<210> SEQ ID NO 514
<211> LENGTH: 122
<212> TYPE: PRT
<213> ORGANISM: Artificial Sequence
<220> FEATURE:
<223> OTHER INFORMATION: Recombinant protein

<400> SEQUENCE: 514

```
Gln Val Gln Leu Gln Glu Ser Gly Pro Gly Leu Val Glu Pro Ser Asp
 1               5                  10                  15
Thr Leu Ser Leu Thr Cys Ala Val Ser Gly Tyr Ser Ile Thr Ser Asp
             20                  25                  30
Ser Ala Trp Ser Trp Ile Arg Gln Pro Pro Gly Lys Lys Leu Glu Trp
         35                  40                  45
Ile Gly Tyr Ile Gln Tyr Ser Gly Ser Thr Asn Tyr Asn Pro Ser Leu
     50                  55                  60
Lys Ser Arg Val Thr Met Ser Arg Asp Thr Ser Lys Asn Gln Phe Ser
 65                  70                  75                  80
Leu Lys Leu Ser Ser Val Thr Ala Leu Asp Thr Ala Val Tyr Tyr Cys
                 85                  90                  95
```

Ala Arg Ser Val Asn Tyr Gly Asn Ser Phe Ala Val Gly Tyr Trp
            100                 105                 110

Gly Gln Gly Thr Leu Val Thr Val Ser Ser
        115                 120

<210> SEQ ID NO 515
<211> LENGTH: 6
<212> TYPE: PRT
<213> ORGANISM: Artificial Sequence
<220> FEATURE:
<223> OTHER INFORMATION: Recombinant protein

<400> SEQUENCE: 515

Ser Asp Ser Ala Trp Ser
1               5

<210> SEQ ID NO 516
<211> LENGTH: 16
<212> TYPE: PRT
<213> ORGANISM: Artificial Sequence
<220> FEATURE:
<223> OTHER INFORMATION: Recombinant protein

<400> SEQUENCE: 516

Tyr Ile Gln Tyr Ser Gly Ser Thr Asn Tyr Asn Pro Ser Leu Lys Ser
1               5                   10                  15

<210> SEQ ID NO 517
<211> LENGTH: 13
<212> TYPE: PRT
<213> ORGANISM: Artificial Sequence
<220> FEATURE:
<223> OTHER INFORMATION: Recombinant protein

<400> SEQUENCE: 517

Ser Val Asn Tyr Tyr Gly Asn Ser Phe Ala Val Gly Tyr
1               5                   10

<210> SEQ ID NO 518
<211> LENGTH: 107
<212> TYPE: PRT
<213> ORGANISM: Artificial Sequence
<220> FEATURE:
<223> OTHER INFORMATION: Recombinant protein

<400> SEQUENCE: 518

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 519
<211> LENGTH: 11

```
<212> TYPE: PRT
<213> ORGANISM: Artificial Sequence
<220> FEATURE:
<223> OTHER INFORMATION: Recombinant protein

<400> SEQUENCE: 519

Arg Ala Ser Gln Gly Ile Ser Asp Tyr Leu Ala
1               5                   10

<210> SEQ ID NO 520
<211> LENGTH: 7
<212> TYPE: PRT
<213> ORGANISM: Artificial Sequence
<220> FEATURE:
<223> OTHER INFORMATION: Recombinant protein

<400> SEQUENCE: 520

Tyr Ala Ser Gln Pro Ala Thr
1               5

<210> SEQ ID NO 521
<211> LENGTH: 9
<212> TYPE: PRT
<213> ORGANISM: Artificial Sequence
<220> FEATURE:
<223> OTHER INFORMATION: Recombinant protein

<400> SEQUENCE: 521

Gln Asn Gly His Ser Phe Pro Leu Thr
1               5

<210> SEQ ID NO 522
<211> LENGTH: 122
<212> TYPE: PRT
<213> ORGANISM: Artificial Sequence
<220> FEATURE:
<223> OTHER INFORMATION: Recombinant protein

<400> SEQUENCE: 522

Gln Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 523
<211> LENGTH: 6
<212> TYPE: PRT
<213> ORGANISM: Artificial Sequence
<220> FEATURE:
<223> OTHER INFORMATION: Recombinant protein

<400> SEQUENCE: 523
```

Ser Asp Ser Ala Trp Ser
1               5

<210> SEQ ID NO 524
<211> LENGTH: 16
<212> TYPE: PRT
<213> ORGANISM: Artificial Sequence
<220> FEATURE:
<223> OTHER INFORMATION: Recombinant protein

<400> SEQUENCE: 524

Tyr Ile Gln Tyr Ser Gly Ser Thr Asn Tyr Asn Pro Ser Leu Lys Ser
1               5                   10                  15

<210> SEQ ID NO 525
<211> LENGTH: 13
<212> TYPE: PRT
<213> ORGANISM: Artificial Sequence
<220> FEATURE:
<223> OTHER INFORMATION: Recombinant protein

<400> SEQUENCE: 525

Ser Val Asn Tyr Tyr Gly Asn Ser Phe Ala Val Gly Pro
1               5                   10

<210> SEQ ID NO 526
<211> LENGTH: 107
<212> TYPE: PRT
<213> ORGANISM: Artificial Sequence
<220> FEATURE:
<223> OTHER INFORMATION: Recombinant protein

<400> SEQUENCE: 526

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
                20                  25                  30

Leu Ala Trp Tyr Gln Gln Lys Pro Gly Gln Ala Pro Arg Leu Leu Ile
            35                  40                  45

Lys Tyr Ala Ser Gln Pro Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 527
<211> LENGTH: 11
<212> TYPE: PRT
<213> ORGANISM: Artificial Sequence
<220> FEATURE:
<223> OTHER INFORMATION: Recombinant protein

<400> SEQUENCE: 527

Arg Ala Ser Gln Gly Ile Ser Asp Tyr Leu Ala
1               5                   10

<210> SEQ ID NO 528
<211> LENGTH: 7
<212> TYPE: PRT
<213> ORGANISM: Artificial Sequence

```
<220> FEATURE:
<223> OTHER INFORMATION: Recombinant protein

<400> SEQUENCE: 528

Tyr Ala Ser Gln Pro Ala Thr
1               5

<210> SEQ ID NO 529
<211> LENGTH: 9
<212> TYPE: PRT
<213> ORGANISM: Artificial Sequence
<220> FEATURE:
<223> OTHER INFORMATION: Recombinant protein

<400> SEQUENCE: 529

Gln Asn Gly His Ser Phe Pro Leu Thr
1               5

<210> SEQ ID NO 530
<211> LENGTH: 122
<212> TYPE: PRT
<213> ORGANISM: Artificial Sequence
<220> FEATURE:
<223> OTHER INFORMATION: Recombinant protein

<400> SEQUENCE: 530

Gln Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120

<210> SEQ ID NO 531
<211> LENGTH: 6
<212> TYPE: PRT
<213> ORGANISM: Artificial Sequence
<220> FEATURE:
<223> OTHER INFORMATION: Recombinant protein

<400> SEQUENCE: 531

Ser Asp Ser Ala Trp Ser
1               5

<210> SEQ ID NO 532
<211> LENGTH: 16
<212> TYPE: PRT
<213> ORGANISM: Artificial Sequence
<220> FEATURE:
<223> OTHER INFORMATION: Recombinant protein

<400> SEQUENCE: 532

Tyr Ile Gln Tyr Ser Gly Ser Thr Asn Tyr Asn Pro Ser Leu Lys Ser
```

```
1               5                    10                   15
```

<210> SEQ ID NO 533
<211> LENGTH: 13
<212> TYPE: PRT
<213> ORGANISM: Artificial Sequence
<220> FEATURE:
<223> OTHER INFORMATION: Recombinant protein

<400> SEQUENCE: 533

```
Ser Val Asn Tyr Tyr Gly Asn Ser Phe Ala Val Gly Tyr
1               5                   10
```

<210> SEQ ID NO 534
<211> LENGTH: 107
<212> TYPE: PRT
<213> ORGANISM: Artificial Sequence
<220> FEATURE:
<223> OTHER INFORMATION: Recombinant protein

<400> SEQUENCE: 534

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105
```

<210> SEQ ID NO 535
<211> LENGTH: 11
<212> TYPE: PRT
<213> ORGANISM: Artificial Sequence
<220> FEATURE:
<223> OTHER INFORMATION: Recombinant protein

<400> SEQUENCE: 535

```
Arg Ala Ser Gln Gly Ile Ser Asp Tyr Leu Ala
1               5                   10
```

<210> SEQ ID NO 536
<211> LENGTH: 7
<212> TYPE: PRT
<213> ORGANISM: Artificial Sequence
<220> FEATURE:
<223> OTHER INFORMATION: Recombinant protein

<400> SEQUENCE: 536

```
Tyr Ala Ser Gln Pro Ala Thr
1               5
```

<210> SEQ ID NO 537
<211> LENGTH: 9
<212> TYPE: PRT
<213> ORGANISM: Artificial Sequence
<220> FEATURE:
<223> OTHER INFORMATION: Recombinant protein

```
<400> SEQUENCE: 537

Gln Asn Gly His Ser Phe Pro Leu Thr
1               5

<210> SEQ ID NO 538
<211> LENGTH: 122
<212> TYPE: PRT
<213> ORGANISM: Artificial Sequence
<220> FEATURE:
<223> OTHER INFORMATION: Recombinant protein

<400> SEQUENCE: 538

Gln Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Pro Pro Gly Lys Lys Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120

<210> SEQ ID NO 539
<211> LENGTH: 6
<212> TYPE: PRT
<213> ORGANISM: Artificial Sequence
<220> FEATURE:
<223> OTHER INFORMATION: Recombinant protein

<400> SEQUENCE: 539

Ser Asp Ser Ala Trp Ser
1               5

<210> SEQ ID NO 540
<211> LENGTH: 16
<212> TYPE: PRT
<213> ORGANISM: Artificial Sequence
<220> FEATURE:
<223> OTHER INFORMATION: Recombinant protein

<400> SEQUENCE: 540

Tyr Ile Gln Tyr Ser Gly Ser Thr Asn Tyr Asn Pro Ser Leu Lys Ser
1               5                   10                  15

<210> SEQ ID NO 541
<211> LENGTH: 13
<212> TYPE: PRT
<213> ORGANISM: Artificial Sequence
<220> FEATURE:
<223> OTHER INFORMATION: Recombinant protein

<400> SEQUENCE: 541

Ser Val Asn Tyr Tyr Gly Asn Ser Phe Ala Val Gly Tyr
1               5                   10
```

<210> SEQ ID NO 542
<211> LENGTH: 107
<212> TYPE: PRT
<213> ORGANISM: Artificial Sequence
<220> FEATURE:
<223> OTHER INFORMATION: Recombinant protein

<400> SEQUENCE: 542

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 543
<211> LENGTH: 11
<212> TYPE: PRT
<213> ORGANISM: Artificial Sequence
<220> FEATURE:
<223> OTHER INFORMATION: Recombinant protein

<400> SEQUENCE: 543

Arg Ala Ser Gln Gly Ile Ser Asp Tyr Leu Ala
1               5                   10

<210> SEQ ID NO 544
<211> LENGTH: 7
<212> TYPE: PRT
<213> ORGANISM: Artificial Sequence
<220> FEATURE:
<223> OTHER INFORMATION: Recombinant protein

<400> SEQUENCE: 544

Tyr Ala Ser Gln Pro Ala Thr
1               5

<210> SEQ ID NO 545
<211> LENGTH: 9
<212> TYPE: PRT
<213> ORGANISM: Artificial Sequence
<220> FEATURE:
<223> OTHER INFORMATION: Recombinant protein

<400> SEQUENCE: 545

Gln Asn Gly His Ser Phe Pro Leu Thr
1               5

<210> SEQ ID NO 546
<211> LENGTH: 122
<212> TYPE: PRT
<213> ORGANISM: Artificial Sequence
<220> FEATURE:
<223> OTHER INFORMATION: Recombinant protein

<400> SEQUENCE: 546

Gln Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Pro Pro Gly Lys Lys Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 547
<211> LENGTH: 6
<212> TYPE: PRT
<213> ORGANISM: Artificial Sequence
<220> FEATURE:
<223> OTHER INFORMATION: Recombinant protein

<400> SEQUENCE: 547

Ser Asp Ser Ala Trp Ser
1               5

<210> SEQ ID NO 548
<211> LENGTH: 16
<212> TYPE: PRT
<213> ORGANISM: Artificial Sequence
<220> FEATURE:
<223> OTHER INFORMATION: Recombinant protein

<400> SEQUENCE: 548

Tyr Ile Gln Tyr Ser Gly Ser Thr Asn Tyr Asn Pro Ser Leu Lys Ser
1               5                   10                  15

<210> SEQ ID NO 549
<211> LENGTH: 13
<212> TYPE: PRT
<213> ORGANISM: Artificial Sequence
<220> FEATURE:
<223> OTHER INFORMATION: Recombinant protein

<400> SEQUENCE: 549

Ser Val Asn Tyr Tyr Gly Asn Ser Phe Ala Val Gly Tyr
1               5                   10

<210> SEQ ID NO 550
<211> LENGTH: 107
<212> TYPE: PRT
<213> ORGANISM: Artificial Sequence
<220> FEATURE:
<223> OTHER INFORMATION: Recombinant protein

<400> SEQUENCE: 550

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

```
Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Asn Gly His Ser Phe Pro Leu
                 85                  90                  95

Thr Phe Gly Gln Gly Thr Lys Leu Glu Ile Lys
            100                 105
```

<210> SEQ ID NO 551
<211> LENGTH: 11
<212> TYPE: PRT
<213> ORGANISM: Artificial Sequence
<220> FEATURE:
<223> OTHER INFORMATION: Recombinant protein

<400> SEQUENCE: 551

```
Arg Ala Ser Gln Gly Ile Ser Asp Tyr Leu Ala
 1               5                  10
```

<210> SEQ ID NO 552
<211> LENGTH: 7
<212> TYPE: PRT
<213> ORGANISM: Artificial Sequence
<220> FEATURE:
<223> OTHER INFORMATION: Recombinant protein

<400> SEQUENCE: 552

```
Tyr Ala Ser Gln Pro Ala Thr
 1               5
```

<210> SEQ ID NO 553
<211> LENGTH: 9
<212> TYPE: PRT
<213> ORGANISM: Artificial Sequence
<220> FEATURE:
<223> OTHER INFORMATION: Recombinant protein

<400> SEQUENCE: 553

```
Gln Asn Gly His Ser Phe Pro Leu Thr
 1               5
```

<210> SEQ ID NO 554
<211> LENGTH: 122
<212> TYPE: PRT
<213> ORGANISM: Artificial Sequence
<220> FEATURE:
<223> OTHER INFORMATION: Recombinant protein

<400> SEQUENCE: 554

```
Gln Val Gln Leu Gln Glu Ser Gly Pro Gly Leu Val Lys Pro Ser Asp
 1               5                  10                  15

Thr Leu Ser Leu Thr Cys Ala Val Ser Gly Tyr Ser Ile Ser Ser Asp
            20                  25                  30

Ser Ala Trp Ser Trp Ile Arg Gln Phe Pro Gly Lys Gly Leu Glu Trp
        35                  40                  45

Ile Gly Tyr Ile Gln Tyr Ser Gly Ser Thr Asn Tyr Asn Pro Ser Leu
 50                  55                  60

Lys Ser Arg Val Thr Met Ser Val Asp Thr Ser Lys Asn Gln Phe Ser
 65                  70                  75                  80
```

```
Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 555
<211> LENGTH: 6
<212> TYPE: PRT
<213> ORGANISM: Artificial Sequence
<220> FEATURE:
<223> OTHER INFORMATION: Recombinant protein

<400> SEQUENCE: 555

Ser Asp Ser Ala Trp Ser
1               5

<210> SEQ ID NO 556
<211> LENGTH: 16
<212> TYPE: PRT
<213> ORGANISM: Artificial Sequence
<220> FEATURE:
<223> OTHER INFORMATION: Recombinant protein

<400> SEQUENCE: 556

Tyr Ile Gln Tyr Ser Gly Ser Thr Asn Tyr Asn Pro Ser Leu Lys Ser
1               5                   10                  15

<210> SEQ ID NO 557
<211> LENGTH: 13
<212> TYPE: PRT
<213> ORGANISM: Artificial Sequence
<220> FEATURE:
<223> OTHER INFORMATION: Recombinant protein

<400> SEQUENCE: 557

Ser Val Asn Tyr Tyr Gly Asn Ser Phe Ala Val Gly Pro
1               5                   10

<210> SEQ ID NO 558
<211> LENGTH: 107
<212> TYPE: PRT
<213> ORGANISM: Artificial Sequence
<220> FEATURE:
<223> OTHER INFORMATION: Recombinant protein

<400> SEQUENCE: 558

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105
```

<210> SEQ ID NO 559
<211> LENGTH: 11
<212> TYPE: PRT
<213> ORGANISM: Artificial Sequence
<220> FEATURE:
<223> OTHER INFORMATION: Recombinant protein

<400> SEQUENCE: 559

Arg Ala Ser Gln Gly Ile Ser Asp Tyr Leu Ala
1               5                   10

<210> SEQ ID NO 560
<211> LENGTH: 7
<212> TYPE: PRT
<213> ORGANISM: Artificial Sequence
<220> FEATURE:
<223> OTHER INFORMATION: Recombinant protein

<400> SEQUENCE: 560

Tyr Ala Ser Gln Pro Ala Thr
1               5

<210> SEQ ID NO 561
<211> LENGTH: 9
<212> TYPE: PRT
<213> ORGANISM: Artificial Sequence
<220> FEATURE:
<223> OTHER INFORMATION: Recombinant protein

<400> SEQUENCE: 561

Gln Asn Gly His Ser Phe Pro Leu Thr
1               5

<210> SEQ ID NO 562
<211> LENGTH: 122
<212> TYPE: PRT
<213> ORGANISM: Artificial Sequence
<220> FEATURE:
<223> OTHER INFORMATION: Recombinant protein

<400> SEQUENCE: 562

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Arg Asp Thr Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 563
<211> LENGTH: 6
<212> TYPE: PRT
<213> ORGANISM: Artificial Sequence
<220> FEATURE:
<223> OTHER INFORMATION: Recombinant protein

<400> SEQUENCE: 563

Ser Asp Ser Ala Trp Ser
1               5

<210> SEQ ID NO 564
<211> LENGTH: 16
<212> TYPE: PRT
<213> ORGANISM: Artificial Sequence
<220> FEATURE:
<223> OTHER INFORMATION: Recombinant protein

<400> SEQUENCE: 564

Tyr Ile Gln Tyr Ser Gly Ser Thr Asn Tyr Asn Pro Ser Leu Lys Ser
1               5                   10                  15

<210> SEQ ID NO 565
<211> LENGTH: 13
<212> TYPE: PRT
<213> ORGANISM: Artificial Sequence
<220> FEATURE:
<223> OTHER INFORMATION: Recombinant protein

<400> SEQUENCE: 565

Ser Val Asn Tyr Tyr Gly Asn Ser Phe Ala Val Gly Pro
1               5                   10

<210> SEQ ID NO 566
<211> LENGTH: 107
<212> TYPE: PRT
<213> ORGANISM: Artificial Sequence
<220> FEATURE:
<223> OTHER INFORMATION: Recombinant protein

<400> SEQUENCE: 566

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
                20                  25                  30

Leu Ala Trp Tyr Gln Gln Lys Pro Gly Gln Ala Pro Arg Leu Leu Ile
            35                  40                  45

Lys Tyr Ala Ser Gln Pro Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 567
<211> LENGTH: 11
<212> TYPE: PRT
<213> ORGANISM: Artificial Sequence
<220> FEATURE:
<223> OTHER INFORMATION: Recombinant protein

<400> SEQUENCE: 567

Arg Ala Ser Gln Gly Ile Ser Asp Tyr Leu Ala
1               5                   10

```
<210> SEQ ID NO 568
<211> LENGTH: 7
<212> TYPE: PRT
<213> ORGANISM: Artificial Sequence
<220> FEATURE:
<223> OTHER INFORMATION: Recombinant protein

<400> SEQUENCE: 568

Tyr Ala Ser Gln Pro Ala Thr
1               5

<210> SEQ ID NO 569
<211> LENGTH: 9
<212> TYPE: PRT
<213> ORGANISM: Artificial Sequence
<220> FEATURE:
<223> OTHER INFORMATION: Recombinant protein

<400> SEQUENCE: 569

Gln Asn Gly His Ser Phe Pro Leu Thr
1               5

<210> SEQ ID NO 570
<211> LENGTH: 122
<212> TYPE: PRT
<213> ORGANISM: Artificial Sequence
<220> FEATURE:
<223> OTHER INFORMATION: Recombinant protein

<400> SEQUENCE: 570

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 571
<211> LENGTH: 6
<212> TYPE: PRT
<213> ORGANISM: Artificial Sequence
<220> FEATURE:
<223> OTHER INFORMATION: Recombinant protein

<400> SEQUENCE: 571

Ser Asp Ser Ala Trp Ser
1               5

<210> SEQ ID NO 572
<211> LENGTH: 16
<212> TYPE: PRT
<213> ORGANISM: Artificial Sequence
<220> FEATURE:
<223> OTHER INFORMATION: Recombinant protein
```

-continued

```
<400> SEQUENCE: 572

Tyr Ile Gln Tyr Ser Gly Ser Thr Asn Tyr Asn Pro Ser Leu Lys Ser
1               5                   10                  15

<210> SEQ ID NO 573
<211> LENGTH: 13
<212> TYPE: PRT
<213> ORGANISM: Artificial Sequence
<220> FEATURE:
<223> OTHER INFORMATION: Recombinant protein

<400> SEQUENCE: 573

Ser Val Asn Tyr Tyr Gly Asn Ser Phe Ala Val Gly Pro
1               5                   10

<210> SEQ ID NO 574
<211> LENGTH: 107
<212> TYPE: PRT
<213> ORGANISM: Artificial Sequence
<220> FEATURE:
<223> OTHER INFORMATION: Recombinant protein

<400> SEQUENCE: 574

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 575
<211> LENGTH: 11
<212> TYPE: PRT
<213> ORGANISM: Artificial Sequence
<220> FEATURE:
<223> OTHER INFORMATION: Recombinant protein

<400> SEQUENCE: 575

Arg Ala Ser Gln Gly Ile Ser Asp Tyr Leu Ala
1               5                   10

<210> SEQ ID NO 576
<211> LENGTH: 7
<212> TYPE: PRT
<213> ORGANISM: Artificial Sequence
<220> FEATURE:
<223> OTHER INFORMATION: Recombinant protein

<400> SEQUENCE: 576

Tyr Ala Ser Gln Pro Ala Thr
1               5

<210> SEQ ID NO 577
<211> LENGTH: 9
```

<212> TYPE: PRT
<213> ORGANISM: Artificial Sequence
<220> FEATURE:
<223> OTHER INFORMATION: Recombinant protein

<400> SEQUENCE: 577

Gln Asn Gly His Ser Phe Pro Leu Thr
1               5

<210> SEQ ID NO 578
<211> LENGTH: 122
<212> TYPE: PRT
<213> ORGANISM: Artificial Sequence
<220> FEATURE:
<223> OTHER INFORMATION: Recombinant protein

<400> SEQUENCE: 578

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 579
<211> LENGTH: 6
<212> TYPE: PRT
<213> ORGANISM: Artificial Sequence
<220> FEATURE:
<223> OTHER INFORMATION: Recombinant protein

<400> SEQUENCE: 579

Ser Asp Ser Ala Trp Ser
1               5

<210> SEQ ID NO 580
<211> LENGTH: 16
<212> TYPE: PRT
<213> ORGANISM: Artificial Sequence
<220> FEATURE:
<223> OTHER INFORMATION: Recombinant protein

<400> SEQUENCE: 580

Tyr Ile Gln Tyr Ser Gly Ser Thr Asn Tyr Asn Pro Ser Leu Lys Ser
1               5                   10                  15

<210> SEQ ID NO 581
<211> LENGTH: 13
<212> TYPE: PRT
<213> ORGANISM: Artificial Sequence
<220> FEATURE:
<223> OTHER INFORMATION: Recombinant protein

<400> SEQUENCE: 581

```
Ser Val Asn Tyr Tyr Gly Asn Ser Phe Ala Val Gly Pro
1               5                   10
```

<210> SEQ ID NO 582
<211> LENGTH: 107
<212> TYPE: PRT
<213> ORGANISM: Artificial Sequence
<220> FEATURE:
<223> OTHER INFORMATION: Recombinant protein

<400> SEQUENCE: 582

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105
```

<210> SEQ ID NO 583
<211> LENGTH: 11
<212> TYPE: PRT
<213> ORGANISM: Artificial Sequence
<220> FEATURE:
<223> OTHER INFORMATION: Recombinant protein

<400> SEQUENCE: 583

```
Arg Ala Ser Gln Gly Ile Ser Asp Tyr Leu Ala
1               5                   10
```

<210> SEQ ID NO 584
<211> LENGTH: 7
<212> TYPE: PRT
<213> ORGANISM: Artificial Sequence
<220> FEATURE:
<223> OTHER INFORMATION: Recombinant protein

<400> SEQUENCE: 584

```
Tyr Ala Ser Gln Pro Ala Thr
1               5
```

<210> SEQ ID NO 585
<211> LENGTH: 9
<212> TYPE: PRT
<213> ORGANISM: Artificial Sequence
<220> FEATURE:
<223> OTHER INFORMATION: Recombinant protein

<400> SEQUENCE: 585

```
Gln Asn Gly His Ser Phe Pro Leu Thr
1               5
```

<210> SEQ ID NO 586
<211> LENGTH: 122
<212> TYPE: PRT
<213> ORGANISM: Artificial Sequence
<220> FEATURE:
<223> OTHER INFORMATION: Recombinant protein

<400> SEQUENCE: 586

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120

<210> SEQ ID NO 587
<211> LENGTH: 6
<212> TYPE: PRT
<213> ORGANISM: Artificial Sequence
<220> FEATURE:
<223> OTHER INFORMATION: Recombinant protein

<400> SEQUENCE: 587

Ser Asp Ser Ala Trp Ser
1               5

<210> SEQ ID NO 588
<211> LENGTH: 16
<212> TYPE: PRT
<213> ORGANISM: Artificial Sequence
<220> FEATURE:
<223> OTHER INFORMATION: Recombinant protein

<400> SEQUENCE: 588

Tyr Ile Gln Tyr Ser Gly Ser Thr Asn Tyr Asn Pro Ser Leu Lys Ser
1               5                   10                  15

<210> SEQ ID NO 589
<211> LENGTH: 13
<212> TYPE: PRT
<213> ORGANISM: Artificial Sequence
<220> FEATURE:
<223> OTHER INFORMATION: Recombinant protein

<400> SEQUENCE: 589

Ser Val Asn Tyr Tyr Gly Asn Ser Phe Ala Val Gly Tyr
1               5                   10

<210> SEQ ID NO 590
<211> LENGTH: 107
<212> TYPE: PRT
<213> ORGANISM: Artificial Sequence
<220> FEATURE:
<223> OTHER INFORMATION: Recombinant protein

<400> SEQUENCE: 590

Glu Ile Val Leu Thr Gln Ser Pro Ala Thr Leu Ser Leu Ser Pro Gly

```
                1               5                   10                  15
        Glu Arg Ala Thr Leu Ser Cys Arg Ala Ser Gln Gly Ile Ser Asp Tyr
                        20                  25                  30

Leu Ala Trp Tyr Gln Gln Lys Pro Gly Gln Ala Pro Arg Leu Leu Ile
                        35                  40                  45

Lys Tyr Ala Ser Gln Pro Ala Thr Gly Ile Pro Ala Arg Phe Ser Gly
                        50                  55                  60

Ser Gly Ser Gly Thr Asp Phe Thr Leu Thr Ile Ser Ser Leu Glu Pro
         65                     70                  75                  80

Glu Asp Phe Ala Val Tyr Tyr Cys Gln Asn Gly His Ser Phe Pro Leu
                        85                  90                  95

Thr Phe Gly Gln Gly Thr Lys Leu Glu Ile Lys
                        100                 105

<210> SEQ ID NO 591
<211> LENGTH: 11
<212> TYPE: PRT
<213> ORGANISM: Artificial Sequence
<220> FEATURE:
<223> OTHER INFORMATION: Recombinant protein

<400> SEQUENCE: 591

Arg Ala Ser Gln Gly Ile Ser Asp Tyr Leu Ala
1               5                   10

<210> SEQ ID NO 592
<211> LENGTH: 7
<212> TYPE: PRT
<213> ORGANISM: Artificial Sequence
<220> FEATURE:
<223> OTHER INFORMATION: Recombinant protein

<400> SEQUENCE: 592

Tyr Ala Ser Gln Pro Ala Thr
1               5

<210> SEQ ID NO 593
<211> LENGTH: 9
<212> TYPE: PRT
<213> ORGANISM: Artificial Sequence
<220> FEATURE:
<223> OTHER INFORMATION: Recombinant protein

<400> SEQUENCE: 593

Gln Asn Gly His Ser Phe Pro Leu Thr
1               5

<210> SEQ ID NO 594
<211> LENGTH: 122
<212> TYPE: PRT
<213> ORGANISM: Artificial Sequence
<220> FEATURE:
<223> OTHER INFORMATION: Recombinant protein

<400> SEQUENCE: 594

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Asp
                20                  25                  30

Ser Ala Trp Ser Trp Ile Arg Gln Pro Pro Gly Lys Lys Leu Glu Trp
                35                  40                  45

Ile Gly Tyr Ile Gln Tyr Ser Gly Ser Thr Asn Tyr Asn Pro Ser Leu
```

```
                50             55                 60
Lys Ser Arg Val Thr Met Ser Val Asp Thr Ser Lys Asn Gln Phe Ser
 65                  70                  75                  80

Leu Lys Leu Ser Ser Val Thr Ala Leu Asp Thr Ala Val Tyr Tyr Cys
                 85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 595
<211> LENGTH: 6
<212> TYPE: PRT
<213> ORGANISM: Artificial Sequence
<220> FEATURE:
<223> OTHER INFORMATION: Recombinant protein

<400> SEQUENCE: 595

Ser Asp Ser Ala Trp Ser
 1               5

<210> SEQ ID NO 596
<211> LENGTH: 16
<212> TYPE: PRT
<213> ORGANISM: Artificial Sequence
<220> FEATURE:
<223> OTHER INFORMATION: Recombinant protein

<400> SEQUENCE: 596

Tyr Ile Gln Tyr Ser Gly Ser Thr Asn Tyr Asn Pro Ser Leu Lys Ser
 1               5                  10                  15

<210> SEQ ID NO 597
<211> LENGTH: 13
<212> TYPE: PRT
<213> ORGANISM: Artificial Sequence
<220> FEATURE:
<223> OTHER INFORMATION: Recombinant protein

<400> SEQUENCE: 597

Ser Val Asn Tyr Tyr Gly Asn Ser Phe Ala Val Gly Pro
 1               5                  10

<210> SEQ ID NO 598
<211> LENGTH: 107
<212> TYPE: PRT
<213> ORGANISM: Artificial Sequence
<220> FEATURE:
<223> OTHER INFORMATION: Recombinant protein

<400> SEQUENCE: 598

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Gly Ile Ser Asp Tyr
             20                  25                  30

Leu Ala Trp Tyr Gln Gln Lys Pro Gly Gln Ala Pro Arg Leu Leu Ile
         35                  40                  45

Lys Tyr Ala Ser Gln Pro Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Asn Gly His Ser Phe Pro Leu
```

```
                 85                  90                  95

Thr Phe Gly Gln Gly Thr Lys Leu Glu Ile Lys
            100                 105

<210> SEQ ID NO 599
<211> LENGTH: 11
<212> TYPE: PRT
<213> ORGANISM: Artificial Sequence
<220> FEATURE:
<223> OTHER INFORMATION: Recombinant protein

<400> SEQUENCE: 599

Arg Ala Ser Gln Gly Ile Ser Asp Tyr Leu Ala
1               5                   10

<210> SEQ ID NO 600
<211> LENGTH: 7
<212> TYPE: PRT
<213> ORGANISM: Artificial Sequence
<220> FEATURE:
<223> OTHER INFORMATION: Recombinant protein

<400> SEQUENCE: 600

Tyr Ala Ser Gln Pro Ala Thr
1               5

<210> SEQ ID NO 601
<211> LENGTH: 9
<212> TYPE: PRT
<213> ORGANISM: Artificial Sequence
<220> FEATURE:
<223> OTHER INFORMATION: Recombinant protein

<400> SEQUENCE: 601

Gln Asn Gly His Ser Phe Pro Leu Thr
1               5

<210> SEQ ID NO 602
<211> LENGTH: 122
<212> TYPE: PRT
<213> ORGANISM: Artificial Sequence
<220> FEATURE:
<223> OTHER INFORMATION: Recombinant protein

<400> SEQUENCE: 602

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120
```

```
<210> SEQ ID NO 603
<211> LENGTH: 6
<212> TYPE: PRT
<213> ORGANISM: Artificial Sequence
<220> FEATURE:
<223> OTHER INFORMATION: Recombinant protein

<400> SEQUENCE: 603

Ser Asp Ser Ala Trp Ser
1               5

<210> SEQ ID NO 604
<211> LENGTH: 16
<212> TYPE: PRT
<213> ORGANISM: Artificial Sequence
<220> FEATURE:
<223> OTHER INFORMATION: Recombinant protein

<400> SEQUENCE: 604

Tyr Ile Gln Tyr Ser Gly Ser Thr Asn Tyr Asn Pro Ser Leu Lys Ser
1               5                   10                  15

<210> SEQ ID NO 605
<211> LENGTH: 13
<212> TYPE: PRT
<213> ORGANISM: Artificial Sequence
<220> FEATURE:
<223> OTHER INFORMATION: Recombinant protein

<400> SEQUENCE: 605

Ser Val Asn Tyr Tyr Gly Asn Ser Phe Ala Val Gly Tyr
1               5                   10

<210> SEQ ID NO 606
<211> LENGTH: 107
<212> TYPE: PRT
<213> ORGANISM: Artificial Sequence
<220> FEATURE:
<223> OTHER INFORMATION: Recombinant protein

<400> SEQUENCE: 606

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 607
<211> LENGTH: 11
<212> TYPE: PRT
<213> ORGANISM: Artificial Sequence
<220> FEATURE:
<223> OTHER INFORMATION: Recombinant protein

<400> SEQUENCE: 607
```

Arg Ala Ser Gln Gly Ile Ser Asp Tyr Leu Ala
1               5                   10

<210> SEQ ID NO 608
<211> LENGTH: 7
<212> TYPE: PRT
<213> ORGANISM: Artificial Sequence
<220> FEATURE:
<223> OTHER INFORMATION: Recombinant protein

<400> SEQUENCE: 608

Tyr Ala Ser Gln Pro Ala Thr
1               5

<210> SEQ ID NO 609
<211> LENGTH: 9
<212> TYPE: PRT
<213> ORGANISM: Artificial Sequence
<220> FEATURE:
<223> OTHER INFORMATION: Recombinant protein

<400> SEQUENCE: 609

Gln Asn Gly His Ser Phe Pro Leu Thr
1               5

<210> SEQ ID NO 610
<211> LENGTH: 122
<212> TYPE: PRT
<213> ORGANISM: Artificial Sequence
<220> FEATURE:
<223> OTHER INFORMATION: Recombinant protein

<400> SEQUENCE: 610

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120

<210> SEQ ID NO 611
<211> LENGTH: 6
<212> TYPE: PRT
<213> ORGANISM: Artificial Sequence
<220> FEATURE:
<223> OTHER INFORMATION: Recombinant protein

<400> SEQUENCE: 611

Ser Asp Ser Ala Trp Ser
1               5

<210> SEQ ID NO 612
<211> LENGTH: 16

```
<212> TYPE: PRT
<213> ORGANISM: Artificial Sequence
<220> FEATURE:
<223> OTHER INFORMATION: Recombinant protein

<400> SEQUENCE: 612

Tyr Ile Gln Tyr Ser Gly Ser Thr Asn Tyr Asn Pro Ser Leu Lys Ser
1               5                   10                  15

<210> SEQ ID NO 613
<211> LENGTH: 13
<212> TYPE: PRT
<213> ORGANISM: Artificial Sequence
<220> FEATURE:
<223> OTHER INFORMATION: Recombinant protein

<400> SEQUENCE: 613

Ser Val Asn Tyr Tyr Gly Asn Ser Phe Ala Val Gly Tyr
1               5                   10

<210> SEQ ID NO 614
<211> LENGTH: 107
<212> TYPE: PRT
<213> ORGANISM: Artificial Sequence
<220> FEATURE:
<223> OTHER INFORMATION: Recombinant protein

<400> SEQUENCE: 614

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 615
<211> LENGTH: 11
<212> TYPE: PRT
<213> ORGANISM: Artificial Sequence
<220> FEATURE:
<223> OTHER INFORMATION: Recombinant protein

<400> SEQUENCE: 615

Arg Ala Ser Gln Gly Ile Ser Asp Tyr Leu Ala
1               5                   10

<210> SEQ ID NO 616
<211> LENGTH: 7
<212> TYPE: PRT
<213> ORGANISM: Artificial Sequence
<220> FEATURE:
<223> OTHER INFORMATION: Recombinant protein

<400> SEQUENCE: 616

Tyr Ala Ser Gln Pro Ala Thr
1               5
```

<210> SEQ ID NO 617
<211> LENGTH: 9
<212> TYPE: PRT
<213> ORGANISM: Artificial Sequence
<220> FEATURE:
<223> OTHER INFORMATION: Recombinant protein

<400> SEQUENCE: 617

```
Gln Asn Gly His Ser Phe Pro Leu Thr
1               5
```

<210> SEQ ID NO 618
<211> LENGTH: 122
<212> TYPE: PRT
<213> ORGANISM: Artificial Sequence
<220> FEATURE:
<223> OTHER INFORMATION: Recombinant protein

<400> SEQUENCE: 618

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Phe Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120
```

<210> SEQ ID NO 619
<211> LENGTH: 6
<212> TYPE: PRT
<213> ORGANISM: Artificial Sequence
<220> FEATURE:
<223> OTHER INFORMATION: Recombinant protein

<400> SEQUENCE: 619

```
Ser Asp Ser Ala Trp Ser
1               5
```

<210> SEQ ID NO 620
<211> LENGTH: 16
<212> TYPE: PRT
<213> ORGANISM: Artificial Sequence
<220> FEATURE:
<223> OTHER INFORMATION: Recombinant protein

<400> SEQUENCE: 620

```
Tyr Ile Gln Tyr Ser Gly Ser Thr Asn Tyr Asn Pro Ser Leu Lys Ser
1               5                   10                  15
```

<210> SEQ ID NO 621
<211> LENGTH: 13
<212> TYPE: PRT
<213> ORGANISM: Artificial Sequence

```
<220> FEATURE:
<223> OTHER INFORMATION: Recombinant protein

<400> SEQUENCE: 621

Ser Val Asn Tyr Tyr Gly Asn Ser Phe Ala Val Gly Pro
1               5                   10

<210> SEQ ID NO 622
<211> LENGTH: 107
<212> TYPE: PRT
<213> ORGANISM: Artificial Sequence
<220> FEATURE:
<223> OTHER INFORMATION: Recombinant protein

<400> SEQUENCE: 622

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 623
<211> LENGTH: 11
<212> TYPE: PRT
<213> ORGANISM: Artificial Sequence
<220> FEATURE:
<223> OTHER INFORMATION: Recombinant protein

<400> SEQUENCE: 623

Arg Ala Ser Gln Gly Ile Ser Asp Tyr Leu Ala
1               5                   10

<210> SEQ ID NO 624
<211> LENGTH: 7
<212> TYPE: PRT
<213> ORGANISM: Artificial Sequence
<220> FEATURE:
<223> OTHER INFORMATION: Recombinant protein

<400> SEQUENCE: 624

Tyr Ala Ser Gln Pro Ala Thr
1               5

<210> SEQ ID NO 625
<211> LENGTH: 9
<212> TYPE: PRT
<213> ORGANISM: Artificial Sequence
<220> FEATURE:
<223> OTHER INFORMATION: Recombinant protein

<400> SEQUENCE: 625

Gln Asn Gly His Ser Phe Pro Leu Thr
1               5
```

```
<210> SEQ ID NO 626
<211> LENGTH: 122
<212> TYPE: PRT
<213> ORGANISM: Artificial Sequence
<220> FEATURE:
<223> OTHER INFORMATION: Recombinant protein

<400> SEQUENCE: 626

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 627
<211> LENGTH: 6
<212> TYPE: PRT
<213> ORGANISM: Artificial Sequence
<220> FEATURE:
<223> OTHER INFORMATION: Recombinant protein

<400> SEQUENCE: 627

Ser Asp Ser Ala Trp Ser
1               5

<210> SEQ ID NO 628
<211> LENGTH: 16
<212> TYPE: PRT
<213> ORGANISM: Artificial Sequence
<220> FEATURE:
<223> OTHER INFORMATION: Recombinant protein

<400> SEQUENCE: 628

Tyr Ile Gln Tyr Ser Gly Ser Thr Asn Tyr Asn Pro Ser Leu Lys Ser
1               5                   10                  15

<210> SEQ ID NO 629
<211> LENGTH: 13
<212> TYPE: PRT
<213> ORGANISM: Artificial Sequence
<220> FEATURE:
<223> OTHER INFORMATION: Recombinant protein

<400> SEQUENCE: 629

Ser Val Asn Tyr Tyr Gly Asn Ser Phe Ala Val Gly Pro
1               5                   10

<210> SEQ ID NO 630
<211> LENGTH: 107
<212> TYPE: PRT
<213> ORGANISM: Artificial Sequence
<220> FEATURE:
<223> OTHER INFORMATION: Recombinant protein
```

<400> SEQUENCE: 630

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 631
<211> LENGTH: 11
<212> TYPE: PRT
<213> ORGANISM: Artificial Sequence
<220> FEATURE:
<223> OTHER INFORMATION: Recombinant protein

<400> SEQUENCE: 631

Arg Ala Ser Gln Gly Ile Ser Asp Tyr Leu Ala
1               5                   10

<210> SEQ ID NO 632
<211> LENGTH: 7
<212> TYPE: PRT
<213> ORGANISM: Artificial Sequence
<220> FEATURE:
<223> OTHER INFORMATION: Recombinant protein

<400> SEQUENCE: 632

Tyr Ala Ser Gln Pro Ala Thr
1               5

<210> SEQ ID NO 633
<211> LENGTH: 9
<212> TYPE: PRT
<213> ORGANISM: Artificial Sequence
<220> FEATURE:
<223> OTHER INFORMATION: Recombinant protein

<400> SEQUENCE: 633

Gln Asn Gly His Ser Phe Pro Leu Thr
1               5

<210> SEQ ID NO 634
<211> LENGTH: 122
<212> TYPE: PRT
<213> ORGANISM: Artificial Sequence
<220> FEATURE:
<223> OTHER INFORMATION: Recombinant protein

<400> SEQUENCE: 634

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

```
Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
 50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
            115                 120
```

<210> SEQ ID NO 635
<211> LENGTH: 6
<212> TYPE: PRT
<213> ORGANISM: Artificial Sequence
<220> FEATURE:
<223> OTHER INFORMATION: Recombinant protein

<400> SEQUENCE: 635

```
Ser Asp Ser Ala Trp Ser
 1               5
```

<210> SEQ ID NO 636
<211> LENGTH: 16
<212> TYPE: PRT
<213> ORGANISM: Artificial Sequence
<220> FEATURE:
<223> OTHER INFORMATION: Recombinant protein

<400> SEQUENCE: 636

```
Tyr Ile Gln Tyr Ser Gly Ser Thr Asn Tyr Asn Pro Ser Leu Lys Ser
 1               5                  10                  15
```

<210> SEQ ID NO 637
<211> LENGTH: 13
<212> TYPE: PRT
<213> ORGANISM: Artificial Sequence
<220> FEATURE:
<223> OTHER INFORMATION: Recombinant protein

<400> SEQUENCE: 637

```
Ser Val Asn Tyr Tyr Gly Asn Ser Phe Ala Val Gly Tyr
 1               5                  10
```

<210> SEQ ID NO 638
<211> LENGTH: 107
<212> TYPE: PRT
<213> ORGANISM: Artificial Sequence
<220> FEATURE:
<223> OTHER INFORMATION: Recombinant protein

<400> SEQUENCE: 638

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
 50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Asn Gly His Ser Phe Pro Leu
                 85                  90                  95

Thr Phe Gly Gln Gly Thr Lys Leu Glu Ile Lys
            100                 105
```

```
<210> SEQ ID NO 639
<211> LENGTH: 11
<212> TYPE: PRT
<213> ORGANISM: Artificial Sequence
<220> FEATURE:
<223> OTHER INFORMATION: Recombinant protein

<400> SEQUENCE: 639

Arg Ala Ser Gln Gly Ile Ser Asp Tyr Leu Ala
1               5                   10
```

```
<210> SEQ ID NO 640
<211> LENGTH: 7
<212> TYPE: PRT
<213> ORGANISM: Artificial Sequence
<220> FEATURE:
<223> OTHER INFORMATION: Recombinant protein

<400> SEQUENCE: 640

Tyr Ala Ser Gln Pro Ala Thr
1               5
```

```
<210> SEQ ID NO 641
<211> LENGTH: 9
<212> TYPE: PRT
<213> ORGANISM: Artificial Sequence
<220> FEATURE:
<223> OTHER INFORMATION: Recombinant protein

<400> SEQUENCE: 641

Gln Asn Gly His Ser Phe Pro Leu Thr
1               5
```

```
<210> SEQ ID NO 642
<211> LENGTH: 122
<212> TYPE: PRT
<213> ORGANISM: Artificial Sequence
<220> FEATURE:
<223> OTHER INFORMATION: Recombinant protein

<400> SEQUENCE: 642

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
                20                  25                  30

Ser Ala Trp Ser Trp Ile Arg Gln Pro Pro Gly Lys Gly Leu Glu Trp
            35                  40                  45

Ile Gly Tyr Ile Tyr Tyr Ser Gly Ser Thr Asn Tyr Asn Pro Ser Leu
        50                  55                  60

Lys Ser Arg Val Thr Ile Ser Val Asp Thr Ser Lys Asn Gln Phe Ser
 65                 70                  75                  80

Leu Lys Leu Ser Ser Val Thr Ala Ala Asp Thr Ala Val Tyr Tyr Cys
                85                  90                  95

Ala Arg Ser Val Asn Tyr Gly Asn Ser Phe Ala Val Gly Tyr Trp
            100                 105                 110
```

```
Gly Gln Gly Thr Ser Val Thr Val Ser Ser
        115                 120
```

<210> SEQ ID NO 643
<211> LENGTH: 6
<212> TYPE: PRT
<213> ORGANISM: Artificial Sequence
<220> FEATURE:
<223> OTHER INFORMATION: Recombinant protein

<400> SEQUENCE: 643

```
Ser Asp Ser Ala Trp Ser
1               5
```

<210> SEQ ID NO 644
<211> LENGTH: 16
<212> TYPE: PRT
<213> ORGANISM: Artificial Sequence
<220> FEATURE:
<223> OTHER INFORMATION: Recombinant protein

<400> SEQUENCE: 644

```
Tyr Ile Tyr Tyr Ser Gly Ser Thr Asn Tyr Asn Pro Ser Leu Lys Ser
1               5                   10                  15
```

<210> SEQ ID NO 645
<211> LENGTH: 13
<212> TYPE: PRT
<213> ORGANISM: Artificial Sequence
<220> FEATURE:
<223> OTHER INFORMATION: Recombinant protein

<400> SEQUENCE: 645

```
Ser Val Asn Tyr Tyr Gly Asn Ser Phe Ala Val Gly Tyr
1               5                   10
```

<210> SEQ ID NO 646
<211> LENGTH: 107
<212> TYPE: PRT
<213> ORGANISM: Artificial Sequence
<220> FEATURE:
<223> OTHER INFORMATION: Recombinant protein

<400> SEQUENCE: 646

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu Ala Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105
```

<210> SEQ ID NO 647
<211> LENGTH: 11
<212> TYPE: PRT
<213> ORGANISM: Artificial Sequence
<220> FEATURE:

```
<223> OTHER INFORMATION: Recombinant protein

<400> SEQUENCE: 647

Arg Ala Ser Gln Gly Ile Ser Asp Tyr Leu Ala
1               5                   10

<210> SEQ ID NO 648
<211> LENGTH: 7
<212> TYPE: PRT
<213> ORGANISM: Artificial Sequence
<220> FEATURE:
<223> OTHER INFORMATION: Recombinant protein

<400> SEQUENCE: 648

Tyr Ala Ser Gln Pro Ala Thr
1               5

<210> SEQ ID NO 649
<211> LENGTH: 9
<212> TYPE: PRT
<213> ORGANISM: Artificial Sequence
<220> FEATURE:
<223> OTHER INFORMATION: Recombinant protein

<400> SEQUENCE: 649

Gln Asn Gly His Ser Phe Pro Leu Thr
1               5

<210> SEQ ID NO 650
<211> LENGTH: 122
<212> TYPE: PRT
<213> ORGANISM: Artificial Sequence
<220> FEATURE:
<223> OTHER INFORMATION: Recombinant protein

<400> SEQUENCE: 650

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Lys Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 651
<211> LENGTH: 6
<212> TYPE: PRT
<213> ORGANISM: Artificial Sequence
<220> FEATURE:
<223> OTHER INFORMATION: Recombinant protein

<400> SEQUENCE: 651

Ser Asp Ser Ala Trp Ser
1               5
```

<210> SEQ ID NO 652
<211> LENGTH: 16
<212> TYPE: PRT
<213> ORGANISM: Artificial Sequence
<220> FEATURE:
<223> OTHER INFORMATION: Recombinant protein

<400> SEQUENCE: 652

Tyr Ile Gln Tyr Ser Gly Ser Thr Asn Tyr Asn Pro Ser Leu Lys Ser
1               5                   10                  15

<210> SEQ ID NO 653
<211> LENGTH: 13
<212> TYPE: PRT
<213> ORGANISM: Artificial Sequence
<220> FEATURE:
<223> OTHER INFORMATION: Recombinant protein

<400> SEQUENCE: 653

Ser Val Asn Tyr Tyr Gly Asn Ser Phe Ala Val Gly Pro
1               5                   10

<210> SEQ ID NO 654
<211> LENGTH: 107
<212> TYPE: PRT
<213> ORGANISM: Artificial Sequence
<220> FEATURE:
<223> OTHER INFORMATION: Recombinant protein

<400> SEQUENCE: 654

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 655
<211> LENGTH: 11
<212> TYPE: PRT
<213> ORGANISM: Artificial Sequence
<220> FEATURE:
<223> OTHER INFORMATION: Recombinant protein

<400> SEQUENCE: 655

Arg Ala Ser Gln Gly Ile Ser Asp Tyr Leu His
1               5                   10

<210> SEQ ID NO 656
<211> LENGTH: 7
<212> TYPE: PRT
<213> ORGANISM: Artificial Sequence
<220> FEATURE:
<223> OTHER INFORMATION: Recombinant protein

<400> SEQUENCE: 656

Tyr Thr Ser Gln Pro Ala Thr
1               5

<210> SEQ ID NO 657
<211> LENGTH: 9
<212> TYPE: PRT
<213> ORGANISM: Artificial Sequence
<220> FEATURE:
<223> OTHER INFORMATION: Recombinant protein

<400> SEQUENCE: 657

Gln Asn Gly His Ser Phe Pro Leu Thr
1               5

<210> SEQ ID NO 658
<211> LENGTH: 122
<212> TYPE: PRT
<213> ORGANISM: Artificial Sequence
<220> FEATURE:
<223> OTHER INFORMATION: Recombinant protein

<400> SEQUENCE: 658

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120

<210> SEQ ID NO 659
<211> LENGTH: 6
<212> TYPE: PRT
<213> ORGANISM: Artificial Sequence
<220> FEATURE:
<223> OTHER INFORMATION: Recombinant protein

<400> SEQUENCE: 659

Ser Asp Ser Ala Trp Ser
1               5

<210> SEQ ID NO 660
<211> LENGTH: 16
<212> TYPE: PRT
<213> ORGANISM: Artificial Sequence
<220> FEATURE:
<223> OTHER INFORMATION: Recombinant protein

<400> SEQUENCE: 660

Tyr Ile Gln Tyr Ser Gly Ser Thr Asn Tyr Asn Pro Ser Leu Lys Ser
1               5                   10                  15

-continued

```
<210> SEQ ID NO 661
<211> LENGTH: 13
<212> TYPE: PRT
<213> ORGANISM: Artificial Sequence
<220> FEATURE:
<223> OTHER INFORMATION: Recombinant protein

<400> SEQUENCE: 661

Ser Val Asn Tyr Tyr Gly Asn Ser Phe Ala Val Gly Tyr
1               5                   10

<210> SEQ ID NO 662
<211> LENGTH: 107
<212> TYPE: PRT
<213> ORGANISM: Artificial Sequence
<220> FEATURE:
<223> OTHER INFORMATION: Recombinant protein

<400> SEQUENCE: 662

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Gln Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 663
<211> LENGTH: 11
<212> TYPE: PRT
<213> ORGANISM: Artificial Sequence
<220> FEATURE:
<223> OTHER INFORMATION: Recombinant protein

<400> SEQUENCE: 663

Arg Ala Ser Gln Gly Ile Ser Asp Tyr Leu His
1               5                   10

<210> SEQ ID NO 664
<211> LENGTH: 7
<212> TYPE: PRT
<213> ORGANISM: Artificial Sequence
<220> FEATURE:
<223> OTHER INFORMATION: Recombinant protein

<400> SEQUENCE: 664

Tyr Thr Ser Gln Pro Ala Thr
1               5

<210> SEQ ID NO 665
<211> LENGTH: 9
<212> TYPE: PRT
<213> ORGANISM: Artificial Sequence
<220> FEATURE:
<223> OTHER INFORMATION: Recombinant protein

<400> SEQUENCE: 665
```

Gln Asn Gly His Ser Phe Pro Leu Thr
1               5

<210> SEQ ID NO 666
<211> LENGTH: 122
<212> TYPE: PRT
<213> ORGANISM: Artificial Sequence
<220> FEATURE:
<223> OTHER INFORMATION: Recombinant protein

<400> SEQUENCE: 666

Gln Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120

<210> SEQ ID NO 667
<211> LENGTH: 6
<212> TYPE: PRT
<213> ORGANISM: Artificial Sequence
<220> FEATURE:
<223> OTHER INFORMATION: Recombinant protein

<400> SEQUENCE: 667

Ser Asp Ser Ala Trp Ser
1               5

<210> SEQ ID NO 668
<211> LENGTH: 16
<212> TYPE: PRT
<213> ORGANISM: Artificial Sequence
<220> FEATURE:
<223> OTHER INFORMATION: Recombinant protein

<400> SEQUENCE: 668

Tyr Ile Gln Tyr Ser Gly Ser Thr Asn Tyr Asn Pro Ser Leu Lys Ser
1               5                   10                  15

<210> SEQ ID NO 669
<211> LENGTH: 13
<212> TYPE: PRT
<213> ORGANISM: Artificial Sequence
<220> FEATURE:
<223> OTHER INFORMATION: Recombinant protein

<400> SEQUENCE: 669

Ser Val Asn Tyr Tyr Gly Asn Ser Phe Ala Val Gly Tyr
1               5                   10

<210> SEQ ID NO 670
<211> LENGTH: 107

```
<212> TYPE: PRT
<213> ORGANISM: Artificial Sequence
<220> FEATURE:
<223> OTHER INFORMATION: Recombinant protein

<400> SEQUENCE: 670

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 671
<211> LENGTH: 11
<212> TYPE: PRT
<213> ORGANISM: Artificial Sequence
<220> FEATURE:
<223> OTHER INFORMATION: Recombinant protein

<400> SEQUENCE: 671

Arg Ala Ser Gln Gly Ile Ser Asp Tyr Leu His
1               5                   10

<210> SEQ ID NO 672
<211> LENGTH: 7
<212> TYPE: PRT
<213> ORGANISM: Artificial Sequence
<220> FEATURE:
<223> OTHER INFORMATION: Recombinant protein

<400> SEQUENCE: 672

Tyr Thr Ser Gln Pro Ala Thr
1               5

<210> SEQ ID NO 673
<211> LENGTH: 9
<212> TYPE: PRT
<213> ORGANISM: Artificial Sequence
<220> FEATURE:
<223> OTHER INFORMATION: Recombinant protein

<400> SEQUENCE: 673

Gln Asn Gly His Ser Phe Pro Leu Thr
1               5

<210> SEQ ID NO 674
<211> LENGTH: 122
<212> TYPE: PRT
<213> ORGANISM: Artificial Sequence
<220> FEATURE:
<223> OTHER INFORMATION: Recombinant protein

<400> SEQUENCE: 674

Gln Val Gln Leu Gln Glu Ser Gly Pro Gly Leu Val Glu Pro Ser Gln
1               5                   10                  15
```

```
Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120
```

<210> SEQ ID NO 675
<211> LENGTH: 6
<212> TYPE: PRT
<213> ORGANISM: Artificial Sequence
<220> FEATURE:
<223> OTHER INFORMATION: Recombinant protein

<400> SEQUENCE: 675

```
Ser Asp Ser Ala Trp Ser
1               5
```

<210> SEQ ID NO 676
<211> LENGTH: 16
<212> TYPE: PRT
<213> ORGANISM: Artificial Sequence
<220> FEATURE:
<223> OTHER INFORMATION: Recombinant protein

<400> SEQUENCE: 676

```
Tyr Ile Gln Tyr Ser Gly Ser Thr Asn Tyr Asn Pro Ser Leu Lys Ser
1               5                   10                  15
```

<210> SEQ ID NO 677
<211> LENGTH: 13
<212> TYPE: PRT
<213> ORGANISM: Artificial Sequence
<220> FEATURE:
<223> OTHER INFORMATION: Recombinant protein

<400> SEQUENCE: 677

```
Ser Val Asn Tyr Tyr Gly Asn Ser Phe Ala Val Gly Pro
1               5                   10
```

<210> SEQ ID NO 678
<211> LENGTH: 107
<212> TYPE: PRT
<213> ORGANISM: Artificial Sequence
<220> FEATURE:
<223> OTHER INFORMATION: Recombinant protein

<400> SEQUENCE: 678

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45
```

```
Lys Tyr Thr Ser Gln Pro Ala Thr Gly Ile Pro Ala Arg Phe Ser Gly
        50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Asn Gly His Ser Phe Pro Leu
                 85                  90                  95

Thr Phe Gly Gln Gly Thr Lys Leu Glu Ile Lys
            100                 105

<210> SEQ ID NO 679
<211> LENGTH: 11
<212> TYPE: PRT
<213> ORGANISM: Artificial Sequence
<220> FEATURE:
<223> OTHER INFORMATION: Recombinant protein

<400> SEQUENCE: 679

Arg Ala Ser Gln Gly Ile Ser Asp Tyr Leu His
 1               5                  10

<210> SEQ ID NO 680
<211> LENGTH: 7
<212> TYPE: PRT
<213> ORGANISM: Artificial Sequence
<220> FEATURE:
<223> OTHER INFORMATION: Recombinant protein

<400> SEQUENCE: 680

Tyr Thr Ser Gln Pro Ala Thr
 1               5

<210> SEQ ID NO 681
<211> LENGTH: 9
<212> TYPE: PRT
<213> ORGANISM: Artificial Sequence
<220> FEATURE:
<223> OTHER INFORMATION: Recombinant protein

<400> SEQUENCE: 681

Gln Asn Gly His Ser Phe Pro Leu Thr
 1               5

<210> SEQ ID NO 682
<211> LENGTH: 122
<212> TYPE: PRT
<213> ORGANISM: Artificial Sequence
<220> FEATURE:
<223> OTHER INFORMATION: Recombinant protein

<400> SEQUENCE: 682

Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Ser Ile Ser Ser Asp
                 20                  25                  30

Ser Ala Trp Ser Trp Ile Arg Gln Pro Pro Gly Lys Gly Leu Glu Trp
             35                  40                  45

Ile Gly Tyr Ile Gln Tyr Ser Gly Ser Thr Asn Tyr Asn Pro Ser Leu
         50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95
```

```
Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120
```

<210> SEQ ID NO 683
<211> LENGTH: 6
<212> TYPE: PRT
<213> ORGANISM: Artificial Sequence
<220> FEATURE:
<223> OTHER INFORMATION: Recombinant protein

<400> SEQUENCE: 683

```
Ser Asp Ser Ala Trp Ser
1               5
```

<210> SEQ ID NO 684
<211> LENGTH: 16
<212> TYPE: PRT
<213> ORGANISM: Artificial Sequence
<220> FEATURE:
<223> OTHER INFORMATION: Recombinant protein

<400> SEQUENCE: 684

```
Tyr Ile Gln Tyr Ser Gly Ser Thr Asn Tyr Asn Pro Ser Leu Lys Ser
1               5                   10                  15
```

<210> SEQ ID NO 685
<211> LENGTH: 13
<212> TYPE: PRT
<213> ORGANISM: Artificial Sequence
<220> FEATURE:
<223> OTHER INFORMATION: Recombinant protein

<400> SEQUENCE: 685

```
Ser Val Asn Tyr Tyr Gly Asn Ser Phe Ala Val Gly Pro
1               5                   10
```

<210> SEQ ID NO 686
<211> LENGTH: 107
<212> TYPE: PRT
<213> ORGANISM: Artificial Sequence
<220> FEATURE:
<223> OTHER INFORMATION: Recombinant protein

<400> SEQUENCE: 686

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Gln Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105
```

<210> SEQ ID NO 687

```
<211> LENGTH: 11
<212> TYPE: PRT
<213> ORGANISM: Artificial Sequence
<220> FEATURE:
<223> OTHER INFORMATION: Recombinant protein

<400> SEQUENCE: 687

Arg Ala Ser Gln Gly Ile Ser Asp Tyr Leu His
1               5                   10

<210> SEQ ID NO 688
<211> LENGTH: 7
<212> TYPE: PRT
<213> ORGANISM: Artificial Sequence
<220> FEATURE:
<223> OTHER INFORMATION: Recombinant protein

<400> SEQUENCE: 688

Tyr Thr Ser Gln Pro Ala Thr
1               5

<210> SEQ ID NO 689
<211> LENGTH: 9
<212> TYPE: PRT
<213> ORGANISM: Artificial Sequence
<220> FEATURE:
<223> OTHER INFORMATION: Recombinant protein

<400> SEQUENCE: 689

Gln Asn Gly His Ser Phe Pro Leu Thr
1               5

<210> SEQ ID NO 690
<211> LENGTH: 122
<212> TYPE: PRT
<213> ORGANISM: Artificial Sequence
<220> FEATURE:
<223> OTHER INFORMATION: Recombinant protein

<400> SEQUENCE: 690

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Phe Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Pro Trp
            100                 105                 110

Gly Gln Gly Thr Leu Val Thr Val Ser Ser
        115                 120

<210> SEQ ID NO 691
<211> LENGTH: 6
<212> TYPE: PRT
<213> ORGANISM: Artificial Sequence
<220> FEATURE:
<223> OTHER INFORMATION: Recombinant protein
```

```
<400> SEQUENCE: 691

Ser Asp Ser Ala Trp Ser
1               5

<210> SEQ ID NO 692
<211> LENGTH: 16
<212> TYPE: PRT
<213> ORGANISM: Artificial Sequence
<220> FEATURE:
<223> OTHER INFORMATION: Recombinant protein

<400> SEQUENCE: 692

Tyr Ile Gln Tyr Ser Gly Ser Thr Asn Tyr Asn Pro Ser Leu Lys Ser
1               5                   10                  15

<210> SEQ ID NO 693
<211> LENGTH: 13
<212> TYPE: PRT
<213> ORGANISM: Artificial Sequence
<220> FEATURE:
<223> OTHER INFORMATION: Recombinant protein

<400> SEQUENCE: 693

Ser Val Asn Tyr Tyr Gly Asn Ser Phe Ala Val Gly Pro
1               5                   10

<210> SEQ ID NO 694
<211> LENGTH: 107
<212> TYPE: PRT
<213> ORGANISM: Mus musculus

<400> SEQUENCE: 694

Asp Ile Val Met Ser Gln Ser Pro Ala Thr Leu Ser Val Thr Pro Gly
1               5                   10                  15

Asp Arg Val Ser Leu Ser Cys Arg Thr Ser Gln Asp Ile Gly Asp Tyr
                20                  25                  30

Leu His Trp Tyr Arg Gln Lys Ser His Glu Ser Pro Arg Leu Leu Ile
            35                  40                  45

Lys Tyr Thr Ser Gln Ser Val Ser Gly Ile Pro Ser Arg Phe Ser Gly
    50                  55                  60

Ser Gly Ser Gly Ser Asp Phe Thr Leu Ser Ile Asn Thr Val Glu Pro
65                  70                  75                  80

Glu Asp Val Gly Leu Tyr Tyr Cys Gln Asn Gly His Ser Phe Pro Leu
                85                  90                  95

Thr Phe Gly Thr Gly Thr Arg Leu Glu Leu Lys
            100                 105

<210> SEQ ID NO 695
<211> LENGTH: 11
<212> TYPE: PRT
<213> ORGANISM: Mus musculus

<400> SEQUENCE: 695

Arg Thr Ser Gln Asp Ile Gly Asp Tyr Leu His
1               5                   10

<210> SEQ ID NO 696
<211> LENGTH: 7
<212> TYPE: PRT
<213> ORGANISM: Mus musculus

<400> SEQUENCE: 696
```

Tyr Thr Ser Gln Ser Val Ser
1               5

<210> SEQ ID NO 697
<211> LENGTH: 9
<212> TYPE: PRT
<213> ORGANISM: Mus musculus

<400> SEQUENCE: 697

Gln Asn Gly His Ser Phe Pro Leu Thr
1               5

<210> SEQ ID NO 698
<211> LENGTH: 122
<212> TYPE: PRT
<213> ORGANISM: Mus musculus

<400> SEQUENCE: 698

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Cys Ala Trp Asn Trp Ile Arg Gln Phe Pro Gly Asn Lys Leu Glu Trp
        35                  40                  45

Met Gly Tyr Ile Asn Tyr Ser Gly Ser Thr Asn Tyr Asn Pro Ser Leu
    50                  55                  60

Lys Ser Arg Ile Ser Ile Thr Arg Asp Thr Ser Gln Asn His Phe Phe
65                  70                  75                  80

Leu Gln Leu Ser Ser Val Thr Ala Glu Asp Thr Ala Thr Tyr Tyr Cys
                85                  90                  95

Thr Arg Ser Val Asn Tyr Tyr Gly Asn Ser Phe Ala Val Gly Tyr Trp
            100                 105                 110

Gly Gln Gly Ile Ser Val Thr Val Ser Ser
        115                 120

<210> SEQ ID NO 699
<211> LENGTH: 6
<212> TYPE: PRT
<213> ORGANISM: Mus musculus

<400> SEQUENCE: 699

Ser Asp Cys Ala Trp Asn
1               5

<210> SEQ ID NO 700
<211> LENGTH: 16
<212> TYPE: PRT
<213> ORGANISM: Mus musculus

<400> SEQUENCE: 700

Tyr Ile Asn Tyr Ser Gly Ser Thr Asn Tyr Asn Pro Ser Leu Lys Ser
1               5                   10                  15

<210> SEQ ID NO 701
<211> LENGTH: 13
<212> TYPE: PRT
<213> ORGANISM: Mus musculus

<400> SEQUENCE: 701

Ser Val Asn Tyr Tyr Gly Asn Ser Phe Ala Val Gly Tyr
1               5                   10

<210> SEQ ID NO 702
<211> LENGTH: 107
<212> TYPE: PRT
<213> ORGANISM: Mus musculus

<400> SEQUENCE: 702

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ser Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 703
<211> LENGTH: 11
<212> TYPE: PRT
<213> ORGANISM: Mus musculus

<400> SEQUENCE: 703

Arg Ala Ser Gln Ser Ile Ser Asp Tyr Leu His
1               5                   10

<210> SEQ ID NO 704
<211> LENGTH: 7
<212> TYPE: PRT
<213> ORGANISM: Mus musculus

<400> SEQUENCE: 704

Tyr Ser Ser Gln Ser Ile Ser
1               5

<210> SEQ ID NO 705
<211> LENGTH: 9
<212> TYPE: PRT
<213> ORGANISM: Mus musculus

<400> SEQUENCE: 705

Gln Asn Gly His Ser Phe Pro Leu Thr
1               5

<210> SEQ ID NO 706
<211> LENGTH: 122
<212> TYPE: PRT
<213> ORGANISM: Mus musculus

<400> SEQUENCE: 706

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Cys Ala Trp Asn Trp Ile Arg Gln Phe Pro Gly Asn Lys Leu Glu Trp
        35                  40                  45

```
Met Gly Tyr Ile Asn Tyr Ser Gly Ser Thr Asn Tyr Asn Pro Ser Leu
    50                  55                  60

Lys Ser Arg Ile Ser Ile Thr Arg Asp Thr Ser Lys Asn His Phe Phe
 65                  70                  75                  80

Leu Gln Leu Asn Ser Val Thr Ala Glu Asp Thr Ala Thr Tyr Tyr Cys
                 85                  90                  95

Ala Arg Ser Val Asp Tyr Phe Gly Asn Ser Phe Ala Val Gly Tyr Trp
            100                 105                 110

Gly Gln Gly Thr Ser Val Ala Val Ser Ser
        115                 120
```

<210> SEQ ID NO 707
<211> LENGTH: 6
<212> TYPE: PRT
<213> ORGANISM: Mus musculus

<400> SEQUENCE: 707

```
Ser Asp Cys Ala Trp Asn
 1               5
```

<210> SEQ ID NO 708
<211> LENGTH: 16
<212> TYPE: PRT
<213> ORGANISM: Mus musculus

<400> SEQUENCE: 708

```
Tyr Ile Asn Tyr Ser Gly Ser Thr Asn Tyr Asn Pro Ser Leu Lys Ser
 1               5                  10                  15
```

<210> SEQ ID NO 709
<211> LENGTH: 13
<212> TYPE: PRT
<213> ORGANISM: Mus musculus

<400> SEQUENCE: 709

```
Ser Val Asp Tyr Phe Gly Asn Ser Phe Ala Val Gly Tyr
 1               5                  10
```

<210> SEQ ID NO 710
<211> LENGTH: 112
<212> TYPE: PRT
<213> ORGANISM: Mus musculus

<400> SEQUENCE: 710

```
Asp Val Met Val Thr Gln Thr Pro Leu Ser Leu Pro Val Asn Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Arg Val Ser Asp Arg Phe Ser Gly Val Pro
     50                 55                  60

Asp Arg Phe Ser Gly Ser Gly Ser Gly Thr Asp Phe Thr Leu Lys Ile
 65                 70                  75                  80

Ser Arg Val Glu Ala Glu Asp Leu Gly Val Tyr Phe Cys Ser Gln Ser
                 85                  90                  95

Thr His Val Pro Pro Thr Phe Gly Gly Gly Thr Lys Leu Glu Ile Lys
            100                 105                 110
```

<210> SEQ ID NO 711

```
<211> LENGTH: 16
<212> TYPE: PRT
<213> ORGANISM: Mus musculus

<400> SEQUENCE: 711

Arg Ser Ser Gln Ser Leu Val His Ser Asn Gly Asn Thr Tyr Leu His
1               5                   10                  15

<210> SEQ ID NO 712
<211> LENGTH: 7
<212> TYPE: PRT
<213> ORGANISM: Mus musculus

<400> SEQUENCE: 712

Arg Val Ser Asp Arg Phe Ser
1               5

<210> SEQ ID NO 713
<211> LENGTH: 9
<212> TYPE: PRT
<213> ORGANISM: Mus musculus

<400> SEQUENCE: 713

Ser Gln Ser Thr His Val Pro Pro Thr
1               5

<210> SEQ ID NO 714
<211> LENGTH: 118
<212> TYPE: PRT
<213> ORGANISM: Mus musculus

<400> SEQUENCE: 714

Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Ile Met Val Trp Met Lys Gln Ser Gln Gly Lys Thr Leu Glu Trp Ile
        35                  40                  45

Gly Lys Ile Asn Pro Tyr Tyr Gly Asp Ile Ser Tyr Asn Leu Lys Phe
    50                  55                  60

Lys Gly Lys Ala Thr Leu Thr Val Asp Lys Ser Ser Ser Thr Val Tyr
65                  70                  75                  80

Met Gln Leu Asn Ser Leu Ala Ser Glu Asp Ser Ala Val Tyr Tyr Cys
                85                  90                  95

Ala Arg Gly Phe Tyr Tyr Asp Tyr Phe Asp Gln Trp Gly Gln Gly Thr
            100                 105                 110

Thr Leu Thr Val Ser Ser
        115

<210> SEQ ID NO 715
<211> LENGTH: 5
<212> TYPE: PRT
<213> ORGANISM: Mus musculus

<400> SEQUENCE: 715

Asp Tyr Ile Met Val
1               5

<210> SEQ ID NO 716
<211> LENGTH: 17
<212> TYPE: PRT
<213> ORGANISM: Mus musculus
```

-continued

```
<400> SEQUENCE: 716

Lys Ile Asn Pro Tyr Tyr Gly Asp Ile Ser Tyr Asn Leu Lys Phe Lys
1               5                   10                  15
Gly

<210> SEQ ID NO 717
<211> LENGTH: 9
<212> TYPE: PRT
<213> ORGANISM: Mus musculus

<400> SEQUENCE: 717

Gly Phe Tyr Tyr Asp Tyr Phe Asp Gln
1               5

<210> SEQ ID NO 718
<211> LENGTH: 107
<212> TYPE: PRT
<213> ORGANISM: Mus musculus

<400> SEQUENCE: 718

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln His Lys Ser His Glu Ser Pro Arg Leu Leu Ile
            35                  40                  45

Lys Tyr Val Ser Gln Pro Ile Ser Gly Ile Pro Ser Arg Phe Ser Gly
        50                  55                  60

Ser Gly Ser Gly Ser Glu Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 719
<211> LENGTH: 11
<212> TYPE: PRT
<213> ORGANISM: Mus musculus

<400> SEQUENCE: 719

Arg Ala Ser Gln Ser Ile Ser Asp Tyr Leu His
1               5                   10

<210> SEQ ID NO 720
<211> LENGTH: 7
<212> TYPE: PRT
<213> ORGANISM: Mus musculus

<400> SEQUENCE: 720

Tyr Val Ser Gln Pro Ile Ser
1               5

<210> SEQ ID NO 721
<211> LENGTH: 9
<212> TYPE: PRT
<213> ORGANISM: Mus musculus

<400> SEQUENCE: 721

Gln Asn Gly His Ser Phe Pro Leu Thr
```

<210> SEQ ID NO 722
<211> LENGTH: 122
<212> TYPE: PRT
<213> ORGANISM: Mus musculus

<400> SEQUENCE: 722

Asp Val Gln Leu Gln Glu Ser Gly Pro Gly Leu Val Glu Pro Ser Gln
1               5                   10                  15

Ser Leu Ser Leu Thr Cys Thr Val Thr Gly Tyr Ser Ile Thr Ser Asp
                20                  25                  30

Cys Ala Trp Ser Trp Ile Arg Gln Phe Pro Gly Asn Lys Leu Glu Trp
            35                  40                  45

Met Gly Tyr Ile Asn Tyr Ser Gly Ser Thr Asn Tyr Asn Pro Ser Leu
        50                  55                  60

Lys Ser Arg Ile Ser Ile Thr Arg Asp Thr Ser Lys Asn Gln Phe Phe
65                  70                  75                  80

Leu Arg Leu Asn Ser Val Thr Gly Glu Asp Thr Ala Thr Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120

<210> SEQ ID NO 723
<211> LENGTH: 6
<212> TYPE: PRT
<213> ORGANISM: Mus musculus

<400> SEQUENCE: 723

Ser Asp Cys Ala Trp Ser
1               5

<210> SEQ ID NO 724
<211> LENGTH: 16
<212> TYPE: PRT
<213> ORGANISM: Mus musculus

<400> SEQUENCE: 724

Tyr Ile Asn Tyr Ser Gly Ser Thr Asn Tyr Asn Pro Ser Leu Lys Ser
1               5                   10                  15

<210> SEQ ID NO 725
<211> LENGTH: 13
<212> TYPE: PRT
<213> ORGANISM: Mus musculus

<400> SEQUENCE: 725

Ser Val Asn Tyr Tyr Gly Asn Ser Phe Ala Val Gly Tyr
1               5                   10

<210> SEQ ID NO 726
<211> LENGTH: 107
<212> TYPE: PRT
<213> ORGANISM: Mus musculus

<400> SEQUENCE: 726

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser

```
                20              25                  30
Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Phe
                85                  90                  95

Thr Phe Gly Ser Gly Thr Lys Leu Glu Ile Lys
            100                 105

<210> SEQ ID NO 727
<211> LENGTH: 11
<212> TYPE: PRT
<213> ORGANISM: Mus musculus

<400> SEQUENCE: 727

Arg Ala Ser Gln Ser Ile Gly Thr Ser Ile His
1               5                   10

<210> SEQ ID NO 728
<211> LENGTH: 7
<212> TYPE: PRT
<213> ORGANISM: Mus musculus

<400> SEQUENCE: 728

Tyr Ala Ser Glu Ser Ile Ser
1               5

<210> SEQ ID NO 729
<211> LENGTH: 9
<212> TYPE: PRT
<213> ORGANISM: Mus musculus

<400> SEQUENCE: 729

Gln Gln Ser Asn Ser Trp Pro Phe Thr
1               5

<210> SEQ ID NO 730
<211> LENGTH: 119
<212> TYPE: PRT
<213> ORGANISM: Mus musculus

<400> SEQUENCE: 730

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Asn Thr Tyr
            20                  25                  30

Trp Ile Glu Trp Val Lys Gln Arg Pro Gly His Gly Leu Glu Trp Ile
        35                  40                  45

Gly Glu Ile Leu Pro Gly Arg Gly Thr Thr Asn Tyr Asn Glu Asn Phe
    50                  55                  60

Lys Gly Lys Ala Thr Ile Thr Ala Asp Ile Ser Ser Asn Thr Ala Tyr
65                  70                  75                  80

Leu Gln Leu Ser Ser Leu Thr Gly Glu Asp Ser Ala Val Tyr Tyr Cys
                85                  90                  95

Ala Arg Leu Thr Pro Leu Ser Leu Arg Thr Gly Tyr Trp Gly Gln Gly
            100                 105                 110
```

```
Thr Thr Leu Thr Val Ser Ser
            115
```

<210> SEQ ID NO 731
<211> LENGTH: 5
<212> TYPE: PRT
<213> ORGANISM: Mus musculus

<400> SEQUENCE: 731

```
Thr Tyr Trp Ile Glu
1               5
```

<210> SEQ ID NO 732
<211> LENGTH: 17
<212> TYPE: PRT
<213> ORGANISM: Mus musculus

<400> SEQUENCE: 732

```
Glu Ile Leu Pro Gly Arg Gly Thr Thr Asn Tyr Asn Glu Asn Phe Lys
1               5                   10                  15

Gly
```

<210> SEQ ID NO 733
<211> LENGTH: 10
<212> TYPE: PRT
<213> ORGANISM: Mus musculus

<400> SEQUENCE: 733

```
Leu Thr Pro Leu Ser Leu Arg Thr Gly Tyr
1               5                   10
```

<210> SEQ ID NO 734
<211> LENGTH: 111
<212> TYPE: PRT
<213> ORGANISM: Mus musculus

<400> SEQUENCE: 734

```
Asp Ile Val Leu Thr Gln Ser Pro Ser Leu Ala Val Ser Leu Gly
1               5                   10                  15

Gln Arg Ala Ile Ile Ser Cys Lys Ala Ser Gln Ser Val Ser Phe Ala
            20                  25                  30

Gly Thr Ser Leu Met Tyr Trp Tyr Gln Gln Lys Pro Gly Gln Gln Pro
        35                  40                  45

Lys Val Leu Met Tyr Arg Ala Ser Asn Leu Glu Ala Gly Val Pro Ile
    50                  55                  60

Arg Phe Ser Gly Ser Gly Ser Gly Thr Asp Phe Thr Leu Asn Ile His
65                  70                  75                  80

Pro Val Glu Glu Asp Asp Val Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110
```

<210> SEQ ID NO 735
<211> LENGTH: 15
<212> TYPE: PRT
<213> ORGANISM: Artificial Sequence
<220> FEATURE:
<223> OTHER INFORMATION: Recombinant protein

<400> SEQUENCE: 735

```
Lys Ala Ser Gln Ser Val Ser Phe Ala Gly Thr Ser Leu Met Tyr
1               5                   10                  15
```

<210> SEQ ID NO 736
<211> LENGTH: 7
<212> TYPE: PRT
<213> ORGANISM: Mus musculus

<400> SEQUENCE: 736

Arg Ala Ser Asn Leu Glu Ala
1               5

<210> SEQ ID NO 737
<211> LENGTH: 9
<212> TYPE: PRT
<213> ORGANISM: Mus musculus

<400> SEQUENCE: 737

Gln Gln Ser Arg Glu Tyr Pro Tyr Thr
1               5

<210> SEQ ID NO 738
<211> LENGTH: 118
<212> TYPE: PRT
<213> ORGANISM: Mus musculus

<400> SEQUENCE: 738

Gln Ile Gln Leu Gln Gln Ser Gly Pro Glu Leu Val Lys Pro Gly Thr
1               5                   10                  15

Ser Val Lys Met Ala Cys Lys Ala Ser Asp Tyr Thr Phe Thr Asp Tyr
            20                  25                  30

Tyr Leu His Trp Val Lys Gln Arg Pro Gly Gln Gly Leu Glu Trp Ile
        35                  40                  45

Gly Trp Ile Tyr Pro Gly Ser Gly Asn Thr Lys Phe Asn Glu Lys Phe
    50                  55                  60

Lys Gly Lys Ala Thr Leu Thr Val Asp Thr Ser Ser Thr Ala Tyr
65                  70                  75                  80

Met His Leu Ser Ser Leu Thr Ser Asp Asp Thr Ala Val Tyr Phe Cys
                85                  90                  95

Thr Arg Val Leu Gly Arg Gly Ala Met Asp Tyr Trp Gly Gln Gly Thr
            100                 105                 110

Ser Val Thr Val Ser Ser
        115

<210> SEQ ID NO 739
<211> LENGTH: 5
<212> TYPE: PRT
<213> ORGANISM: Mus musculus

<400> SEQUENCE: 739

Asp Tyr Tyr Leu His
1               5

<210> SEQ ID NO 740
<211> LENGTH: 17
<212> TYPE: PRT
<213> ORGANISM: Mus musculus

<400> SEQUENCE: 740

Trp Ile Tyr Pro Gly Ser Gly Asn Thr Lys Phe Asn Glu Lys Phe Lys
1               5                   10                  15

Gly

```
<210> SEQ ID NO 741
<211> LENGTH: 9
<212> TYPE: PRT
<213> ORGANISM: Mus musculus

<400> SEQUENCE: 741

Val Leu Gly Arg Gly Ala Met Asp Tyr
1               5

<210> SEQ ID NO 742
<211> LENGTH: 106
<212> TYPE: PRT
<213> ORGANISM: Mus musculus

<400> SEQUENCE: 742

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

Phe Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys
            100                 105

<210> SEQ ID NO 743
<211> LENGTH: 10
<212> TYPE: PRT
<213> ORGANISM: Mus musculus

<400> SEQUENCE: 743

Ser Ala Ser Ser Val Ser Tyr Met Phe
1               5                   10

<210> SEQ ID NO 744
<211> LENGTH: 7
<212> TYPE: PRT
<213> ORGANISM: Mus musculus

<400> SEQUENCE: 744

Ser Thr Ser Asn Leu Ala Ser
1               5

<210> SEQ ID NO 745
<211> LENGTH: 9
<212> TYPE: PRT
<213> ORGANISM: Mus musculus

<400> SEQUENCE: 745

Gln Gln Arg Ser Ser Tyr Pro Leu Thr
1               5

<210> SEQ ID NO 746
<211> LENGTH: 118
<212> TYPE: PRT
<213> ORGANISM: Mus musculus
```

<400> SEQUENCE: 746

Gln Val Gln Leu Gln Gln Ser Gly Ala Glu Leu Leu Lys Pro Gly Ala
1               5                   10                  15

Ser Val Lys Ile Ser Cys Lys Ala Thr Asp Tyr Thr Phe Ser Arg Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Val Asn Ile Lys Tyr Asn Glu Ile Phe
    50                  55                  60

Lys Gly Lys Ala Thr Phe Thr Ala Glu Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Arg Thr Pro Tyr Leu Gln Arg Gly Ala Tyr Trp Gly Gln Gly Thr
            100                 105                 110

Leu Val Thr Val Ser Ala
        115

<210> SEQ ID NO 747
<211> LENGTH: 5
<212> TYPE: PRT
<213> ORGANISM: Mus musculus

<400> SEQUENCE: 747

Arg Tyr Trp Ile Glu
1               5

<210> SEQ ID NO 748
<211> LENGTH: 17
<212> TYPE: PRT
<213> ORGANISM: Mus musculus

<400> SEQUENCE: 748

Glu Ile Leu Pro Gly Ser Val Asn Ile Lys Tyr Asn Glu Ile Phe Lys
1               5                   10                  15

Gly

<210> SEQ ID NO 749
<211> LENGTH: 9
<212> TYPE: PRT
<213> ORGANISM: Mus musculus

<400> SEQUENCE: 749

Thr Pro Tyr Leu Gln Arg Gly Ala Tyr
1               5

<210> SEQ ID NO 750
<211> LENGTH: 107
<212> TYPE: PRT
<213> ORGANISM: Mus musculus

<400> SEQUENCE: 750

Asp Ile Val Met Thr Gln Ser Pro Ala Thr Leu Ser Val Thr Ala Gly
1               5                   10                  15

Asp Arg Val Ser Leu Ser Cys Arg Ala Ser Gln Gly Ile Ser Asp Tyr
            20                  25                  30

Leu His Trp Tyr Gln Gln Lys Ser His Glu Ser Pro Arg Leu Leu Ile
        35                  40                  45

Lys Tyr Thr Ser Gln Pro Val Ser Gly Ile Pro Ser Arg Phe Ser Gly

```
                    50                  55                  60
Ser Gly Ser Gly Ser Glu Phe Thr Leu Ser Ile Asn Ser Val Glu Pro
 65                  70                  75                  80

Glu Asp Val Gly Val Tyr Tyr Cys Gln Asn Gly His Ser Phe Pro Leu
                 85                  90                  95

Thr Phe Gly Ala Gly Thr Lys Leu Glu Leu Lys
            100                 105

<210> SEQ ID NO 751
<211> LENGTH: 11
<212> TYPE: PRT
<213> ORGANISM: Mus musculus

<400> SEQUENCE: 751

Arg Ala Ser Gln Gly Ile Ser Asp Tyr Leu His
 1               5                  10

<210> SEQ ID NO 752
<211> LENGTH: 7
<212> TYPE: PRT
<213> ORGANISM: Mus musculus

<400> SEQUENCE: 752

Tyr Thr Ser Gln Pro Val Ser
 1               5

<210> SEQ ID NO 753
<211> LENGTH: 9
<212> TYPE: PRT
<213> ORGANISM: Mus musculus

<400> SEQUENCE: 753

Gln Asn Gly His Ser Phe Pro Leu Thr
 1               5

<210> SEQ ID NO 754
<211> LENGTH: 122
<212> TYPE: PRT
<213> ORGANISM: Mus musculus

<400> SEQUENCE: 754

Asp Val Gln Leu Gln Glu Ser Gly Pro Gly Leu Val Glu Pro Ser Gln
 1               5                  10                  15

Ser Leu Ser Leu Thr Cys Thr Val Thr Gly Tyr Ser Ile Thr Ser Asp
                 20                  25                  30

Cys Ala Trp Ser Trp Ile Arg Gln Phe Pro Gly Asn Lys Leu Glu Trp
             35                  40                  45

Met Gly Tyr Ile Asn Tyr Ser Gly Ser Thr Asn Tyr Asn Pro Ser Leu
         50                  55                  60

Lys Ser Arg Ile Ser Val Thr Arg Asp Thr Ser Lys Asn Gln Phe Phe
 65                  70                  75                  80

Leu Arg Leu Ser Ser Val Thr Ala Glu Asp Thr Ala Thr Tyr Tyr Cys
                 85                  90                  95

Thr Arg Ser Val Asn Tyr Tyr Gly Asn Ser Phe Ala Val Gly Tyr Trp
                100                 105                 110

Gly Gln Gly Thr Ser Val Thr Val Ser Ser
            115                 120

<210> SEQ ID NO 755
<211> LENGTH: 6
```

```
<212> TYPE: PRT
<213> ORGANISM: Mus musculus

<400> SEQUENCE: 755

Ser Asp Cys Ala Trp Ser
1               5

<210> SEQ ID NO 756
<211> LENGTH: 16
<212> TYPE: PRT
<213> ORGANISM: Mus musculus

<400> SEQUENCE: 756

Tyr Ile Asn Tyr Ser Gly Ser Thr Asn Tyr Asn Pro Ser Leu Lys Ser
1               5                   10                  15

<210> SEQ ID NO 757
<211> LENGTH: 13
<212> TYPE: PRT
<213> ORGANISM: Mus musculus

<400> SEQUENCE: 757

Ser Val Asn Tyr Tyr Gly Asn Ser Phe Ala Val Gly Tyr
1               5                   10

<210> SEQ ID NO 758
<211> LENGTH: 107
<212> TYPE: PRT
<213> ORGANISM: Artificial Sequence
<220> FEATURE:
<223> OTHER INFORMATION: Recombinant protein

<400> SEQUENCE: 758

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
                20                  25                  30

Leu His Trp Tyr Gln Gln Lys Pro Gly Glu Ala Pro Arg Leu Leu Ile
            35                  40                  45

Lys Tyr Thr Ser Gln Pro Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 759
<211> LENGTH: 11
<212> TYPE: PRT
<213> ORGANISM: Artificial Sequence
<220> FEATURE:
<223> OTHER INFORMATION: Recombinant protein

<400> SEQUENCE: 759

Arg Ala Ser Gln Gly Ile Ser Asp Tyr Leu His
1               5                   10

<210> SEQ ID NO 760
<211> LENGTH: 7
<212> TYPE: PRT
<213> ORGANISM: Artificial Sequence
```

<220> FEATURE:
<223> OTHER INFORMATION: Recombinant protein

<400> SEQUENCE: 760

Tyr Thr Ser Gln Pro Ala Thr
1               5

<210> SEQ ID NO 761
<211> LENGTH: 9
<212> TYPE: PRT
<213> ORGANISM: Artificial Sequence
<220> FEATURE:
<223> OTHER INFORMATION: Recombinant protein

<400> SEQUENCE: 761

Gln Asn Gly His Ser Phe Pro Leu Thr
1               5

<210> SEQ ID NO 762
<211> LENGTH: 122
<212> TYPE: PRT
<213> ORGANISM: Artificial Sequence
<220> FEATURE:
<223> OTHER INFORMATION: Recombinant protein

<400> SEQUENCE: 762

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120

<210> SEQ ID NO 763
<211> LENGTH: 6
<212> TYPE: PRT
<213> ORGANISM: Artificial Sequence
<220> FEATURE:
<223> OTHER INFORMATION: Recombinant protein

<400> SEQUENCE: 763

Ser Asp Ser Ala Trp Ser
1               5

<210> SEQ ID NO 764
<211> LENGTH: 16
<212> TYPE: PRT
<213> ORGANISM: Artificial Sequence
<220> FEATURE:
<223> OTHER INFORMATION: Recombinant protein

<400> SEQUENCE: 764

Tyr Ile Gln Tyr Ser Gly Ser Thr Asn Tyr Asn Pro Ser Leu Lys Ser

```
<210> SEQ ID NO 765
<211> LENGTH: 13
<212> TYPE: PRT
<213> ORGANISM: Artificial Sequence
<220> FEATURE:
<223> OTHER INFORMATION: Recombinant protein

<400> SEQUENCE: 765

Ser Val Asn Tyr Tyr Gly Asn Ser Phe Ala Val Gly Tyr
1               5                   10

<210> SEQ ID NO 766
<211> LENGTH: 107
<212> TYPE: PRT
<213> ORGANISM: Artificial Sequence
<220> FEATURE:
<223> OTHER INFORMATION: Recombinant protein

<400> SEQUENCE: 766

Asp Ile Val Met Thr Gln Ser His Lys Ile Met Ser Thr Leu Val Gly
1               5                   10                  15

Asp Arg Val Ser Ile Thr Cys Lys Ala Ser Gln Asp Val Asp Pro Ala
            20                  25                  30

Val Ala Trp Tyr Gln Gln Lys Pro Gly Gln Tyr Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Lys Tyr Pro Tyr
                85                  90                  95

Thr Phe Gly Gly Gly Thr Lys Leu Glu Ile Lys
            100                 105

<210> SEQ ID NO 767
<211> LENGTH: 11
<212> TYPE: PRT
<213> ORGANISM: Artificial Sequence
<220> FEATURE:
<223> OTHER INFORMATION: Recombinant protein

<400> SEQUENCE: 767

Lys Ala Ser Gln Asp Val Asp Pro Ala Val Ala
1               5                   10

<210> SEQ ID NO 768
<211> LENGTH: 7
<212> TYPE: PRT
<213> ORGANISM: Artificial Sequence
<220> FEATURE:
<223> OTHER INFORMATION: Recombinant protein

<400> SEQUENCE: 768

Trp Ala Ser Thr Arg His Thr
1               5

<210> SEQ ID NO 769
<211> LENGTH: 9
<212> TYPE: PRT
<213> ORGANISM: Artificial Sequence
<220> FEATURE:
<223> OTHER INFORMATION: Recombinant protein
```

<400> SEQUENCE: 769

Gln Gln Tyr Ser Lys Tyr Pro Tyr Thr
1               5

<210> SEQ ID NO 770
<211> LENGTH: 118
<212> TYPE: PRT
<213> ORGANISM: Artificial Sequence
<220> FEATURE:
<223> OTHER INFORMATION: Recombinant protein

<400> SEQUENCE: 770

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Ser Trp Ile Arg Gln Pro Pro Gly Lys Gly Leu Glu Trp Leu
        35                  40                  45

Gly Val Ile Trp Gly Gly Gly Asn Thr Tyr Asn Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Ala Asp Asp Thr Ala Met Tyr Phe Cys Ala
                85                  90                  95

Lys His Gly Tyr Tyr Gly Tyr Val Met Asp Tyr Trp Gly Gln Gly Thr
            100                 105                 110

Ser Val Thr Val Ser Ser
        115

<210> SEQ ID NO 771
<211> LENGTH: 5
<212> TYPE: PRT
<213> ORGANISM: Artificial Sequence
<220> FEATURE:
<223> OTHER INFORMATION: Recombinant protein

<400> SEQUENCE: 771

Asp Tyr Gly Val Ser
1               5

<210> SEQ ID NO 772
<211> LENGTH: 16
<212> TYPE: PRT
<213> ORGANISM: Artificial Sequence
<220> FEATURE:
<223> OTHER INFORMATION: Recombinant protein

<400> SEQUENCE: 772

Val Ile Trp Gly Gly Gly Asn Thr Tyr Asn Asn Ser Ala Leu Lys Ser
1               5                   10                  15

<210> SEQ ID NO 773
<211> LENGTH: 10
<212> TYPE: PRT
<213> ORGANISM: Artificial Sequence
<220> FEATURE:
<223> OTHER INFORMATION: Recombinant protein

<400> SEQUENCE: 773

His Gly Tyr Tyr Gly Tyr Val Met Asp Tyr
1               5                   10

<210> SEQ ID NO 774
<211> LENGTH: 107
<212> TYPE: PRT
<213> ORGANISM: Artificial Sequence
<220> FEATURE:
<223> OTHER INFORMATION: Recombinant protein

<400> SEQUENCE: 774

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Gly Ile Ser Asp Tyr
            20                  25                  30
Leu His Trp Tyr Gln Gln Lys Pro Gly Glu Ala Pro Arg Leu Leu Ile
        35                  40                  45
Lys Tyr Thr Ser Gln Pro Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Asn Gly His Ser Phe Pro Leu
                85                  90                  95
Thr Phe Gly Gln Gly Thr Lys Leu Glu Ile Lys
            100                 105

<210> SEQ ID NO 775
<211> LENGTH: 11
<212> TYPE: PRT
<213> ORGANISM: Artificial Sequence
<220> FEATURE:
<223> OTHER INFORMATION: Recombinant protein

<400> SEQUENCE: 775

Arg Ala Ser Gln Gly Ile Ser Asp Tyr Leu His
1               5                   10

<210> SEQ ID NO 776
<211> LENGTH: 7
<212> TYPE: PRT
<213> ORGANISM: Artificial Sequence
<220> FEATURE:
<223> OTHER INFORMATION: Recombinant protein

<400> SEQUENCE: 776

Tyr Thr Ser Gln Pro Ala Thr
1               5

<210> SEQ ID NO 777
<211> LENGTH: 9
<212> TYPE: PRT
<213> ORGANISM: Artificial Sequence
<220> FEATURE:
<223> OTHER INFORMATION: Recombinant protein

<400> SEQUENCE: 777

Gln Asn Gly His Ser Phe Pro Leu Thr
1               5

<210> SEQ ID NO 778
<211> LENGTH: 122
<212> TYPE: PRT
<213> ORGANISM: Artificial Sequence
<220> FEATURE:
<223> OTHER INFORMATION: Recombinant protein

<400> SEQUENCE: 778

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120
```

<210> SEQ ID NO 779
<211> LENGTH: 6
<212> TYPE: PRT
<213> ORGANISM: Artificial Sequence
<220> FEATURE:
<223> OTHER INFORMATION: Recombinant protein

<400> SEQUENCE: 779

```
Ser Asp Ser Ala Trp Ser
1               5
```

<210> SEQ ID NO 780
<211> LENGTH: 16
<212> TYPE: PRT
<213> ORGANISM: Artificial Sequence
<220> FEATURE:
<223> OTHER INFORMATION: Recombinant protein

<400> SEQUENCE: 780

```
Tyr Ile Gln Tyr Ser Gly Ser Thr Asn Tyr Asn Pro Ser Leu Lys Ser
1               5                   10                  15
```

<210> SEQ ID NO 781
<211> LENGTH: 13
<212> TYPE: PRT
<213> ORGANISM: Artificial Sequence
<220> FEATURE:
<223> OTHER INFORMATION: Recombinant protein

<400> SEQUENCE: 781

```
Ser Val Asn Tyr Tyr Gly Asn Ser Phe Ala Val Gly Tyr
1               5                   10
```

<210> SEQ ID NO 782
<211> LENGTH: 107
<212> TYPE: PRT
<213> ORGANISM: Artificial Sequence
<220> FEATURE:
<223> OTHER INFORMATION: Recombinant protein

<400> SEQUENCE: 782

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30
```

-continued

```
Leu His Trp Tyr Gln Gln Lys Pro Gly Glu Ala Pro Arg Leu Leu Ile
           35                  40                  45

Lys Tyr Thr Ser Gln Pro Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Val Gly Val Tyr Tyr Cys Gln Ser Gly His Ser Phe Pro Leu
                 85                  90                  95

Thr Phe Gly Ala Gly Thr Lys Leu Glu Leu Lys
            100                 105

<210> SEQ ID NO 783
<211> LENGTH: 11
<212> TYPE: PRT
<213> ORGANISM: Artificial Sequence
<220> FEATURE:
<223> OTHER INFORMATION: Recombinant protein

<400> SEQUENCE: 783

Arg Ala Ser Gln Gly Ile Ser Asp Tyr Leu His
 1               5                  10

<210> SEQ ID NO 784
<211> LENGTH: 7
<212> TYPE: PRT
<213> ORGANISM: Artificial Sequence
<220> FEATURE:
<223> OTHER INFORMATION: Recombinant protein

<400> SEQUENCE: 784

Tyr Thr Ser Gln Pro Ala Thr
 1               5

<210> SEQ ID NO 785
<211> LENGTH: 9
<212> TYPE: PRT
<213> ORGANISM: Artificial Sequence
<220> FEATURE:
<223> OTHER INFORMATION: Recombinant protein

<400> SEQUENCE: 785

Gln Ser Gly His Ser Phe Pro Leu Thr
 1               5

<210> SEQ ID NO 786
<211> LENGTH: 122
<212> TYPE: PRT
<213> ORGANISM: Artificial Sequence
<220> FEATURE:
<223> OTHER INFORMATION: Recombinant protein

<400> SEQUENCE: 786

Asp Val Gln Leu Gln Glu Ser Gly Pro Gly Leu Val Glu Pro Ser Gln
 1               5                  10                  15

Ser Leu Ser Leu Thr Cys Thr Val Thr Gly Tyr Ser Ile Thr Ser Asp
                 20                  25                  30

Ser Ala Trp Ser Trp Ile Arg Gln Phe Pro Gly Asn Lys Leu Glu Trp
             35                  40                  45

Met Gly Tyr Ile Gln Tyr Ser Gly Ser Thr Asn Tyr Asn Pro Ser Leu
     50                  55                  60

Lys Ser Arg Ile Ser Val Thr Arg Asp Thr Ser Lys Asn Gln Phe Phe
 65                  70                  75                  80
```

```
Leu Arg Leu Ser Ser Val Thr Ala Glu Asp Thr Ala Thr Tyr Tyr Cys
                85                  90                  95

Thr Arg Ser Val Asn Tyr Tyr Gly Asn Ser Phe Ala Val Gly Tyr Trp
            100                 105                 110

Gly Gln Gly Thr Ser Val Thr Val Ser Ser
        115                 120
```

<210> SEQ ID NO 787
<211> LENGTH: 6
<212> TYPE: PRT
<213> ORGANISM: Artificial Sequence
<220> FEATURE:
<223> OTHER INFORMATION: Recombinant protein

<400> SEQUENCE: 787

```
Ser Asp Ser Ala Trp Ser
1               5
```

<210> SEQ ID NO 788
<211> LENGTH: 16
<212> TYPE: PRT
<213> ORGANISM: Artificial Sequence
<220> FEATURE:
<223> OTHER INFORMATION: Recombinant protein

<400> SEQUENCE: 788

```
Tyr Ile Gln Tyr Ser Gly Ser Thr Asn Tyr Asn Pro Ser Leu Lys Ser
1               5                   10                  15
```

<210> SEQ ID NO 789
<211> LENGTH: 13
<212> TYPE: PRT
<213> ORGANISM: Artificial Sequence
<220> FEATURE:
<223> OTHER INFORMATION: Recombinant protein

<400> SEQUENCE: 789

```
Ser Val Asn Tyr Tyr Gly Asn Ser Phe Ala Val Gly Tyr
1               5                   10
```

<210> SEQ ID NO 790
<211> LENGTH: 107
<212> TYPE: PRT
<213> ORGANISM: Artificial Sequence
<220> FEATURE:
<223> OTHER INFORMATION: Recombinant protein

<400> SEQUENCE: 790

```
Asp Ile Val Met Thr Gln Ser Pro Ala Thr Leu Ser Val Thr Ala Gly
1               5                   10                  15

Asp Arg Val Ser Leu Ser Cys Arg Ala Ser Gln Gly Ile Ser Asp Tyr
            20                  25                  30

Leu His Trp Tyr Gln Gln Lys Ser His Glu Ser Pro Arg Leu Leu Ile
        35                  40                  45

Lys Tyr Thr Ser Gln Pro Val Ser Gly Ile Pro Ser Arg Phe Ser Gly
    50                  55                  60

Ser Gly Ser Gly Ser Glu Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105
```

<210> SEQ ID NO 791
<211> LENGTH: 11
<212> TYPE: PRT
<213> ORGANISM: Artificial Sequence
<220> FEATURE:
<223> OTHER INFORMATION: Recombinant protein

<400> SEQUENCE: 791

Arg Ala Ser Gln Gly Ile Ser Asp Tyr Leu His
1               5                   10

<210> SEQ ID NO 792
<211> LENGTH: 7
<212> TYPE: PRT
<213> ORGANISM: Artificial Sequence
<220> FEATURE:
<223> OTHER INFORMATION: Recombinant protein

<400> SEQUENCE: 792

Tyr Thr Ser Gln Pro Val Ser
1               5

<210> SEQ ID NO 793
<211> LENGTH: 9
<212> TYPE: PRT
<213> ORGANISM: Artificial Sequence
<220> FEATURE:
<223> OTHER INFORMATION: Recombinant protein

<400> SEQUENCE: 793

Gln Asn Gly His Ser Phe Pro Leu Thr
1               5

<210> SEQ ID NO 794
<211> LENGTH: 122
<212> TYPE: PRT
<213> ORGANISM: Artificial Sequence
<220> FEATURE:
<223> OTHER INFORMATION: Recombinant protein

<400> SEQUENCE: 794

Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Trp Val Asp Pro Trp
            100                 105                 110

Gly Gln Gly Thr Leu Val Thr Val Ser Ser
        115                 120

<210> SEQ ID NO 795
<211> LENGTH: 6
<212> TYPE: PRT
<213> ORGANISM: Artificial Sequence

```
<220> FEATURE:
<223> OTHER INFORMATION: Recombinant protein

<400> SEQUENCE: 795

Ser Asp Ser Ala Trp Ser
1               5

<210> SEQ ID NO 796
<211> LENGTH: 16
<212> TYPE: PRT
<213> ORGANISM: Artificial Sequence
<220> FEATURE:
<223> OTHER INFORMATION: Recombinant protein

<400> SEQUENCE: 796

Tyr Ile Gln Tyr Ser Gly Ser Thr Asn Tyr Asn Pro Ser Leu Lys Ser
1               5                   10                  15

<210> SEQ ID NO 797
<211> LENGTH: 13
<212> TYPE: PRT
<213> ORGANISM: Artificial Sequence
<220> FEATURE:
<223> OTHER INFORMATION: Recombinant protein

<400> SEQUENCE: 797

Ser Val Asn Tyr Tyr Gly Asn Ser Phe Trp Val Asp Pro
1               5                   10

<210> SEQ ID NO 798
<211> LENGTH: 107
<212> TYPE: PRT
<213> ORGANISM: Artificial Sequence
<220> FEATURE:
<223> OTHER INFORMATION: Recombinant protein

<400> SEQUENCE: 798

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
                20                  25                  30

Leu His Trp Tyr Gln Gln Lys Pro Gly Glu Ala Pro Arg Leu Leu Ile
            35                  40                  45

Lys Tyr Thr Ser Gln Pro Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 799
<211> LENGTH: 11
<212> TYPE: PRT
<213> ORGANISM: Artificial Sequence
<220> FEATURE:
<223> OTHER INFORMATION: Recombinant protein

<400> SEQUENCE: 799

Arg Ala Ser Gln Gly Ile Ser Asp Tyr Leu His
1               5                   10
```

<210> SEQ ID NO 800
<211> LENGTH: 7
<212> TYPE: PRT
<213> ORGANISM: Artificial Sequence
<220> FEATURE:
<223> OTHER INFORMATION: Recombinant protein

<400> SEQUENCE: 800

Tyr Thr Ser Gln Pro Ala Thr
1               5

<210> SEQ ID NO 801
<211> LENGTH: 9
<212> TYPE: PRT
<213> ORGANISM: Artificial Sequence
<220> FEATURE:
<223> OTHER INFORMATION: Recombinant protein

<400> SEQUENCE: 801

Gln Asn Gly His Ser Phe Pro Leu Thr
1               5

<210> SEQ ID NO 802
<211> LENGTH: 122
<212> TYPE: PRT
<213> ORGANISM: Artificial Sequence
<220> FEATURE:
<223> OTHER INFORMATION: Recombinant protein

<400> SEQUENCE: 802

Asp Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Phe Pro Gly Lys Lys Leu Glu Trp
        35                  40                  45

Met Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Ser Val Asn Tyr Tyr Gly Asn Ser Phe Ala Val Asp Tyr Trp
                100                 105                 110

Gly Gln Gly Thr Ser Val Thr Val Ser Ser
        115                 120

<210> SEQ ID NO 803
<211> LENGTH: 6
<212> TYPE: PRT
<213> ORGANISM: Artificial Sequence
<220> FEATURE:
<223> OTHER INFORMATION: Recombinant protein

<400> SEQUENCE: 803

Ser Asp Ser Ala Trp Ser
1               5

<210> SEQ ID NO 804
<211> LENGTH: 16
<212> TYPE: PRT
<213> ORGANISM: Artificial Sequence
<220> FEATURE:
<223> OTHER INFORMATION: Recombinant protein -continued

<400> SEQUENCE: 804

Tyr Ile Gln Tyr Ser Gly Ser Thr Asn Tyr Asn Pro Ser Leu Lys Ser
1               5                   10                  15

<210> SEQ ID NO 805
<211> LENGTH: 13
<212> TYPE: PRT
<213> ORGANISM: Artificial Sequence
<220> FEATURE:
<223> OTHER INFORMATION: Recombinant protein

<400> SEQUENCE: 805

Ser Val Asn Tyr Tyr Gly Asn Ser Phe Ala Val Asp Tyr
1               5                   10

<210> SEQ ID NO 806
<211> LENGTH: 107
<212> TYPE: PRT
<213> ORGANISM: Artificial Sequence
<220> FEATURE:
<223> OTHER INFORMATION: Recombinant protein

<400> SEQUENCE: 806

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 807
<211> LENGTH: 11
<212> TYPE: PRT
<213> ORGANISM: Artificial Sequence
<220> FEATURE:
<223> OTHER INFORMATION: Recombinant protein

<400> SEQUENCE: 807

Arg Ala Ser Gln Gly Val Ser Asp Tyr Leu His
1               5                   10

<210> SEQ ID NO 808
<211> LENGTH: 7
<212> TYPE: PRT
<213> ORGANISM: Artificial Sequence
<220> FEATURE:
<223> OTHER INFORMATION: Recombinant protein

<400> SEQUENCE: 808

Tyr Ala Ser Gln Pro Ala Thr
1               5

<210> SEQ ID NO 809
<211> LENGTH: 9

```
<212> TYPE: PRT
<213> ORGANISM: Artificial Sequence
<220> FEATURE:
<223> OTHER INFORMATION: Recombinant protein

<400> SEQUENCE: 809

Gln Asn Gly His Ser Phe Pro Leu Thr
1               5

<210> SEQ ID NO 810
<211> LENGTH: 122
<212> TYPE: PRT
<213> ORGANISM: Artificial Sequence
<220> FEATURE:
<223> OTHER INFORMATION: Recombinant protein

<400> SEQUENCE: 810

Gln Val Gln Leu Gln Glu Ser Gly Pro Gly Leu Val Glu Pro Ser Gln
1               5                   10                  15

Thr Leu Ser Leu Thr Cys Thr Val Ser Gly Tyr Ser Ile Thr Ser Asp
            20                  25                  30

Ser Ala Trp Ser Trp Ile Arg Gln Pro Pro Gly Lys Lys Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120

<210> SEQ ID NO 811
<211> LENGTH: 6
<212> TYPE: PRT
<213> ORGANISM: Artificial Sequence
<220> FEATURE:
<223> OTHER INFORMATION: Recombinant protein

<400> SEQUENCE: 811

Ser Asp Ser Ala Trp Ser
1               5

<210> SEQ ID NO 812
<211> LENGTH: 16
<212> TYPE: PRT
<213> ORGANISM: Artificial Sequence
<220> FEATURE:
<223> OTHER INFORMATION: Recombinant protein

<400> SEQUENCE: 812

Tyr Ile Gln Tyr Ser Gly Ser Thr Asn Tyr Asn Pro Ser Leu Lys Ser
1               5                   10                  15

<210> SEQ ID NO 813
<211> LENGTH: 13
<212> TYPE: PRT
<213> ORGANISM: Artificial Sequence
<220> FEATURE:
<223> OTHER INFORMATION: Recombinant protein

<400> SEQUENCE: 813
```

Ser Val Asn Tyr Tyr Gly Asn Ser Phe Ala Val Gly Tyr
1               5                   10

<210> SEQ ID NO 814
<211> LENGTH: 107
<212> TYPE: PRT
<213> ORGANISM: Artificial Sequence
<220> FEATURE:
<223> OTHER INFORMATION: Recombinant protein

<400> SEQUENCE: 814

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 815
<211> LENGTH: 11
<212> TYPE: PRT
<213> ORGANISM: Artificial Sequence
<220> FEATURE:
<223> OTHER INFORMATION: Recombinant protein

<400> SEQUENCE: 815

Arg Ala Ser Gln Gly Ile Ser Asp Tyr Leu His
1               5                   10

<210> SEQ ID NO 816
<211> LENGTH: 7
<212> TYPE: PRT
<213> ORGANISM: Artificial Sequence
<220> FEATURE:
<223> OTHER INFORMATION: Recombinant protein

<400> SEQUENCE: 816

Tyr Thr Ser Gln Pro Ala Thr
1               5

<210> SEQ ID NO 817
<211> LENGTH: 9
<212> TYPE: PRT
<213> ORGANISM: Artificial Sequence
<220> FEATURE:
<223> OTHER INFORMATION: Recombinant protein

<400> SEQUENCE: 817

Gln Asn Gly His Ser Phe Pro Leu Thr
1               5

<210> SEQ ID NO 818
<211> LENGTH: 122
<212> TYPE: PRT
<213> ORGANISM: Artificial Sequence

```
<220> FEATURE:
<223> OTHER INFORMATION: Recombinant protein

<400> SEQUENCE: 818

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120

<210> SEQ ID NO 819
<211> LENGTH: 6
<212> TYPE: PRT
<213> ORGANISM: Artificial Sequence
<220> FEATURE:
<223> OTHER INFORMATION: Recombinant protein

<400> SEQUENCE: 819

Ser Asp Ser Ala Trp Ser
1               5

<210> SEQ ID NO 820
<211> LENGTH: 16
<212> TYPE: PRT
<213> ORGANISM: Artificial Sequence
<220> FEATURE:
<223> OTHER INFORMATION: Recombinant protein

<400> SEQUENCE: 820

Tyr Ile Gln Tyr Ser Gly Ser Thr Asn Tyr Asn Pro Ser Leu Lys Ser
1               5                   10                  15

<210> SEQ ID NO 821
<211> LENGTH: 13
<212> TYPE: PRT
<213> ORGANISM: Artificial Sequence
<220> FEATURE:
<223> OTHER INFORMATION: Recombinant protein

<400> SEQUENCE: 821

Ser Val Asn Tyr Tyr Gly Asn Ser Phe Ala Val Gly Tyr
1               5                   10

<210> SEQ ID NO 822
<211> LENGTH: 107
<212> TYPE: PRT
<213> ORGANISM: Artificial Sequence
<220> FEATURE:
<223> OTHER INFORMATION: Recombinant protein

<400> SEQUENCE: 822

Asp Ile Gln Met Thr Gln Ser Pro Ser Ser Leu Ser Ala Ser Val Gly
```

```
  1               5                  10                 15
Asp Arg Val Thr Ile Thr Cys Gln Ala Ser Gln Asp Ile Ser Asn Tyr
            20                 25                 30

Leu Asn Trp Tyr Gln Gln Lys Pro Gly Lys Ala Pro Lys Leu Leu Ile
            35                 40                 45

Tyr Asp Ala Ser Asn Leu Glu Thr Gly Val Pro Ser Arg Phe Ser Gly
            50                 55                 60

Ser Gly Ser Gly Thr Asp Phe Thr Phe Thr Ile Ser Ser Leu Gln Pro
65                  70                 75                 80

Glu Asp Ile Ala Thr Tyr Tyr Cys Gln Gln Val Ala Ala Leu Pro Pro
                85                 90                 95

Thr Phe Gly Gly Gly Thr Lys Val Glu Ile Lys
            100                105
```

<210> SEQ ID NO 823
<211> LENGTH: 11
<212> TYPE: PRT
<213> ORGANISM: Artificial Sequence
<220> FEATURE:
<223> OTHER INFORMATION: Recombinant protein

<400> SEQUENCE: 823

```
Gln Ala Ser Gln Asp Ile Ser Asn Tyr Leu Asn
1               5                  10
```

<210> SEQ ID NO 824
<211> LENGTH: 7
<212> TYPE: PRT
<213> ORGANISM: Artificial Sequence
<220> FEATURE:
<223> OTHER INFORMATION: Recombinant protein

<400> SEQUENCE: 824

```
Asp Ala Ser Asn Leu Glu Thr
1               5
```

<210> SEQ ID NO 825
<211> LENGTH: 9
<212> TYPE: PRT
<213> ORGANISM: Artificial Sequence
<220> FEATURE:
<223> OTHER INFORMATION: Recombinant protein

<400> SEQUENCE: 825

```
Gln Gln Val Ala Ala Leu Pro Pro Thr
1               5
```

<210> SEQ ID NO 826
<211> LENGTH: 123
<212> TYPE: PRT
<213> ORGANISM: Artificial Sequence
<220> FEATURE:
<223> OTHER INFORMATION: Recombinant protein

<400> SEQUENCE: 826

```
Glu Val Gln Leu Val Glu Ser Gly Gly Gly Leu Val Lys Pro Gly Gly
1               5                  10                 15

Ser Leu Arg Leu Ser Cys Ala Ala Ser Gly Phe Thr Phe Thr Ser Tyr
            20                 25                 30

Ser Met Ser Trp Val Arg Gln Ala Pro Gly Lys Gly Leu Glu Trp Val
            35                 40                 45

Ser Ser Ile Ser Ser Arg Ser Ser Tyr Ile Cys Tyr Ala Asp Ser Val
```

```
                     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                     85                  90                  95

Ala Arg Glu Gly Asp Thr Gly Ser Ile Gly Gly Asp Tyr Met Asp Val
                100                 105                 110

Trp Gly Lys Gly Thr Thr Val Thr Val Ser Ser
            115                 120
```

<210> SEQ ID NO 827
<211> LENGTH: 5
<212> TYPE: PRT
<213> ORGANISM: Artificial Sequence
<220> FEATURE:
<223> OTHER INFORMATION: Recombinant protein

<400> SEQUENCE: 827

```
Ser Tyr Ser Met Ser
 1               5
```

<210> SEQ ID NO 828
<211> LENGTH: 17
<212> TYPE: PRT
<213> ORGANISM: Artificial Sequence
<220> FEATURE:
<223> OTHER INFORMATION: Recombinant protein

<400> SEQUENCE: 828

```
Ser Ile Ser Ser Arg Ser Ser Tyr Ile Cys Tyr Ala Asp Ser Val Lys
 1               5                  10                  15

Gly
```

<210> SEQ ID NO 829
<211> LENGTH: 14
<212> TYPE: PRT
<213> ORGANISM: Artificial Sequence
<220> FEATURE:
<223> OTHER INFORMATION: Recombinant protein

<400> SEQUENCE: 829

```
Glu Gly Asp Thr Gly Ser Ile Gly Gly Asp Tyr Met Asp Val
 1               5                  10
```

<210> SEQ ID NO 830
<211> LENGTH: 107
<212> TYPE: PRT
<213> ORGANISM: Artificial Sequence
<220> FEATURE:
<223> OTHER INFORMATION: Recombinant protein

<400> SEQUENCE: 830

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Gly Ile Ser Asp Tyr
                20                  25                  30

Leu His Trp Tyr Gln Gln Lys Pro Gly Glu Ala Pro Arg Leu Leu Ile
            35                  40                  45

Lys Tyr Thr Ser Gln Pro Ala Thr Gly Ile Pro Ala Arg Phe Ser Gly
        50                  55                  60

Ser Gly Ser Gly Thr Asp Phe Thr Leu Thr Ile Ser Ser Leu Glu Pro
 65                  70                  75                  80
```

```
Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105
```

<210> SEQ ID NO 831
<211> LENGTH: 11
<212> TYPE: PRT
<213> ORGANISM: Artificial Sequence
<220> FEATURE:
<223> OTHER INFORMATION: Recombinant protein

<400> SEQUENCE: 831

```
Arg Ala Ser Gln Gly Ile Ser Asp Tyr Leu His
1               5                   10
```

<210> SEQ ID NO 832
<211> LENGTH: 7
<212> TYPE: PRT
<213> ORGANISM: Artificial Sequence
<220> FEATURE:
<223> OTHER INFORMATION: Recombinant protein

<400> SEQUENCE: 832

```
Tyr Thr Ser Gln Pro Ala Thr
1               5
```

<210> SEQ ID NO 833
<211> LENGTH: 9
<212> TYPE: PRT
<213> ORGANISM: Artificial Sequence
<220> FEATURE:
<223> OTHER INFORMATION: Recombinant protein

<400> SEQUENCE: 833

```
Gln Asn Gly His Ser Phe Pro Leu Thr
1               5
```

<210> SEQ ID NO 834
<211> LENGTH: 122
<212> TYPE: PRT
<213> ORGANISM: Artificial Sequence
<220> FEATURE:
<223> OTHER INFORMATION: Recombinant protein

<400> SEQUENCE: 834

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120
```

<210> SEQ ID NO 835
<211> LENGTH: 6
<212> TYPE: PRT
<213> ORGANISM: Artificial Sequence
<220> FEATURE:
<223> OTHER INFORMATION: Recombinant protein

<400> SEQUENCE: 835

Ser Asp Ser Ala Trp Ser
1               5

<210> SEQ ID NO 836
<211> LENGTH: 16
<212> TYPE: PRT
<213> ORGANISM: Artificial Sequence
<220> FEATURE:
<223> OTHER INFORMATION: Recombinant protein

<400> SEQUENCE: 836

Tyr Ile Gln Tyr Ser Gly Ser Thr Asn Tyr Asn Pro Ser Leu Lys Ser
1               5                   10                  15

<210> SEQ ID NO 837
<211> LENGTH: 13
<212> TYPE: PRT
<213> ORGANISM: Artificial Sequence
<220> FEATURE:
<223> OTHER INFORMATION: Recombinant protein

<400> SEQUENCE: 837

Ser Val Asn Tyr Tyr Gly Asn Ser Phe Ala Val Gly Tyr
1               5                   10

<210> SEQ ID NO 838
<211> LENGTH: 112
<212> TYPE: PRT
<213> ORGANISM: Artificial Sequence
<220> FEATURE:
<223> OTHER INFORMATION: Recombinant protein

<400> SEQUENCE: 838

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Arg
            20                  25                  30

Gln Gly Asn Thr Tyr Phe His Trp Leu Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 839
<211> LENGTH: 16
<212> TYPE: PRT
<213> ORGANISM: Artificial Sequence
<220> FEATURE:
<223> OTHER INFORMATION: Recombinant protein

<400> SEQUENCE: 839

Arg Ser Ser Gln Ser Leu Val His Arg Gln Gly Asn Thr Tyr Phe His
1               5                   10                  15

<210> SEQ ID NO 840
<211> LENGTH: 7
<212> TYPE: PRT
<213> ORGANISM: Artificial Sequence
<220> FEATURE:
<223> OTHER INFORMATION: Recombinant protein

<400> SEQUENCE: 840

Lys Val Ser Asn Arg Phe Ser
1               5

<210> SEQ ID NO 841
<211> LENGTH: 9
<212> TYPE: PRT
<213> ORGANISM: Artificial Sequence
<220> FEATURE:
<223> OTHER INFORMATION: Recombinant protein

<400> SEQUENCE: 841

Ser Gln Ser Thr His Val Pro Tyr Thr
1               5

<210> SEQ ID NO 842
<211> LENGTH: 114
<212> TYPE: PRT
<213> ORGANISM: Artificial Sequence
<220> FEATURE:
<223> OTHER INFORMATION: Recombinant protein

<400> SEQUENCE: 842

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Thr Trp Val Arg Gln Ala Pro Gly Lys Gly Leu Val Trp Val
        35                  40                  45

Gly Glu Ile Asn Pro Asp Ser Ser Thr Ile Asn Tyr Ala Pro Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Val Phe Thr Ser Trp Gly Gln Gly Thr Leu Val Thr Val
            100                 105                 110

Ser Ser

<210> SEQ ID NO 843
<211> LENGTH: 5
<212> TYPE: PRT
<213> ORGANISM: Artificial Sequence
<220> FEATURE:
<223> OTHER INFORMATION: Recombinant protein

<400> SEQUENCE: 843

Arg Tyr Trp Met Thr
1               5

<210> SEQ ID NO 844

<211> LENGTH: 17
<212> TYPE: PRT
<213> ORGANISM: Artificial Sequence
<220> FEATURE:
<223> OTHER INFORMATION: Recombinant protein

<400> SEQUENCE: 844

Glu Ile Asn Pro Asp Ser Ser Thr Ile Asn Tyr Ala Pro Ser Val Lys
1               5                   10                  15
Gly

<210> SEQ ID NO 845
<211> LENGTH: 5
<212> TYPE: PRT
<213> ORGANISM: Artificial Sequence
<220> FEATURE:
<223> OTHER INFORMATION: Recombinant protein

<400> SEQUENCE: 845

Gly Val Phe Thr Ser
1               5

<210> SEQ ID NO 846
<211> LENGTH: 107
<212> TYPE: PRT
<213> ORGANISM: Artificial Sequence
<220> FEATURE:
<223> OTHER INFORMATION: Recombinant protein

<400> SEQUENCE: 846

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Ile Ser Asp Tyr
            20                  25                  30

Leu His Trp Tyr Gln Gln Lys Pro Gly Glu Ala Pro Arg Leu Leu Ile
        35                  40                  45

Lys Tyr Thr Ser Gln Pro Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 847
<211> LENGTH: 11
<212> TYPE: PRT
<213> ORGANISM: Artificial Sequence
<220> FEATURE:
<223> OTHER INFORMATION: Recombinant protein

<400> SEQUENCE: 847

Arg Ala Ser Gln Gly Ile Ser Asp Tyr Leu His
1               5                   10

<210> SEQ ID NO 848
<211> LENGTH: 7
<212> TYPE: PRT
<213> ORGANISM: Artificial Sequence
<220> FEATURE:
<223> OTHER INFORMATION: Recombinant protein

<400> SEQUENCE: 848

Tyr Thr Ser Gln Pro Ala Thr
1               5

<210> SEQ ID NO 849
<211> LENGTH: 9
<212> TYPE: PRT
<213> ORGANISM: Artificial Sequence
<220> FEATURE:
<223> OTHER INFORMATION: Recombinant protein

<400> SEQUENCE: 849

Gln Asn Gly His Ser Phe Pro Leu Thr
1               5

<210> SEQ ID NO 850
<211> LENGTH: 122
<212> TYPE: PRT
<213> ORGANISM: Artificial Sequence
<220> FEATURE:
<223> OTHER INFORMATION: Recombinant protein

<400> SEQUENCE: 850

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Ser Ala Trp Ser Trp Ile Arg Gln Pro Pro Gly Lys Gly Leu Glu Trp
        35                  40                  45

Ile Gly Tyr Ile Gln Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Val Asn Tyr Tyr Gly Asn Ser Phe Ala Val Gly Tyr Trp
            100                 105                 110

Gly Gln Gly Thr Leu Val Thr Val Ser Ser
        115                 120

<210> SEQ ID NO 851
<211> LENGTH: 6
<212> TYPE: PRT
<213> ORGANISM: Artificial Sequence
<220> FEATURE:
<223> OTHER INFORMATION: Recombinant protein

<400> SEQUENCE: 851

Ser Asp Ser Ala Trp Ser
1               5

<210> SEQ ID NO 852
<211> LENGTH: 16
<212> TYPE: PRT
<213> ORGANISM: Artificial Sequence
<220> FEATURE:
<223> OTHER INFORMATION: Recombinant protein

<400> SEQUENCE: 852

Tyr Ile Gln Tyr Ser Gly Ser Thr Asn Tyr Asn Pro Ser Leu Lys Ser
1               5                   10                  15

<210> SEQ ID NO 853

```
<211> LENGTH: 13
<212> TYPE: PRT
<213> ORGANISM: Artificial Sequence
<220> FEATURE:
<223> OTHER INFORMATION: Recombinant protein

<400> SEQUENCE: 853

Ser Val Asn Tyr Tyr Gly Asn Ser Phe Ala Val Gly Tyr
1               5                   10

<210> SEQ ID NO 854
<211> LENGTH: 112
<212> TYPE: PRT
<213> ORGANISM: Artificial Sequence
<220> FEATURE:
<223> OTHER INFORMATION: Recombinant protein

<400> SEQUENCE: 854

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Arg
            20                  25                  30

Gln Gly Asn Thr Tyr Phe His Trp Leu Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 855
<211> LENGTH: 16
<212> TYPE: PRT
<213> ORGANISM: Artificial Sequence
<220> FEATURE:
<223> OTHER INFORMATION: Recombinant protein

<400> SEQUENCE: 855

Arg Ser Ser Gln Ser Leu Val His Arg Gln Gly Asn Thr Tyr Phe His
1               5                   10                  15

<210> SEQ ID NO 856
<211> LENGTH: 7
<212> TYPE: PRT
<213> ORGANISM: Artificial Sequence
<220> FEATURE:
<223> OTHER INFORMATION: Recombinant protein

<400> SEQUENCE: 856

Lys Val Ser Asn Arg Phe Ser
1               5

<210> SEQ ID NO 857
<211> LENGTH: 9
<212> TYPE: PRT
<213> ORGANISM: Artificial Sequence
<220> FEATURE:
<223> OTHER INFORMATION: Recombinant protein

<400> SEQUENCE: 857

Ser Gln Ser Thr His Val Pro Tyr Thr
```

-continued

```
1               5
```

<210> SEQ ID NO 858
<211> LENGTH: 114
<212> TYPE: PRT
<213> ORGANISM: Artificial Sequence
<220> FEATURE:
<223> OTHER INFORMATION: Recombinant protein

<400> SEQUENCE: 858

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Thr Trp Val Arg Gln Ala Pro Gly Lys Gly Leu Val Trp Val
        35                  40                  45

Gly Glu Ile Asn Pro Asp Ser Ser Thr Ile Asn Tyr Ala Pro Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Val Phe Thr Ser Trp Gly Gln Gly Thr Leu Val Thr Val
            100                 105                 110

Ser Ser
```

<210> SEQ ID NO 859
<211> LENGTH: 5
<212> TYPE: PRT
<213> ORGANISM: Artificial Sequence
<220> FEATURE:
<223> OTHER INFORMATION: Recombinant protein

<400> SEQUENCE: 859

```
Arg Tyr Trp Met Thr
1               5
```

<210> SEQ ID NO 860
<211> LENGTH: 17
<212> TYPE: PRT
<213> ORGANISM: Artificial Sequence
<220> FEATURE:
<223> OTHER INFORMATION: Recombinant protein

<400> SEQUENCE: 860

```
Glu Ile Asn Pro Asp Ser Ser Thr Ile Asn Tyr Ala Pro Ser Val Lys
1               5                   10                  15

Gly
```

<210> SEQ ID NO 861
<211> LENGTH: 5
<212> TYPE: PRT
<213> ORGANISM: Artificial Sequence
<220> FEATURE:
<223> OTHER INFORMATION: Recombinant protein

<400> SEQUENCE: 861

```
Gly Val Phe Thr Ser
1               5
```

<210> SEQ ID NO 862
<211> LENGTH: 112

```
<212> TYPE: PRT
<213> ORGANISM: Artificial Sequence
<220> FEATURE:
<223> OTHER INFORMATION: Recombinant protein

<400> SEQUENCE: 862

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Arg
            20                  25                  30

Asn Gly Asn Thr Tyr Phe His Trp Cys Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 863
<211> LENGTH: 16
<212> TYPE: PRT
<213> ORGANISM: Artificial Sequence
<220> FEATURE:
<223> OTHER INFORMATION: Recombinant protein

<400> SEQUENCE: 863

Arg Ser Ser Gln Ser Leu Val His Arg Asn Gly Asn Thr Tyr Phe His
1               5                   10                  15

<210> SEQ ID NO 864
<211> LENGTH: 7
<212> TYPE: PRT
<213> ORGANISM: Artificial Sequence
<220> FEATURE:
<223> OTHER INFORMATION: Recombinant protein

<400> SEQUENCE: 864

Lys Val Ser Asn Arg Phe Ser
1               5

<210> SEQ ID NO 865
<211> LENGTH: 9
<212> TYPE: PRT
<213> ORGANISM: Artificial Sequence
<220> FEATURE:
<223> OTHER INFORMATION: Recombinant protein

<400> SEQUENCE: 865

Ser Gln Ser Thr His Val Pro Tyr Thr
1               5

<210> SEQ ID NO 866
<211> LENGTH: 114
<212> TYPE: PRT
<213> ORGANISM: Artificial Sequence
<220> FEATURE:
<223> OTHER INFORMATION: Recombinant protein

<400> SEQUENCE: 866

Glu Val Lys Leu Leu Glu Ser Gly Gly Gly Leu Val Gln Pro Gly Gly
1               5                   10                  15
```

Ser Leu Lys Leu Ser Cys Ala Ala Ser Gly Phe Asp Phe Ser Arg Tyr
            20                  25                  30

Trp Met Thr Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Glu Val Arg Ser Glu Asp Thr Ala Leu Tyr Tyr Cys
                85                  90                  95

Ala Ser Gly Val Phe Thr Ser Trp Gly Gln Gly Thr Leu Val Thr Val
            100                 105                 110

Ser Ala

<210> SEQ ID NO 867
<211> LENGTH: 5
<212> TYPE: PRT
<213> ORGANISM: Artificial Sequence
<220> FEATURE:
<223> OTHER INFORMATION: Recombinant protein

<400> SEQUENCE: 867

Arg Tyr Trp Met Thr
1               5

<210> SEQ ID NO 868
<211> LENGTH: 17
<212> TYPE: PRT
<213> ORGANISM: Artificial Sequence
<220> FEATURE:
<223> OTHER INFORMATION: Recombinant protein

<400> SEQUENCE: 868

Glu Ile Asn Pro Asp Ser Ser Thr Ile Asn Tyr Thr Pro Ser Leu Lys
1               5                   10                  15

Asp

<210> SEQ ID NO 869
<211> LENGTH: 5
<212> TYPE: PRT
<213> ORGANISM: Artificial Sequence
<220> FEATURE:
<223> OTHER INFORMATION: Recombinant protein

<400> SEQUENCE: 869

Gly Val Phe Thr Ser
1               5

<210> SEQ ID NO 870
<211> LENGTH: 112
<212> TYPE: PRT
<213> ORGANISM: Artificial Sequence
<220> FEATURE:
<223> OTHER INFORMATION: Recombinant protein

<400> SEQUENCE: 870

Asp Ile Val Val Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln

```
                35                  40                  45
Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
                100                 105                 110

<210> SEQ ID NO 871
<211> LENGTH: 17
<212> TYPE: PRT
<213> ORGANISM: Artificial Sequence
<220> FEATURE:
<223> OTHER INFORMATION: Recombinant protein

<400> SEQUENCE: 871

Lys Ser Ser Gln Ser Leu Leu Asn Ser Arg Thr Arg Lys Asn Tyr Leu
 1               5                  10                  15

Ala

<210> SEQ ID NO 872
<211> LENGTH: 7
<212> TYPE: PRT
<213> ORGANISM: Artificial Sequence
<220> FEATURE:
<223> OTHER INFORMATION: Recombinant protein

<400> SEQUENCE: 872

Trp Ala Ser Thr Arg Glu Ser
 1               5

<210> SEQ ID NO 873
<211> LENGTH: 8
<212> TYPE: PRT
<213> ORGANISM: Artificial Sequence
<220> FEATURE:
<223> OTHER INFORMATION: Recombinant protein

<400> SEQUENCE: 873

Lys Gln Ser Tyr Asn Leu Leu Thr
 1               5

<210> SEQ ID NO 874
<211> LENGTH: 121
<212> TYPE: PRT
<213> ORGANISM: Artificial Sequence
<220> FEATURE:
<223> OTHER INFORMATION: Recombinant protein

<400> SEQUENCE: 874

Glu Val Arg Leu Val Glu Ser Gly Gly Gly Leu Val Gln Pro Gly Gly
 1               5                  10                  15

Ser Leu Lys Leu Ser Cys Ala Thr Ser Gly Phe Thr Phe Ser Asp Tyr
                20                  25                  30

Phe Met Tyr Trp Ile Arg Gln Thr Pro Glu Lys Arg Leu Glu Trp Val
                35                  40                  45

Ala Tyr Ile Ser Asn Gly Gly Asp Ser Ser Tyr Pro Asp Thr Val
 50                  55                  60

Lys Gly Arg Phe Thr Ile Ser Arg Asp Asn Ala Lys Asn Thr Leu Tyr
 65                  70                  75                  80
```

```
Leu Gln Met Ser Arg Leu Lys Ser Glu Asp Thr Ala Met Tyr Tyr Cys
                85                  90                  95

Ala Thr Asn Lys Asn Trp Asp Asp Tyr Tyr Asp Met Asp Tyr Trp Gly
            100                 105                 110

Gln Gly Thr Ser Val Thr Val Ser Ser
        115                 120

<210> SEQ ID NO 875
<211> LENGTH: 5
<212> TYPE: PRT
<213> ORGANISM: Artificial Sequence
<220> FEATURE:
<223> OTHER INFORMATION: Recombinant protein

<400> SEQUENCE: 875

Asp Tyr Phe Met Tyr
1               5

<210> SEQ ID NO 876
<211> LENGTH: 17
<212> TYPE: PRT
<213> ORGANISM: Artificial Sequence
<220> FEATURE:
<223> OTHER INFORMATION: Recombinant protein

<400> SEQUENCE: 876

Tyr Ile Ser Asn Gly Gly Asp Ser Ser Tyr Pro Asp Thr Val Lys
1               5                   10                  15

Gly

<210> SEQ ID NO 877
<211> LENGTH: 12
<212> TYPE: PRT
<213> ORGANISM: Artificial Sequence
<220> FEATURE:
<223> OTHER INFORMATION: Recombinant protein

<400> SEQUENCE: 877

Asn Lys Asn Trp Asp Asp Tyr Tyr Asp Met Asp Tyr
1               5                   10

<210> SEQ ID NO 878
<211> LENGTH: 107
<212> TYPE: PRT
<213> ORGANISM: Artificial Sequence
<220> FEATURE:
<223> OTHER INFORMATION: Recombinant protein

<400> SEQUENCE: 878

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Asn Tyr Ala Ser Ser Arg Tyr Thr Gly Ile Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95
```

```
Thr Phe Gly Gly Gly Thr Lys Leu Glu Ile Glu
                100                 105
```

<210> SEQ ID NO 879
<211> LENGTH: 11
<212> TYPE: PRT
<213> ORGANISM: Artificial Sequence
<220> FEATURE:
<223> OTHER INFORMATION: Recombinant protein

<400> SEQUENCE: 879

```
Lys Ala Ser Gln Ser Val Ser Asn Asp Val Ala
1               5                   10
```

<210> SEQ ID NO 880
<211> LENGTH: 7
<212> TYPE: PRT
<213> ORGANISM: Artificial Sequence
<220> FEATURE:
<223> OTHER INFORMATION: Recombinant protein

<400> SEQUENCE: 880

```
Tyr Ala Ser Ser Arg Tyr Thr
1               5
```

<210> SEQ ID NO 881
<211> LENGTH: 9
<212> TYPE: PRT
<213> ORGANISM: Artificial Sequence
<220> FEATURE:
<223> OTHER INFORMATION: Recombinant protein

<400> SEQUENCE: 881

```
Gln Gln Asp Tyr Ser Ser Pro Tyr Thr
1               5
```

<210> SEQ ID NO 882
<211> LENGTH: 121
<212> TYPE: PRT
<213> ORGANISM: Artificial Sequence
<220> FEATURE:
<223> OTHER INFORMATION: Recombinant protein

<400> SEQUENCE: 882

```
Gln Val Gln Leu Glu Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ser Met His Trp Val Lys Gln Ser His Ala Lys Ser Leu Glu Trp Ile
        35                  40                  45

Gly Val Ile Ser Thr Tyr Tyr Gly Asp Val Arg Tyr Asn Gln Lys Phe
    50                  55                  60

Lys Gly Lys Ala Thr Met Thr Val Asp Lys Ser Ser Ser Thr Ala Tyr
65                  70                  75                  80

Met Ala Leu Ala Arg Leu Thr Ser Glu Asp Ser Ala Ile Tyr Tyr Cys
                85                  90                  95

Ala Arg Ala Pro Met Ile Thr Thr Gly Ala Trp Phe Ala Tyr Trp Gly
                100                 105                 110

Gln Gly Thr Leu Val Thr Val Ser Ala
            115                 120
```

<210> SEQ ID NO 883
<211> LENGTH: 5

```
<212> TYPE: PRT
<213> ORGANISM: Artificial Sequence
<220> FEATURE:
<223> OTHER INFORMATION: Recombinant protein

<400> SEQUENCE: 883

Asp Tyr Ser Met His
1               5

<210> SEQ ID NO 884
<211> LENGTH: 17
<212> TYPE: PRT
<213> ORGANISM: Artificial Sequence
<220> FEATURE:
<223> OTHER INFORMATION: Recombinant protein

<400> SEQUENCE: 884

Val Ile Ser Thr Tyr Tyr Gly Asp Val Arg Tyr Asn Gln Lys Phe Lys
1               5                   10                  15

Gly

<210> SEQ ID NO 885
<211> LENGTH: 12
<212> TYPE: PRT
<213> ORGANISM: Artificial Sequence
<220> FEATURE:
<223> OTHER INFORMATION: Recombinant protein

<400> SEQUENCE: 885

Ala Pro Met Ile Thr Thr Gly Ala Trp Phe Ala Tyr
1               5                   10

<210> SEQ ID NO 886
<211> LENGTH: 112
<212> TYPE: PRT
<213> ORGANISM: Artificial Sequence
<220> FEATURE:
<223> OTHER INFORMATION: Recombinant protein

<400> SEQUENCE: 886

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
                20                  25                  30

Asn Gly Asn Thr Tyr Phe His Trp Ala Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 887
<211> LENGTH: 16
<212> TYPE: PRT
<213> ORGANISM: Artificial Sequence
<220> FEATURE:
<223> OTHER INFORMATION: Recombinant protein

<400> SEQUENCE: 887
```

Arg Ser Ser Gln Ser Leu Val His Arg Asn Gly Asn Thr Tyr Phe His
1               5                   10                  15

<210> SEQ ID NO 888
<211> LENGTH: 7
<212> TYPE: PRT
<213> ORGANISM: Artificial Sequence
<220> FEATURE:
<223> OTHER INFORMATION: Recombinant protein

<400> SEQUENCE: 888

Lys Val Ser Asn Arg Phe Ser
1               5

<210> SEQ ID NO 889
<211> LENGTH: 9
<212> TYPE: PRT
<213> ORGANISM: Artificial Sequence
<220> FEATURE:
<223> OTHER INFORMATION: Recombinant protein

<400> SEQUENCE: 889

Ser Gln Ser Thr His Val Pro Tyr Thr
1               5

<210> SEQ ID NO 890
<211> LENGTH: 114
<212> TYPE: PRT
<213> ORGANISM: Artificial Sequence
<220> FEATURE:
<223> OTHER INFORMATION: Recombinant protein

<400> SEQUENCE: 890

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Thr Trp Val Arg Gln Ala Pro Gly Lys Gly Leu Glu Trp Ile
        35                  40                  45

Gly Glu Ile Asn Pro Asp Ser Ser Thr Ile Asn Tyr Asn Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Glu Val Arg Ser Glu Asp Thr Ala Leu Tyr Tyr Cys
                85                  90                  95

Ala Ser Gly Val Phe Thr Ser Trp Gly Gln Gly Thr Leu Val Thr Val
            100                 105                 110

Ser Ala

<210> SEQ ID NO 891
<211> LENGTH: 5
<212> TYPE: PRT
<213> ORGANISM: Artificial Sequence
<220> FEATURE:
<223> OTHER INFORMATION: Recombinant protein

<400> SEQUENCE: 891

Arg Tyr Trp Met Thr
1               5

<210> SEQ ID NO 892
<211> LENGTH: 17
<212> TYPE: PRT

```
<213> ORGANISM: Artificial Sequence
<220> FEATURE:
<223> OTHER INFORMATION: Recombinant protein

<400> SEQUENCE: 892

Glu Ile Asn Pro Asp Ser Ser Thr Ile Asn Tyr Asn Pro Ser Leu Lys
1               5                   10                  15

Asp

<210> SEQ ID NO 893
<211> LENGTH: 5
<212> TYPE: PRT
<213> ORGANISM: Artificial Sequence
<220> FEATURE:
<223> OTHER INFORMATION: Recombinant protein

<400> SEQUENCE: 893

Gly Val Phe Thr Ser
1               5

<210> SEQ ID NO 894
<211> LENGTH: 107
<212> TYPE: PRT
<213> ORGANISM: Artificial Sequence
<220> FEATURE:
<223> OTHER INFORMATION: Recombinant protein

<400> SEQUENCE: 894

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Phe Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Asp Thr Lys Leu Pro Tyr
                85                  90                  95

Thr Phe Gly Gly Gly Thr Lys Leu Glu Met Lys
            100                 105

<210> SEQ ID NO 895
<211> LENGTH: 11
<212> TYPE: PRT
<213> ORGANISM: Artificial Sequence
<220> FEATURE:
<223> OTHER INFORMATION: Recombinant protein

<400> SEQUENCE: 895

Arg Ala Ser Gln Asp Ile Ser Asn Tyr Leu Asn
1               5                   10

<210> SEQ ID NO 896
<211> LENGTH: 7
<212> TYPE: PRT
<213> ORGANISM: Artificial Sequence
<220> FEATURE:
<223> OTHER INFORMATION: Recombinant protein

<400> SEQUENCE: 896

Tyr Thr Ser Arg Leu His Ser
```

<210> SEQ ID NO 897
<211> LENGTH: 9
<212> TYPE: PRT
<213> ORGANISM: Artificial Sequence
<220> FEATURE:
<223> OTHER INFORMATION: Recombinant protein

<400> SEQUENCE: 897

Gln Gln Asp Thr Lys Leu Pro Tyr Thr
1               5

<210> SEQ ID NO 898
<211> LENGTH: 122
<212> TYPE: PRT
<213> ORGANISM: Artificial Sequence
<220> FEATURE:
<223> OTHER INFORMATION: Recombinant protein

<400> SEQUENCE: 898

Gln Val Gln Leu Gln Gln Ser Gly Ala Glu Pro Met Lys Pro Gly Ala
1               5                   10                  15

Ser Val Lys Ile Ser Cys Lys Ala Thr Gly Tyr Thr Phe Ser Ser His
            20                  25                  30

Trp Ile Glu Trp Ile Lys Gln Arg Pro Gly His Gly Leu Glu Trp Ile
        35                  40                  45

Gly Glu Ile Leu Pro Gly Ser Gly Asn Thr Asn Tyr Asn Glu Lys Phe
    50                  55                  60

Lys Gly Lys Ala Thr Phe Thr Ala Asp Thr Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Tyr Tyr Gly Leu Asn Tyr Asp Trp Tyr Phe Asp Val Trp
            100                 105                 110

Gly Ala Gly Thr Thr Val Thr Val Ser Ser
        115                 120

<210> SEQ ID NO 899
<211> LENGTH: 5
<212> TYPE: PRT
<213> ORGANISM: Artificial Sequence
<220> FEATURE:
<223> OTHER INFORMATION: Recombinant protein

<400> SEQUENCE: 899

Ser His Trp Ile Glu
1               5

<210> SEQ ID NO 900
<211> LENGTH: 17
<212> TYPE: PRT
<213> ORGANISM: Artificial Sequence
<220> FEATURE:
<223> OTHER INFORMATION: Recombinant protein

<400> SEQUENCE: 900

Glu Ile Leu Pro Gly Ser Gly Asn Thr Asn Tyr Asn Glu Lys Phe Lys
1               5                   10                  15

Gly

<210> SEQ ID NO 901

```
<211> LENGTH: 13
<212> TYPE: PRT
<213> ORGANISM: Artificial Sequence
<220> FEATURE:
<223> OTHER INFORMATION: Recombinant protein

<400> SEQUENCE: 901

Gly Tyr Tyr Gly Leu Asn Tyr Asp Trp Tyr Phe Asp Val
1               5                   10

<210> SEQ ID NO 902
<211> LENGTH: 112
<212> TYPE: PRT
<213> ORGANISM: Artificial Sequence
<220> FEATURE:
<223> OTHER INFORMATION: Recombinant protein

<400> SEQUENCE: 902

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Phe His Trp Ala Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 903
<211> LENGTH: 16
<212> TYPE: PRT
<213> ORGANISM: Artificial Sequence
<220> FEATURE:
<223> OTHER INFORMATION: Recombinant protein

<400> SEQUENCE: 903

Arg Ser Ser Gln Ser Leu Val His Arg Asn Gly Asn Thr Tyr Phe His
1               5                   10                  15

<210> SEQ ID NO 904
<211> LENGTH: 7
<212> TYPE: PRT
<213> ORGANISM: Artificial Sequence
<220> FEATURE:
<223> OTHER INFORMATION: Recombinant protein

<400> SEQUENCE: 904

Lys Val Ser Asn Arg Phe Ser
1               5

<210> SEQ ID NO 905
<211> LENGTH: 9
<212> TYPE: PRT
<213> ORGANISM: Artificial Sequence
<220> FEATURE:
<223> OTHER INFORMATION: Recombinant protein

<400> SEQUENCE: 905

Ser Gln Ser Thr His Val Pro Tyr Thr
```

-continued

<210> SEQ ID NO 906
<211> LENGTH: 114
<212> TYPE: PRT
<213> ORGANISM: Artificial Sequence
<220> FEATURE:
<223> OTHER INFORMATION: Recombinant protein

<400> SEQUENCE: 906

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Thr Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Glu Val Arg Ser Glu Asp Thr Ala Leu Tyr Tyr Cys
                85                  90                  95

Ala Ser Gly Val Phe Thr Ser Trp Gly Gln Gly Thr Leu Val Thr Val
            100                 105                 110

Ser Ala

<210> SEQ ID NO 907
<211> LENGTH: 5
<212> TYPE: PRT
<213> ORGANISM: Artificial Sequence
<220> FEATURE:
<223> OTHER INFORMATION: Recombinant protein

<400> SEQUENCE: 907

Arg Tyr Trp Met Thr
1               5

<210> SEQ ID NO 908
<211> LENGTH: 17
<212> TYPE: PRT
<213> ORGANISM: Artificial Sequence
<220> FEATURE:
<223> OTHER INFORMATION: Recombinant protein

<400> SEQUENCE: 908

Glu Ile Asn Pro Asp Ser Ser Thr Ile Asn Tyr Ala Pro Ser Leu Lys
1               5                   10                  15

Asp

<210> SEQ ID NO 909
<211> LENGTH: 5
<212> TYPE: PRT
<213> ORGANISM: Artificial Sequence
<220> FEATURE:
<223> OTHER INFORMATION: Recombinant protein

<400> SEQUENCE: 909

Gly Val Phe Thr Ser
1               5

<210> SEQ ID NO 910
<211> LENGTH: 112

```
<212> TYPE: PRT
<213> ORGANISM: Artificial Sequence
<220> FEATURE:
<223> OTHER INFORMATION: Recombinant protein

<400> SEQUENCE: 910

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Arg
            20                  25                  30

Pro Gly Asn Thr Tyr Phe His Trp Leu Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 911
<211> LENGTH: 16
<212> TYPE: PRT
<213> ORGANISM: Artificial Sequence
<220> FEATURE:
<223> OTHER INFORMATION: Recombinant protein

<400> SEQUENCE: 911

Arg Ser Ser Gln Ser Leu Val His Arg Pro Gly Asn Thr Tyr Phe His
1               5                   10                  15

<210> SEQ ID NO 912
<211> LENGTH: 7
<212> TYPE: PRT
<213> ORGANISM: Artificial Sequence
<220> FEATURE:
<223> OTHER INFORMATION: Recombinant protein

<400> SEQUENCE: 912

Lys Val Ser Asn Arg Phe Ser
1               5

<210> SEQ ID NO 913
<211> LENGTH: 9
<212> TYPE: PRT
<213> ORGANISM: Artificial Sequence
<220> FEATURE:
<223> OTHER INFORMATION: Recombinant protein

<400> SEQUENCE: 913

Ser Gln Ser Thr His Val Pro Tyr Thr
1               5

<210> SEQ ID NO 914
<211> LENGTH: 114
<212> TYPE: PRT
<213> ORGANISM: Artificial Sequence
<220> FEATURE:
<223> OTHER INFORMATION: Recombinant protein

<400> SEQUENCE: 914

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Asp Phe Ser Arg Tyr
            20                  25                  30

Trp Met Thr Trp Val Arg Gln Ala Pro Gly Lys Gly Leu Val Trp Val
        35                  40                  45

Gly Glu Ile Asn Pro Asp Ser Ser Thr Ile Asn Tyr Ala Pro Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ser Gly Val Phe Thr Ser Trp Gly Gln Gly Thr Leu Val Thr Val
            100                 105                 110

Ser Ser

<210> SEQ ID NO 915
<211> LENGTH: 5
<212> TYPE: PRT
<213> ORGANISM: Artificial Sequence
<220> FEATURE:
<223> OTHER INFORMATION: Recombinant protein

<400> SEQUENCE: 915

Arg Tyr Trp Met Thr
1               5

<210> SEQ ID NO 916
<211> LENGTH: 17
<212> TYPE: PRT
<213> ORGANISM: Artificial Sequence
<220> FEATURE:
<223> OTHER INFORMATION: Recombinant protein

<400> SEQUENCE: 916

Glu Ile Asn Pro Asp Ser Ser Thr Ile Asn Tyr Ala Pro Ser Val Lys
1               5                   10                  15

Gly

<210> SEQ ID NO 917
<211> LENGTH: 5
<212> TYPE: PRT
<213> ORGANISM: Artificial Sequence
<220> FEATURE:
<223> OTHER INFORMATION: Recombinant protein

<400> SEQUENCE: 917

Gly Val Phe Thr Ser
1               5

<210> SEQ ID NO 918
<211> LENGTH: 112
<212> TYPE: PRT
<213> ORGANISM: Artificial Sequence
<220> FEATURE:
<223> OTHER INFORMATION: Recombinant protein

<400> SEQUENCE: 918

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Arg
            20                  25                  30

Asn Gly Asn Thr Tyr Phe His Trp Leu Gln Gln Arg Pro Gly Gln Pro
```

```
              35                  40                  45
Pro Arg Leu Ile Tyr Lys Val Ser Asn Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Tyr Thr Phe Gly Gln Gly Thr Lys Leu Glu Ile Lys
             100                 105                 110

<210> SEQ ID NO 919
<211> LENGTH: 16
<212> TYPE: PRT
<213> ORGANISM: Artificial Sequence
<220> FEATURE:
<223> OTHER INFORMATION: Recombinant protein

<400> SEQUENCE: 919

Arg Ser Ser Gln Ser Leu Val His Arg Asn Gly Asn Thr Tyr Phe His
  1               5                  10                  15

<210> SEQ ID NO 920
<211> LENGTH: 7
<212> TYPE: PRT
<213> ORGANISM: Artificial Sequence
<220> FEATURE:
<223> OTHER INFORMATION: Recombinant protein

<400> SEQUENCE: 920

Lys Val Ser Asn Arg Phe Ser
  1               5

<210> SEQ ID NO 921
<211> LENGTH: 9
<212> TYPE: PRT
<213> ORGANISM: Artificial Sequence
<220> FEATURE:
<223> OTHER INFORMATION: Recombinant protein

<400> SEQUENCE: 921

Ser Gln Ser Thr His Val Pro Tyr Thr
  1               5

<210> SEQ ID NO 922
<211> LENGTH: 114
<212> TYPE: PRT
<213> ORGANISM: Artificial Sequence
<220> FEATURE:
<223> OTHER INFORMATION: Recombinant protein

<400> SEQUENCE: 922

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asp Phe Ser Arg Tyr
                 20                  25                  30

Trp Met Thr Trp Val Arg Gln Ala Pro Gly Lys Gly Leu Val Trp Val
             35                  40                  45

Gly Glu Ile Asn Pro Asp Ser Ser Thr Ile Asn Tyr Ala Pro Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
```

85                  90                  95
Ala Arg Gly Val Phe Thr Ser Trp Gly Gln Gly Thr Leu Val Thr Val
                100                 105                 110

Ser Ser

<210> SEQ ID NO 923
<211> LENGTH: 5
<212> TYPE: PRT
<213> ORGANISM: Artificial Sequence
<220> FEATURE:
<223> OTHER INFORMATION: Recombinant protein

<400> SEQUENCE: 923

Arg Tyr Trp Met Thr
1               5

<210> SEQ ID NO 924
<211> LENGTH: 17
<212> TYPE: PRT
<213> ORGANISM: Artificial Sequence
<220> FEATURE:
<223> OTHER INFORMATION: Recombinant protein

<400> SEQUENCE: 924

Glu Ile Asn Pro Asp Ser Ser Thr Ile Asn Tyr Ala Pro Ser Val Lys
1               5                   10                  15

Gly

<210> SEQ ID NO 925
<211> LENGTH: 5
<212> TYPE: PRT
<213> ORGANISM: Artificial Sequence
<220> FEATURE:
<223> OTHER INFORMATION: Recombinant protein

<400> SEQUENCE: 925

Gly Val Phe Thr Ser
1               5

<210> SEQ ID NO 926
<211> LENGTH: 112
<212> TYPE: PRT
<213> ORGANISM: Artificial Sequence
<220> FEATURE:
<223> OTHER INFORMATION: Recombinant protein

<400> SEQUENCE: 926

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Arg
            20                  25                  30

Asn Gly Asn Thr Tyr Phe His Trp Leu Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
                100                 105                 110

<210> SEQ ID NO 927
<211> LENGTH: 16
<212> TYPE: PRT
<213> ORGANISM: Artificial Sequence
<220> FEATURE:
<223> OTHER INFORMATION: Recombinant protein

<400> SEQUENCE: 927

```
Arg Ser Ser Gln Ser Leu Val His Arg Asn Gly Asn Thr Tyr Phe His
1               5                   10                  15
```

<210> SEQ ID NO 928
<211> LENGTH: 7
<212> TYPE: PRT
<213> ORGANISM: Artificial Sequence
<220> FEATURE:
<223> OTHER INFORMATION: Recombinant protein

<400> SEQUENCE: 928

```
Lys Val Ser Asn Arg Phe Ser
1               5
```

<210> SEQ ID NO 929
<211> LENGTH: 9
<212> TYPE: PRT
<213> ORGANISM: Artificial Sequence
<220> FEATURE:
<223> OTHER INFORMATION: Recombinant protein

<400> SEQUENCE: 929

```
Ser Gln Ser Thr His Val Pro Tyr Thr
1               5
```

<210> SEQ ID NO 930
<211> LENGTH: 114
<212> TYPE: PRT
<213> ORGANISM: Artificial Sequence
<220> FEATURE:
<223> OTHER INFORMATION: Recombinant protein

<400> SEQUENCE: 930

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Thr Trp Val Arg Gln Ala Pro Gly Lys Gly Leu Val Trp Val
        35                  40                  45

Gly Glu Ile Asn Pro Asp Ser Ser Thr Ile Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Phe Thr Ser Trp Gly Gln Gly Thr Leu Val Thr Val
            100                 105                 110

Ser Ser
```

<210> SEQ ID NO 931
<211> LENGTH: 5
<212> TYPE: PRT
<213> ORGANISM: Artificial Sequence
<220> FEATURE:
<223> OTHER INFORMATION: Recombinant protein

<400> SEQUENCE: 931

Arg Tyr Trp Met Thr
1               5

<210> SEQ ID NO 932
<211> LENGTH: 17
<212> TYPE: PRT
<213> ORGANISM: Artificial Sequence
<220> FEATURE:
<223> OTHER INFORMATION: Recombinant protein

<400> SEQUENCE: 932

Glu Ile Asn Pro Asp Ser Ser Thr Ile Asn Tyr Ala Asp Ser Val Lys
1               5                   10                  15

Gly

<210> SEQ ID NO 933
<211> LENGTH: 5
<212> TYPE: PRT
<213> ORGANISM: Artificial Sequence
<220> FEATURE:
<223> OTHER INFORMATION: Recombinant protein

<400> SEQUENCE: 933

Gly Val Phe Thr Ser
1               5

<210> SEQ ID NO 934
<211> LENGTH: 112
<212> TYPE: PRT
<213> ORGANISM: Artificial Sequence
<220> FEATURE:
<223> OTHER INFORMATION: Recombinant protein

<400> SEQUENCE: 934

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Arg
            20                  25                  30

Gln Gly Asn Thr Tyr Phe His Trp Leu Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 935
<211> LENGTH: 16
<212> TYPE: PRT
<213> ORGANISM: Artificial Sequence
<220> FEATURE:
<223> OTHER INFORMATION: Recombinant protein

<400> SEQUENCE: 935

Arg Ser Ser Gln Ser Leu Val His Arg Gln Gly Asn Thr Tyr Phe His
1               5                   10                  15

```
<210> SEQ ID NO 936
<211> LENGTH: 7
<212> TYPE: PRT
<213> ORGANISM: Artificial Sequence
<220> FEATURE:
<223> OTHER INFORMATION: Recombinant protein

<400> SEQUENCE: 936

Lys Val Ser Asn Arg Phe Ser
1               5

<210> SEQ ID NO 937
<211> LENGTH: 9
<212> TYPE: PRT
<213> ORGANISM: Artificial Sequence
<220> FEATURE:
<223> OTHER INFORMATION: Recombinant protein

<400> SEQUENCE: 937

Ser Gln Ser Thr His Val Pro Tyr Thr
1               5

<210> SEQ ID NO 938
<211> LENGTH: 114
<212> TYPE: PRT
<213> ORGANISM: Artificial Sequence
<220> FEATURE:
<223> OTHER INFORMATION: Recombinant protein

<400> SEQUENCE: 938

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Thr Trp Val Arg Gln Ala Pro Gly Lys Gly Leu Val Trp Val
        35                  40                  45

Gly Glu Ile Asn Pro Asp Ser Ser Thr Ile Asn Tyr Ala Pro Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Val Phe Thr Ser Trp Gly Gln Gly Thr Leu Val Thr Val
            100                 105                 110

Ser Ser

<210> SEQ ID NO 939
<211> LENGTH: 5
<212> TYPE: PRT
<213> ORGANISM: Artificial Sequence
<220> FEATURE:
<223> OTHER INFORMATION: Recombinant protein

<400> SEQUENCE: 939

Arg Tyr Trp Met Thr
1               5

<210> SEQ ID NO 940
<211> LENGTH: 17
<212> TYPE: PRT
<213> ORGANISM: Artificial Sequence
<220> FEATURE:
<223> OTHER INFORMATION: Recombinant protein
```

-continued

```
<400> SEQUENCE: 940

Glu Ile Asn Pro Asp Ser Ser Thr Ile Asn Tyr Ala Pro Ser Val Lys
1               5                   10                  15

Gly

<210> SEQ ID NO 941
<211> LENGTH: 5
<212> TYPE: PRT
<213> ORGANISM: Artificial Sequence
<220> FEATURE:
<223> OTHER INFORMATION: Recombinant protein

<400> SEQUENCE: 941

Gly Val Phe Thr Ser
1               5

<210> SEQ ID NO 942
<211> LENGTH: 326
<212> TYPE: PRT
<213> ORGANISM: Artificial Sequence
<220> FEATURE:
<223> OTHER INFORMATION: Recombinant protein

<400> SEQUENCE: 942

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
```

```
            260                 265                 270
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 943
<211> LENGTH: 326
<212> TYPE: PRT
<213> ORGANISM: Artificial Sequence
<220> FEATURE:
<223> OTHER INFORMATION: Recombinant protein

<400> SEQUENCE: 943

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Leu Leu Tyr Ser
        275                 280                 285

Lys Leu Thr Val Asp Lys Ser Arg Trp Gln Glu Gly Asn Val Phe Ser
```

```
                       290                 295                 300
Cys Ser Val Met His Glu Ala Leu His Asn His Tyr Thr Gln Lys Ser
305                     310                 315                 320

Leu Ser Leu Ser Leu Gly
                325
```